(12) United States Patent
Schwab et al.

(10) Patent No.: US 9,138,308 B2
(45) Date of Patent: Sep. 22, 2015

(54) MUCOSAL TISSUE ADHESION VIA TEXTURED SURFACE

(75) Inventors: Justin J. Schwab, Santa Barbara, CA (US); Joseph S. Raven, Tigard, OR (US); Futian Liu, Sunnyvale, CA (US)

(73) Assignee: APOLLO ENDOSURGERY, INC., Austin, TX (US)

( * ) Notice: Subject to any disclaimer, the term of this patent is extended or adjusted under 35 U.S.C. 154(b) by 348 days.

(21) Appl. No.: 13/565,670

(22) Filed: Aug. 2, 2012

(65) Prior Publication Data

US 2013/0197661 A1 Aug. 1, 2013

Related U.S. Application Data

(63) Continuation-in-part of application No. 13/245,518, filed on Sep. 26, 2011, now abandoned, which is a continuation-in-part of application No. 13/104,820, filed on May 10, 2011, now abandoned, application No. 13/565,670, which is a continuation-in-part of (Continued)

(51) Int. Cl.
*A61F 2/04* (2013.01)
*B29C 41/02* (2006.01)
*A61F 2/00* (2006.01)
*A61B 5/00* (2006.01)
*A61L 27/16* (2006.01)
*A61L 27/18* (2006.01)
*A61L 27/56* (2006.01)

(Continued)

(52) U.S. Cl.
CPC . *A61F 2/04* (2013.01); *A61B 5/686* (2013.01); *A61B 5/6871* (2013.01); *A61B 5/6879* (2013.01); *A61F 2/0077* (2013.01); *A61L 27/165* (2013.01); *A61L 27/18* (2013.01); *A61L 27/56* (2013.01); *A61L 31/049* (2013.01); *A61L 31/06* (2013.01); *A61L 31/146* (2013.01); *B29C 41/02* (2013.01); *A61F 2002/045* (2013.01); *A61L 2400/08* (2013.01)

(58) Field of Classification Search
CPC .................................. A61F 2/04; A61F 2/042
USPC .......................................... 623/23.64–23.65
See application file for complete search history.

(56) References Cited

U.S. PATENT DOCUMENTS 2,324,735 A 7/1943 Spanelabrahamn
2,805,208 A 9/1957 Roche (Continued)

FOREIGN PATENT DOCUMENTS

EP 0230672 8/1987
EP 0315814 A2 5/1989

(Continued)

OTHER PUBLICATIONS

Alvarez, Sonia et al., 'Synthesis of Macro/Mesoporous Silica and Carbon Monoliths by Using a Commercial Polyurethane Foam as Sacrificial Template', Materials Letters, 61, 2378-2381 (2007).

(Continued)

*Primary Examiner* — Suzette J Gherbi
(74) *Attorney, Agent, or Firm* — Gordon & Jacobson, PC

(57) ABSTRACT

The present specification discloses porous materials, methods of forming such porous material, biocompatible implantable devices comprising such porous materials, and methods of making such biocompatible implantable devices. The porous material may be used to fix to the interior mucosal lining of a patient's gastrointestinal tract.

13 Claims, 26 Drawing Sheets

Related U.S. Application Data application No. 13/104,820, filed on May 10, 2011, now abandoned, application No. 13/565,670, which is a continuation-in-part of application No. 13/247,535, filed on Sep. 28, 2011, now Pat. No. 9,044,897, application No. 13/565,670, which is a continuation-in-part of application No. 13/247,835, filed on Sep. 28, 2011, now Pat. No. 8,889,751, application No. 13/565,670, which is a continuation-in-part of application No. 13/246,568, filed on Sep. 27, 2011, now Pat. No. 8,877,822, application No. 13/565,670, which is a continuation-in-part of application No. 13/104,395, filed on May 10, 2011, now abandoned, application No. 13/565,670, which is a continuation-in-part of application No. 13/104,888, filed on May 10, 2011, now abandoned, said application No. 13/565,670 is a continuation-in-part of application No. 13/104,811, filed on May 10, 2011, now Pat. No. 8,685,296, application No. 13/565,670, which is a continuation-in-part of application No. 13/104,893, filed on May 10, 2011, which is a continuation-in-part of application No. 13/021,615, filed on Feb. 4, 2011, which is a continuation-in-part of application No. 13/015,309, filed on Jan. 27, 2011, now abandoned.

(60) Provisional application No. 61/333,146, filed on May 10, 2010, provisional application No. 61/387,381, filed on Sep. 28, 2010, provisional application No. 61/387,115, filed on Sep. 28, 2010, provisional application No. 61/387,074, filed on Sep. 28, 2010, provisional application No. 61/387,083, filed on Sep. 28, 2010, provisional application No. 61/333,120, filed on May 10, 2010, provisional application No. 61/333,613, filed on May 11, 2010, provisional application No. 61/333,599, filed on May 11, 2010, provisional application No. 61/301,104, filed on Feb. 3, 2010, provisional application No. 61/375,338, filed on Aug. 20, 2010, provisional application No. 61/301,864, filed on Feb. 5, 2010.

(51) Int. Cl.
*A61L 31/04* (2006.01)
*A61L 31/06* (2006.01)
*A61L 31/14* (2006.01)

(56) References Cited

U.S. PATENT DOCUMENTS

| | | |
|---|---|---|
| 2,997,746 A | 8/1961 | OBrien |
| 3,189,921 A | 6/1965 | Pangman |
| 3,293,663 A | 12/1966 | Cronin |
| 3,366,975 A | 2/1968 | Pangman |
| 3,376,238 A | 4/1968 | Gregorian |
| 3,559,214 A | 2/1971 | Pangman |
| 3,600,718 A | 8/1971 | Boone |
| 3,665,520 A | 5/1972 | Perras |
| 3,700,380 A | 10/1972 | Kitrilakis |
| 3,852,832 A | 12/1974 | McGhan |
| 3,923,939 A | 12/1975 | Baker |
| 3,934,274 A | 1/1976 | Hartley |
| 4,034,751 A | 7/1977 | Hung |
| 4,150,076 A | 4/1979 | Baris |
| 4,157,085 A | 6/1979 | Austad |
| 4,231,979 A | 11/1980 | White |
| 4,264,990 A | 5/1981 | Hamas |
| 4,298,997 A | 11/1981 | Rybka |
| 4,298,998 A | 11/1981 | Naficy |
| 4,329,385 A | 5/1982 | Banks |
| 4,428,082 A | 1/1984 | Naficy |
| 4,433,440 A | 2/1984 | Cohen |
| 4,470,160 A | 9/1984 | Cavon |
| 4,472,226 A | 9/1984 | Redinger |
| 4,482,577 A | 11/1984 | Goldstein |
| 4,499,211 A | 2/1985 | Walch |
| 4,531,244 A | 7/1985 | Hamas |
| 4,573,999 A | 3/1986 | Netto |
| 4,584,324 A | 4/1986 | Baumann |
| 4,592,755 A | 6/1986 | Penton |
| 4,610,690 A | 9/1986 | Tiffamy |
| 4,636,213 A | 1/1987 | Pakiam |
| 4,643,733 A | 2/1987 | Becker |
| 4,647,618 A | 3/1987 | Baumann |
| 4,648,880 A | 3/1987 | Brauman |
| 4,650,487 A | 3/1987 | Chaglassian |
| 4,651,717 A | 3/1987 | Jakubczak |
| 4,681,587 A | 7/1987 | Eberl |
| 4,740,208 A | 4/1988 | Cavon |
| 4,772,285 A | 9/1988 | Ksander |
| 4,773,908 A | 9/1988 | Becker |
| 4,773,909 A | 9/1988 | Chaglassian |
| 4,790,848 A | 12/1988 | Cronin |
| 4,795,464 A | 1/1989 | Eberl |
| 4,803,025 A | 2/1989 | Brockmeyer |
| 4,828,560 A | 5/1989 | Heyler |
| 4,840,628 A | 6/1989 | Cavon |
| 4,841,992 A | 6/1989 | Sasaki |
| 4,859,383 A | 8/1989 | Dillon |
| 4,859,712 A | 8/1989 | Cox |
| 4,889,744 A | 12/1989 | Quaid |
| 4,899,764 A | 2/1990 | Gauger |
| 4,902,294 A | 2/1990 | Gosserez |
| 4,906,423 A | 3/1990 | Frisch |
| 4,936,858 A | 6/1990 | OKeeffe |
| 4,944,749 A | 7/1990 | Becker |
| 4,944,750 A | 7/1990 | Cox |
| 4,950,292 A | 8/1990 | Audretsch |
| 4,955,907 A | 9/1990 | Ledergerber |
| 4,955,909 A | 9/1990 | Ersek |
| 4,960,425 A | 10/1990 | Yan |
| 4,965,430 A | 10/1990 | Curtis |
| 4,969,899 A | 11/1990 | Cox |
| 5,002,572 A | 3/1991 | Picha |
| 5,007,929 A | 4/1991 | Quaid |
| 5,007,940 A | 4/1991 | Berg |
| 5,011,494 A | 4/1991 | von Recum |
| 5,022,942 A | 6/1991 | Yan |
| 5,026,394 A | 6/1991 | Baker |
| 5,034,422 A | 7/1991 | Triolo |
| 5,035,249 A | 7/1991 | Sasaki |
| 5,066,398 A | 11/1991 | Soria |
| 5,092,348 A | 3/1992 | Dubrul |
| 5,092,882 A | 3/1992 | Lynn |
| 5,104,409 A | 4/1992 | Baker |
| 5,116,387 A | 5/1992 | Berg |
| 5,128,088 A | 7/1992 | Shimomura |
| 5,135,959 A | 8/1992 | Hill |
| 5,146,933 A | 9/1992 | Boyd |
| 5,147,398 A | 9/1992 | Lynn |
| 5,158,571 A | 10/1992 | Picha |
| 5,158,573 A | 10/1992 | Berg |
| 5,171,269 A | 12/1992 | Bark |
| 5,185,297 A | 2/1993 | Park |
| 5,207,709 A | 5/1993 | Picha |
| 5,219,361 A | 6/1993 | von Recum |
| 5,236,453 A | 8/1993 | Picha |
| 5,236,454 A | 8/1993 | Miller |
| 5,236,457 A | 8/1993 | Devanathan |
| 5,246,454 A | 9/1993 | Petersen |
| 5,282,856 A | 2/1994 | Ledergerber |
| 5,296,069 A | 3/1994 | Robert |
| 5,348,788 A | 9/1994 | White |
| 5,354,338 A | 10/1994 | Ledergerber |
| 5,358,521 A | 10/1994 | Shane |
| 5,376,117 A | 12/1994 | Pinchuk |
| 5,383,929 A | 1/1995 | Ledergerber |
| 5,437,824 A | 8/1995 | Carlisle |
| 5,441,919 A | 8/1995 | Park |
| 5,447,535 A | 9/1995 | Muller |

(56) References Cited

U.S. PATENT DOCUMENTS

| | | | |
|---|---|---|---|
| 5,455,100 A | 10/1995 | White | |
| 5,460,621 A * | 10/1995 | Gertzman et al. | 604/358 |
| 5,480,430 A | 1/1996 | Carlisle | |
| 5,496,367 A | 3/1996 | Fisher | |
| 5,496,370 A | 3/1996 | Hamas | |
| 5,507,808 A | 4/1996 | Becker | |
| 5,522,896 A | 6/1996 | Prescott | |
| 5,525,275 A | 6/1996 | Iverson | |
| 5,531,899 A | 7/1996 | Yen | |
| 5,534,023 A | 7/1996 | Henley | |
| 5,545,217 A | 8/1996 | Offray | |
| 5,545,220 A | 8/1996 | Andrews | |
| 5,549,671 A | 8/1996 | Waybright | |
| 5,571,179 A | 11/1996 | Manders | |
| RE35,391 E | 12/1996 | Brauman | |
| 5,589,176 A | 12/1996 | Seare | |
| 5,605,693 A | 2/1997 | Seare | |
| 5,607,473 A | 3/1997 | Weber-Unger | |
| 5,624,674 A | 4/1997 | Seare | |
| 5,630,843 A | 5/1997 | Rosenberg | |
| 5,630,844 A | 5/1997 | Dogan et al. | |
| 5,633,290 A | 5/1997 | Frechet | |
| 5,653,755 A | 8/1997 | Ledergerber | |
| 5,656,710 A | 8/1997 | Newberth | |
| 5,658,330 A | 8/1997 | Carlisle | |
| 5,674,285 A | 10/1997 | Quaid | |
| 5,681,572 A | 10/1997 | Seare | |
| 5,728,457 A | 3/1998 | Frechet | |
| 5,776,159 A | 7/1998 | Young | |
| 5,779,734 A | 7/1998 | Ledergerber | |
| 5,798,065 A | 8/1998 | Picha | |
| 5,824,081 A | 10/1998 | Knapp | |
| 5,843,189 A | 12/1998 | Perouse | |
| 5,855,588 A | 1/1999 | Young | |
| 5,863,957 A | 1/1999 | Li | |
| 5,871,497 A | 2/1999 | Young | |
| 5,882,353 A | 3/1999 | VanBeek | |
| 5,895,423 A | 4/1999 | Becker | |
| 5,935,164 A | 8/1999 | Iversen | |
| 5,961,552 A | 10/1999 | Iversen | |
| 5,964,803 A | 10/1999 | Iversen | |
| 5,965,076 A | 10/1999 | Banks | |
| 5,984,943 A | 11/1999 | Young | |
| 5,993,716 A | 11/1999 | Draenert | |
| 6,060,530 A | 5/2000 | Chaouk | |
| 6,071,309 A | 6/2000 | Knowlton | |
| 6,074,421 A | 6/2000 | Murphy | |
| 6,083,262 A | 7/2000 | Caravel | |
| 6,099,565 A | 8/2000 | Sakura | |
| 6,100,306 A | 8/2000 | Li | |
| 6,107,357 A | 8/2000 | Hawker | |
| 6,113,634 A | 9/2000 | Weber-Unger | |
| 6,146,418 A | 11/2000 | Berman | |
| 6,160,030 A | 12/2000 | Chaouk | |
| 6,183,514 B1 | 2/2001 | Becker | |
| 6,187,043 B1 | 2/2001 | Ledergerber | |
| 6,203,570 B1 | 3/2001 | Baeke | |
| 6,206,930 B1 | 3/2001 | Burg | |
| 6,214,045 B1 * | 4/2001 | Corbitt et al. | 623/8 |
| 6,214,926 B1 | 4/2001 | Winn | |
| 6,225,367 B1 | 5/2001 | Chaouk | |
| 6,315,796 B1 | 11/2001 | Eaton | |
| 6,335,438 B1 | 1/2002 | Fonnum | |
| 6,340,648 B1 | 1/2002 | Imura | |
| 6,380,270 B1 | 4/2002 | Yates | |
| 6,387,133 B1 | 5/2002 | Perouse | |
| 6,432,138 B1 | 8/2002 | Offray | |
| 6,464,726 B1 | 10/2002 | Heljenek | |
| 6,471,993 B1 | 10/2002 | Shastri | |
| 6,520,989 B1 | 2/2003 | Eaton | |
| 6,531,523 B1 | 3/2003 | Davankov | |
| 6,540,789 B1 * | 4/2003 | Silverman et al. | 623/23.65 |
| 6,541,865 B2 | 4/2003 | Hawker | |
| 6,544,287 B1 | 4/2003 | Johnson | |
| 6,575,896 B2 * | 6/2003 | Silverman et al. | 600/29 |
| 6,602,452 B2 | 8/2003 | Schuessler | |
| 6,602,804 B2 | 8/2003 | Allen | |
| 6,605,116 B2 | 8/2003 | Falcon | |
| 6,638,308 B2 | 10/2003 | Corbitt | |
| 6,663,668 B1 | 12/2003 | Chaouk | |
| 6,672,385 B2 | 1/2004 | Kilaas | |
| 6,673,285 B2 | 1/2004 | Ma | |
| 6,692,527 B1 | 2/2004 | Bellin | |
| 6,693,159 B1 | 2/2004 | Holmes | |
| 6,726,991 B2 | 4/2004 | Kaeding | |
| 6,755,861 B2 | 6/2004 | Nakao | |
| 6,802,861 B1 | 10/2004 | Hamas | |
| 6,802,868 B2 * | 10/2004 | Silverman et al. | 623/23.65 |
| 6,811,570 B1 | 11/2004 | Gehl | |
| 6,818,673 B2 | 11/2004 | Ferguson | |
| 6,875,233 B1 | 4/2005 | Turner | |
| 6,881,226 B2 | 4/2005 | Corbitt | |
| 6,900,055 B1 | 5/2005 | Fuller | |
| 6,913,626 B2 | 7/2005 | McGhan | |
| 6,916,339 B1 | 7/2005 | Missana | |
| 6,921,418 B2 | 7/2005 | Ledergerber | |
| 6,932,840 B1 | 8/2005 | Bretz | |
| 6,936,068 B1 | 8/2005 | Knisley | |
| 6,967,222 B2 | 11/2005 | Khanarian | |
| 6,998,148 B1 | 2/2006 | You | |
| 7,018,918 B2 | 3/2006 | Kloster | |
| 7,026,374 B2 * | 4/2006 | Nathan et al. | 523/113 |
| 7,044,979 B2 * | 5/2006 | Silverman et al. | 623/23.65 |
| 7,056,277 B2 * | 6/2006 | Silverman et al. | 600/29 |
| 7,081,135 B2 | 7/2006 | Smith | |
| 7,081,136 B1 | 7/2006 | Becker | |
| 7,087,200 B2 | 8/2006 | Taboas | |
| 7,087,982 B2 | 8/2006 | Huang | |
| 7,105,116 B2 | 9/2006 | Bellin | |
| 7,109,249 B2 | 9/2006 | Bruza | |
| 7,112,615 B2 | 9/2006 | Gleason | |
| 7,169,180 B2 | 1/2007 | Brennan | |
| 7,176,273 B2 | 2/2007 | Yuan | |
| 7,192,450 B2 | 3/2007 | Brauker | |
| 7,241,704 B1 | 7/2007 | Wu | |
| 7,244,270 B2 | 7/2007 | Lesh | |
| 7,323,208 B2 | 1/2008 | Ma | |
| 7,332,445 B2 | 2/2008 | Lukas | |
| 7,364,591 B2 * | 4/2008 | Silverman et al. | 623/23.65 |
| 7,368,483 B2 | 5/2008 | Connor | |
| 7,419,772 B2 | 9/2008 | Watkins | |
| 7,425,288 B2 | 9/2008 | Flodin | |
| 7,425,350 B2 | 9/2008 | Todd | |
| 7,439,272 B2 | 10/2008 | Xu | |
| 7,466,025 B2 | 12/2008 | Goodner | |
| 7,476,249 B2 | 1/2009 | Frank | |
| 7,520,896 B2 | 4/2009 | Benslimane | |
| 7,547,393 B2 | 6/2009 | Ramaswamy | |
| 7,557,167 B2 | 7/2009 | Swetlin | |
| 7,575,759 B2 | 8/2009 | Murphy | |
| 7,625,405 B2 | 12/2009 | Purkait | |
| 7,628,604 B2 | 12/2009 | Schuessler | |
| 7,629,224 B1 | 12/2009 | van den Hoek et al. | |
| 7,632,228 B2 | 12/2009 | Brauker | |
| 7,632,291 B2 | 12/2009 | Stephens | |
| 7,641,688 B2 | 1/2010 | Lesh | |
| 7,645,475 B2 | 1/2010 | Prewett | |
| 7,651,762 B2 | 1/2010 | Xu | |
| 7,651,872 B2 | 1/2010 | Hart | |
| 7,674,521 B2 | 3/2010 | Gates | |
| 7,771,347 B2 * | 8/2010 | Silverman et al. | 600/29 |
| 7,771,644 B2 | 8/2010 | Flather | |
| 8,202,317 B2 | 6/2012 | Becker | |
| 8,313,527 B2 | 11/2012 | Powell | |
| 8,487,012 B2 | 7/2013 | Goraltchouk | |
| 8,506,627 B2 | 8/2013 | Van Epps | |
| 8,845,753 B2 * | 9/2014 | Stack et al. | 623/23.7 |
| 2002/0005600 A1 | 1/2002 | Ma | |
| 2002/0038147 A1 | 3/2002 | Miller | |
| 2002/0065331 A1 | 5/2002 | Zampini | |
| 2002/0193885 A1 | 12/2002 | Legeay | |
| 2003/0036803 A1 | 2/2003 | McGhan | |
| 2003/0093151 A1 | 5/2003 | Zhang | |
| 2003/0099630 A1 | 5/2003 | DiBenedetto | |

(56) References Cited

U.S. PATENT DOCUMENTS

| | | |
|---|---|---|
| 2003/0105469 A1 | 6/2003 | Karmon |
| 2003/0205846 A1 | 11/2003 | Bellin |
| 2003/0208269 A1 | 11/2003 | Eaton |
| 2003/0234462 A1 | 12/2003 | Pearce |
| 2004/0010225 A1 | 1/2004 | Schuessler |
| 2004/0077739 A1 | 4/2004 | Flodin |
| 2004/0115241 A1 | 6/2004 | Calhoun |
| 2004/0127985 A1 | 7/2004 | Bellin |
| 2004/0143327 A1 | 7/2004 | Ku |
| 2004/0148024 A1 | 7/2004 | Williams |
| 2004/0153151 A1 | 8/2004 | Gonzales de Vicente |
| 2004/0213986 A1 | 10/2004 | Kim |
| 2005/0055093 A1 | 3/2005 | Brennan |
| 2005/0070124 A1 | 3/2005 | Miller |
| 2005/0112169 A1 | 5/2005 | Brauker |
| 2005/0122169 A1 | 6/2005 | Watanabe |
| 2005/0196452 A1 | 9/2005 | Boyan |
| 2005/0216094 A1 | 9/2005 | Prewett |
| 2005/0251083 A1 | 11/2005 | Carr-Brendel |
| 2006/0002810 A1 | 1/2006 | Grohowski |
| 2006/0036266 A1 | 2/2006 | Sulmanidze |
| 2006/0036320 A1 | 2/2006 | Job |
| 2006/0051392 A1 | 3/2006 | Heruth |
| 2006/0136056 A1 | 6/2006 | Wohl |
| 2006/0147492 A1 | 7/2006 | Hunter |
| 2006/0224239 A1 | 10/2006 | Tiahrt |
| 2006/0229721 A1 | 10/2006 | Ku |
| 2006/0235094 A1 | 10/2006 | Habibi-Naini |
| 2006/0246121 A1 | 11/2006 | Ma |
| 2006/0247383 A1 | 11/2006 | Hedrick |
| 2007/0036844 A1 | 2/2007 | Ma |
| 2007/0093911 A1 | 4/2007 | Fricke |
| 2007/0104693 A1 | 5/2007 | Quijano |
| 2007/0104695 A1 | 5/2007 | Quijano |
| 2007/0116735 A1 | 5/2007 | Calhoun |
| 2007/0135916 A1 | 6/2007 | Maxwell |
| 2007/0154525 A1 | 7/2007 | Calhoun |
| 2007/0190108 A1 | 8/2007 | Datta |
| 2007/0198085 A1 | 8/2007 | Benslimane |
| 2007/0202084 A1* | 8/2007 | Sadozai et al. ............... 424/93.7 |
| 2007/0233273 A1 | 10/2007 | Connell |
| 2007/0287009 A1 | 12/2007 | Okude |
| 2008/0009830 A1 | 1/2008 | Fujimoto |
| 2008/0071371 A1 | 3/2008 | Elshout |
| 2008/0075752 A1 | 3/2008 | Ratner |
| 2008/0154366 A1 | 6/2008 | Frank |
| 2008/0241212 A1 | 10/2008 | Moses |
| 2008/0246180 A1 | 10/2008 | Appleby |
| 2008/0268019 A1 | 10/2008 | Badylak |
| 2008/0292939 A1 | 11/2008 | Xie |
| 2008/0312739 A1 | 12/2008 | Agerup |
| 2009/0018603 A1* | 1/2009 | Mitelberg et al. ............... 607/40 |
| 2009/0022770 A1 | 1/2009 | Andersson |
| 2009/0030515 A1 | 1/2009 | Schuessler |
| 2009/0045119 A1 | 2/2009 | Hosoya |
| 2009/0045166 A1 | 2/2009 | Li |
| 2009/0082864 A1 | 3/2009 | Chen |
| 2009/0087641 A1 | 4/2009 | Favis |
| 2009/0093878 A1 | 4/2009 | Glicksman |
| 2009/0118829 A1 | 5/2009 | Powell |
| 2009/0125107 A1 | 5/2009 | Maxwell |
| 2009/0157180 A1 | 6/2009 | Schraga |
| 2009/0164014 A1 | 6/2009 | Liljensten |
| 2009/0169716 A1 | 7/2009 | Linhardt |
| 2009/0198331 A1 | 8/2009 | Kesten |
| 2009/0198332 A1 | 8/2009 | Becker |
| 2009/0198333 A1 | 8/2009 | Becker |
| 2009/0214652 A1 | 8/2009 | Hunter |
| 2010/0042211 A1 | 2/2010 | Van Epps |
| 2010/0042212 A1 | 2/2010 | Van Epps |
| 2010/0049317 A1 | 2/2010 | Schuessler |
| 2010/0075056 A1 | 3/2010 | Axisa |
| 2010/0204719 A1* | 8/2010 | Balbierz et al. ............... 606/157 |
| 2010/0292790 A1 | 11/2010 | Stroumpoulis |
| 2011/0035004 A1 | 2/2011 | Maxwell |
| 2011/0054604 A1 | 3/2011 | Becker |
| 2011/0054605 A1 | 3/2011 | Becker |
| 2011/0093069 A1 | 4/2011 | Goraltchouk |
| 2011/0104395 A1 | 5/2011 | Kumagai |
| 2011/0106249 A1 | 5/2011 | Becker |
| 2011/0117267 A1 | 5/2011 | Powell |
| 2011/0184531 A1 | 7/2011 | Goraltchouk |
| 2011/0196488 A1 | 8/2011 | Goraltchouk |
| 2011/0196489 A1 | 8/2011 | Van Epps |
| 2011/0257623 A1 | 10/2011 | Marshall |
| 2011/0276133 A1 | 11/2011 | Liu |
| 2011/0276134 A1 | 11/2011 | Manesis |
| 2011/0278755 A1 | 11/2011 | Liu |
| 2011/0282444 A1 | 11/2011 | Liu |
| 2011/0309541 A1 | 12/2011 | Thompson |
| 2011/0310488 A1 | 12/2011 | Tomotoshi |
| 2011/0313073 A1 | 12/2011 | Goraltchouk |
| 2012/0004722 A1 | 1/2012 | Goraltchouk |
| 2012/0041555 A1 | 2/2012 | Manesis |
| 2012/0077010 A1 | 3/2012 | Manesis |
| 2012/0077012 A1 | 3/2012 | Liu |
| 2012/0077891 A1 | 3/2012 | Liu |
| 2012/0101574 A1 | 4/2012 | Goraltchouk |
| 2012/0142798 A1 | 6/2012 | Thompson |
| 2012/0245685 A1 | 9/2012 | Yu |
| 2012/0321777 A1 | 12/2012 | Stroumpoulis |
| 2013/0013062 A1 | 1/2013 | Thompson |
| 2013/0023987 A1 | 1/2013 | Liu |
| 2013/0032962 A1 | 2/2013 | Liu |
| 2013/0053956 A1 | 2/2013 | Powell |
| 2013/0158657 A1 | 6/2013 | Nofrey |
| 2013/0209661 A1 | 8/2013 | Goraltchouk |
| 2014/0081419 A1* | 3/2014 | Silverman et al. ......... 623/23.65 |
| 2014/0219963 A1* | 8/2014 | Badylak et al. ............... 424/93.1 |

FOREIGN PATENT DOCUMENTS

| | | |
|---|---|---|
| EP | 0522585 | 1/1993 |
| EP | 1532942 | 5/2005 |
| FR | 2840617 A1 | 12/2003 |
| JP | 2003062062 | 4/2003 |
| JP | 2007029717 | 8/2007 |
| WO | 2004037318 A2 | 5/2004 |
| WO | 2004062531 A1 | 7/2004 |
| WO | 2006133366 | 12/2006 |
| WO | 2008121409 A1 | 10/2008 |
| WO | 2009061672 | 5/2009 |
| WO | 2009110917 A1 | 9/2009 |
| WO | 2010019761 A1 | 2/2010 |
| WO | 2010022130 A1 | 2/2010 |
| WO | 2011094155 A2 | 8/2011 |
| WO | 2011097499 A1 | 8/2011 |
| WO | 2011143213 A1 | 11/2011 |
| WO | 2011143219 A1 | 11/2011 |

OTHER PUBLICATIONS

Barr, S. et al, 'Current Implant Surface Technology: An Examination of Their Nanostructure and Their Influence on Fibroblast Alignment and Biocompatibility', Elastic, 2009, 9, 198-217.

Brauker et al., 'Neovascularization of synthetic membranes directed by membrane microarchitecture', Journal of Biomedical Materials Research, 1995, pp. 1517-1524, vol. 29, John Wiley & Sons, Inc.

Ma, Peter, 'Scaffolds for tissue fabrication', Materials Today, 2004, 7, 30-40.

Mikos, Antonios et al., 'Formation of Highly Porous Biodegradable Scaffolds for Tissue Engineering', Electronic Journal of Biotechnology, 2000, 3(2), 114-119.

Murphy, William et al, 'Salt Fusion: An Approach to Improve Pore Interconnectivity Within Tissue Engineering Scaffolds', Tissue Engineering, vol. 8, Iss, 1, 2004.

Sharkawy et al. 'Engineering the tissue which encapsulates subcutaneous implants', II. Plasma—tissue exchange properties, 1998, pp. 586-597, John Wiley & Sons, Inc.

(56) References Cited

OTHER PUBLICATIONS

Wei, Guobao et al., 'Macroporous and Nanofibers Polymer Scaffolds and Polymer/bone-like Apatite Composite Scaffolds Generated by Sugar Spheres', Journal of Biomedical Materials Research Part A, 2006, 306-315.

Zhang, Yuan et al, 'Macroporous Alumina Monoliths Prepared by Filling Polymer Foams With Alumina Hydrosols', J. Mater Sci., 44, 931-938 (2009).

* cited by examiner

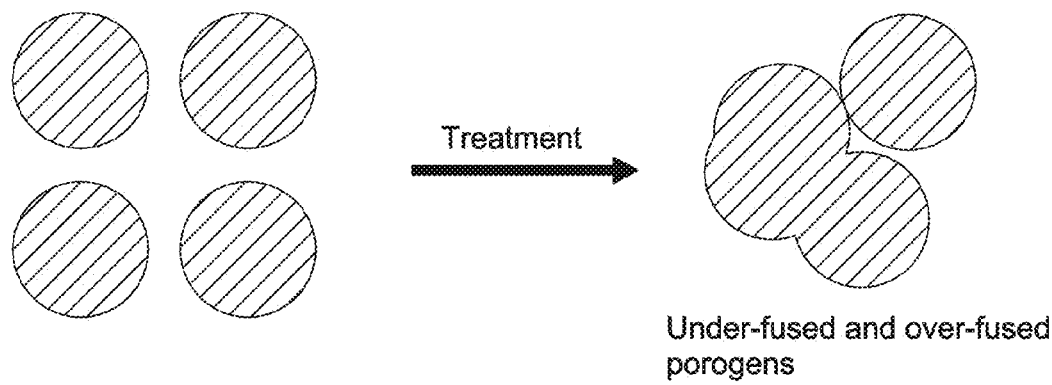
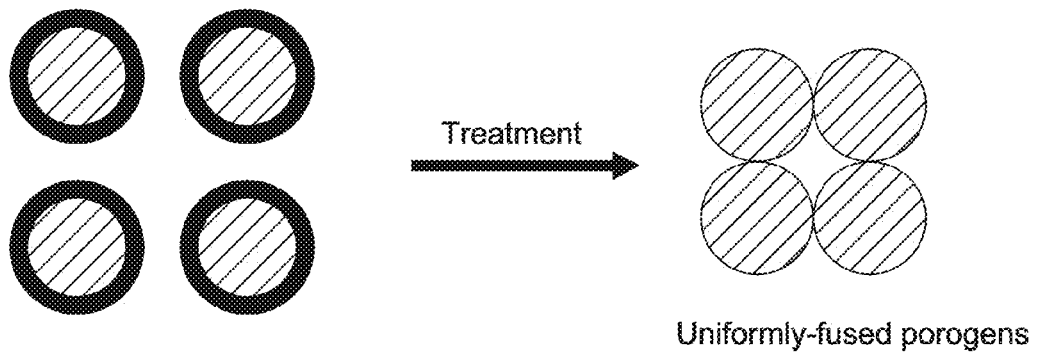
FIG. 1

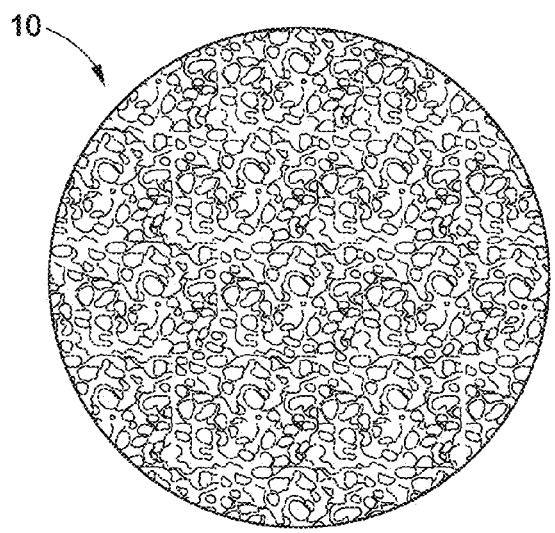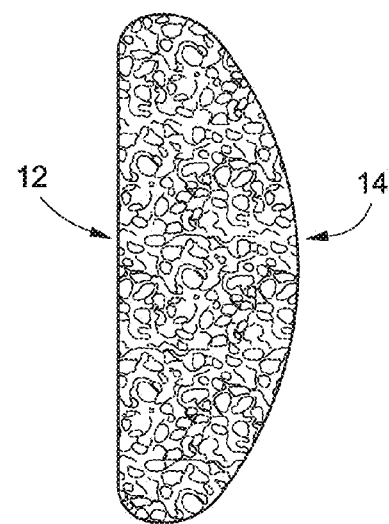
FIG. 4A  FIG. 4B
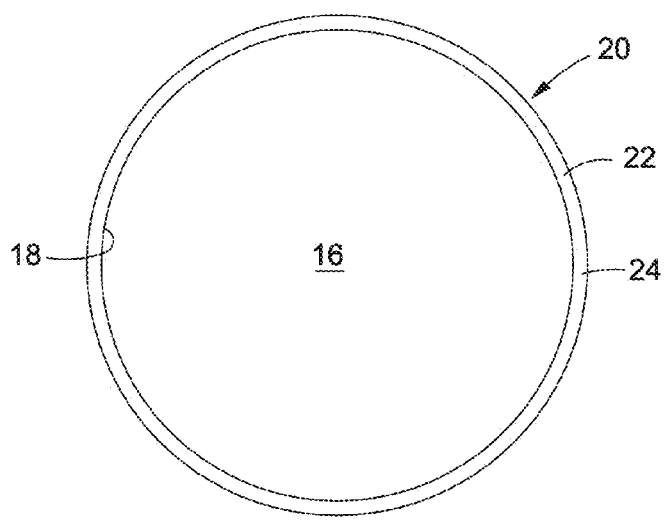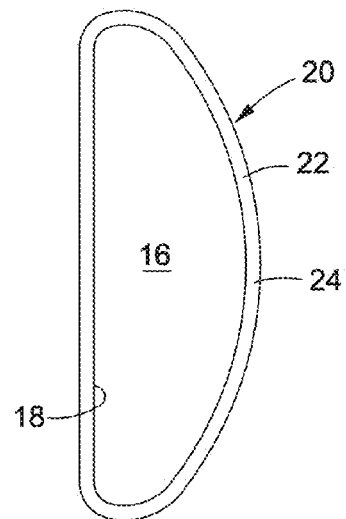
FIG. 4C  FIG. 4D

MUCOSAL TISSUE ADHESION VIA TEXTURED SURFACE

RELATED APPLICATIONS

This application is a continuation-in-part of U.S. application Ser. No. 13/245,518, filed Sep. 26, 2011, which is a continuation-in-part of U.S. application Ser. No. 13/104,820, filed May 10, 2011, which claims priority to U.S. Provisional Application No. 61/333,146, filed May 10, 2010, and also claims priority to U.S. Provisional Application No. 61/387,381, filed Sep. 28, 2010; and is also a continuation-in-part of U.S. application Ser. No. 13/104,820, which claims the benefit of Provisional Application No. 61/333,146; and is also a continuation-in-part of U.S. application Ser. No. 13/247,535, filed Sep. 28, 2011, which claims the benefit of Provisional Application No. 61/387,381, filed Sep. 28, 2010, and claims the benefit of Provisional Application No. 61/387,115, filed Sep. 28, 2010; and is also a continuation-in-part of U.S. application Ser. No. 13/247,835, filed Sep. 28, 2011, which claims the benefit of Provisional Application No. 61/387,074, filed Sep. 28, 2010; and is also a continuation-in-part of U.S. application Ser. No. 13/246,568, filed Sep. 27, 2011, which claims the benefit of Provisional Application No. 61/387,083, filed Sep. 28, 2010; and is also a continuation-in-part of U.S. application Ser. No. 13/104,395, filed May 10, 2011, which claims the benefit of Provisional Application No. 61/333,120, filed May 10, 2010; and is also a continuation-in-part of U.S. application Ser. No. 13/104,888, filed May 10, 2011, which claims the benefit of Provisional Application No. 61/333,613, filed May 11, 2010; and is also a continuation-in-part of U.S. application Ser. No. 13/104,811, filed May 10, 2011, which claims the benefit of Provisional Application No. 61/333,599, filed May 11, 2010; and is also a continuation-in-part of U.S. application Ser. No. 13/104,893, filed May 10, 2011, which is a continuation-in-part of U.S. application Ser. No. 13/015,309, filed Jan. 27, 2011, which claims priority to U.S. Provisional Application No. 61/301,104, filed Feb. 3, 2010, and U.S. Provisional Application No. 61/375,338, filed Aug. 20, 2010, and is also a continuation-in-part of U.S. application Ser. No. 13/021,615, filed Feb. 4, 2011, which claims priority to U.S. Provisional Application No. 61/301,864, filed Feb. 5, 2010; the entire disclosure of each of these applications is incorporated herein by reference in their entireties.

FIELD OF THE INVENTION

The present disclosure related to porous materials for use in biomedical applications.

BACKGROUND OF INVENTION

Porous materials are widely used in biomedical, industrial, and household applications. In the biomedical field, porous materials have been used as scaffolds (templates) for tissue engineering/regeneration, wound dressings, drug release matrices, membranes for separations and filtration, sterile filters, artificial kidneys, absorbents, hemostatic devices, and the like. In various industrial and household applications, porous materials have been used as insulating materials, packaging materials, impact absorbers, liquid or gas absorbents, membranes, filters and so forth.

Implantable medical devices frequently induce a foreign body response that results in the formation of an avascular, fibrous capsule around the implant, which limits the performance of the device. For example, formation of these fibrous capsules can result in capsular contracture, the tightening and hardening of the capsule that surrounds the implanted device. Capsular contractions not only distort the aesthetic appearance of the surrounding are where the implant is placed, but also cause pain to the individual. Problems with capsular formation and contracture occur in many types of implantable medical devices, such as, e.g., pacemakers, orthopedic joint prosthetics, dura matter substitutes, implantable cardiac defibrillators, tissue expanders, and tissue implants used for prosthetic, reconstructive, or aesthetic purposes, like breast implants, muscle implants, or implants that reduce or prevent scarring. Correction of capsular contracture may require surgical removal or release of the capsule, or removal and possible replacement of the device itself.

Scar tissue formation in the healing of a wound or surgical incision is also a process involving the formation of fibrous tissue. A visible scar results from this healing process because the fibrous tissue is aligned in one direction. However, it is often aesthetically desirable to prevent scar formation, especially in certain types of plastic surgery.

The biological response to implantable medical devices and wound healing appears dependent on the microarchitecture of the surface of the implants. Implants with smooth surfaces in particular are most susceptible to capsular formation and contracture. One means of reducing capsular formation and contracture has been to texture the surface of an implantable medical device. In these methods, a textured surface is imprinted onto the surface of a device forming "hills" and "valleys" architecture. See, e.g., U.S. Pat. No. 4,960,425, Textured Surface Prosthesis Implants; U.S. Pat. No. 5,022,942, Method of Making Textured Surface Prosthesis Implants. However, capsular contracture can still occur in implantable medical devices textured in that manner.

In addition, medical devices for implantation within a patient's gastrointestinal tract are typically anchored in place with sutures or other barbs. Capsular contracture is typically a remote issue for such kinds of implantation. However, such implantation methods may cause an adverse effect in the patient's body, such as a prolonged puncture or penetration of the gastrointestinal tract. It is thus desirable to produce a less invasive manner of fixing implantable devices within the gastrointestinal tract.

SUMMARY OF THE INVENTION

Aspects of the present specification disclose a porous material comprising a substantially non-resorbable, biocompatible, elastomer matrix defining an array of interconnected pores.

In one embodiment, the present specification discloses a method of anchoring an implant device to a mucosal lining of a patient's gastrointestinal tract. At least a portion of the implant device is formed of a substantially non-resorbable, biocompatible, elastomer matrix defining an array of interconnected pores structured to receive tissue ingrowth from the mucosal lining of the patient's gastrointestinal tract to anchor the implant device to the mucosal lining. The method includes inserting the implant device into the patient's gastrointestinal tract. The method also includes placing the implant device within the patient's gastrointestinal tract such that the array of interconnected pores contacts the mucosal lining and receives tissue ingrowth from the mucosal lining to anchor the implant device to the mucosal lining.

In one embodiment, the present specification discloses an apparatus for implantation within a patient's gastrointestinal tract. The apparatus includes a non-resorbable, biocompatible, elastomer matrix being made of at least one of a fluoro-type silicone, polybutadiene, or styrenebutadiene. The elastomer matrix defines an array of interconnected pores and has a porosity of at least 10% and exhibits an elastic elongation of at least 80%.

In one embodiment, the present specification discloses an implant device structured to be anchored within a patient's gastrointestinal tract and to form a stoma therein. As least a portion of the implant device is made of an elastomer material made by the steps of: a) providing porogens each having a core material and a shell material surrounding the core material; b) fusing the shell material of the porogens to form a porogen scaffold of fused porogens; c) coating the porogen scaffold with an elastomer base to form an elastomer coated porogen scaffold; d) curing the elastomer coated porogen scaffold to form a cured elastomer coated porogen scaffold; and e) removing the porogen scaffold from the cured elastomer coated porogen scaffold, wherein removal of the porogen scaffold results in the elastomer material.

BRIEF DESCRIPTION OF THE DRAWINGS

Features and advantages of the present invention will become appreciated as the same become better understood with reference to the specification, claims, and appended drawings wherein:

FIG. 1 illustrates the porogens consisting of a single material and porogens comprising a shell material and a core material as disclosed in the present specification. Controlled fusion of porogens consisting of a single material is difficult due to the random timing that each porogen transitions from its solid phase to its liquid phase. As such, fusing porogens under a treatment results in insufficient fusion of the porogens (or under-fusion) and/or too much fusion of porogens (over-fusion). Controlled fusion of porogens can be accomplished using the porogen compositions disclosed in the present specification. Treatment is done under conditions that allow the shell material to transition from its solid phase to its liquid phase, but maintain the core material in its solid phase. As such, fusion of porogen compositions disclosed herein result in a more uniform porogen scaffold.

FIG. 3 shows an analysis of a porous material as disclosed in the present specification.

FIG. 4 illustrates a representative biocompatible implantable device covered with a porous material of the present specification. FIG. 4A is a top view of an implantable device covered with a porous material. FIG. 4B is a side view of an implantable device covered with a porous material. FIGS. 4C and 4D illustrate a cross-sectional view of the biocompatible implantable device covered with a porous material.

FIG. 5 illustrates a representative porous material shell of the present specification.

FIG. 6 illustrates a representative biocompatible implantable device covered with a porous material of the present specification.

FIG. 7 includes bar graphs showing data of thickness and disorganization of capsules from various biomaterials, normalized to Textured 1 biomaterial.

FIG. 27 shows an analysis of a porous material as disclosed in the present specification.

FIG. 28 shows an analysis of a porous material as disclosed in the present specification.

FIG. 29 shows an analysis of a porous material as disclosed in the present specification.

FIG. 30 shows an analysis of a porous material as disclosed in the present specification.

DETAILED DESCRIPTION OF THE PREFERRED EMBODIMENTS

Figure 2:
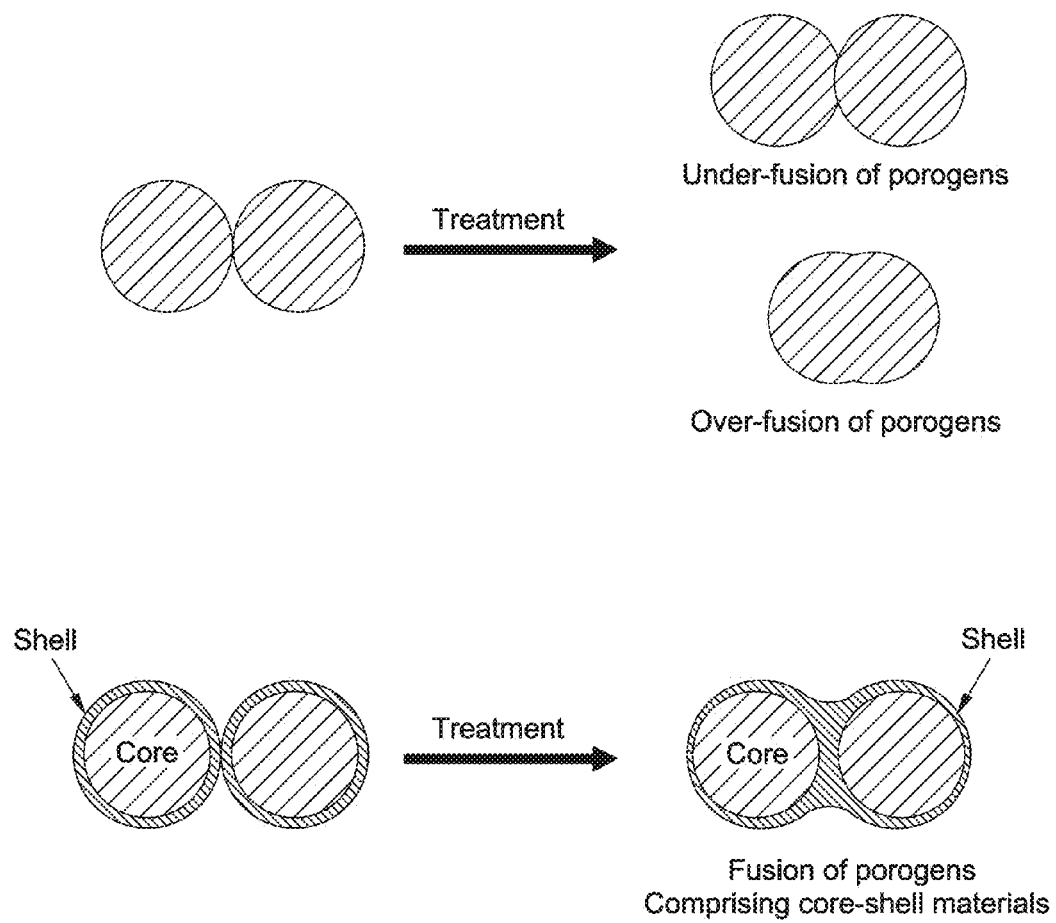
FIG. 2 illustrates fusion of the shells of porogens without the cores of the porogens fusing.

The porogen compositions disclosed herein provide a means to control the degree and amount of fusion that occurs during a treatment. This is accomplished, in part, by providing a shell material and a core material, where the shell material has a lower melting point temperature and/or glass transition temperature relative to the core material. Currently, porogens are composed of a single material. Controlling the fusion of these single material porogens is difficult, due, in part, to the random timing that each individual porogen transitions from its solid phase to its liquid phase. As such, under any given treatment condition designed to cause porogen fusion, there will be a population of porogens that have remained in the solid phase, and yet at the same time, a population of porogens that have completely transitioned into their liquid or rubbery phase (FIG. 1). This unequal or uncontrolled transition from the solid phase to the liquid or rubbery phase results in a porogen scaffold that comprises regions of insufficient porogen fusion (or under-fusion) and/or too much porogen fusion (over-fusion). The uncontrolled nature of the fusion process produces an un-uniform porogen scaffold that ultimately results in porous materials with a matrix of un-uniform pore sizes and interconnections. Such a disorganized structure can reduce the utility of porous materials. The porogen compositions disclosed herein overcome the uncontrollable fusion rates observed in single material porogens. The compositions disclosed herein comprise porogens comprising a shell material and a core material. Controlled fusion of porogens is achieved because fusion treatment is performed under conditions that allow the shell material to transition from its solid phase to its liquid or rubbery phase, but the core material is maintained in its solid phase. As such, fusion of porogen compositions disclosed herein result in a more uniform porogen scaffold (FIG. 1). FIG. 2 also shows fusion of the shells of porogens without the cores of the porogens fusing. Thus, a method of making a porous material that utilizes a porogen composition of the present specification will produce a porous material with a more uniform matrix of pore size and interconnections.

The present specification discloses, in part, a porogen composition. As used herein, the term "porogen composition" or "porogen(s)" refers to any structured material that can be used to create a porous material.

Porogens have a shape sufficient to allow formation of a porogen scaffold useful in making an elastomer matrix as disclosed in the present specification. Any porogen shape is useful with the proviso that the porogen shape is sufficient to allow formation of a porogen scaffold useful in making an elastomer matrix as disclosed in the present specification. Useful porogen shapes include, without limitation, roughly spherical, perfectly spherical, ellipsoidal, polyhedronal, triangular, pyramidal, quadrilateral like squares, rectangles, parallelograms, trapezoids, rhombus and kites, and other types of polygonal shapes.

In an embodiment, porogens have a shape sufficient to allow formation of a porogen scaffold useful in making an elastomer matrix that allows tissue growth within its array of interconnected pores. In aspects of this embodiment, porogens have a shape that is roughly spherical, perfectly spherical, ellipsoidal, polyhedronal, triangular, pyramidal, quadrilateral, or polygonal.

Porogens have a roundness sufficient to allow formation of a porogen scaffold useful in making a matrix defining an array of interconnected pores. As used herein, "roundness" is defined as $(6 \times V)/(\pi \times D^3)$, where V is the volume and D is the diameter. Any porogen roundness is useful with the proviso that the porogen roundness is sufficient to allow formation of a porogen scaffold useful in making an elastomer matrix as disclosed in the present specification.

In an embodiment, porogens have a roundness sufficient to allow formation of a porogen scaffold useful in making a matrix defining an array of interconnected pores. In aspects of this embodiment, porogens have a mean roundness of, e.g., about 0.1, about 0.2, about 0.3, about 0.4, about 0.5, about 0.6, about 0.7, about 0.8, about 0.9, or about 1.0. In other aspects of this embodiment, porogens have a mean roundness of, e.g., at least 0.1, at least 0.2, at least 0.3, at least 0.4, at least 0.5, at least 0.6, at least 0.7, at least 0.8, at least 0.9, or at least 1.0. In yet other aspects of this embodiment, porogens have a mean roundness of, e.g., at most 0.1, at most 0.2, at most 0.3, at most 0.4, at most 0.5, at most 0.6, at most 0.7, at most 0.8, at most 0.9, or at most 1.0. In still other aspects of this embodiment, porogens have a mean roundness of, e.g., about 0.1 to about 1.0, about 0.2 to about 1.0, about 0.3 to about 1.0, about 0.4 to about 1.0, about 0.5 to about 1.0, about 0.6 to about 1.0, about 0.7 to about 1.0, about 0.8 to about 1.0, about 0.9 to about 1.0, about 0.1 to about 0.9, about 0.2 to about 0.9, about 0.3 to about 0.9, about 0.4 to about 0.9, about 0.5 to about 0.9, about 0.6 to about 0.9, about 0.7 to about 0.9, about 0.8 to about 0.9, about 0.1 to about 0.8, about 0.2 to about 0.8, about 0.3 to about 0.8, about 0.4 to about 0.8, about 0.5 to about 0.8, about 0.6 to about 0.8, about 0.7 to about 0.8, about 0.1 to about 0.7, about 0.2 to about 0.7, about 0.3 to about 0.7, about 0.4 to about 0.7, about 0.5 to about 0.7, about 0.6 to about 0.7, about 0.1 to about 0.6, about 0.2 to about 0.6, about 0.3 to about 0.6, about 0.4 to about 0.6, about 0.5 to about 0.6, about 0.1 to about 0.5, about 0.2 to about 0.5, about 0.3 to about 0.5, or about 0.4 to about 0.5.

A porogen has a thickness sufficient to allow formation of a porogen scaffold. As such, a porogen can be of any thickness, with the proviso that the thickness of the porogen is sufficient to create a porogen scaffold useful for its intended purpose. The thickness of a porogen can be measured based on its shape. For example, for spherical and elliptical porogens, thickness is measured based on the diameter of the core material. For example, for sided-shaped porogens, like polyhedrons, triangles, pyramids, quadrilateral, or polygons, thickness is measured based on the base width of the porogen.

In another embodiment, a porogen comprises a mean porogen diameter sufficient to allow formation of a porogen scaffold useful in making a matrix defining an array of interconnected pores. In aspects of this embodiment, a porogen comprises a mean porogen diameter of, e.g., about 50 μm, about 75 μm, about 100 μm, about 150 μm, about 200 μm, about 250 μm, about 300 μm, about 350 μm, about 400 μm, about 450 μm, or about 500 μm. In other aspects, a porogen comprises a mean porogen diameter of, e.g., about 500 μm, about 600 μm, about 700 μm, about 800 μm, about 900 μm, about 1000 μm, about 1500 μm, about 2000 μm, about 2500 μm, or about 3000 μm.

In yet other aspects of this embodiment, a porogen comprises a mean porogen diameter of, e.g., at least 50 μm, at least 75 μm, at least 100 μm, at least 150 μm, at least 200 μm, at least 250 μm, at least 300 μm, at least 350 μm, at least 400 μm, at least 450 μm, or at least 500 μm. In still other aspects, a porogen comprises a mean porogen diameter of, e.g., at least 500 μm, at least 600 μm, at least 700 μm, at least 800 μm, at least 900 μm, at least 1000 μm, at least 1500 μm, at least 2000 μm, at least 2500 μm, or at least 3000 μm. In further aspects of this embodiment, a porogen comprises a mean porogen diameter of, e.g., at most 50 μm, at most 75 μm, at most 100 μm, at most 150 μm, at most 200 μm, at most 250 μm, at most 300 μm, at most 350 μm, at most 400 μm, at most 450 μm, or at most 500 μm. In yet further aspects of this embodiment, a porogen comprises a mean porogen diameter of, e.g., at most 500 μm, at most 600 μm, at most 700 μm, at most 800 μm, at most 900 μm, at most 1000 μm, at most 1500 μm, at most 2000 μm, at most 2500 μm, or at most 3000 μm. In still further aspects of this embodiment, a porogen comprises a mean porogen diameter of, e.g., about 300 μm to about 600 μm, about 200 μm to about 700 μm, about 100 μm to about 800 μm, about 500 μm to about 800 μm, about 50 μm to about 500 μm, about 75 μm to about 500 μm, about 100 μm to about 500 μm, about 200 μm to about 500 μm, about 300 μm to about 500 μm, about 50 μm to about 1000 μm, about 75 μm to about 1000 μm, about 100 μm to about 1000 μm, about 200 μm to about 1000 μm, about 300 μm to about 1000 μm, about 50 μm to about 1000 μm, about 75 μm to about 3000 μm, about 100 μm to about 3000 μm, about 200 μm to about 3000 μm, or about 300 μm to about 3000 μm.

In another embodiment, a porogen comprises a mean porogen base sufficient to allow formation of a porogen scaffold useful in making a matrix defining an array of interconnected pores. In aspects of this embodiment, a porogen comprises a mean porogen base of, e.g., about 50 μm, about 75 μm, about 100 μm, about 150 μm, about 200 μm, about 250 μm, about 300 μm, about 350 μm, about 400 μm, about 450 μm, or about 500 μm. In other aspects, a porogen comprises a mean porogen base of, e.g., about 500 μm, about 600 μm, about 700 μm, about 800 μm, about 900 μm, about 1000 μm, about 1500 μm, about 2000 μm, about 2500 μm, or about 3000 μm. In yet other aspects of this embodiment, a porogen comprises a mean porogen base of, e.g., at least 50 μm, at least 75 μm, at least 100 μm, at least 150 μm, at least 200 μm, at least 250 μm, at least 300 μm, at least 350 μm, at least 400 μm, at least 450 μm, or at least 500 μm. In still other aspects, a porogen comprises a mean porogen base of, e.g., at least 500 μm, at least 600 μm, at least 700 μm, at least 800 μm, at least 900 μm, at least 1000 μm, at least 1500 μm, at least 2000 μm, at least 2500 μm, or at least 3000 μm. In further aspects of this embodiment, a porogen comprises a mean porogen base of, e.g., at most 50 μm, at most 75 μm, at most 100 μm, at most 150 μm, at most 200 μm, at most 250 μm, at most 300 μm, at most 350 μm, at most 400 μm, at most 450 μm, or at most 500 μm. In yet further aspects of this embodiment, a porogen comprises a mean porogen base of, e.g., at most 500 μm, at most 600 μm, at most 700 μm, at most 800 μm, at most 900 μm, at most 1000 μm, at most 1500 μm, at most 2000 μm, at most 2500 μm, or at most 3000 μm. In still further aspects of this embodiment, a porogen comprises a mean porogen base of, e.g., about 300 μm to about 600 μm, about 200 μm to about 700 μm, about 100 μm to about 800 μm, about 500 μm to about 800 μm, about 50 μm to about 500 μm, about 75 μm to about 500 μm, about 100 μm to about 500 μm, about 200 μm to about 500 μm, about 300 μm to about 500 μm, about 50 μm to about 1000 μm, about 75 μm to about 1000 μm, about 100 μm to about 1000 μm, about 200 μm to about 1000 μm, about 300 μm to about 1000 μm, about 50 μm to about 1000 μm, about 75 μm to about 3000 μm, about 100 μm to about 3000 μm, about 200 μm to about 3000 μm, or about 300 μm to about 3000 μm.

The present specification discloses, in part, a porogen comprising a shell material. A shell material of a porogen can be made of any material with the proviso that 1) the melting point temperature ($T_m$) of the shell material is lower than the melting point temperature of the core material; and/or 2) the glass transition temperature ($T_g$) of the shell material is lower than the glass transition temperature of the core material. As used herein, the term "melting point temperature" or "melting point" refers to the temperature at which the solid and liquid phases of a material exist in equilibrium, at any fixed pressure, and is the temperature at which the first trace of liquid appears. For a material made of a pure substance, the melting, or fusion, process occurs at a single temperature. For a material made of two or more substances, the melting process normally occurs over a range of temperatures, and a distinction is made between the melting point and the freezing point temperature. As used herein, the term "freezing point temperature" or "freezing point" refers to the temperature at which the solid and liquid phases of a material exist in equilibrium, at any fixed pressure, and is the temperature at which the last trace of solid disappears. The freezing point temperature is usually higher than the melting point temperature in materials made from two or more substances.

Amorphous materials, as well as some polymers, do not have a true melting point temperature as there is no abrupt phase change from a solid phase to a liquid phase at any specific temperature. Instead, amorphous materials and polymers exhibit a gradual change in viscoelastic properties over a range of temperatures. Such materials are characterized by vitrification, or glass transition, the process of converting a material into a glassy amorphous solid that is free from crystalline structure. Vitrification occurs at a glass transition temperature. As used herein, the term "glass transition temperature" refers to the temperature at which the glass and liquid phases of an amorphous material exist in equilibrium, at any fixed pressure, and is the temperature that roughly defined the "knee" point of the material's density vs. temperature graph. The glass transition temperature of an amorphous material is lower than its melting temperature.

A shell material can comprise a natural or synthetic, inorganic or organic material. Exemplary materials suitable as a shell material disclosed in the present specification, include, without limitation, natural and synthetic salt and its derivatives, natural and synthetic ceramic and/or its derivatives, natural and synthetic sugar and its derivatives, natural and synthetic polysaccharide and its derivatives, natural and synthetic wax and its derivatives, natural and synthetic metal and its derivatives, natural and synthetic surfactant and its derivatives, natural and synthetic organic solid and its derivatives, natural and synthetic water soluble solid and its derivatives, and/or natural and synthetic polymer and its derivatives, composites thereof, and/or combinations thereof.

A natural or synthetic salt and its derivatives refer to ionic compounds composed of cations and anions so that the product is electrically neutral. The component ions of a salt can be inorganic or organic, as well as, a monoatomic ion or a polyatomic ion. Common salt-forming cations include, without limitation, Ammonium $NH_4^+$, Calcium $Ca^{2+}$, Iron $Fe^{2+}$ and $Fe^{3+}$, Magnesium $Mg^{2+}$, Potassium $K^+$, Pyridinium $C_5H_5NH^+$, Quaternary ammonium $NR_4^+$ and Sodium $Na^+$. Common salt-forming anions include, without limitation, Acetate $CH_3COO^-$, Carbonate $CO_3^{2-}$, Chloride $Cl^-$, Citrate $HOC(COO^-)(CH_2COO^-)_2$, Cyanide $C\equiv N^-$, Hydroxide $OH^-$, Nitrate $NO_3^-$, Nitrite $NO_2^-$, Oxide $O^{2-}$, Phosphate $PO_4^{3-}$, and Sulfate $SO_4^{2-}$. Non-limiting examples of salts include, cobalt chloride hexahydrate, copper sulfate pentahydrate, ferric hexacyanoferrate, lead diacetate, magnesium sulfate, manganese dioxide, mercury sulfide, monosodium glutamate, nickel chloride hexahydrate, potassium bitartrate, potassium chloride, potassium dichromate, potassium fluoride, potassium permanganate, sodium alginate, sodium chromate, sodium chloride, sodium fluoride, sodium iodate, sodium iodide, sodium nitrate, sodium sulfate, and/or mixtures thereof.

A natural or synthetic ceramic and its derivatives refer to inorganic, non-metallic solids that can have a crystalline or partly crystalline structure, or can be amorphous (e.g., a glass). Ceramics include oxides, such as, e.g., alumina and zirconium dioxide, non-oxides, such as, e.g., carbides, borides, nitrides, and silicides; and composites comprising combinations of oxides and non-oxides. Non-limiting examples of salts include, alumina, barium titanate, bismuth strontium calcium copper oxide, boron nitride, lead zirconate titanate, magnesium diboride, Silicon aluminium oxynitride, silicon carbide, silicon nitride, strontium titanate, titanium carbide, uranium oxide, yttrium barium copper oxide, zinc oxide, and zirconium dioxide.

A natural or synthetic sugar and its derivatives refer to a compound comprising one to 10 monosaccharide units, e.g., a monosaccharide, a disaccharide, a trisaccharide, and an oligosaccharide comprising four to ten monosaccharide units. Monosaccharides are polyhydroxy aldehydes or polyhydroxy ketones with three or more carbon atoms, including aldoses, dialdoses, aldoketoses, ketoses and diketoses, as well as cyclic forms, deoxy sugars and amino sugars, and their derivatives, provided that the parent monosaccharide has a (potential) carbonyl group. Oligosaccharides are compounds in which at least two monosaccharide units are joined by glycosidic linkages. According to the number of units, they are called disaccharides, trisaccharides, tetrasaccharides, pentasaccharides, hexoaccharides, heptoaccharides, octoaccharides, nonoaccharides, decoaccharides, etc. An oligosaccharide can be unbranched, branched or cyclic. Non-limiting examples of sugars include, monosacchrides, such as, e.g., trioses, like glyceraldehyde and dihydroxyacetone; tetroses, like erythrose, threose and erythrulose; pentoses, like arabinose, lyxose, ribose, xylose, ribulose, xylulose; hexoses, like allose, altrose, galactose, glucose, gulose, idose, mannose, talose, fructose, psicose, sorbose, tagatose, fucose, rhamnose; heptoses, like sedoheptulose and mannoheptulose; octooses, like octulose and 2-keto-3-deoxy-manno-octonate; nonoses like sialose; and decose; and oligosaccharides, such as, e.g., disaccharides, like sucrose, lactose, maltose, trehalose, cellobiose, gentiobiose, kojibiose, laminaribiose, mannobiose, melibiose, nigerose, rutinose, and xylobiose; trisaccharides like raffinose, acarbose, maltotriose, and melezitose and/or mixtures thereof. Sugars also include sugar substitutes like acesulfame potassium, alitame, aspartame, acesulfame, cyclamate, dulcin, glucin, neohesperidin dihydrochalcone, neotame, saccharin, and sucralose.

A natural or synthetic polysaccharide and its derivatives refer to a polymeric carbohydrate compound comprising more than 10 repeating monosaccharide of disaccharide units joined by glycosidic bonds. A polysaccharide can be linear or contain various degrees of branching. Depending on the structure, these macromolecules can have distinct properties from their monosaccharide building blocks. They may be amorphous or even insoluble in water. When all the monosaccharides in a polysaccharide are the same type the polysaccharide is called a homopolysaccharide, but when more than one type of monosaccharide is present they are called heteropolysaccharides. Non-limiting examples of polysaccharides include, amylose; cellulose; cellulose derivatives (like FICOLL, alkyl cellulose, carboxy cellulose, methyl cellulose, carboxymethyl cellulose, hemicellulose, hydroxyethyl cellulose, hydroxypropyl cellulose, hydroxyethyl methyl cellulose, hydroxypropyl methyl cellulose); chitin; chitosan; dextrans (like dextran 1K, dextran 4K, dextran 40K, dextran 60K, and dextran 70K); dextrin; glycogen; inulin; glcosaminoglycans (like chondrotin sulfates, keratin sulfates, heparin sulfates, alginic acid, hyaluronic acid); pectin; pullulan; starch; hetastarch; starch derivatives (like hydroxymethyl starch, hydroxyethyl starch, hydroxypropyl starch, hydroxybutyl starch, and hydroxypentyl starch); xanthan; and salts thereof.

A natural or synthetic wax and its derivatives refer to a type of lipid that contain a wide variety of long-chain alkanes, esters, polyesters and hydroxy esters of long-chain primary alcohols and fatty acids. Waxes are usually distinguished from fats by the lack of triglyceride esters of glycerin (propan-1,2,3-triol) and three fatty acids. Waxes include animal waxes, vegetable waxes, mineral waxes, petroleum waxes, synthetic waxes and/or mixtures thereof. Non-limiting examples of waxes include animal waxes like beeswax, Chinese wax, lanolin (wool wax), shellac wax, spermaceti; vegetable waxes like bayberry wax, candelilla wax, carnauba wax, castor wax, esparto wax, Japan wax, jojoba wax, ouricury wax, rice bran wax, soy wax; mineral waxes like ceresin wax, montan wax, ozocerite, peat wax; petroleum waxes like paraffin wax, microcrystalline wax, petroleum jelly; and synthetic waxes like polyethylene wax, Fischer-Tropsch wax, esterified wax, saponified wax, substituted amide wax, polymerized α-olefin wax.

A natural or synthetic metal and its derivatives refer to an element, compound, or alloy characterized by high electrical conductivity. An alloy is a mixture of two or more elements in solid solution in which the major component is a metal. A metal can be a base metal, a ferrous metal, a noble metal, or a precious metal. Non limiting examples of metals include alkali metals, like Lithium, Sodium, Potassium, Rubidium, Caesium, and Francium; alkaline earth metals like Beryllium, Magnesium, Calcium, Strontium, Barium, and Radium; transition metals like Zinc, Molybdenum, Cadmium, Scandium, Titanium, Vanadium, Chromium, Manganese, Iron, Cobalt, Nickel, Copper, Yttrium, Zirconium, Niobium, Technetium, Ruthenium, Rhodium, Palladium, Silver, Hafnium, Tantalum, Tungsten, Rhenium, Osmium, Iridium, Platinum, Gold, Mercury, Rutherfordium, Dubnium, Seaborgium, Bohrium, Hassium, Meitnerium, Darmstadtium, Roentgenium, and Copernicium; post-transition metals like Aluminium, Gallium, Indium, Tin, Thallium, Lead, Bismuth, Ununtrium, Ununquadium, Ununpentium, and Ununhexium; lanthanoids like Lanthanum, Cerium, Praseodymium, Neodymium, Promethium, Samarium, Europium, Gadolinium, Terbium, Dysprosium, Holmium, Erbium, Thulium, Ytterbium, and Lutetium; and actinoids like Actinium, Thorium, Protactinium, Uranium, Neptunium, Plutonium, Americium, Curium, Berkelium, Californium, Einsteinium, Fermium, Mendelevium, Nobelium, and Lawrencium.

A natural or synthetic surfactant and its derivatives refer to organic compounds that are amphiphilic and are soluble in both organic solvents and water. A surfactant includes, without limitation, ionic surfactants like cationic surfactants (based on quaternary ammonium cations) and anionic surfactants (based on sulfate, sulfonate or carboxylate anions), zwitterionic (amphoteric) surfactants, and/or non-ionic surfactants. Non-limiting examples of surfactants include anionic surfactants like perfluorooctanoate (PFOA or PFO), perfluorooctanesulfonate (PFOS), sodium dodecyl sulfate (SDS), ammonium lauryl sulfate, and other alkyl sulfate salts, sodium laureth sulfate, also known as sodium lauryl ether sulfate (SLES), alkyl benzene sulfonate, soaps, and fatty acid salts; cationic surfactants like cetyl trimethylammonium bromide (CTAB), also known as hexadecyl trimethyl ammonium bromide, and other alkyltrimethylammonium salts, cetylpyridinium chloride (CPC), polyethoxylated tallow amine (POEA), benzalkonium chloride (BAC), benzethonium chloride (BZT); zwitterionic surfactants like dodecyl betaine, cocamidopropyl betaine, coco ampho glycinate; and non-ionic surfactants like sucrose monolaurate, sodium cholate, dodecyl dimethylamine oxide, alkyl naphthalene sulfonates (ANS), alkyl poly(ethylene oxide), alkylphenol poly(ethylene oxide), poly(ethylene oxide) and poly(propylene oxide) co-polymers, also known as Poloxamers or Poloxamines including Poloxamer 124 (PLURONIC® L44), Poloxamer 181 (PLURONIC® L61), Poloxamer 182 (PLURONIC® L62), Poloxamer 184 (PLURONIC® L64), Poloxamer 188 (PLURONIC® F68), Poloxamer 237 (PLURONIC® F87), Poloxamer 338 (PLURONIC® L108), and Poloxamer 407 (PLURONIC® F127), alkyl polyglucosides, including octyl glucoside and decyl maltoside, fatty alcohols including cetyl alcohol and oleyl alcohol, cocamide MEA, cocamide DEA, polysorbates including polysorbate 20 (TWEEN® 20), polysorbate 40 (TWEEN® 40), polysorbate 60 (TWEEN® 60), polysorbate 61 (TWEEN® 61), polysorbate 65 (TWEEN® 65), polysorbate (TWEEN® 80), and polysorbate 81 (TWEEN® 81); polyoxyethyleneglycol dodecyl ethers, like BRIJ® 30, and BRIJ® 35; 2-dodecoxyethanol (LUBROL®⁻PX); polyoxyethylene octyl phenyl ether (TRITON® X-100); sodium dodecyl sulfate (SDS); 3-[(3-Cholamidopropyl)dimethylammonio]-1-propanesulfonate (CHAPS); and 3-[(3-Cholamidopropyl)dimethyl ammonio]-2-hydroxy-1-propanesulfonate (CHAPSO).

A natural or synthetic inorganic solid and its derivatives refer to a mineral not of biological origin. Non-limiting examples of inorganic solids include hydroxyapatite (HAP), carbonated hydroxyapatite, fluorinated hydroxyapatite, various calcium phosphates (CAP), glass, salts, oxides, silicates, and/or the like, and/or mixtures thereof.

A natural or synthetic water-soluble solid and its derivatives refer to any material that can be dissolved in water. Non-limiting examples of inorganic solids include sodium hydroxide and naphthalene.

A natural or synthetic polymer and its derivatives, refer to natural and synthetic macromolecules composed of repeating structural units typically connected by covalent chemical bonds. A polymer includes natural or synthetic hydrophilic polymers, natural or synthetic hydrophobic polymers, natural or synthetic amphiphilic polymers, degradable polymers, partially degradable polymers, non-degradable polymers, and combinations thereof. Polymers may be homopolymers or copolymers. Copolymers may be random copolymers, blocked copolymers, graft copolymers, and/or mixtures thereof. Non-limiting examples of polymers include poly (alkylene oxide), poly(acrylamide), poly(acrylic acid), poly (acrylamide-co-arylic acid), poly(acrylamide-co-diallyldimethylammonium chloride), poly(acrylonitrile), poly (allylamine), poly(amide), poly(anhydride), poly(butylene), poly(∈-caprolactone), poly(carbonate), poly(ester), poly (etheretherketone), poly(ethersulphone), poly(ethylene), poly(ethylene alcohol), poly(ethylenimine), poly(ethylene glycol), poly(ethylene oxide), poly(glycolide) ((like poly(glycolic acid)), poly(hydroxy butyrate), poly(hydroxyethylmethacrylate), poly(hydroxypropylmethacrylate), poly(hydroxystrene), poly(imide), poly(lactide), poly(L-lactic acid), poly(D,L-lactic acid), poly(lactide-co-glycolide), poly (lysine), poly(methacrylate), poly(methacrylic acid), poly (methylmethacrylate), poly(orthoester), poly(phenylene oxide), poly(phosphazene), poly(phosphoester), poly(propylene fumarate), poly(propylene), poly(propylene glycol), poly(propylene oxide), poly(styrene), poly(sulfone), poly (tetrafluoroethylene), poly(vinyl acetate), poly(vinyl alcohol), poly(vinyl chloride), poly(vinylidene fluoride), poly(vinyl pyrrolidone), poly(urethane), collagen, gelatin, any copolymer thereof (like poly(ethylene oxide) poly(propylene oxide) copolymers (poloxamers), poly(vinyl alcohol-co-ethylene), poly(styrene-co-allyl alcohol, and poly(ethylene)-block-poly(ethylene glycol), and/or any mixtures thereof.

A shell material has a thickness sufficient to allow formation of a porogen scaffold. As such, a shell material can be of any thickness, with the proviso that the amount of shell material is sufficient to create a porogen scaffold useful for its intended purpose. The thickness of the shell material is measured from the interior surface of the shell that is adjacent of the core material to the exterior surface of the shell.

Thus, in an embodiment, a porogen composition comprises a shell material. In an aspect of this embodiment, a porogen composition comprises a shell material having a melting point temperature that is lower than a melting point temperature of the core material. In aspects of this embodiment, a porogen composition comprises a shell material having a melting point temperature that is lower than a melting point temperature of the core material by, e.g., about 1° C., about 2° C., about 3° C., about 4° C., about 5° C., about 6° C., about 7° C., about 8° C., about 9° C., about 10° C., about 15° C., about 20° C., about 25° C., about 30° C., about 35° C., about 40° C., about 45° C., or about 50° C. In other aspects of this embodiment, a porogen composition comprises a shell material having a melting point temperature that is lower than a melting point temperature of the core material by, e.g., at least 1° C., at least 2° C., at least 3° C., at least 4° C., at least 5° C., at least 6° C., at least 7° C., at least 8° C., at least 9° C., at least 10° C., at least 15° C., at least 20° C., at least 25° C., at least 30° C., at least 35° C., at least 40° C., at least 45° C., or at least 50° C. In yet other aspects of this embodiment, a porogen composition comprises a shell material having a melting point temperature that is lower than a melting point temperature of the core material by, e.g., about 5° C. to about 50° C., about 5° C. to about 75° C., about 5° C. to about 100° C., about 5° C. to about 200° C., about 5° C. to about 300° C., about 10° C. to about 50° C., about 10° C. to about 75° C., about 10° C. to about 100° C., about 10° C. to about 200° C., or about 10° C. to about 300° C.

In an aspect of this embodiment, a porogen composition comprises a shell material having a glass transition temperature that is lower than a glass transition temperature of the core material. In aspects of this embodiment, a porogen composition comprises a shell material having a glass transition temperature that is lower than a glass transition temperature of the core material by, e.g., about 1° C., about 2° C., about 3° C., about 4° C., about 5° C., about 6° C., about 7° C., about 8° C., about 9° C., about 10° C., about 15° C., about 20° C., about 25° C., about 30° C., about 35° C., about 40° C., about 45° C., or about 50° C. In other aspects of this embodiment, a porogen composition comprises a shell material having a glass transition temperature that is lower than a glass transition temperature of the core material by, e.g., at least 1° C., at least 2° C., at least 3° C., at least 4° C., at least 5° C., at least 6° C., at least 7° C., at least 8° C., at least 9° C., at least 10° C., at least 15° C., at least 20° C., at least 25° C., at least 30° C., at least 35° C., at least 40° C., at least 45° C., or at least 50° C. In yet other aspects of this embodiment, a porogen composition comprises a shell material having a glass transition temperature that is lower than a glass transition temperature of the core material by, e.g., about 5° C. to about 50° C., about 5° C. to about °C., about 5° C. to about 100° C., about 5° C. to about 200° C., about 5° C. to about 300° C., about 10° C. to about 50° C., about 10° C. to about 75° C., about 10° C. to about 100° C., about 10° C. to about 200° C., or about 10° C. to about 300° C.

In another embodiment, a porogen composition comprises a shell material having a thickness sufficient to allow formation of a porogen scaffold. In aspects of this embodiment, a porogen composition comprises a shell material having a thickness of, e.g., about 1 µm, about 2 µm, about 3 µm, about 4 µm, about 5 µm, about 6 µm, about 7 µm, about 8 µm, about 9 µm, about 10 µm, about 15 µm, about 20 µm, about 25 µm, about 30 µm, about 35 µm, about 40 µm, about 45 µm, or about 50 µm. In other aspects of this embodiment, a porogen composition comprises a shell material having a thickness of, e.g., at least 1 µm, at least 2 µm, at least 3 µm, at least 4 µm, at least 5 µm, at least 6 µm, at least 7 µm, at least 8 µm, at least 9 µm, at least 10 µm, at least 15 µm, at least 20 µm, at least 25 µm, at least 30 µm, at least 35 µm, at least 40 µm, at least 45 µm, or at least 50 µm. In yet other aspects of this embodiment, a porogen composition comprises a shell material having a thickness of, e.g., about 5 µm to about 50 µm, about 5 µm to about 75 µm, about 5 µm to about 100 µm, about 5 µm to about 200 µm, about 5 µm to about 300 µm, about 10 µm to about 50 µm, about 10 µm to about 75 µm, about 10 µm to about 100 µm, about 10 µm to about 200 µm, about 10 µm to about 300 µm, about 15 µm to about 50 µm, about 15 µm to about 75 µm, about 15 µm to about 100 µm, about 15 µm to about 200 µm, or about 15 µm to about 300 µm.

In another embodiment, a shell material comprises an inorganic material. In another embodiment, a shell material comprises an organic material. In another embodiment, a shell material comprises a salt and/or its derivatives, a ceramic and/or its derivatives, a sugar and/or its derivatives, a polysaccharide and/or its derivatives, a wax and/or its derivatives, a metal and/or its derivatives, a surfactant and/or its derivatives, a water soluble solid and/or its derivatives, or a polymer and/or its derivatives.

The present specification discloses, in part, a porogen comprising a core material. A core material of a porogen can be made of any material with the proviso that 1) the melting point temperature ($T_m$) of the core material is higher than the melting point temperature of the shell material; and/or 2) the glass transition temperature ($T_g$) of the core material is higher than the glass transition temperature of the shell material. A core material can be of any shape, with the proviso that the shape is useful to create a porogen scaffold. Useful core shapes include, without limitation, roughly spherical, perfectly spherical, ellipsoidal, polyhedronal, triangular, pyramidal, quadrilateral like squares, rectangles, parallelograms, trapezoids, rhombus and kites, and other types of polygonal shapes.

A core material has a thickness sufficient to allow formation of a porogen scaffold. As such, a core material can be of any thickness, with the proviso that the amount of core material is sufficient to create a porogen scaffold useful for its intended purpose. The thickness of a core material can be measured based on its shape. For example, for triangular cores, quadrilateral cores, and any other type of polygonal shape, thickness is measured based on the base width of the core material. For example, for sided-shaped cores, like polyhedrons, triangles, pyramids, quadrilateral, or polygons, thickness is measured based on the base width of the core.

A core material can comprise a natural or synthetic, inorganic or organic material. Exemplary materials suitable as a core material disclosed in the present specification, include, without limitation, natural and synthetic salts and its derivatives, natural and synthetic ceramics and/or its derivatives, natural and synthetic sugars and its derivatives, natural and synthetic polysaccharides and its derivatives, natural and synthetic waxes and its derivatives, natural and synthetic metals and its derivatives, natural and synthetic organic solids and its derivatives, natural and synthetic water soluble solids and its derivatives, and/or natural and synthetic polymers and its derivatives, composites thereof, and/or combinations thereof. Exemplary materials suitable as a core material are described above in the present specification.

Thus, in an embodiment, a porogen composition comprises a core material. In an aspect of this embodiment, a porogen composition comprises a core material having a melting point temperature that is higher than a melting point temperature of the shell material. In aspects of this embodiment, a porogen composition comprises a core material having a melting point temperature that is higher than a melting point temperature of the shell material by, e.g., about 1° C., about 2° C., about 3° C., about 4° C., about 5° C., about 6° C., about 7° C., about 8° C., about 9° C., about 10° C., about 15° C., about 20° C., about 25° C., about 30° C., about 35° C., about 40° C., about 45° C., or about 50° C. In other aspects of this embodiment, a porogen composition comprises a core material having a melting point temperature that is higher than a melting point temperature of the shell material by, e.g., at least 1° C., at least 2° C., at least 3° C., at least 4° C., at least 5° C., at least 6° C., at least 7° C., at least 8° C., at least 9° C., at least 10° C., at least 15° C., at least 20° C., at least 25° C., at least 30° C., at least 35° C., at least 40° C., at least 45° C., or at least 50° C. In yet other aspects of this embodiment, a porogen composition comprises a core material having a melting point temperature that is higher than a melting point temperature of the shell material by, e.g., about 5° C. to about 50° C., about 5° C. to about 75° C., about 5° C. to about 100° C., about 5° C. to about 200° C., about 5° C. to about 300° C., about 10° C. to about 50° C., about 10° C. to about 75° C., about 10° C. to about 100° C., about 10° C. to about 200° C., or about 10° C. to about 300° C.

In an aspect of this embodiment, a porogen composition comprises a core material having a glass transition temperature that is higher than a glass transition temperature of the shell material. In aspects of this embodiment, a porogen composition comprises a core material having a glass transition temperature that is higher than a glass transition temperature of the shell material by, e.g., about 1° C., about 2° C., about 3° C., about 4° C., about 5° C., about 6° C., about 7° C., about 8° C., about 9° C., about 10° C., about 15° C., about 20° C., about 25° C., about 30° C., about 35° C., about 40° C., about 45° C., or about 50° C. In other aspects of this embodiment, a porogen composition comprises a core material having a glass transition temperature that is higher than a glass transition temperature of the shell material by, e.g., at least 1° C., at least 2° C., at least 3° C., at least 4° C., at least 5° C., at least 6° C., at least 7° C., at least 8° C., at least 9° C., at least 10° C., at least 15° C., at least 20° C., at least 25° C., at least 30° C., at least 35° C., at least 40° C., at least 45° C., or at least 50° C. In yet other aspects of this embodiment, a porogen composition comprises a core material having a glass transition temperature that is higher than a glass transition temperature of the shell material by, e.g., about 5° C. to about 50° C., about 5° C. to about ° C., about 5° C. to about 100° C., about 5° C. to about 200° C., about 5° C. to about 300° C., about 10° C. to about 50° C., about 10° C. to about 75° C., about 10° C. to about 100° C., about 10° C. to about 200° C., or about 10° C. to about 300° C.

In another embodiment, a porogen composition comprises a core material having a thickness sufficient to allow formation of a porogen scaffold. In aspects of this embodiment, a porogen composition comprises a core material having a thickness of, e.g., about 10 µm, about 20 µm, about 30 µm, about 40 µm, about 50 µm, about 60 µm, about 70 µm, about 80 µm, about 90 µm, about 100 µm, about 200 µm, about 300 µm, about 400 µm, about 500 µm, about 600 µm, about 700 µm, about 800 µm, or about 900 µm. In other aspects of this embodiment, a porogen composition comprises a shell material having a thickness of, e.g., at least 10 µm, at least 20 µm, at least 30 µm, at least 40 µm, at least 50 µm, at least 60 µm, at least 70 µm, at least 80 µm, at least 90 µm, at least 100 µm, at least 200 µm, at least 300 µm, at least 400 µm, at least 500 µm, at least 600 µm, at least 700 µm, at least 800 µm, or at least 900 µm. In yet other aspects of this embodiment, a porogen composition comprises a shell material having a thickness of, e.g., about 10 µm to about 500 µm, about 10 µm to about 750 µm, about 10 µm to about 1000 µm, about 10 µm to about 2000 µm, about 10 µm to about 3000 µm, about 25 µm to about 500 µm, about 25 µm to about 750 µm, about 25 µm to about 1000 µm, about 25 µm to about 2000 µm, about 25 µm to about 3000 µm, about 50 µm to about 500 µm, about 50 µm to about 750 µm, about 50 µm to about 1000 µm, about 50 µm to about 2000 µm, about 50 µm to about 3000 µm, about 100 µm to about 500 µm, about 100 µm to about 750 µm, about 100 µm to about 1000 µm, about 100 µm to about 2000 µm, or about 100 µm to about 3000 µm.

In another embodiment, a core material comprises an inorganic material. In another embodiment, a core material comprises an organic material. In another embodiment, a core material comprises a salt and/or its derivatives, a ceramic and/or its derivatives, a sugar and/or its derivatives, a polysaccharide and/or its derivatives, a wax and/or its derivatives, a metal and/or its derivatives, a water soluble solid and/or its derivatives, or a polymer and/or its derivatives.

The present specification discloses, in part, a porogen comprising a shell material and a core material, where the core material has a higher melting point temperature or glass transition temperature relative to the melting point temperature or the glass transition temperature of the shell material. The melting point temperature or glass transition temperature of any of the shell and core materials is well known to a person of ordinary skill and is publicly available information. See, e.g., Polymer Physics, pp. 454 (Ed. Michael Rubinstein, Edmund T. Rolls, Ralph H. Colby, Oxford University Press, 2003); Inorganic Chemistry, pp. 822 (Ed. Peter Atkins, Duward F. Shriver, Tina Overton, Jonathan Rourke, W.H. Freeman, 2006); and Carbohydrate Chemistry, pp. 96 (B. G. Davis and A. J. Fairbanks, Oxford University Press 2002), each of which is incorporated by reference in its entirety.

Thus, in an embodiment, a porogen comprises a shell material comprising an inorganic material and a core material comprising an inorganic material, where the core material has a higher melting point temperature or glass transition temperature relative to the melting point temperature or the glass transition temperature of the shell material. In another embodiment, a porogen comprises a shell material comprising an organic material and a core material comprising an inorganic material, where the core material has a higher melting point temperature or glass transition temperature relative to the melting point temperature or the glass transition temperature of the shell material. In another embodiment, a porogen comprises a shell material comprising an inorganic material and a core material comprising an organic material, where the core material has a higher melting point temperature or glass transition temperature relative to the melting point temperature or the glass transition temperature of the shell material. In another embodiment, a porogen comprises a shell material comprising an organic material and a core material comprising an organic material, where the core material has a higher melting point temperature or glass transition temperature relative to the melting point temperature or the glass transition temperature of the shell material.

In another embodiment, a porogen comprises a shell material comprising a salt and/or its derivatives and a core material comprising a salt and/or its derivatives, where the core material has a higher melting point temperature or glass transition temperature relative to the melting point temperature or the glass transition temperature of the shell material. In another embodiment, a porogen comprises a shell material comprising a ceramic and/or its derivatives and a core material comprising a salt and/or its derivatives, where the core material has a higher melting point temperature or glass transition temperature relative to the melting point temperature or the glass transition temperature of the shell material. In another embodiment, a porogen comprises a shell material comprising a surfactant and/or its derivatives and a core material comprising a salt and/or its derivatives, where the core material has a higher melting point temperature or glass transition temperature relative to the melting point temperature or the glass transition temperature of the shell material. In another embodiment, a porogen comprises a shell material comprising a polysaccharide and/or its derivatives and a core material comprising a salt and/or its derivatives, where the core material has a higher melting point temperature or glass transition temperature relative to the melting point temperature or the glass transition temperature of the shell material. In another embodiment, a porogen comprises a shell material comprising a wax and/or its derivatives and a core material comprising a salt and/or its derivatives, where the core material has a higher melting point temperature or glass transition temperature relative to the melting point temperature or the glass transition temperature of the shell material. In another embodiment, a porogen comprises a shell material comprising a metal and/or its derivatives and a core material comprising a salt and/or its derivatives, where the core material has a higher melting point temperature or glass transition temperature relative to the melting point temperature or the glass transition temperature of the shell material. In another embodiment, a porogen comprises a shell material comprising a surfactant and/or its derivatives and a core material comprising a salt and/or its derivatives, where the core material has a higher melting point temperature or glass transition temperature relative to the melting point temperature or the glass transition temperature of the shell material. In another embodiment, a porogen comprises a shell material comprising a water-soluble solid and/or its derivatives and a core material comprising a salt and/or its derivatives, where the core material has a higher melting point temperature or glass transition temperature relative to the melting point temperature or the glass transition temperature of the shell material. In another embodiment, a porogen comprises a shell material comprising a polymer and/or its derivatives and a core material comprising a salt and/or its derivatives, where the core material has a higher melting point temperature or glass transition temperature relative to the melting point temperature or the glass transition temperature of the shell material.

In another embodiment, a porogen comprises a shell material comprising a salt and/or its derivatives and a core material comprising a ceramic and/or its derivatives, where the core material has a higher melting point temperature or glass transition temperature relative to the melting point temperature or the glass transition temperature of the shell material. In another embodiment, a porogen comprises a shell material comprising a ceramic and/or its derivatives and a core material comprising a ceramic and/or its derivatives, where the core material has a higher melting point temperature or glass transition temperature relative to the melting point temperature or the glass transition temperature of the shell material. In another embodiment, a porogen comprises a shell material comprising a sugar and/or its derivatives and a core material comprising a ceramic and/or its derivatives, where the core material has a higher melting point temperature or glass transition temperature relative to the melting point temperature or the glass transition temperature of the shell material. In another embodiment, a porogen comprises a shell material comprising a polysaccharide and/or its derivatives and a core material comprising a ceramic and/or its derivatives, where the core material has a higher melting point temperature or glass transition temperature relative to the melting point temperature or the glass transition temperature of the shell material. In another embodiment, a porogen comprises a shell material comprising a wax and/or its derivatives and a core material comprising a ceramic and/or its derivatives, where the core material has a higher melting point temperature or glass transition temperature relative to the melting point temperature or the glass transition temperature of the shell material. In another embodiment, a porogen comprises a shell material comprising a metal and/or its derivatives and a core material comprising a ceramic and/or its derivatives, where the core material has a higher melting point temperature or glass transition temperature relative to the melting point temperature or the glass transition temperature of the shell material. In another embodiment, a porogen comprises a shell material comprising a surfactant and/or its derivatives and a core material comprising a ceramic and/or its derivatives, where the core material has a higher melting point temperature or glass transition temperature relative to the melting point temperature or the glass transition temperature of the shell material. In another embodiment, a porogen comprises a shell material comprising a water-soluble solid and/or its derivatives and a core material comprising a ceramic and/or its derivatives, where the core material has a higher melting point temperature or glass transition temperature relative to the melting point temperature or the glass transition temperature of the shell material. In another embodiment, a porogen comprises a shell material comprising a polymer and/or its derivatives and a core material comprising a ceramic and/or its derivatives, where the core material has a higher melting point temperature or glass transition temperature relative to the melting point temperature or the glass transition temperature of the shell material.

In another embodiment, a porogen comprises a shell material comprising a salt and/or its derivatives and a core material comprising a sugar and/or its derivatives, where the core material has a higher melting point temperature or glass transition temperature relative to the melting point temperature or the glass transition temperature of the shell material. In another embodiment, a porogen comprises a shell material comprising a ceramic and/or its derivatives and a core material comprising a sugar and/or its derivatives, where the core material has a higher melting point temperature or glass transition temperature relative to the melting point temperature or the glass transition temperature of the shell material. In another embodiment, a porogen comprises a shell material comprising a sugar and/or its derivatives and a core material comprising a sugar and/or its derivatives, where the core material has a higher melting point temperature or glass transition temperature relative to the melting point temperature or the glass transition temperature of the shell material. In another embodiment, a porogen comprises a shell material comprising a polysaccharide and/or its derivatives and a core material comprising a sugar and/or its derivatives, where the core material has a higher melting point temperature or glass transition temperature relative to the melting point temperature or the glass transition temperature of the shell material. In another embodiment, a porogen comprises a shell material comprising a wax and/or its derivatives and a core material comprising a sugar and/or its derivatives, where the core material has a higher melting point temperature or glass transition temperature relative to the melting point temperature or the glass transition temperature of the shell material. In another embodiment, a porogen comprises a shell material comprising a metal and/or its derivatives and a core material comprising a sugar and/or its derivatives, where the core material has a higher melting point temperature or glass transition temperature relative to the melting point temperature or the glass transition temperature of the shell material. In another embodiment, a porogen comprises a shell material comprising a surfactant and/or its derivatives and a core material comprising a sugar and/or its derivatives, where the core material has a higher melting point temperature or glass transition temperature relative to the melting point temperature or the glass transition temperature of the shell material. In another embodiment, a porogen comprises a shell material comprising a water-soluble solid and/or its derivatives and a core material comprising a sugar and/or its derivatives, where the core material has a higher melting point temperature or glass transition temperature relative to the melting point temperature or the glass transition temperature of the shell material. In another embodiment, a porogen comprises a shell material comprising a polymer and/or its derivatives and a core material comprising a sugar and/or its derivatives, where the core material has a higher melting point temperature or glass transition temperature relative to the melting point temperature or the glass transition temperature of the shell material.

In another embodiment, a porogen comprises a shell material comprising a salt and/or its derivatives and a core material comprising a polysaccharide and/or its derivatives, where the core material has a higher melting point temperature or glass transition temperature relative to the melting point temperature or the glass transition temperature of the shell material. In another embodiment, a porogen comprises a shell material comprising a ceramic and/or its derivatives and a core material comprising a polysaccharide and/or its derivatives, where the core material has a higher melting point temperature or glass transition temperature relative to the melting point temperature or the glass transition temperature of the shell material. In another embodiment, a porogen comprises a shell material comprising a sugar and/or its derivatives and a core material comprising a polysaccharide and/or its derivatives, where the core material has a higher melting point temperature or glass transition temperature relative to the melting point temperature or the glass transition temperature of the shell material. In another embodiment, a porogen comprises a shell material comprising a polysaccharide and/or its derivatives and a core material comprising a polysaccharide and/or its derivatives, where the core material has a higher melting point temperature or glass transition temperature relative to the melting point temperature or the glass transition temperature of the shell material. In another embodiment, a porogen comprises a shell material comprising a wax and/or its derivatives and a core material comprising a polysaccharide and/or its derivatives, where the core material has a higher melting point temperature or glass transition temperature relative to the melting point temperature or the glass transition temperature of the shell material. In another embodiment, a porogen comprises a shell material comprising a metal and/or its derivatives and a core material comprising a polysaccharide and/or its derivatives, where the core material has a higher melting point temperature or glass transition temperature relative to the melting point temperature or the glass transition temperature of the shell material. In another embodiment, a porogen comprises a shell material comprising a surfactant and/or its derivatives and a core material comprising a polysaccharide and/or its derivatives, where the core material has a higher melting point temperature or glass transition temperature relative to the melting point temperature or the glass transition temperature of the shell material. In another embodiment, a porogen comprises a shell material comprising a water-soluble solid and/or its derivatives and a core material comprising a polysaccharide and/or its derivatives, where the core material has a higher melting point temperature or glass transition temperature relative to the melting point temperature or the glass transition temperature of the shell material. In another embodiment, a porogen comprises a shell material comprising a polymer and/or its derivatives and a core material comprising a polysaccharide and/or its derivatives, where the core material has a higher melting point temperature or glass transition temperature relative to the melting point temperature or the glass transition temperature of the shell material.

In another embodiment, a porogen comprises a shell material comprising a salt and/or its derivatives and a core material comprising a wax and/or its derivatives, where the core material has a higher melting point temperature or glass transition temperature relative to the melting point temperature or the glass transition temperature of the shell material. In another embodiment, a porogen comprises a shell material comprising a ceramic and/or its derivatives and a core material comprising a wax and/or its derivatives, where the core material has a higher melting point temperature or glass transition temperature relative to the melting point temperature or the glass transition temperature of the shell material. In another embodiment, a porogen comprises a shell material comprising a sugar and/or its derivatives and a core material comprising a wax and/or its derivatives, where the core material has a higher melting point temperature or glass transition temperature relative to the melting point temperature or the glass transition temperature of the shell material. In another embodiment, a porogen comprises a shell material comprising a polysaccharide and/or its derivatives and a core material comprising a wax and/or its derivatives, where the core material has a higher melting point temperature or glass transition temperature relative to the melting point temperature or the glass transition temperature of the shell material. In another embodiment, a porogen comprises a shell material comprising a wax and/or its derivatives and a core material comprising a wax and/or its derivatives, where the core material has a higher melting point temperature or glass transition temperature relative to the melting point temperature or the glass transition temperature of the shell material. In another embodiment, a porogen comprises a shell material comprising a metal and/or its derivatives and a core material comprising a wax and/or its derivatives, where the core material has a higher melting point temperature or glass transition temperature relative to the melting point temperature or the glass transition temperature of the shell material. In another embodiment, a porogen comprises a shell material comprising a surfactant and/or its derivatives and a core material comprising a wax and/or its derivatives, where the core material has a higher melting point temperature or glass transition temperature relative to the melting point temperature or the glass transition temperature of the shell material. In another embodiment, a porogen comprises a shell material comprising a water-soluble solid and/or its derivatives and a core material comprising a wax and/or its derivatives, where the core material has a higher melting point temperature or glass transition temperature relative to the melting point temperature or the glass transition temperature of the shell material. In another embodiment, a porogen comprises a shell material comprising a polymer and/or its derivatives and a core material comprising a wax and/or its derivatives, where the core material has a higher melting point temperature or glass transition temperature relative to the melting point temperature or the glass transition temperature of the shell material.

In another embodiment, a porogen comprises a shell material comprising a salt and/or its derivatives and a core material comprising a metal and/or its derivatives, where the core material has a higher melting point temperature or glass transition temperature relative to the melting point temperature or the glass transition temperature of the shell material. In another embodiment, a porogen comprises a shell material comprising a ceramic and/or its derivatives and a core material comprising a metal and/or its derivatives, where the core material has a higher melting point temperature or glass transition temperature relative to the melting point temperature or the glass transition temperature of the shell material. In another embodiment, a porogen comprises a shell material comprising a sugar and/or its derivatives and a core material comprising a metal and/or its derivatives, where the core material has a higher melting point temperature or glass transition temperature relative to the melting point temperature or the glass transition temperature of the shell material. In another embodiment, a porogen comprises a shell material comprising a polysaccharide and/or its derivatives and a core material comprising a metal and/or its derivatives, where the core material has a higher melting point temperature or glass transition temperature relative to the melting point temperature or the glass transition temperature of the shell material. In another embodiment, a porogen comprises a shell material comprising a wax and/or its derivatives and a core material comprising a metal and/or its derivatives, where the core material has a higher melting point temperature or glass transition temperature relative to the melting point temperature or the glass transition temperature of the shell material. In another embodiment, a porogen comprises a shell material comprising a metal and/or its derivatives and a core material comprising a metal and/or its derivatives, where the core material has a higher melting point temperature or glass transition temperature relative to the melting point temperature or the glass transition temperature of the shell material. In another embodiment, a porogen comprises a shell material comprising a surfactant and/or its derivatives and a core material comprising a metal and/or its derivatives, where the core material has a higher melting point temperature or glass transition temperature relative to the melting point temperature or the glass transition temperature of the shell material. In another embodiment, a porogen comprises a shell material comprising a water-soluble solid and/or its derivatives and a core material comprising a metal and/or its derivatives, where the core material has a higher melting point temperature or glass transition temperature relative to the melting point temperature or the glass transition temperature of the shell material. In another embodiment, a porogen comprises a shell material comprising a polymer and/or its derivatives and a core material comprising a metal and/or its derivatives, where the core material has a higher melting point temperature or glass transition temperature relative to the melting point temperature or the glass transition temperature of the shell material.

In another embodiment, a porogen comprises a shell material comprising a salt and/or its derivatives and a core material comprising a water-soluble solid and/or its derivatives, where the core material has a higher melting point temperature or glass transition temperature relative to the melting point temperature or the glass transition temperature of the shell material. In another embodiment, a porogen comprises a shell material comprising a ceramic and/or its derivatives and a core material comprising a water-soluble solid and/or its derivatives, where the core material has a higher melting point temperature or glass transition temperature relative to the melting point temperature or the glass transition temperature of the shell material. In another embodiment, a porogen comprises a shell material comprising a sugar and/or its derivatives and a core material comprising a water-soluble solid and/or its derivatives, where the core material has a higher melting point temperature or glass transition temperature relative to the melting point temperature or the glass transition temperature of the shell material. In another embodiment, a porogen comprises a shell material comprising a polysaccharide and/or its derivatives and a core material comprising a water-soluble solid and/or its derivatives, where the core material has a higher melting point temperature or glass transition temperature relative to the melting point temperature or the glass transition temperature of the shell material. In another embodiment, a porogen comprises a shell material comprising a wax and/or its derivatives and a core material comprising a water-soluble solid and/or its derivatives, where the core material has a higher melting point temperature or glass transition temperature relative to the melting point temperature or the glass transition temperature of the shell material. In another embodiment, a porogen comprises a shell material comprising a metal and/or its derivatives and a core material comprising a water-soluble solid and/or its derivatives, where the core material has a higher melting point temperature or glass transition temperature relative to the melting point temperature or the glass transition temperature of the shell material. In another embodiment, a porogen comprises a shell material comprising a surfactant and/or its derivatives and a core material comprising a water-soluble solid and/or its derivatives, where the core material has a higher melting point temperature or glass transition temperature relative to the melting point temperature or the glass transition temperature of the shell material. In another embodiment, a porogen comprises a shell material comprising a water-soluble solid and/or its derivatives and a core material comprising a water-soluble solid and/or its derivatives, where the core material has a higher melting point temperature or glass transition temperature relative to the melting point temperature or the glass transition temperature of the shell material. In another embodiment, a porogen comprises a shell material comprising a polymer and/or its derivatives and a core material comprising a water-soluble solid and/or its derivatives, where the core material has a higher melting point temperature or glass transition temperature relative to the melting point temperature or the glass transition temperature of the shell material.

In another embodiment, a porogen comprises a shell material comprising a salt and/or its derivatives and a core material comprising a polymer and/or its derivatives, where the core material has a higher melting point temperature or glass transition temperature relative to the melting point temperature or the glass transition temperature of the shell material. In another embodiment, a porogen comprises a shell material comprising a ceramic and/or its derivatives and a core material comprising a polymer and/or its derivatives, where the core material has a higher melting point temperature or glass transition temperature relative to the melting point temperature or the glass transition temperature of the shell material. In another embodiment, a porogen comprises a shell material comprising a sugar and/or its derivatives and a core material comprising a polymer and/or its derivatives, where the core material has a higher melting point temperature or glass transition temperature relative to the melting point temperature or the glass transition temperature of the shell material. In another embodiment, a porogen comprises a shell material comprising a polysaccharide and/or its derivatives and a core material comprising a polymer and/or its derivatives, where the core material has a higher melting point temperature or glass transition temperature relative to the melting point temperature or the glass transition temperature of the shell material. In another embodiment, a porogen comprises a shell material comprising a wax and/or its derivatives and a core material comprising a polymer and/or its derivatives, where the core material has a higher melting point temperature or glass transition temperature relative to the melting point temperature or the glass transition temperature of the shell material. In another embodiment, a porogen comprises a shell material comprising a metal and/or its derivatives and a core material comprising a polymer and/or its derivatives, where the core material has a higher melting point temperature or glass transition temperature relative to the melting point temperature or the glass transition temperature of the shell material. In another embodiment, a porogen comprises a shell material comprising a surfactant and/or its derivatives and a core material comprising a polymer and/or its derivatives, where the core material has a higher melting point temperature or glass transition temperature relative to the melting point temperature or the glass transition temperature of the shell material. In another embodiment, a porogen comprises a shell material comprising a water-soluble solid and/or its derivatives and a core material comprising a polymer and/or its derivatives, where the core material has a higher melting point temperature or glass transition temperature relative to the melting point temperature or the glass transition temperature of the shell material. In another embodiment, a porogen comprises a shell material comprising a polymer and/or its derivatives and a core material comprising a polymer and/or its derivatives, where the core material has a higher melting point temperature or glass transition temperature relative to the melting point temperature or the glass transition temperature of the shell material.

Aspects of the present specification disclose, in part, a porogen comprising a core material and shell material where the shell material is fusible and the core material is non-fusible under a given physical or physicochemical treatment. As used herein, the term "under a given physical or physicochemical treatment" refers to a physical or physicochemical treatment that permits the shell material to transition from its solid phase to its liquid phase, but maintains the core material in its solid phase.

Thus, in an embodiment, a porogen comprises a shell material comprising an inorganic material and a core material comprising an inorganic material, where under a given physical or physicochemical treatment the shell material is fusible and the core material is non-fusible. In another embodiment, a porogen comprises a shell material comprising an organic material and a core material comprising an inorganic material, where under a given physical or physicochemical treatment the shell material is fusible and the core material is non-fusible. In another embodiment, a porogen comprises a shell material comprising an inorganic material and a core material comprising an organic material, where under a given physical or physicochemical treatment the shell material is fusible and the core material is non-fusible. In another embodiment, a porogen comprises a shell material comprising an organic material and a core material comprising an organic material, where under a given physical or physicochemical treatment the shell material is fusible and the core material is non-fusible.

In another embodiment, a porogen comprises a shell material comprising a salt and/or its derivatives and a core material comprising a salt and/or its derivatives, where under a given physical or physicochemical treatment the shell material is fusible and the core material is non-fusible. In another embodiment, a porogen comprises a shell material comprising a ceramic and/or its derivatives and a core material comprising a salt and/or its derivatives, where under a given physical or physicochemical treatment the shell material is fusible and the core material is non-fusible. In another embodiment, a porogen comprises a shell material comprising a sugar and/or its derivatives and a core material comprising a salt and/or its derivatives, where under a given physical or physicochemical treatment the shell material is fusible and the core material is non-fusible. In another embodiment, a porogen comprises a shell material comprising a polysaccharide and/or its derivatives and a core material comprising a salt and/or its derivatives, where under a given physical or physicochemical treatment the shell material is fusible and the core material is non-fusible. In another embodiment, a porogen comprises a shell material comprising a wax and/or its derivatives and a core material comprising a salt and/or its derivatives, where under a given physical or physicochemical treatment the shell material is fusible and the core material is non-fusible. In another embodiment, a porogen comprises a shell material comprising a metal and/or its derivatives and a core material comprising a salt and/or its derivatives, where under a given physical or physicochemical treatment the shell material is fusible and the core material is non-fusible. In another embodiment, a porogen comprises a shell material comprising a surfactant and/or its derivatives and a core material comprising a salt and/or its derivatives, where under a given physical or physicochemical treatment the shell material is fusible and the core material is non-fusible. In another embodiment, a porogen comprises a shell material comprising a water-soluble solid and/or its derivatives and a core material comprising a salt and/or its derivatives, where under a given physical or physicochemical treatment the shell material is fusible and the core material is non-fusible. In another embodiment, a porogen comprises a shell material comprising a polymer and/or its derivatives and a core material comprising a salt and/or its derivatives, where under a given physical or physicochemical treatment the shell material is fusible and the core material is non-fusible.

In another embodiment, a porogen comprises a shell material comprising a salt and/or its derivatives and a core material comprising a ceramic and/or its derivatives, where under a given physical or physicochemical treatment the shell material is fusible and the core material is non-fusible. In another embodiment, a porogen comprises a shell material comprising a ceramic and/or its derivatives and a core material comprising a ceramic and/or its derivatives, where under a given physical or physicochemical treatment the shell material is fusible and the core material is non-fusible. In another embodiment, a porogen comprises a shell material comprising a sugar and/or its derivatives and a core material comprising a ceramic and/or its derivatives, where under a given physical or physicochemical treatment the shell material is fusible and the core material is non-fusible. In another embodiment, a porogen comprises a shell material comprising a polysaccharide and/or its derivatives and a core material comprising a ceramic and/or its derivatives, where under a given physical or physicochemical treatment the shell material is fusible and the core material is non-fusible. In another embodiment, a porogen comprises a shell material comprising a wax and/or its derivatives and a core material comprising a ceramic and/or its derivatives, where under a given physical or physicochemical treatment the shell material is fusible and the core material is non-fusible. In another embodiment, a porogen comprises a shell material comprising a metal and/or its derivatives and a core material comprising a ceramic and/or its derivatives, where under a given physical or physicochemical treatment the shell material is fusible and the core material is non-fusible. In another embodiment, a porogen comprises a shell material comprising a surfactant and/or its derivatives and a core material comprising a ceramic and/or its derivatives, where under a given physical or physicochemical treatment the shell material is fusible and the core material is non-fusible. In another embodiment, a porogen comprises a shell material comprising a water-soluble solid and/or its derivatives and a core material comprising a ceramic and/or its derivatives, where under a given physical or physicochemical treatment the shell material is fusible and the core material is non-fusible. In another embodiment, a porogen comprises a shell material comprising a polymer and/or its derivatives and a core material comprising a ceramic and/or its derivatives, where under a given physical or physicochemical treatment the shell material is fusible and the core material is non-fusible.

In another embodiment, a porogen comprises a shell material comprising a salt and/or its derivatives and a core material comprising a sugar and/or its derivatives, where under a given physical or physicochemical treatment the shell material is fusible and the core material is non-fusible. In another embodiment, a porogen comprises a shell material comprising a ceramic and/or its derivatives and a core material comprising a sugar and/or its derivatives, where under a given physical or physicochemical treatment the shell material is fusible and the core material is non-fusible. In another embodiment, a porogen comprises a shell material comprising a sugar and/or its derivatives and a core material comprising a sugar and/or its derivatives, where under a given physical or physicochemical treatment the shell material is fusible and the core material is non-fusible. In another embodiment, a porogen comprises a shell material comprising a polysaccharide and/or its derivatives and a core material comprising a sugar and/or its derivatives, where under a given physical or physicochemical treatment the shell material is fusible and the core material is non-fusible. In another embodiment, a porogen comprises a shell material comprising a wax and/or its derivatives and a core material comprising a sugar and/or its derivatives, where under a given physical or physicochemical treatment the shell material is fusible and the core material is non-fusible. In another embodiment, a porogen comprises a shell material comprising a metal and/or its derivatives and a core material comprising a sugar and/or its derivatives, where under a given physical or physicochemical treatment the shell material is fusible and the core material is non-fusible. In another embodiment, a porogen comprises a shell material comprising a surfactant and/or its derivatives and a core material comprising a sugar and/or its derivatives, where under a given physical or physicochemical treatment the shell material is fusible and the core material is non-fusible. In another embodiment, a porogen comprises a shell material comprising a water-soluble solid and/or its derivatives and a core material comprising a sugar and/or its derivatives, where under a given physical or physicochemical treatment the shell material is fusible and the core material is non-fusible. In another embodiment, a porogen comprises a shell material comprising a polymer and/or its derivatives and a core material comprising a sugar and/or its derivatives, where under a given physical or physicochemical treatment the shell material is fusible and the core material is non-fusible.

In another embodiment, a porogen comprises a shell material comprising a salt and/or its derivatives and a core material comprising a polysaccharide and/or its derivatives, where under a given physical or physicochemical treatment the shell material is fusible and the core material is non-fusible. In another embodiment, a porogen comprises a shell material comprising a ceramic and/or its derivatives and a core material comprising a polysaccharide and/or its derivatives, where under a given physical or physicochemical treatment the shell material is fusible and the core material is non-fusible. In another embodiment, a porogen comprises a shell material comprising a sugar and/or its derivatives and a core material comprising a polysaccharide and/or its derivatives, where under a given physical or physicochemical treatment the shell material is fusible and the core material is non-fusible. In another embodiment, a porogen comprises a shell material comprising a polysaccharide and/or its derivatives and a core material comprising a polysaccharide and/or its derivatives, where under a given physical or physicochemical treatment the shell material is fusible and the core material is non-fusible. In another embodiment, a porogen comprises a shell material comprising a wax and/or its derivatives and a core material comprising a polysaccharide and/or its derivatives, where under a given physical or physicochemical treatment the shell material is fusible and the core material is non-fusible. In another embodiment, a porogen comprises a shell material comprising a metal and/or its derivatives and a core material comprising a polysaccharide and/or its derivatives, where under a given physical or physicochemical treatment the shell material is fusible and the core material is non-fusible. In another embodiment, a porogen comprises a shell material comprising a surfactant and/or its derivatives and a core material comprising a polysaccharide and/or its derivatives, where under a given physical or physicochemical treatment the shell material is fusible and the core material is non-fusible. In another embodiment, a porogen comprises a shell material comprising a water-soluble solid and/or its derivatives and a core material comprising a polysaccharide and/or its derivatives, where under a given physical or physicochemical treatment the shell material is fusible and the core material is non-fusible. In another embodiment, a porogen comprises a shell material comprising a polymer and/or its derivatives and a core material comprising a polysaccharide and/or its derivatives, where under a given physical or physicochemical treatment the shell material is fusible and the core material is non-fusible.

In another embodiment, a porogen comprises a shell material comprising a salt and/or its derivatives and a core material comprising a wax and/or its derivatives, where under a given physical or physicochemical treatment the shell material is fusible and the core material is non-fusible. In another embodiment, a porogen comprises a shell material comprising a ceramic and/or its derivatives and a core material comprising a wax and/or its derivatives, where under a given physical or physicochemical treatment the shell material is fusible and the core material is non-fusible. In another embodiment, a porogen comprises a shell material comprising a sugar and/or its derivatives and a core material comprising a wax and/or its derivatives, where under a given physical or physicochemical treatment the shell material is fusible and the core material is non-fusible. In another embodiment, a porogen comprises a shell material comprising a polysaccharide and/or its derivatives and a core material comprising a wax and/or its derivatives, where under a given physical or physicochemical treatment the shell material is fusible and the core material is non-fusible. In another embodiment, a porogen comprises a shell material comprising a wax and/or its derivatives and a core material comprising a wax and/or its derivatives, where under a given physical or physicochemical treatment the shell material is fusible and the core material is non-fusible. In another embodiment, a porogen comprises a shell material comprising a metal and/or its derivatives and a core material comprising a wax and/or its derivatives, where under a given physical or physicochemical treatment the shell material is fusible and the core material is non-fusible. In another embodiment, a porogen comprises a shell material comprising a surfactant and/or its derivatives and a core material comprising a wax and/or its derivatives, where under a given physical or physicochemical treatment the shell material is fusible and the core material is non-fusible. In another embodiment, a porogen comprises a shell material comprising a water-soluble solid and/or its derivatives and a core material comprising a wax and/or its derivatives, where under a given physical or physicochemical treatment the shell material is fusible and the core material is non-fusible. In another embodiment, a porogen comprises a shell material comprising a polymer and/or its derivatives and a core material comprising a wax and/or its derivatives, where under a given physical or physicochemical treatment the shell material is fusible and the core material is non-fusible.

In another embodiment, a porogen comprises a shell material comprising a salt and/or its derivatives and a core material comprising a metal and/or its derivatives, where under a given physical or physicochemical treatment the shell material is fusible and the core material is non-fusible. In another embodiment, a porogen comprises a shell material comprising a ceramic and/or its derivatives and a core material comprising a metal and/or its derivatives, where under a given physical or physicochemical treatment the shell material is fusible and the core material is non-fusible. In another embodiment, a porogen comprises a shell material comprising a sugar and/or its derivatives and a core material comprising a metal and/or its derivatives, where under a given physical or physicochemical treatment the shell material is fusible and the core material is non-fusible. In another embodiment, a porogen comprises a shell material comprising a polysaccharide and/or its derivatives and a core material comprising a metal and/or its derivatives, where under a given physical or physicochemical treatment the shell material is fusible and the core material is non-fusible. In another embodiment, a porogen comprises a shell material comprising a wax and/or its derivatives and a core material comprising a metal and/or its derivatives, where under a given physical or physicochemical treatment the shell material is fusible and the core material is non-fusible. In another embodiment, a porogen comprises a shell material comprising a metal and/or its derivatives and a core material comprising a metal and/or its derivatives, where under a given physical or physicochemical treatment the shell material is fusible and the core material is non-fusible. In another embodiment, a porogen comprises a shell material comprising a surfactant and/or its derivatives and a core material comprising a metal and/or its derivatives, where under a given physical or physicochemical treatment the shell material is fusible and the core material is non-fusible. In another embodiment, a porogen comprises a shell material comprising a water-soluble solid and/or its derivatives and a core material comprising a metal and/or its derivatives, where under a given physical or physicochemical treatment the shell material is fusible and the core material is non-fusible. In another embodiment, a porogen comprises a shell material comprising a polymer and/or its derivatives and a core material comprising a metal and/or its derivatives, where under a given physical or physicochemical treatment the shell material is fusible and the core material is non-fusible.

In another embodiment, a porogen comprises a shell material comprising a salt and/or its derivatives and a core material comprising a water-soluble solid and/or its derivatives, where under a given physical or physicochemical treatment the shell material is fusible and the core material is non-fusible. In another embodiment, a porogen comprises a shell material comprising a ceramic and/or its derivatives and a core material comprising a water-soluble solid and/or its derivatives, where under a given physical or physicochemical treatment the shell material is fusible and the core material is non-fusible. In another embodiment, a porogen comprises a shell material comprising a sugar and/or its derivatives and a core material comprising a water-soluble solid and/or its derivatives, where under a given physical or physicochemical treatment the shell material is fusible and the core material is non-fusible. In another embodiment, a porogen comprises a shell material comprising a polysaccharide and/or its derivatives and a core material comprising a water-soluble solid and/or its derivatives, where under a given physical or physicochemical treatment the shell material is fusible and the core material is non-fusible. In another embodiment, a porogen comprises a shell material comprising a wax and/or its derivatives and a core material comprising a water-soluble solid and/or its derivatives, where under a given physical or physicochemical treatment the shell material is fusible and the core material is non-fusible. In another embodiment, a porogen comprises a shell material comprising a metal and/or its derivatives and a core material comprising a water-soluble solid and/or its derivatives, where under a given physical or physicochemical treatment the shell material is fusible and the core material is non-fusible. In another embodiment, a porogen comprises a shell material comprising a surfactant and/or its derivatives and a core material comprising a water-soluble solid and/or its derivatives, where under a given physical or physicochemical treatment the shell material is fusible and the core material is non-fusible. In another embodiment, a porogen comprises a shell material comprising a water-soluble solid and/or its derivatives and a core material comprising a water-soluble solid and/or its derivatives, where under a given physical or physicochemical treatment the shell material is fusible and the core material is non-fusible. In another embodiment, a porogen comprises a shell material comprising a polymer and/or its derivatives and a core material comprising a water-soluble solid and/or its derivatives, where under a given physical or physicochemical treatment the shell material is fusible and the core material is non-fusible.

In another embodiment, a porogen comprises a shell material comprising a salt and/or its derivatives and a core material comprising a polymer and/or its derivatives, where under a given physical or physicochemical treatment the shell material is fusible and the core material is non-fusible. In another embodiment, a porogen comprises a shell material comprising a ceramic and/or its derivatives and a core material comprising a polymer and/or its derivatives, where under a given physical or physicochemical treatment the shell material is fusible and the core material is non-fusible. In another embodiment, a porogen comprises a shell material comprising a sugar and/or its derivatives and a core material comprising a polymer and/or its derivatives, where under a given physical or physicochemical treatment the shell material is fusible and the core material is non-fusible. In another embodiment, a porogen comprises a shell material comprising a polysaccharide and/or its derivatives and a core material comprising a polymer and/or its derivatives, where under a given physical or physicochemical treatment the shell material is fusible and the core material is non-fusible. In another embodiment, a porogen comprises a shell material comprising a wax and/or its derivatives and a core material comprising a polymer and/or its derivatives, where under a given physical or physicochemical treatment the shell material is fusible and the core material is non-fusible. In another embodiment, a porogen comprises a shell material comprising a metal and/or its derivatives and a core material comprising a polymer and/or its derivatives, where under a given physical or physicochemical treatment the shell material is fusible and the core material is non-fusible. In another embodiment, a porogen comprises a shell material comprising a surfactant and/or its derivatives and a core material comprising a polymer and/or its derivatives, where under a given physical or physicochemical treatment the shell material is fusible and the core material is non-fusible. In another embodiment, a porogen comprises a shell material comprising a water-soluble solid and/or its derivatives and a core material comprising a polymer and/or its derivatives, where under a given physical or physicochemical treatment the shell material is fusible and the core material is non-fusible. In another embodiment, a porogen comprises a shell material comprising a polymer and/or its derivatives and a core material comprising a polymer and/or its derivatives, where under a given physical or physicochemical treatment the shell material is fusible and the core material is non-fusible.

The present specification discloses methods of making a porogen composition.

In one aspect, methods of making a porogen composition comprise the steps of: a) forming a particle out of a core material; and b) coating the particle with a shell material.

The present specification discloses, in part, forming a particle out of a core material. Suitable core materials are as described above. Forming a particle out of a core material can be accomplished by any suitable means, including, without limitation, pelletization by fluidized bed granulation, rotor granulation, or extrusion-spheronization; grinding by roller mills and sieving; solvent evaporation; or emulsion. Suitable particles of a core material are also commercially available from, e.g., Fisher Scientific (Pittsburg, Pa.), Boehringer Ingelheim Pharmaceuticals, Inc. (Ridgefield, Conn.); and Paulaur Corp., (Cranbury, N.J.).

The present specification discloses, in part, coating a particle with a shell material. Suitable shell materials are as described above. Coating a particle with a shell material can be accomplished by any suitable means, including, without limitation, mechanical application such as, e.g., dipping, spraying, filtration, knifing, curtaining, brushing, or vapor deposition; physical adsorption application; thermal application; fluidization application; adhering application; chemical bonding application; self-assembling application; molecular entrapment application, and/or any combination thereof. The shell material is applied to the particle of core material in such a manner as to coat the particle with the desired thickness of shell material. Removal of excess shell material can be accomplished by any suitable means, including, without limitation, gravity-based filtering or sieving, vacuum-based filtering or sieving, blowing, and/or any combination thereof.

The present specification discloses in part, methods of making a porous material using the porogen compositions disclosed in the present specification. The porogens disclosed herein can be used in any methods of making a porous material that utilized previously described porogens. Examples of such methods are described in, e.g., Gates, et al., Materials Containing Voids with Void Size Controlled on the Nanometer Scale, U.S. Pat. No. 7,674,521; Hart, et al., Discrete Nano-Textured Structures in Biomolecular Arrays and Method of Use, U.S. Pat. No. 7,651,872; Xu and Grenz, Methods and Devices Using a Shrinkable Support for Porous Monolithic Materials, U.S. Pat. No. 7,651,762; van den Hoek, et al., VLSI Fabrication Processes for Introducing Pores into Dielectric Materials, U.S. Pat. No. 7,629,224; Murphy, et al., Tissue Engineering Scaffolds, U.S. Pat. No. 7,575,759; Swetlin, et al., Polyester Compositions, Methods of Manufacturing Said Compositions, and Articles Made Therefrom, U.S. Pat. No. 7,557,167; Goodner, et al., Formation of Interconnect Structures by Removing Sacrificial Material with Supercritical Carbon Dioxide, U.S. Pat. No. 7,466,025; Xu, Ultraporous Sol Gel Monoliths, U.S. Pat. No. 7,439,272; Todd, Apparatus, Precursors and Deposition Methods for Silicon-Containing Materials, U.S. Pat. No. 7,425,350; Flodin and Aurell, Method for Preparing an Open Porous Polymer Material and an Open Porous Polymer Material, U.S. Pat. No. 7,425,288; Watkins and Pai, Mesoporous Materials and Methods, U.S. Pat. No. 7,419,772; Connor, et al., Porous Composition of Matter, and Method of Making Same, U.S. Pat. No. 7,368,483; Lukas, et al., Porous Low Dielectric Constant Compositions and Methods for Making and Using Same, U.S. Pat. No. 7,332,445; Wu, et al., Methods for Producing Low Stress Porous Low-K Dielectric Materials Using Precursors with Organic Functional Groups, U.S. Pat. No. 7,241,704; Yuan and Ding, Functionalized Porous Poly(Aryl Ether Ketone) Materials and Their Use, U.S. Pat. No. 7,176,273; Gleason, et al., Porous Material Formation by Chemical Vapor Deposition onto Colloidal Crystal Templates, U.S. Pat. No. 7,112,615; Bruza, et al., Composition Containing a Cross-Linkable Matrix Precursor and a Porogen, and Porous Matrix Prepared Therefrom, U.S. Pat. No. 7,109,249; Huang, et al., Nitrogen-Containing Polymers as Porogens in the Preparation of Highly Porous, Low Dielectric Constant Materials, U.S. Pat. No. 7,087,982; Taboas, et al., Controlled Local/Global and Micro/Macro-Porous 3D Plastic, Polymer and Ceramic/Cement Composite Scaffold Fabrication and applications Thereof, U.S. Pat. No. 7,087,200; Kloster, et al., Method of Forming a Selectively Converted Inter-Layer Dielectric Using A Porogen Material, U.S. Pat. No. 7,018,918; You, et al., Porous Materials, U.S. Pat. No. 6,998,148; Khanarian, et al., Porous Optical Materials, U.S. Pat. No. 6,967,222; Holmes and Cooper, Manufacturing Porous Cross-Linked Polymer Monoliths, U.S. Pat. No. 6,693,159; Ma, Reverse Fabrication of Porous Materials, U.S. Pat. No. 6,673,285; Kilaas, et al., Combined Liner and Matrix System, U.S. Pat. No. 6,672,385; Chaouk and Meijs, Hydratable Siloxane Comprising Porous Polymers, U.S. Pat. No. 6,663,668; Allen, et al., Porous Materials, U.S. Pat. No. 6,602,804; Hawker, et al., Porous Dielectric Material and Electronic Devices Fabricated Therewith, U.S. Pat. No. 6,541,865; Davankov, et al., Method of Making Biocompatible Polymeric Adsorbing Material for Purification of Physiological Fluids of Organism, U.S. Pat. No. 6,531,523; Shastri, et al., Three-Dimensional Polymer Matrices, U.S. Pat. No. 6,471,993; Yates, Photogenerated Nanoporous Materials, U.S. Pat. No. 6,380,270; Formum, Method for the Manufacture of Amino Group Containing Support Matrices, Support Matrices Prepared by the Method, and Use of the Support Matrices, U.S. Pat. No. 6,335,438; Chaouk, et al., Polymers, U.S. Pat. No. 6,225,367; Chaouk, et al., High Water Content Porous Polymer, U.S. Pat. No. 6,160,030; Hawker, et al., Dielectric Compositions and Method for Their Manufacture, U.S. Pat. No. 6,107,357; Li, et al., Polymeric Microbeads and Methods of Preparation, U.S. Pat. No. 6,100,306; Chaouk, et al., Process for Manufacture of A Porous Polymer by Use of A Porogen, U.S. Pat. No. 6,060,530; Li, et al., Polymeric Microbeads, U.S. Pat. No. 5,863,957; Frechet and Svec, Porous Polymeric Material with Gradients, U.S. Pat. No. 5,728,457; Frechet and Svec, Pore-Size Selective Modification of Porous Materials, U.S. Pat. No. 5,633,290; Yen, et al., Ion Exchange Polyethylene Membrane and Process, U.S. Pat. No. 5,531,899; Soria, et al., Membrane for a Filtration, Gas or Liquid Separation or Pervaporation Apparatus and A Manufacturing Method for Such Membrane, U.S. Pat. No. 5,066,398; Axisa, et al., Method of Fabricating A Porous Elastomer, U.S. Patent Publication 2010/0075056; Liljensten and Persoon, Biodegradable Ostochondreal Implant, U.S. Patent Publication 2009/0164014; Favis, et al., Porous Nanosheath Networks, Method of Making and Uses Thereof, U.S. Patent Publication 2009/0087641; Hosoya, et al., Porous Polymer and Process For Producing the Same, U.S. Patent Publication 2009/0045119; Andersson, Chitosan Compositions, U.S. Patent Publication 2009/0022770; Xie, Three-Dimensional Hydrophilic Porous Structures for Fuel Cell Plates, U.S. Patent Publication 2008/0292939; Ratner and Marshall, Novel Porous Materials, U.S. Patent Publication 2008/0075752; Ma and Chen, Porous Materials having Multi-Sized Geometries, U.S. Patent Publication 2007/0036844; Ma, Reverse Fabrication of Porous Materials, U.S. Patent Publication 2002/0005600; Liu, et al., Porous Materials, Methods of Making and Uses, and U.S. patent application Ser. No. 13/104,888, filed May 10, 2011; and Liu, et al., Porous Materials, Methods of Making and Uses, and U.S. patent application Ser. No. 13/104,395, filed May 10, 2011; each of which is incorporated by reference in its entirety.

In one aspect, the method of making a porous material comprises the steps of: a) coating porogens comprising a shell material and a core material with a substance base to form a substance coated porogen mixture; b) treating the substance coated porogen mixture to allow fusing of the porogens to form a porogen scaffold and stabilization of the substance; and c) removing the porogen scaffold, wherein porogen scaffold removal results in a porous material, the porous material comprising a substance matrix defining an array of interconnected pores.

In another aspect, a method of making a porous material comprises the steps of a) coating porogens comprising a shell material and a core material with a substance base to form a substance coated porogen mixture; b) packing the substance coated porogen mixture into a mold; c) treating the substance coated porogen mixture to allow fusing of the porogens to form a porogen scaffold and stabilization of the substance; and d) removing the porogen scaffold, wherein porogen scaffold removal results in a porous material, the porous material comprising a substance matrix defining an array of interconnected pores.

As used herein, the term "substance base" is synonymous with "uncured substance" and refers to a substance disclosed herein that is in its uncured state. As used herein, the term "elastomer base" is synonymous with "uncured elastomer" and refers to an elastomer disclosed herein that is in its uncured state. As used herein, the term "silicon-based elastomer base" is synonymous with "uncured silicon-based elastomer" and refers to a silicon-based elastomer disclosed herein that is in its uncured state.

The present specification discloses, in part, packing porogens into a mold prior to fusion. Any mold shape may be used for packing the porogens. Porogens can be packed into the mold before coating of a substance base, or can be first coated with a substance base before packing into a mold. If coated first, the substance coated porogen mixture may first have to be devolitalized before packing into a mold. As a non-limiting example, a mold shape can be a shell that outlines the contours an implantable device, such as, e.g., a shell for a breast implant, or a shell for a muscle implant. As another non-limiting example, the mold shape can be one that forms sheets. Such sheets can be made in a wide variety or proportions based on the needed application. For example, the sheets can be made in a size slightly bigger that an implantable device so that there is sufficient material to cover the device and allow for trimming of the excess. As another example, the sheets can be produced as a continuous roll that allows a person skilled in the art to take only the desired amount for an application, such as, e.g., creating strips having a textured surface for control of scar formation. The porogens may be packed into a mold using ultrasonic agitation, mechanical agitation, or any other suitable method for obtaining a closely packed array of porogens.

In an embodiment, a substance coated porogen mixture is packed into a mold. In an aspect of this embodiment, a substance coated porogen mixture is packed into a mold in a manner suitable to obtain a closely packed array of porogens. In other aspects of this embodiment, a substance coated porogen mixture is packed into a mold using sonic agitation or mechanical agitation.

In another embodiment, porogens are packed into a mold. In an aspect of this embodiment, porogens are packed into a mold in a manner suitable to obtain a closely packed array of porogens. In other aspects of this embodiment, porogens are packed into a mold using sonic agitation or mechanical agitation.

As used herein, the term "porogen scaffold" refers to a three-dimensional structural framework composed of fused porogens that serves as the negative replica of a matrix defining an interconnected array of pores. The porogen compositions disclosed herein comprise a shell material and a core material.

The present specification discloses, in part, coating porogens with a substance base to form a substance coated porogen mixture. Coating the porogens with a substance base can be accomplished by any suitable means, including, without limitation, mechanical application such as, e.g., dipping, spraying, knifing, curtaining, brushing, or vapor deposition, thermal application, adhering application, chemical bonding, self-assembling, molecular entrapment, and/or any combination thereof. The substance is applied to the porogens in such a manner as to coat the porogens with the desired thickness of substance. Removal of excess substance base can be accomplished by any suitable means, including, without limitation, gravity-based filtering or sieving, vacuum-based filtering or sieving, blowing, and/or any combination thereof.

Any substance base can be used to coat the porogens with the proviso that the substance base is a suitable material to form a porous material. A substance base can be any organic or inorganic material, composites thereof, and/or combinations thereof. Suitable substance bases include, without limitation, natural and synthetic ceramics and/or its derivatives, natural and synthetic polysaccharides and its derivatives, natural and synthetic metals and its derivatives, natural and synthetic polymers and its derivatives, and/or natural and synthetic elastomers and its derivatives, composites thereof, and/or combinations thereof.

A natural or synthetic elastomer or elastic polymer refers to an amorphous polymer that exists above its glass transition temperature at ambient temperatures, thereby conferring the property of viscoelasticity so that considerable segmental motion is possible, and includes, without limitation, carbon-based elastomers, silicon-based elastomers, thermoset elastomers, and thermoplastic elastomers. As used herein, the term "ambient temperature" refers to a temperature of about 18° C. to about 22° C. Elastomers, ether naturally occurring or synthetically made, comprise monomers usually made of carbon, hydrogen, oxygen, and/or silicon which are linked together to form long polymer chains. Elastomers are typically covalently cross-linked to one another, although non-covalently cross-linked elastomers are known. Elastomers may be homopolymers or copolymers, degradable, substantially non-degradable, or non-degradable. Copolymers may be random copolymers, blocked copolymers, graft copolymers, and/or mixtures thereof. Unlike other polymers classes, elastomers can be stretched many times their original length without breaking by reconfiguring themselves to distribute an applied stress, and the cross-linkages ensure that the elastomers will return to their original configuration when the stress is removed. Elastomers can be a non-medical grade elastomer or a medical grade elastomer. Medical grade elastomers are typically divided into three categories: non-implantable, short term implantable and long-term implantable. Exemplary substantially non-degradable and/or non-degradable, biocompatible, elastomers include, without limitation, bromo isobutylene isoprene (BIIR), polybutadiene (BR), chloro isobutylene isoprene (CIIR), polychloroprene (CR), chlorosulphonated polyethylene (CSM), ethylene propylene (EP), ethylene propylene diene monomer (EPDM), fluoronated hydrocarbon (FKM), fluoro silicone (FVQM), hydrogenated nitrile butadiene (HNBR), polyisoprene (IR), isobutylene isoprene butyl (IIR), methyl vinyl silicone (MVQ), acrylonitrile butadiene (NBR), polyurethane (PU), styrene butadiene (SBR), styrene ethylene/butylene styrene (SEBS), polydimethylsiloxane (PDMS), polysiloxane (SI), and acrylonitrile butadiene carboxy monomer (XNBR).

Thus, in an embodiment, porogens are coated with a substance base to a thickness sufficient to allow formation of a porous material comprising a matrix defining an interconnected array of pores. In aspects of this embodiment, porogens are coated with a substance base to a thickness of, e.g., about 1 µm, about 2 µm, about 3 µm, about 4 µm, about 5 µm, about 6 µm, about 7 µm, about 8 µm, about 9 µm, about 10 µm, about 20 µm, about 30 µm, about 40 µm, about 50 µm, about 60 µm, about 70 µm, about 80 µm, about 90 µm, or about 100 µm. In other aspects of this embodiment, porogens are coated with a substance base to a thickness of, e.g., at least 1 µm, at least 2 µm, at least 3 µm, at least 4 µm, at least 5 µm, at least 6 μm, at least 7 μm, at least 8 μm, at least 9 μm, at least 10 μm, at least 20 μm, at least 30 μm, at least 40 μm, at least 50 μm, at least 60 μm, at least 70 μm, at least 80 μm, at least 90 μm, or at least 100 μm. In yet other aspects of this embodiment, porogens are coated with a substance base to a thickness of, e.g., at most 1 μm, at most 2 μm, at most 3 μm, at most 4 μm, at most 5 μm, at most 6 μm, at most 7 μm, at most 8 μm, at most 9 μm, at most 10 μm, at most 20 μm, at most 30 μm, at most 40 μm, at most 50 μm, at most 60 μm, at most 70 μm, at most 80 μm, at most 90 μm, or at most 100 μm. In still other aspects of this embodiment, porogens are coated with a substance base to a thickness of, e.g., about 1 μm to about 5 μm, about 1 μm to about 10 μm, about 5 μm to about 10 μm, about 5 μm to about 25 μm, about 5 μm to about 50 μm, about 10 μm to about 50 μm, about 10 μm to about 75 μm, about 10 μm to about 100 μm, about 25 μm to about 100 μm, or about 50 μm to about 100 μm.

The present specification discloses, in part, devolitalizing substance coated porogens. As used herein, the term "devolitalizing" or "devolitalization" refers to a process that removes volatile components from the substance coated porogens. Devolitalization of the substance coated porogens can be accomplished by any suitable means that substantially removes all the volatile components from the substance coated porogens. Non-limiting examples of devolitalizing procedures include evaporation, freeze-drying, sublimination, extraction, and/or any combination thereof.

In an embodiment, substance coated porogens are devolitalized at a single temperature for a time sufficient to allow the evaporation of substantially all volatile components from the substance coated porogens. In an aspect of this embodiment, substance coated porogens are devolitalized at ambient temperature for about 1 minute to about 5 minutes. In another aspect of this embodiment, substance coated porogens are devolitalized at ambient temperature for about 45 minutes to about 75 minutes. In yet another aspect of this embodiment, substance coated porogens are devolitalized at ambient temperature for about 90 minutes to about 150 minutes. In another aspect of this embodiment, substance coated porogens are devolitalized at about 18° C. to about 22° C. for about 1 minute to about 5 minutes. In yet another aspect of this embodiment, substance coated porogens are devolitalized at about 18° C. to about 22° C. for about 45 minutes to about 75 minutes. In still another aspect of this embodiment, substance coated porogens are devolitalized at about 18° C. to about 22° C. for about 90 minutes to about 150 minutes.

The present specification discloses, in part, treating a substance coated porogen mixture to allow fusing of the porogens to form a porogen scaffold and stabilization of the substance. As used herein, the term "treating" refers to a process that 1) fuses the porogens to form a porogen scaffold useful to make a porous material comprising a matrix of an interconnected array of pores and 2) stabilizes the substance. Non-limiting examples of treating include thermal treating like heating or freezing, chemical treating, catalyst treating, radiation treating, and physical treating. Treating of a substance coated porogen scaffold can be done under any condition for any length of time with the proviso that the treating fuses the porogens to form a porogen scaffold useful to make a porous material comprising a matrix of an interconnected array of pores and stabilizes the substance.

Thermal treating a substance coated porogen mixture can be at any temperature or temperatures for any length of time or times with the proviso that the thermal treatment fuses the porogens to form a porogen scaffold and stabilizes the substance base to form a substance matrix as disclosed in the present specification. A non-limiting example of temperatures useful in a thermal treatment are temperatures higher than the glass transition temperature or melting temperature of the porogens, such as between about 5° C. to about 50° C. higher than the glass transition temperature or melting temperature of the porogens. Any temperature can be used in a thermal treatment with the proviso that the temperature is sufficient to cause fusion of the porogens. As a non-limiting example, the thermal treatment can be from about 30° C. to about 250° C. Increasing the duration of the thermal treatment at a given temperature increases the connection size; increases the sintering temperature, and increases the growth rate of the connections. Any time can be used in a thermal treatment with the proviso that the time is sufficient to cause fusion of the porogens and cures the substance. Suitable times are generally from about 0.5 hours to about 48 hours.

Thus, in an embodiment, a substance coated porogen scaffold is treated by thermal treatment, chemical treatment, catalyst treatment, radiation treatment, or physical treatment where the treatment is sufficient to stabilize a substance. In another embodiment, a substance coated porogen scaffold is treated at a single time, where the treating time is sufficient to stabilize a substance.

In another embodiment, substance coated porogens are thermal treated at a single temperature for a single time, where the treating temperature and time is sufficient to fuse the porogens to form a porogen scaffold and cure the substance to form a substance matrix sufficient to allow tissue growth within its array of interconnected pores.

In other aspects of this embodiment, the thermal treatment comprises heating substance coated porogens for a time at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the porogens, where the treating temperature and time is sufficient to fuse the porogens to form a porogen scaffold and cure the substance to form a substance matrix sufficient to allow tissue growth within its array of interconnected pores. In yet other aspects of this embodiment, the thermal treatment comprises heating substance coated porogens for a time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least 50° C. higher than the melting temperature or glass transition temperature of the porogens, where the treating temperature and time is sufficient to fuse the porogens to form a porogen scaffold and cure the substance to form a substance matrix sufficient to allow tissue growth within its array of interconnected pores. In still other aspects of this embodiment, the thermal treatment comprises heating substance coated porogens for a time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, where the treating temperature and time is sufficient to fuse the porogens to form a porogen scaffold and cure the substance to form a substance matrix sufficient to allow tissue growth within its array of interconnected pores. In further aspects of this embodiment, the thermal treatment comprises heating substance coated porogens for a time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, where the treating temperature and time is sufficient to fuse the porogens to form a porogen scaffold and cure the substance to form a substance matrix sufficient to allow tissue growth within its array of interconnected pores.

In another aspect of this embodiment, a substance on a substance coated porogen scaffold is treated at about 30° C. to about 130° C. for about 10 minutes to about 360 minutes, where the treating temperature and time is sufficient to fuse the porogens to form a porogen scaffold and cure the substance to form a substance matrix sufficient to allow tissue growth within its array of interconnected pores.

In yet another embodiment, substance-coated porogens are thermal treated at a plurality of temperatures for a plurality of times, where the treating temperatures and times are sufficient to fuse the porogens to form a porogen scaffold and cure the substance to form a substance matrix sufficient to allow tissue growth within its array of interconnected pores. In an aspect of this embodiment, substance coated porogens are treated at a first temperature for a first time, and then a second temperature for a second time, where the treating temperatures and times are sufficient to fuse the porogens to form a porogen scaffold and cure the substance to form a substance matrix sufficient to allow tissue growth within its array of interconnected pores, and where the first and second temperatures are different.

In aspects of this embodiment, thermal treatment comprises heating the substance coated porogens at a first temperature for a first time, and then heating the porogens at a second temperature for a second time, where the treating temperatures and times are sufficient to fuse the porogens to form a porogen scaffold and cure the substance to form a substance matrix sufficient to allow tissue growth within its array of interconnected pores, and where the first and second temperatures are different, and where the first and second temperatures are different. In other aspects of this embodiment, the thermal treatment comprises heating substance coated porogens for a first time at, e.g., about 5 C higher, about 10° C. higher, about 15° C. higher, about 2° C. higher, about 25° C. higher, about 30° C. higher, about 35° C. higher, about 40° C. higher, about 45° C. higher, or about 50° C. higher than the melting temperature or glass transition temperature of the substance coated porogens, then heating for a second time the porogens at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the porogens, where the treating temperatures and times are sufficient to fuse the porogens to form a porogen scaffold and cure the substance to form a substance matrix sufficient to allow tissue growth within its array of interconnected pores, and where the first and second temperatures are different. In yet other aspects of this embodiment, the thermal treatment comprises heating substance coated porogens for a first time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least 50° C. higher than the melting temperature or glass transition temperature of the porogens, then heating substance coated porogens for a second time at, e.g., at least 5° C. higher, at least 10° C. higher, at least 15° C. higher, at least 20° C. higher, at least 25° C. higher, at least ° C. higher, at least 35° C. higher, at least 40° C. higher, at least 45° C. higher, or at least 50° C. higher than the melting temperature or glass transition temperature of the porogens, where the treating temperatures and times are sufficient to fuse the porogens to form a porogen scaffold and cure the substance to form a substance matrix sufficient to allow tissue growth within its array of interconnected pores, and where the first and second temperatures are different. In still other aspects of this embodiment, the thermal treatment comprises heating substance coated porogens for a first time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, then heating substance coated porogens for a second time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, where the treating temperatures and times are sufficient to fuse the porogens to form a porogen scaffold and cure the substance to form a substance matrix sufficient to allow tissue growth within its array of interconnected pores, and where the first and second temperatures are different.

In further aspects of this embodiment, the thermal treatment comprises heating substance coated porogens for a first time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, then heating substance coated porogens for a second time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, where the treating temperatures and times are sufficient to fuse the porogens to form a porogen scaffold and cure the substance to form a substance matrix sufficient to allow tissue growth within its array of interconnected pores, and where the first and second temperatures are different.

In other aspects of this embodiment, thermal treatment comprises heating the substance coated porogens at a first temperature for a first time, heating the porogens at a second temperature for a second time, and then heating the porogens at a third temperature at a third time, where the treating temperatures and times are sufficient to fuse the porogens to form a porogen scaffold and cure the substance to form a substance matrix sufficient to allow tissue growth within its array of interconnected pores, and where the first temperature is different from the second temperature and the second temperature is different form the third temperature.

In other aspects of this embodiment, the thermal treatment comprises heating substance coated porogens for a first time at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the porogens, then heating substance coated porogens for a second time at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the porogens, then heating substance coated porogens for a third time at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the porogens, where the treating temperatures and times are sufficient to fuse the porogens to form a porogen scaffold and cure the substance to form a substance matrix sufficient to allow tissue growth within its array of interconnected pores, and where the first temperature is different from the second temperature and the second temperature is different form the third temperature. In yet other aspects of this embodiment, the thermal treatment comprises heating substance coated porogens for a first time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least ° C. higher than the melting temperature or glass transition temperature of the porogens, then heating substance coated porogens for a second time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least 50° C. higher than the melting temperature or glass transition temperature of the porogens, then heating substance coated porogens for a third time at, e.g., at least 5° C. higher, at least 10° C. higher, at least 15° C. higher, at least 20° C. higher, at least 25° C. higher, at least ° C. higher, at least 35° C. higher, at least 40° C. higher, at least 45° C. higher, or at least 50° C. higher than the melting temperature or glass transition temperature of the porogens, where the treating temperatures and times are sufficient to fuse the porogens to form a porogen scaffold and cure the substance to form a substance matrix sufficient to allow tissue growth within its array of interconnected pores, and where the first temperature is different from the second temperature and the second temperature is different from the third temperature. In still other aspects of this embodiment, the thermal treatment comprises heating substance coated porogens for a first time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, then heating substance coated porogens for a second time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, then heating substance coated porogens for a third time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, where the treating temperatures and times are sufficient to fuse the porogens to form a porogen scaffold and cure the substance to form a substance matrix sufficient to allow tissue growth within its array of interconnected pores, and where the first temperature is different from the second temperature and the second temperature is different from the third temperature.

In further aspects of this embodiment, the thermal treatment comprises heating substance coated porogens for a first time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, then heating substance coated porogens for a second time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, then heating substance coated porogens for a third time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, where the treating temperatures and times are sufficient to fuse the porogens to form a porogen scaffold and cure the substance to form a substance matrix sufficient to allow tissue growth within its array of interconnected pores, and where the first temperature is different from the second temperature and the second temperature is different from the third temperature.

In still other aspect of this embodiment, substance coated porogens are treated at about 60° C. to about 75° C. for about 15 minutes to about 45 minutes, and then at about 120° C. to about 130° C. for about 60 minutes to about 90 minutes, where the treating temperatures and times is sufficient to fuse the porogens to form a porogen scaffold and cure the substance to form a substance matrix sufficient to allow tissue growth within its array of interconnected pores. In a further aspect of this embodiment, a substance coated porogen mixture is treated at about 60° C. to about 75° C. for about 15 minutes to about 45 minutes, then at about 135° C. to about 150° C. for about 90 minutes to about 150 minutes, and then at about 150° C. to about 165° C. for about 15 minutes to about 45 minutes.

The present specification discloses, in part, to form a porogen scaffold that serves as the negative replica of an elastomer matrix defining an interconnected array of pores as disclosed in the present specification.

The porogen scaffold is formed in such a manner that substantially all the fused porogens in the porogen scaffold have a similar diameter. As used herein, the term "substantially," when used to describe fused porogens, refers to at least 90% of the porogen comprising the porogen scaffold are fused, such as, e.g., at least 95% of the porogens are fused or at least 97% of the porogen are fused. As used herein, the term "similar diameter," when used to describe fused porogens, refers to a difference in the diameters of the two fused porogen that is less than about 20% of the larger diameter. As used herein, the term "diameter," when used to describe a fused porogen, refers to the longest line segment that can be drawn that connects two points within the fused porogen, regardless of whether the line passes outside the boundary of the fused porogen. Any fused porogen diameter is useful with the proviso that the fused porogen diameter is sufficient to allow formation of a porogen scaffold useful in making an elastomer matrix as disclosed in the present specification.

The porogen scaffold is formed in such a manner that the diameter of the connections between each fused porogen is sufficient to allow formation of a porogen scaffold useful in making an elastomer matrix as disclosed in the present specification. As used herein, the term "diameter," when describing the connection between fused porogens, refers to the diameter of the cross-section of the connection between two fused porogens in the plane normal to the line connecting the centroids of the two fused porogens, where the plane is chosen so that the area of the cross-section of the connection is at its minimum value. As used herein, the term "diameter of a cross-section of a connection," when describing the connection between fused porogens refers to the average length of a straight line segment that passes through the center, or centroid (in the case of a connection having a cross-section that lacks a center), of the cross-section of a connection and terminates at the periphery of the cross-section. As used herein, the term "substantially," when used to describe the connections between fused porogens refers to at least 90% of the fused porogens comprising the porogen scaffold make connections between each other, such as, e.g., at least 95% of the fused porogens make connections between each other or at least 97% of the fused porogens make connections between each other.

In an embodiment, a porogen scaffold comprises fused porogens where substantially all the fused porogens have a similar diameter. In aspects of this embodiment, at least 90% of all the fused porogens that have a similar diameter, at least 95% of all the fused porogens have a similar diameter, or at least 97% of all the fused porogens have a similar diameter. In another aspect of this embodiment, difference in the diameters of two fused porogens is, e.g., less than about 20% of the larger diameter, less than about 15% of the larger diameter, less than about 10% of the larger diameter, or less than about 5% of the larger diameter.

In another embodiment, a porogen scaffold comprises fused porogens having a mean diameter sufficient to allow tissue growth into the array of interconnected porogens. In aspects of this embodiment, a porogen scaffold comprises fused porogens comprising a mean fused porogen diameter of, e.g., about 50 µm, about 75 µm, about 100 µm, about 150 µm, about 200 µm, about 250 µm, about 300 µm, about 350 µm, about 400 µm, about 450 µm, or about 500 µm. In other aspects, a porogen scaffold comprises fused porogens comprising a mean fused porogen diameter of, e.g., about 500 µm, about 600 µm, about 700 µm, about 800 µm, about 900 µm, about 1000 µm, about 1500 µm, about 2000 µm, about 2500 µm, or about 3000 µm. In yet other aspects of this embodiment, a porogen scaffold comprises fused porogens comprising a mean fused porogen diameter of, e.g., at least 50 µm, at least 75 µm, at least 100 µm, at least 150 µm, at least 200 µm, at least 250 µm, at least 300 µm, at least 350 µm, at least 400 µm, at least 450 µm, or at least 500 µm. In still other aspects, an elastomer matrix comprises fused porogens comprising a mean fused porogen diameter of, e.g., at least 500 µm, at least 600 µm, at least 700 µm, at least 800 µm, at least 900 µm, at least 1000 µm, at least 1500 µm, at least 2000 µm, at least 2500 µm, or at least 3000 µm. In further aspects of this embodiment, a porogen scaffold comprises fused porogens comprising a mean fused porogen diameter of, e.g., at most 50 µm, at most 75 µm, at most 100 µm, at most 150 µm, at most 200 µm, at most 250 µm, at most 300 µm, at most 350 µm, at most 400 µm, at most 450 µm, or at most 500 µm. In yet further aspects of this embodiment, an elastomer matrix comprises fused porogens comprising a mean fused porogen diameter of, e.g., at most 500 µm, at most 600 µm, at most 700 µm, at most 800 µm, at most 900 µm, at most 1000 µm, at most 1500 µm, at most 2000 µm, at most 2500 µm, or at most 3000 µm. In still further aspects of this embodiment, a porogen scaffold comprises fused porogens comprising a mean fused porogen diameter in a range from, e.g., about 300 µm to about 600 µm, about 200 µm to about 700 µm, about 100 µm to about 800 µm, about 500 µm to about 800 µm, about 50 µm to about 500 µm, about 75 µm to about 500 µm, about 100 µm to about 500 µm, about 200 µm to about 500 µm, about 300 µm to about 500 µm, about 50 µm to about 1000 µm, about 75 µm to about 1000 µm, about 100 µm to about 1000 µm, about 200 µm to about 1000 µm, about 300 µm to about 1000 µm, about 50 µm to about 1000 µm, about 75 µm to about 3000 µm, about 100 µm to about 3000 µm, about 200 µm to about 3000 µm, or about 300 µm to about 3000 µm.

In another embodiment, a porogen scaffold comprises fused porogens connected to a plurality of other porogens. In aspects of this embodiment, a porogen scaffold comprises a mean fused porogen connectivity, e.g., about two other fused porogens, about three other fused porogens, about four other fused porogens, about five other fused porogens, about six other fused porogens, about seven other fused porogens, about eight other fused porogens, about nine other fused porogens, about ten other fused porogens, about 11 other fused porogens, or about 12 other fused porogens. In other aspects of this embodiment, a porogen scaffold comprises a mean fused porogen connectivity, e.g., at least two other fused porogens, at least three other fused porogens, at least four other fused porogens, at least five other fused porogens, at least six other fused porogens, at least seven other fused porogens, at least eight other fused porogens, at least nine other fused porogens, at least ten other fused porogens, at least 11 other fused porogens, or at least 12 other fused porogens. In yet other aspects of this embodiment, a porogen scaffold comprises a mean fused porogen connectivity, e.g., at most two other fused porogens, at most three other fused porogens, at most four other fused porogens, at most five other fused porogens, at most six other fused porogens, at most seven other fused porogens, at most eight other fused porogens, at most nine other fused porogens, at most ten other fused porogens, at most 11 other fused porogens, or at most 12 other fused porogens.

In still other aspects of this embodiment, a porogen scaffold comprises fused porogens connected to, e.g., about two other fused porogens to about 12 other fused porogens, about two other fused porogens to about 11 other fused porogens, about two other fused porogens to about ten other fused porogens, about two other fused porogens to about nine other fused porogens, about two other fused porogens to about eight other fused porogens, about two other fused porogens to about seven other fused porogens, about two other fused porogens to about six other fused porogens, about two other fused porogens to about five other fused porogens, about three other fused porogens to about 12 other fused porogens, about three other fused porogens to about 11 other fused porogens, about three other fused porogens to about ten other fused porogens, about three other fused porogens to about nine other fused porogens, about three other fused porogens to about eight other fused porogens, about three other fused porogens to about seven other fused porogens, about three other fused porogens to about six other fused porogens, about three other fused porogens to about five other fused porogens, about four other fused porogens to about 12 other fused porogens, about four other fused porogens to about 11 other fused porogens, about four other fused porogens to about ten other fused porogens, about four other fused porogens to about nine other fused porogens, about four other fused porogens to about eight other fused porogens, about four other fused porogens to about seven other fused porogens, about four other fused porogens to about six other fused porogens, about four other fused porogens to about five other fused porogens, about five other fused porogens to about 12 other fused porogens, about five other fused porogens to about 11 other fused porogens, about five other fused porogens to about ten other fused porogens, about five other fused porogens to about nine other fused porogens, about five other fused porogens to about eight other fused porogens, about five other fused porogens to about seven other fused porogens, or about five other fused porogens to about six other fused porogens.

In another embodiment, a porogen scaffold comprises fused porogens where the diameter of the connections between the fused porogens is sufficient to allow formation of a porogen scaffold useful in making an elastomer matrix that allows tissue growth within its array of interconnected pores. In aspects of this embodiment, the porogen scaffold comprises fused porogens where the diameter of the connections between the fused porogens is, e.g., about 10% the mean fused porogen diameter, about 20% the mean fused porogen diameter, about 30% the mean fused porogen diameter, about 40% the mean fused porogen diameter, about 50% the mean fused porogen diameter, about 60% the mean fused porogen diameter, about 70% the mean fused porogen diameter, about 80% the mean fused porogen diameter, or about 90% the mean fused porogen diameter. In other aspects of this embodiment, the porogen scaffold comprises fused porogens where the diameter of the connections between the fused porogens is, e.g., at least 10% the mean fused porogen diameter, at least 20% the mean fused porogen diameter, at least 30% the mean fused porogen diameter, at least 40% the mean fused porogen diameter, at least 50% the mean fused porogen diameter, at least 60% the mean fused porogen diameter, at least 70% the mean fused porogen diameter, at least 80% the mean fused porogen diameter, or at least 90% the mean fused porogen diameter. In yet other aspects of this embodiment, the porogen scaffold comprises fused porogens where the diameter of the connections between the fused porogens is, e.g., at most 10% the mean fused porogen diameter, at most 20% the mean fused porogen diameter, at most 30% the mean fused porogen diameter, at most 40% the mean fused porogen diameter, at most 50% the mean fused porogen diameter, at most 60% the mean fused porogen diameter, at most 70% the mean fused porogen diameter, at most 80% the mean fused porogen diameter, or at most 90% the mean fused porogen diameter.

In still other aspects of this embodiment, a porogen scaffold comprises fused porogens where the diameter of the connections between the fused porogens is, e.g., about 10% to about 90% the mean fused porogen diameter, about 15% to about 90% the mean fused porogen diameter, about 20% to about 90% the mean fused porogen diameter, about 25% to about 90% the mean fused porogen diameter, about 30% to about 90% the mean fused porogen diameter, about 35% to about 90% the mean fused porogen diameter, about 40% to about 90% the mean fused porogen diameter, about 10% to about 80% the mean fused porogen diameter, about 15% to about 80% the mean fused porogen diameter, about 20% to about 80% the mean fused porogen diameter, about 25% to about 80% the mean fused porogen diameter, about 30% to about 80% the mean fused porogen diameter, about 35% to about 80% the mean fused porogen diameter, about 40% to about 80% the mean fused porogen diameter, about 10% to about 70% the mean fused porogen diameter, about 15% to about 70% the mean fused porogen diameter, about 20% to about 70% the mean fused porogen diameter, about 25% to about 70% the mean fused porogen diameter, about 30% to about 70% the mean fused porogen diameter, about 35% to about 70% the mean fused porogen diameter, about 40% to about 70% the mean fused porogen diameter, about 10% to about 60% the mean fused porogen diameter, about 15% to about 60% the mean fused porogen diameter, about 20% to about 60% the mean fused porogen diameter, about 25% to about 60% the mean fused porogen diameter, about 30% to about 60% the mean fused porogen diameter, about 35% to about 60% the mean fused porogen diameter, about 40% to about 60% the mean fused porogen diameter, about 10% to about 50% the mean fused porogen diameter, about 15% to about 50% the mean fused porogen diameter, about 20% to about 50% the mean fused porogen diameter, about 25% to about 50% the mean fused porogen diameter, about 30% to about 50% the mean fused porogen diameter, about 10% to about 40% the mean fused porogen diameter, about 15% to about 40% the mean fused porogen diameter, about 20% to about 40% the mean fused porogen diameter, about 25% to about 40% the mean fused porogen diameter, about 40% the mean fused porogen diameter, or about 30% to about 40% the mean fused porogen diameter.

The present specification discloses, in part, stabilizing a substance. As used herein, the term "stabilizing" refers to a process that exposes the substance base to an element which activates a phase change in the substance base to a more stable state, such as, e.g., by physically or chemically, cross-linking components of the substance to one another. Such a stabilization forms, e.g., a substance matrix. Non-limiting examples of stabilizing include curing, such as, e.g., thermal curing, chemical curing, catalyst curing, radiation curing, and physical curing. Stabilizing of a substance coated porogen scaffold can be done under any condition for any length of time with the proviso that the conditions used stabilize the substance.

The present specification discloses, in part, removing a porogen scaffold from a treated substance. Removal of the porogen scaffold can be accomplished by any suitable means, with the proviso that removal results in a porous material comprising a matrix defining an array of interconnected pores. Non-limiting examples of porogen removal include solvent extraction, thermal decomposition extraction, degradation extraction, mechanical extraction, and/or any combination thereof. As such, it is beneficial to use shell and core materials that are removable using an extraction method, but such method leaves the porous material intact. In extraction methods requiring exposure to another solution, such as, e.g., solvent extraction, the extraction can incorporate a plurality of solution changes over time to facilitate removal of the porogen scaffold. Non-limiting examples of solvents useful for solvent extraction include water, methylene chloride, acetic acid, formic acid, pyridine, tetrahydrofuran, dimethylsulfoxide, dioxane, benzene, and/or mixtures thereof. A mixed solvent can be in a ratio of higher than about 1:1, first solvent to second solvent or lower than about 1:1, first solvent to second solvent.

In an embodiment, a porogen scaffold is removed by extraction, where the extraction removes substantially all the porogen scaffold leaving a porous material comprising a matrix defining an array of interconnected pores. In aspects of this embodiment, a porogen scaffold is removed by extraction, where the extraction removes, e.g., about 75% of the porogen scaffold, about 80% of the porogen scaffold, about 85% of the porogen scaffold, about 90% of the porogen scaffold, or about 95% of the porogen scaffold. In other aspects of this embodiment, a porogen scaffold is removed by extraction, where the extraction removes, e.g., at least 75% of the porogen scaffold, at least 80% of the porogen scaffold, at least 85% of the porogen scaffold, at least 90% of the porogen scaffold, or at least 95% of the porogen scaffold. In aspects of this embodiment, a porogen scaffold is removed by extraction, where the extraction removes, e.g., about 75% to about 90% of the porogen scaffold, about 75% to about 95% of the porogen scaffold, about 75% to about 100% of the porogen scaffold, about 80% to about 90% of the porogen scaffold, about 80% to about 95% of the porogen scaffold, about 80% to about 100% of the porogen scaffold, about 85% to about 90% of the porogen scaffold, about 85% to about 95% of the porogen scaffold, or about 85% to about 100% of the porogen scaffold. In an aspect, a porogen scaffold is removed by a solvent extraction, a thermal extraction, a degradation extraction, a mechanical extraction, and/or any combination thereof.

In another embodiment, a porogen scaffold is removed by solvent extraction, where the extraction removes substantially all the porogen scaffold leaving a porous material comprising a matrix defining an array of interconnected pores. In aspects of this embodiment, a porogen scaffold is removed by solvent extraction, where the extraction removes, e.g., about 75% of the porogen scaffold, about 80% of the porogen scaffold, about 85% of the porogen scaffold, about 90% of the porogen scaffold, or about 95% of the porogen scaffold. In other aspects of this embodiment, a porogen scaffold is removed by solvent extraction, where the extraction removes, e.g., at least 75% of the porogen scaffold, at least 80% of the porogen scaffold, at least 85% of the porogen scaffold, at least 90% of the porogen scaffold, or at least 95% of the porogen scaffold. In aspects of this embodiment, a porogen scaffold is removed by solvent extraction, where the extraction removes, e.g., about 75% to about 90% of the porogen scaffold, about 75% to about 95% of the porogen scaffold, about 75% to about 100% of the porogen scaffold, about 80% to about 90% of the porogen scaffold, about 80% to about 95% of the porogen scaffold, about 80% to about 100% of the porogen scaffold, about 85% to about 90% of the porogen scaffold, about 85% to about 95% of the porogen scaffold, or about 85% to about 100% of the porogen scaffold.

In yet another embodiment, a porogen scaffold is removed by thermal decomposition extraction, where the extraction removes substantially all the porogen scaffold leaving a porous material comprising a matrix defining an array of interconnected pores. In aspects of this embodiment, a porogen scaffold is removed by thermal decomposition extraction, where the extraction removes, e.g., about 75% of the porogen scaffold, about 80% of the porogen scaffold, about 85% of the porogen scaffold, about 90% of the porogen scaffold, or about 95% of the porogen scaffold. In other aspects of this embodiment, a porogen scaffold is removed by thermal decomposition extraction, where the extraction removes, e.g., at least 75% of the porogen scaffold, at least 80% of the porogen scaffold, at least 85% of the porogen scaffold, at least 90% of the porogen scaffold, or at least 95% of the porogen scaffold. In aspects of this embodiment, a porogen scaffold is removed by thermal decomposition extraction, where the extraction removes, e.g., about 75% to about 90% of the porogen scaffold, about 75% to about 95% of the porogen scaffold, about 75% to about 100% of the porogen scaffold, about 80% to about 90% of the porogen scaffold, about 80% to about 95% of the porogen scaffold, about 80% to about 100% of the porogen scaffold, about 85% to about 90% of the porogen scaffold, about 85% to about 95% of the porogen scaffold, or about 85% to about 100% of the porogen scaffold.

In still another embodiment, a porogen scaffold is removed by degradation extraction, where the extraction removes substantially all the porogen scaffold leaving a porous material comprising a matrix defining an array of interconnected pores. In aspects of this embodiment, a porogen scaffold is removed by degradation extraction, where the extraction removes, e.g., about 75% of the porogen scaffold, about 80% of the porogen scaffold, about 85% of the porogen scaffold, about 90% of the porogen scaffold, or about 95% of the porogen scaffold. In other aspects of this embodiment, a porogen scaffold is removed by degradation extraction, where the extraction removes, e.g., at least 75% of the porogen scaffold, at least 80% of the porogen scaffold, at least 85% of the porogen scaffold, at least 90% of the porogen scaffold, or at least 95% of the porogen scaffold. In aspects of this embodiment, a porogen scaffold is removed by degradation extraction, where the extraction removes, e.g., about 75% to about 90% of the porogen scaffold, about 75% to about 95% of the porogen scaffold, about 75% to about 100% of the porogen scaffold, about 80% to about 90% of the porogen scaffold, about 80% to about 95% of the porogen scaffold, about 80% to about 100% of the porogen scaffold, about 85% to about 90% of the porogen scaffold, about 85% to about 95% of the porogen scaffold, or about 85% to about 100% of the porogen scaffold.

In still another embodiment, a porogen scaffold is removed by mechanical extraction, where the extraction removes substantially all the porogen scaffold leaving a porous material comprising a matrix defining an array of interconnected pores. In aspects of this embodiment, a porogen scaffold is removed by mechanical extraction, where the extraction removes, e.g., about 75% of the porogen scaffold, about 80% of the porogen scaffold, about 85% of the porogen scaffold, about 90% of the porogen scaffold, or about 95% of the porogen scaffold. In other aspects of this embodiment, a porogen scaffold is removed by mechanical extraction, where the extraction removes, e.g., at least 75% of the porogen scaffold, at least 80% of the porogen scaffold, at least 85% of the porogen scaffold, at least 90% of the porogen scaffold, or at least 95% of the porogen scaffold. In aspects of this embodiment, a porogen scaffold is removed by mechanical extraction, where the extraction removes, e.g., about 75% to about 90% of the porogen scaffold, about 75% to about 95% of the porogen scaffold, about 75% to about 100% of the porogen scaffold, about 80% to about 90% of the porogen scaffold, about 80% to about 95% of the porogen scaffold, about 80% to about 100% of the porogen scaffold, about 85% to about 90% of the porogen scaffold, about 85% to about 95% of the porogen scaffold, or about 85% to about 100% of the porogen scaffold.

The methods of forming a porogen scaffold, and extracting porogens to form a porous material or elastomer material may result in a porous material or a elastomer material disclosed in this application. In one embodiment, the disclosed porous material may have a high porosity and interconnected pore structures that favor tissue growth into the porous material, such as, e.g., by facilitating cell migration, cell proliferation, cell differentiation, nutrient exchange, and/or waste removal. The interconnected pore structure may encourage cell infiltration and growth therein, which disrupt the planar arrangement of capsule formation. Interconnection of the pores is achieved without sacrificing mechanical strength of the porous material, that is, the material's hardness, tensile strength, elongation, tear strength, abrasion and resistance, are preserved. As such, the porous material, its application in creating biocompatible implantable devices, and other aspects disclosed herein are useful in preventing capsular contraction, and in reducing or preventing scar formation.

Even further, it may be important to anchor a biocompatible implantable device to surrounding tissue in order to prevent slippage or unwanted movement. For example, it may be important to anchor securely facial and breast implants into position to prevent slippage or any other unwanted movement. As such, the porous material, its application in creating biocompatible implantable devices, and other aspects disclosed herein are useful in anchoring biocompatible implantable devices.

A porous material disclosed herein may be implanted into the soft tissue of an animal. Such a porous material may be completely implanted into the soft tissue of an animal body (i.e., the entire material is within the body), or the device may be partially implanted into an animal body (i.e., only part of the material is implanted within an animal body, the remainder of the material being located outside of the animal body). A porous material disclosed herein can also be affixed to one or more soft tissues of an animal, typically to the skin of an animal body. For example, a strip of porous material can be placed subcutaneously underneath a healing wound or incision to prevent the fibrous tissue from aligning and thereby reducing or preventing scar formation.

The present specification discloses, in part, a porous material comprising a substantially non-degradable, biocompatible, elastomer matrix. As used herein, the term "non-degradable" refers to a material that is not prone to degrading, decomposing, or breaking down to any substantial or significant degree while implanted in the host. The term "non-resorbable" refers to a material that is not prone to degrading, decomposing, or breaking down to any substantial or significant degree while implanted in the host and being assimilated in the host's body. Non-limiting examples of substantial non-degradation include less than 10% degradation of a porous material over a time period measured, less than 5% degradation of a porous material over a time period measured, less than 3% degradation of a porous material over a time period measured, less than 1% degradation of a porous material over a time period measured. As used herein, the term "biocompatible" refers to a material's ability to perform its intended function, with a desired degree of incorporation in the host, without eliciting any undesirable local or systemic effects in that host.

In an embodiment, a porous material comprises an elastomer matrix defining an array of interconnected pores that is substantially non-degradable. In aspects of this embodiment, a porous material comprising an elastomer matrix defining an array of interconnected pores is substantially non-degradable for, e.g., about five years, about ten years, about 15 years, about 20 years, about 25 years, about 30 years, about 35 years, about 40 years, about 45 years, or about 50 years. In other aspects of this embodiment, a porous material comprising an elastomer matrix defining an array of interconnected pores is substantially non-degradable for, e.g., at least five years, at least ten years, at least 15 years, at least 20 years, at least 25 years, at least 30 years, at least 35 years, at least 40 years, at least 45 years, or at least 50 years. In yet other aspects of this embodiment, a porous material comprising an elastomer matrix defining an array of interconnected pores exhibits less than 5% degradation, less than 3% degradation, or less than 1% degradation over for, e.g., about five years, about ten years, about 15 years, about 20 years, about 25 years, about 30 years, about 35 years, about 40 years, about 45 years, or about 50 years. In still other aspects of this embodiment, a porous material comprising an elastomer matrix defining an array of interconnected pores exhibits less than 5% degradation, less than 3% degradation, or less than 1% degradation over for, e.g., at least five years, at least ten years, at least 15 years, at least 20 years, at least 25 years, at least 30 years, at least 35 years, at least 40 years, at least 45 years, or at least 50 years.

In another embodiment, a porous material comprises an elastomer matrix defining an array of interconnected pores that is substantially biocompatible. In aspects of this embodiment, a porous material comprising an elastomer matrix defining an array of interconnected pores is substantially biocompatible for, e.g., at least five years, at least ten years, at least 15 years, at least 20 years, at least 25 years, at least 30 years, at least 35 years, at least 40 years, at least 45 years, or at least 50 years.

As used herein, the term "elastomer" or "elastic polymer" refers to an amorphous polymer that exists above its glass transition temperature (TO at ambient temperatures, thereby conferring the property of viscoelasticity so that considerable segmental motion is possible, and includes, without limitation, carbon-based elastomers, silicon-based elastomers, thermoset elastomers, and thermoplastic elastomers. The term "ambient temperature" refers to a temperature of about 18° C. to about 22° C. Elastomers, either naturally-occurring or synthetically-made, comprise monomers commonly made of carbon, hydrogen, oxygen, and/or silicon which are linked together to form long polymer chains. Elastomers are typically covalently cross-linked to one another, although non-covalently cross-linked elastomers are known. Elastomers may be homopolymers or copolymers, degradable, substantially non-degradable, or non-degradable. Copolymers may be random copolymers, blocked copolymers, graft copolymers, and/or mixtures thereof. Unlike other polymers classes, an elastomer can be stretched many times its original length without breaking by reconfiguring themselves to distribute an applied stress, and the cross-linkages ensure that the elastomers will return to their original configuration when the stress is removed. Elastomers can be a non-medical grade elastomer or a medical grade elastomer. Medical grade elastomers are typically divided into three categories: non implantable, short term implantable and long-term implantable. Exemplary substantially non-degradable and/or non-degradable, biocompatible, elastomers include, without limitation, bromo isobutylene isoprene (BIIR), polybutadiene (BR), chloro isobutylene isoprene (CIIR), polychloroprene (CR), chlorosulphonated polyethylene (CSM), ethylene propylene (EP), ethylene propylene diene monomer (EPDM), fluoronated hydrocarbon (FKM), fluoro silicone (FVQM), hydrogenated nitrile butadiene (HNBR), polyisoprene (IR), isobutylene isoprene butyl (IIR), methyl vinyl silicone (MVQ), acrylonitrile butadiene (NBR), polyurethane (PU), styrene butadiene (SBR), styrene ethylene/butylene styrene (SEBS), polydimethylsiloxane (PDMS), polysiloxane (SI), and acrylonitrile butadiene carboxy monomer (XNBR).

The present specification discloses, in part, an elastomer that is a silicon-based elastomer. As used herein, the term "silicon-based elastomer" refers to any silicon containing elastomer, such as, e.g., methyl vinyl silicone, polydimethylsiloxane, or polysiloxane. A silicone-based elastomer can be a high temperature vulcanization (HTV) silicone or a room temperature vulcanization (RTV). A silicon-based elastomer can be a non-medical grade silicon-based elastomer or a medical grade silicon-based elastomer. As used herein, the term "medical grade silicon-based elastomer" refers to a silicon-based elastomer approved by the U.S. Pharmacopedia (USP) as at least Class V. Medical grade silicon-based elastomers are typically divided into three categories: non implantable, short term implantable and long-term implantable.

Thus, in an embodiment, an elastomer is a medical grade elastomer. In aspects of this embodiment, a medical grade elastomer is, e.g., a medical grade carbon-based elastomer, a medical grade silicon-based elastomer, a medical grade thermoset elastomer, or a medical grade thermoplastic elastomer. In other aspects of this embodiment, an elastomer is, e.g., a medical grade, long-term implantable, carbon-based elastomer, a medical grade, long-term implantable, silicon-based elastomer, a medical grade, long-term implantable, thermoset elastomer, or a medical grade, long-term implantable, thermoplastic elastomer. In still other aspects, a medical grade elastomer is, e.g., a medical grade bromo isobutylene isoprene, a medical grade polybutadiene, a medical grade chloro isobutylene isoprene, a medical grade polychloroprene, a medical grade chlorosulphonated polyethylene, a medical grade ethylene propylene, a medical grade ethylene propylene diene monomer, a medical grade fluoronated hydrocarbon, a medical grade fluoro silicone, a medical grade hydrogenated nitrile butadiene, a medical grade polyisoprene, a medical grade isobutylene isoprene butyl, a medical grade methyl vinyl silicone, a medical grade acrylonitrile butadiene, a medical grade polyurethane, a medical grade styrene butadiene, a medical grade styrene ethylene/butylene styrene, a medical grade polydimethylsiloxane, a medical grade polysiloxane, or a medical grade acrylonitrile butadiene carboxy monomer.

In another embodiment, an elastomer is a silicon-based elastomer. In an aspect of this embodiment, a silicon-based elastomer is a medical grade silicon-based elastomer. In aspects of this embodiment, a medical grade silicon-based elastomer is, e.g., at least a USP Class V silicon-based elastomer, at least a USP Class VI silicon-based elastomer, or USP Class VII silicon-based elastomer. In yet other aspects, a medical grade silicon-based elastomer is a long-term implantable silicon-based elastomer. In yet other aspects, a medical grade silicon-based elastomer is, e.g., a medical grade, long-term implantable, methyl vinyl silicone, a medical grade, long-term implantable, polydimethylsiloxane, or a medical grade, long-term implantable, polysiloxane.

Elastomers have the property of viscoelasticity. Viscoelasticity is the property of materials that exhibit both viscous and elastic characteristics when undergoing deformation. Viscous materials resist shear flow and strain linearly with time when a stress is applied. Elastic materials strain instantaneously when stretched and just as quickly return to their original state once the stress is removed. Viscoelastic materials have elements of both of these properties and, as such, exhibit time dependent strain. A viscoelastic material has the following properties: 1) hysteresis, or memory, is seen in the stress-strain curve; 2) stress relaxation occurs: step constant strain causes decreasing stress; and 3) creep occurs: step constant stress causes increasing strain. The viscoelasticity of elastomers confer a unique set of properties involving elongation, tensile strength, shear strength compressive modulus, and hardness that distinguish elastomers from other classes of polymers.

The present specification discloses, in part, a porous material comprising an elastomer matrix defining an array of interconnected pores. As used herein, the term "matrix" or "elastomer matrix" is synonymous with "cured elastomer" and refers to a three-dimensional structural framework composed of a substantially non-degradable, biocompatible elastomer in its cured state. As used herein, the term "silicon-based elastomer matrix" is synonymous with "cured silicon-based elastomer" and refers to a three-dimensional structural framework composed of a substantially non-degradable, biocompatible silicon-based elastomer in its cured state.

In one embodiment, a porous material comprising an elastomer matrix defining an array of interconnected pores exhibits high resistance to deformation. Resistance to deformation is the ability of an elastomeric material to maintain its original form after being exposed to stress, and can be calculated as the original form of the elastomeric material ($L_o$), divided by the form of an elastomeric material after it is released from a stress ($L_R$), and then multiplied by 100.

In an embodiment, a porous material comprising an elastomer matrix defining an array of interconnected pores exhibits high resistance to deformation. In aspects of this embodiment, a porous material comprising an elastomer matrix defining an array of interconnected pores exhibits resistance to deformation of, e.g., about 100%, about 99%, about 98%, about 97%, about 96%, about 95%, about 94%, about 93%, about 92%, about 91%, about 90%, about 89%, about 88%, about 87%, about 86%, or about 85%. In other aspects of this embodiment, a porous material comprising an elastomer matrix defining an array of interconnected pores exhibits resistance to deformation of, e.g., at least 99%, at least 98%, at least 97%, at least 96%, at least 95%, at least 94%, at least 93%, at least 92%, at least 91%, at least 90%, at least 89%, at least 88%, at least 87%, at least 86%, or at least 85%. In yet other aspects of this embodiment, a porous material comprising an elastomer matrix defining an array of interconnected pores exhibits resistance to deformation of, e.g., at most 99%, at most 98%, at most 97%, at most 96%, at most 95%, at most 94%, at most 93%, at most 92%, at most 91%, at most 90%, at most 89%, at most 88%, at most 87%, at most 86%, or at most 85%. In still aspects of this embodiment, a porous material comprising an elastomer matrix defining an array of interconnected pores exhibits resistance to deformation of, e.g., about 85% to about 100%, about 87% to about 100%, about 90% to about 100%, about 93% to about 100%, about 95% to about 100%, or about 97% to about 100%.

In one embodiment, a porous material comprising an elastomer matrix defines an array of interconnected pores exhibiting high elastic elongation. Elongation is a type of deformation caused when an elastomer stretches under a tensile stress. Deformation is simply a change in shape that anything undergoes under stress. The elongation property of an elastomeric material can be expressed as percent elongation, which is calculated as the length of an elastomer after it is stretched (L), divided by the original length of the elastomer ($L_O$), and then multiplied by 100. In addition, this elastic elongation is reversible. Reversible elongation is the ability of an elastomeric material to return to its original length after being released from a tensile stress, and can be calculated as the original length of the elastomeric material ($L_O$), divided by the length of an elastomeric material after it is released from a tensile stress ($L_R$), and then multiplied by 100.

In an embodiment, a porous material comprising an elastomer matrix defining an array of interconnected pores exhibits high elastic elongation. In aspects of this embodiment, a porous material comprising an elastomer matrix defining an array of interconnected pores exhibits an elastic elongation of, e.g., about 50%, about 80%, about 100%, about 200%, about 300%, about 400%, about 500%, about 600%, about 700%, about 800%, about 900%, about 1000%, about 1100%, about 1200%, about 1300%, about 1400%, about 1500%, about 1600%, about 1700%, about 1800%, about 1900%, or about 2000%. In other aspects of this embodiment, a porous material comprising an elastomer matrix defining an array of interconnected pores exhibits an elastic elongation of, e.g., at least 50%, at least 80%, at least 100%, at least 200%, at least 300%, at least 400%, at least 500%, at least 600%, at least 700%, at least 800%, at least 900%, at least 1000%, at least 1100%, at least 1200%, at least 1300%, at least 1400%, at least 1500%, at least 1600%, at least 1700%, at least 1800%, at least 1900%, or at least 2000%. In yet other aspects of this embodiment, a porous material comprising an elastomer matrix defining an array of interconnected pores exhibits an elastic elongation of, e.g., at most 50%, at most 80%, at most 100%, at most 200%, at most 300%, at most 400%, at most 500%, at most 600%, at most 700%, at most 800%, at most 900%, at most 1000%, at most 1100%, at most 1200%, at most 1300%, at most 1400%, at most 1500%, at most 1600%, at most 1700%, at most 1800%, at most 1900%, or at most 2000%. In still aspects of this embodiment, a porous material comprising an elastomer matrix defining an array of interconnected pores exhibits an elastic elongation of, e.g., about 50% to about 600%, about 50% to about 700%, about 50% to about 800%, about 50% to about 900%, about 50% to about 1000%, about 80% to about 600%, about 80% to about 700%, about 80% to about 800%, about 80% to about 900%, about 80% to about 1000%, about 100% to about 600%, about 100% to about 700%, about 100% to about 800%, about 100% to about 900%, about 100% to about 1000%, about 200% to about 600%, about 200% to about 700%, about 200% to about 800%, about 200% to about 900%, or about 200% to about 1000%.

In another embodiment, a porous material comprises an elastomer matrix that defines an array of interconnected pores exhibiting reversible elongation. In aspects of this embodiment, a porous material comprising an elastomer matrix defining an array of interconnected pores exhibits a reversible elastic elongation of, e.g., about 100%, about 99%, about 98%, about 97%, about 96%, about 95%, about 94%, about 93%, about 92%, about 91%, about 90%, about 89%, about 88%, about 87%, about 86%, or about 85%. In other aspects of this embodiment, a porous material comprising an elastomer matrix defining an array of interconnected pores exhibits a reversible elastic elongation of, e.g., at least 99%, at least 98%, at least 97%, at least 96%, at least 95%, at least 94%, at least 93%, at least 92%, at least 91%, at least 90%, at least 89%, at least 88%, at least 87%, at least 86%, or at least 85%. In yet other aspects of this embodiment, a porous material comprising an elastomer matrix defining an array of interconnected pores exhibits a reversible elastic elongation of, e.g., at most 99%, at most 98%, at most 97%, at most 96%, at most 95%, at most 94%, at most 93%, at most 92%, at most 91%, at most 90%, at most 89%, at most 88%, at most 87%, at most 86%, or at most 85%. In still aspects of this embodiment, a porous material comprising an elastomer matrix defining an array of interconnected pores exhibits a reversible elastic elongation of, e.g., about 85% to about 100%, about 87% to about 100%, about 90% to about 100%, about 93% to about 100%, about 95% to about 100%, or about 97% to about 100%.

In one embodiment, a porous material comprises an elastomer matrix defining an array of interconnected pores exhibiting low elastic modulus. Elastic modulus, or modulus of elasticity, refers to the ability of an elastomeric material to resist deformation, or, conversely, an object's tendency to be non-permanently deformed when a force is applied to it. The elastic modulus of an object is defined as the slope of its stress-strain curve in the elastic deformation region: A=stress/strain, where A is the elastic modulus in Pascal's; stress is the force causing the deformation divided by the area to which the force is applied; and strain is the ratio of the change caused by the stress to the original state of the object. Specifying how stresses are to be measured, including directions, allows for many types of elastic moduli to be defined. The three primary elastic moduli are tensile modulus, shear modulus, and bulk modulus.

Tensile modulus (E) or Young's modulus is an object's response to linear strain, or the tendency of an object to deform along an axis when opposing forces are applied along that axis. It is defined as the ratio of tensile stress to tensile strain. It is often referred to simply as the elastic modulus. The shear modulus or modulus of rigidity refers to an object's tendency to shear (the deformation of shape at constant volume) when acted upon by opposing forces. It is defined as shear stress over shear strain. The shear modulus is part of the derivation of viscosity. The shear modulus is concerned with the deformation of a solid when it experiences a force parallel to one of its surfaces while its opposite face experiences an opposing force (such as friction). The bulk modulus (K) describes volumetric elasticity or an object's resistance to uniform compression, and is the tendency of an object to deform in all directions when uniformly loaded in all directions. It is defined as volumetric stress over volumetric strain, and is the inverse of compressibility. The bulk modulus is an extension of Young's modulus to three dimensions.

In another embodiment, a porous material comprises an elastomer matrix defining an array of interconnected pores that exhibits low tensile modulus. In aspects of this embodiment, a porous material comprising an elastomer matrix defining an array of interconnected pores exhibits a tensile modulus of, e.g., about 0.01 Mega Pascals ("MPa"), about 0.02 MPa, about 0.03 MPa, about 0.04 MPa, about 0.05 MPa, about 0.06 MPa, about 0.07 MPa, about 0.08 MPa, about 0.09 MPa, about 0.1 MPa, about 0.15 MPa, about 0.2 MPa, about 0.25 MPa, about 0.3 MPa, about 0.35 MPa, about 0.4 MPa, about 0.45 MPa, about 0.5 MPa, about 0.55 MPa, about 0.6 MPa, about 0.65 MPa, or about 0.7 MPa. In other aspects of this embodiment, a porous material comprising an elastomer matrix defining an array of interconnected pores exhibits a tensile modulus of, e.g., at most 0.01 MPa, at most 0.02 MPa, at most 0.03 MPa, at most 0.04 MPa, at most 0.05 MPa, at most 0.06 MPa, at most 0.07 MPa, at most 0.08 MPa, at most 0.09 MPa, at most 0.1 MPa, at most 0.15 MPa, at most 0.2 MPa, at most 0.25 MPa, at most 0.3 MPa, at most 0.35 MPa, at most 0.4 MPa, at most 0.45 MPa, at most 0.5 MPa, at most 0.55 MPa, at most 0.6 MPa, at most 0.65 MPa, or at most 0.7 MPa. In yet other aspects of this embodiment, a porous material comprising an elastomer matrix defining an array of interconnected pores exhibits a tensile modulus of, e.g., about 0.01 MPa to about 0.1 MPa, about 0.01 MPa to about 0.2 MPa, about 0.01 MPa to about 0.3 MPa, about 0.01 MPa to about 0.4 MPa, about 0.01 MPa to about 0.5 MPa, about 0.01 MPa to about 0.6 MPa, or about 0.01 MPa to about 0.7 MPa.

In another embodiment, a porous material comprises an elastomer matrix defining an array of interconnected pores that exhibits low shear modulus. In aspects of this embodiment, a porous material comprising an elastomer matrix defining an array of interconnected pores exhibits a shear modulus of, e.g., about 0.1 MPa, about 0.2 MPa, about 0.3 MPa, about 0.4 MPa, about 0.5 MPa, about 0.6 MPa, about 0.7 MPa, about 0.8 MPa, about 0.9 MPa, about 1 MPa, about 1.5 MPa, about 2 MPa, about 2.5 MPa, or about 3 MPa. In other aspects of this embodiment, a porous material comprising an elastomer matrix defining an array of interconnected pores exhibits a shear modulus of, e.g., at most 0.1 MPa, at most 0.2 MPa, at most 0.3 MPa, at most 0.4 MPa, at most 0.5 MPa, at most 0.6 MPa, at most 0.7 MPa, at most 0.8 MPa, at most 0.9 MPa, at most 1 MPa, at most 1.5 MPa, at most 2 MPa, at most 2.5 MPa, or at most 3 MPa. In yet other aspects of this embodiment, a porous material comprising an elastomer matrix defining an array of interconnected pores exhibits a shear modulus of, e.g., about 0.1 MPa to about 1 MPa, about 0.1 MPa to about 1.5 MPa, about 0.1 MPa to about 2 MPa, about 0.1 MPa to about 2.5 MPa, or about 0.1 MPa to about 3 MPa.

In another embodiment, a porous material comprises an elastomer matrix defining an array of interconnected pores that exhibits low bulk modulus. In aspects of this embodiment, a porous material comprising an elastomer matrix defining an array of interconnected pores exhibits a bulk modulus of, e.g., about 0.5 Giga Pascals ("GPa"), about 0.6 GPa, about 0.7 GPa, about 0.8 GPa, about 0.9 GPa, about 1 GPa, about 1.5 GPa, about 2 GPa, about 2.5 GPa, about 3 GPa, about 3.5 GPa, about 4 GPa, about 4.5 GPa, or about 5 GPa. In other aspects of this embodiment, a porous material comprising an elastomer matrix defining an array of interconnected pores exhibits a bulk modulus of, e.g., at most 0.5 GPa, at most 0.6 GPa, at most 0.7 GPa, at most 0.8 GPa, at most 0.9 GPa, at most 1 GPa, at most 1.5 GPa, at most 2 GPa, at most 2.5 GPa, at most 3 GPa, at most 3.5 GPa, at most 4 GPa, at most 4.5 GPa, or at most 5 GPa. In yet other aspects of this embodiment, a porous material comprising an elastomer matrix defining an array of interconnected pores exhibits a bulk modulus of, e.g., about 0.5 GPa to about 5 GPa, about 0.5 GPa to about 1 GPa, or about 1 GPa to about 5 GPa.

In one embodiment, a porous material comprises an elastomer matrix defining an array of interconnected pores that exhibit high tensile strength relative to other polymer classes. Other polymer classes include any other polymer not classified as an elastomer. Tensile strength has three different definitional points of stress maxima. Yield strength refers to the stress at which material strain changes from elastic deformation to plastic deformation, causing it to deform permanently. Ultimate strength refers to the maximum stress a material can withstand when subjected to tension, compression or shearing. It is the maximum stress on the stress-strain curve. Breaking strength refers to the stress coordinate on the stress-strain curve at the point of rupture, or when the material pulls apart.

In another embodiment, a porous material comprises an elastomer matrix defining an array of interconnected pores that exhibits high yield strength relative to other polymer classes. In aspects of this embodiment, a porous material comprising an elastomer matrix defining an array of interconnected pores exhibits a yield strength of, e.g., about 1 MPa, about 5 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa, about 600 MPa, about 700 MPa, about 800 MPa, about 900 MPa, about 1000 MPa, about 1500 MPa, or about 2000 MPa. In other aspects of this embodiment, a porous material comprising an elastomer matrix defining an array of interconnected pores exhibits a yield strength of, e.g., at least 1 MPa, at least 5 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa, at least 600 MPa, at least 700 MPa, at least 800 MPa, at least 900 MPa, at least 1000 MPa, at least 1500 MPa, or at least 2000 MPa. In yet other aspects of this embodiment, a porous material comprising an elastomer matrix defining an array of interconnected pores exhibits a yield strength of, e.g., at most 1 MPa, at most 5 MPa, at most 10 MPa, at most 20 MPa, at most 30 MPa, at most 40 MPa, at most 50 MPa, at most 60 MPa, at most 70 MPa, at most 80 MPa, at most 90 MPa, at most 100 MPa, at most 200 MPa, at most 300 MPa, at most 400 MPa, at most 500 MPa, at most 600 MPa, at most 700 MPa, at most 800 MPa, at most 900 MPa, at most 1000 MPa, at most 1500 MPa, or at most 2000 MPa. In still other aspects of this embodiment, a porous material comprising an elastomer matrix defining an array of interconnected pores exhibits a yield strength of, e.g., about 1 MPa to about 50 MPa, about 1 MPa to about 60 MPa, about 1 MPa to about 70 MPa, about 1 MPa to about 80 MPa, about 1 MPa to about 90 MPa, about 1 MPa to about 100 MPa, about 10 MPa to about 50 MPa, about 10 MPa to about 60 MPa, about 10 MPa to about 70 MPa, about 10 MPa to about 80 MPa, about 10 MPa to about 90 MPa, about 10 MPa to about 100 MPa, about 100 MPa to about 500 MPA, about 300 MPa to about 500 MPA, about 300 MPa to about 1000 MPa, about 500 MPa to about 1000 MPa, about 700 MPa to about 1000 MPa, about 700 MPa to about 1500 MPa, about 1000 MPa to about 1500 MPa, or about 1200 MPa to about 1500 MPa.

In another embodiment, a porous material comprises an elastomer matrix defining an array of interconnected pores that exhibit high ultimate strength relative to other polymer classes. In aspects of this embodiment, a porous material comprising an elastomer matrix defining an array of interconnected pores exhibits an ultimate strength of, e.g., about 1 MPa, about 5 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa, about 600 MPa, about 700 MPa, about 800 MPa, about 900 MPa, about 1000 MPa, about 1500 MPa, or about 2000 MPa. In other aspects of this embodiment, a porous material comprising an elastomer matrix defining an array of interconnected pores exhibits an ultimate strength of, e.g., at least 1 MPa, at least 5 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100

MPa, at least 200 MPa, at least 300 MPa, at least 400 MPa, at least 500 MPa, at least 600 MPa, at least 700 MPa, at least 800 MPa, at least 900 MPa, at least 1000 MPa, at least 1500 MPa, or at least 2000 MPa. In yet other aspects of this embodiment, a porous material comprising an elastomer matrix defining an array of interconnected pores exhibits an ultimate strength of, e.g., at most 1 MPa, at most 5 MPa, at most 10 MPa, at most 20 MPa, at most 30 MPa, at most 40 MPa, at most 50 MPa, at most 60 MPa, at most 70 MPa, at most 80 MPa, at most 90 MPa, at most 100 MPa, at most 200 MPa, at most 300 MPa, at most 400 MPa, at most 500 MPa, at most 600 MPa, at most 700 MPa, at most 800 MPa, at most 900 MPa, at most 1000 MPa, at most 1500 MPa, or at most 2000 MPa. In still other aspects of this embodiment, a porous material comprising an elastomer matrix defining an array of interconnected pores exhibits an ultimate strength of, e.g., about 1 MPa to about 50 MPa, about 1 MPa to about 60 MPa, about 1 MPa to about 70 MPa, about 1 MPa to about 80 MPa, about 1 MPa to about 90 MPa, about 1 MPa to about 100 MPa, about 10 MPa to about 50 MPa, about 10 MPa to about 60 MPa, about 10 MPa to about 70 MPa, about 10 MPa to about 80 MPa, about 10 MPa to about 90 MPa about 10 MPa to about 100 MPa, about 100 MPa to about 500 MPA, about 300 MPa to about 500 MPA, about 300 MPa to about 1000 MPa, about 500 MPa to about 1000 MPa, about 700 MPa to about 1000 MPa, about 700 MPa to about 1500 MPa, about 1000 MPa to about 1500 MPa, or about 1200 MPa to about 1500 MPa.

In another embodiment, a porous material comprises an elastomer matrix defining an array of interconnected pores that exhibit high breaking strength relative to other polymer classes. In aspects of this embodiment, a porous material comprising an elastomer matrix defining an array of interconnected pores exhibits a breaking strength of, e.g., about 1 MPa, about 5 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa, about 600 MPa, about 700 MPa, about 800 MPa, about 900 MPa, about 1000 MPa, about 1500 MPa, or about 2000 MPa. In other aspects of this embodiment, a porous material comprising an elastomer matrix defining an array of interconnected pores exhibits a breaking strength of, e.g., at least 1 MPa, at least 5 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa, at least 600 MPa, at least 700 MPa, at least 800 MPa, at least 900 MPa, at least 1000 MPa, at least 1500 MPa, or at least 2000 MPa. In yet other aspects of this embodiment, a porous material comprising an elastomer matrix defining an array of interconnected pores exhibits a breaking strength of, e.g., at most 1 MPa, at most 5 MPa, at most 10 MPa, at most 20 MPa, at most 30 MPa, at most 40 MPa, at most 50 MPa, at most 60 MPa, at most 70 MPa, at most 80 MPa, at most 90 MPa, at most 100 MPa, at most 200 MPa, at most 300 MPa, at most 400 MPa, at most 500 MPa, at most 600 MPa, at most 700 MPa, at most 800 MPa, at most 900 MPa, at most 1000 MPa, at most 1500 MPa, or at most 2000 MPa. In still other aspects of this embodiment, a porous material comprising an elastomer matrix defining an array of interconnected pores exhibits a breaking strength of, e.g., about 1 MPa to about 50 MPa, about 1 MPa to about 60 MPa, about 1 MPa to about 70 MPa about 1 MPa to about 80 MPa, about 1 MPa to about 90 MPa, about 1 MPa to about 100 MPa, about 10 MPa to about 50 MPa, about 10 MPa to about 60 MPa, about 10 MPa to about 70 MPa, about 10 MPa to about 80 MPa, about 10 MPa to about 90 MPa, about 10 MPa to about 100 MPa, about 100 MPa to about 500 MPA, about 300 MPa to about 500 MPA, about 300 MPa to about 1000 MPa, about 500 MPa to about 1000 MPa, about 700 MPa to about 1000 MPa, about 700 MPa to about 1500 MPa, about 1000 MPa to about 1500 MPa, or about 1200 MPa to about 1500 MPa.

In one embodiment, a porous material comprises an elastomer matrix defining an array of interconnected pores that exhibits low flexural strength relative to other polymer classes. Flexural strength, also known as bend strength or modulus of rupture, refers to an object's ability to resist deformation under load and represents the highest stress experienced within the object at its moment of rupture. It is measured in terms of stress.

In an embodiment, a porous material comprises an elastomer matrix defining an array of interconnected pores that exhibits low flexural strength relative to other polymer classes. In aspects of this embodiment, a porous material comprising an elastomer matrix defining an array of interconnected pores exhibits a flexural strength of, e.g., about 1 MPa, about 5 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa, about 600 MPa, about 700 MPa, about 800 MPa, about 900 MPa, about 1000 MPa, about 1500 MPa, or about 2000 MPa. In other aspects of this embodiment, a porous material comprising an elastomer matrix defining an array of interconnected pores exhibits a flexural strength of, e.g., at least 1 MPa, at least 5 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa, at least 600 MPa, at least 700 MPa, at least 800 MPa, at least 900 MPa, at least 1000 MPa, at least 1500 MPa, or at least 2000 MPa. In yet other aspects of this embodiment, a porous material comprising an elastomer matrix defining an array of interconnected pores exhibits a flexural strength of, e.g., at most 1 MPa, at most 5 MPa, at most 10 MPa, at most 20 MPa, at most 30 MPa, at most 40 MPa, at most 50 MPa, at most 60 MPa, at most 70 MPa, at most 80 MPa, at most 90 MPa, at most 100 MPa, at most 200 MPa, at most 300 MPa, at most 400 MPa, at most 500 MPa, at most 600 MPa, at most 700 MPa, at most 800 MPa, at most 900 MPa, at most 1000 MPa, at most 1500 MPa, or at most 2000 MPa. In still other aspects of this embodiment, a porous material comprising an elastomer matrix defining an array of interconnected pores exhibits a flexural strength of, e.g., about 1 MPa to about 50 MPa, about 1 MPa to about 60 MPa, about 1 MPa to about 70 MPa, about 1 MPa to about 80 MPa, about 1 MPa to about 90 MPa, about 1 MPa to about 100 MPa, about 10 MPa to about 50 MPa, about 10 MPa to about 60 MPa, about 10 MPa to about 70 MPa, about 10 MPa to about 80 MPa, about 10 MPa to about 90 MPa about 10 MPa to about 100 MPa, about 100 MPa to about 500 MPA, about 300 MPa to about 500 MPA, about 300 MPa to about 1000 MPa, about 500 MPa to about 1000 MPa, about 700 MPa to about 1000 MPa, about 700 MPa to about 1500 MPa, about 1000 MPa to about 1500 MPa, or about 1200 MPa to about 1500 MPa.

In one embodiment, a porous material comprises an elastomer matrix defining an array of interconnected pores that exhibits high compressibility. Compressibility refers to the relative volume change in response to a pressure (or mean stress) change, and is the reciprocal of the bulk modulus.

In an embodiment, a porous material comprises an elastomer matrix defining an array of interconnected pores that exhibits high compressibility. In aspects of this embodiment, a porous material comprising an elastomer matrix defining an array of interconnected pores exhibits a compressibility of, e.g., about 0.1 kilo Pascals ("kPa"), about 0.5 kPa, about 1 kPa, about 5 kPa, about 10 kPa, about 15 kPa, about 20 kPa, about 30 kPa, about 40 kPa, about 50 kPa, about 60 kPa, about 70 kPa, about 80 kPa, about 90 kPa, or about 100 kPa. In other aspects of this embodiment, a porous material comprising an elastomer matrix defining an array of interconnected pores exhibits a compressibility of, e.g., at least 0.1 kPa, at least 0.5 kPa, at least 1 kPa, at least 5 kPa, at least 10 kPa, at least 15 kPa, at least 20 kPa, at least 30 kPa, at least 40 kPa, at least 50 kPa, at least 60 kPa, at least 70 kPa, at least 80 kPa, at least 90 kPa, or at least 100 kPa. In yet other aspects of this embodiment, a porous material comprising an elastomer matrix defining an array of interconnected pores exhibits a compressibility of, e.g., at most 0.1 kPa, at most 0.5 kPa, at most 1 kPa, at most 5 kPa, at most 10 kPa, at most 15 kPa, at most 20 kPa, at most 30 kPa, at most 40 kPa, at most 50 kPa, at most 60 kPa, at most 70 kPa, at most 80 kPa, at most 90 kPa, or at most 100 kPa. In still other aspects of this embodiment, a porous material comprising an elastomer matrix defining an array of interconnected pores exhibits a compressibility of, e.g., about 0.1 kPa to about 100 kPa, about 0.5 kPa to about 100 kPa, about 1 kPa to about 100 kPa, about 5 kPa to about 100 kPa, about 10 kPa to about 100 kPa, about 1 kPa to about 30 kPa, about 1 kPa to about 40 kPa, about 1 kPa to about 50 kPa, or about 1 kPa to about 60 kPa.

In one embodiment, a porous material comprises an elastomer matrix defining an array of interconnected pores that exhibits low hardness. Hardness refers to various properties of an object in the solid phase that gives it high resistance to various kinds of shape change when force is applied. Hardness is measured using a durometer and is a unitless value that ranges from zero to 100.

In an embodiment, a porous material comprises an elastomer matrix defining an array of interconnected pores that exhibits low hardness. In aspects of this embodiment, a porous material comprising an elastomer matrix defining an array of interconnected pores exhibits a hardness of, e.g., about 5, about 10, about 15, about 20, about 25, about 30, about 35, about 40, about 45, about 50, about 55, or about 60. In other aspects of this embodiment, a porous material comprising an elastomer matrix defining an array of interconnected pores exhibits a hardness of, e.g., at least 5, at least 10, at least 15, at least 20, at least 25, at least 30, at least 35, at least 40, at least 45, at least 50, at least 55, or at least 60. In yet other aspects of this embodiment, a porous material comprising an elastomer matrix defining an array of interconnected pores exhibits a hardness of, e.g., at most 5, at most 10, at most 15, at most 20, at most 25, at most 30, at most 35, at most 40, at most 45, at most 50, at most 55, or at most 60. In still other aspects of this embodiment, a porous material comprising an elastomer matrix defining an array of interconnected pores exhibits a hardness of, e.g., about 5 to about 60, about 10 to about 50, about 15 to about 45, about 20 to about 40, or about 25 to about 35.

In one embodiment, a porous material comprises an elastomer matrix including pores having a shape sufficient to allow tissue growth into the array of interconnected pores. As such, the pore shape should support aspects of tissue growth such as, e.g., cell migration, cell proliferation, cell differentiation, nutrient exchange, and/or waste removal. Any pore shape is useful with the proviso that the pore shape is sufficient to allow tissue growth into the array of interconnected pores. Useful pore shapes include, without limitation, roughly spherical, perfectly spherical, dodecahedrons (such as pentagonal dodecahedrons), and ellipsoids.

In one embodiment, a porous material comprises an elastomer matrix including pores having a roundness sufficient to allow tissue growth into the array of interconnected pores. As such, the pore roundness should support aspects of tissue growth such as, e.g., cell migration, cell proliferation, cell differentiation, nutrient exchange, and/or waste removal. "Roundness" is $(6 \times V)/(\pi \times D^3)$ where V is the volume and D is the diameter. Any pore roundness is useful with the proviso that the pore roundness is sufficient to allow tissue growth into the array of interconnected pores.

In one embodiment, a porous material comprises an elastomer matrix, formed in such a manner that substantially all the pores in the elastomer matrix have a similar diameter. As used herein, the term "substantially," when used to describe pores, refers to at least 90% of the pores within the elastomer matrix such as, e.g., at least 95% or at least 97% of the pores. As used herein, the term "similar diameter," when used to describe pores, refers to a difference in the diameters of the two pores that is less than about 20% of the larger diameter. As used herein, the term "diameter," when used to describe pores, refers to the longest line segment that can be drawn that connects two points within the pore, regardless of whether the line passes outside the boundary of the pore. Any pore diameter is useful with the proviso that the pore diameter is sufficient to allow tissue growth into the porous material. As such, the pore diameter size should support aspects of tissue growth such as, e.g., cell migration, cell proliferation, cell differentiation, nutrient exchange, and/or waste removal.

In one embodiment, a porous material comprises an elastomer matrix that is formed in such a manner that the diameter of the connections between pores is sufficient to allow tissue growth into the array of interconnected pores. As such, the diameter of the connections between pores should support aspects of tissue growth such as, e.g., cell migration, cell proliferation, cell differentiation, nutrient exchange, and/or waste removal. As used herein, the term "diameter," when describing the connection between pores, refers to the diameter of the cross-section of the connection between two pores in the plane normal to the line connecting the centroids of the two pores, where the plane is chosen so that the area of the cross-section of the connection is at its minimum value. As used herein, the term "diameter of a cross-section of a connection," when describing the connection between pores, refers to the average length of a straight line segment that passes through the center, or centroid (in the case of a connection having a cross-section that lacks a center), of the cross-section of a connection and terminates at the periphery of the cross-section. As used herein, the term "substantially," when used to describe the connections between pores refers to at least 90% of the connections made between each pore comprising the elastomer matrix, such as, e.g., at least 95% or at least 97% of the connections.

Thus, in an embodiment, a porous material comprises an elastomer matrix includes pores having a roundness sufficient to allow tissue growth into the array of interconnected pores. In aspects of this embodiment, a porous material comprising an elastomer matrix includes pores having a roundness of, e.g., about 0.1, about 0.2, about 0.3, about 0.4, about 0.5, about 0.6, about 0.7, about 0.8, about 0.9, or about 1.0. In other aspects of this embodiment, a porous material comprising an elastomer matrix includes pores having a roundness of, e.g., at least 0.1, at least 0.2, at least 0.3, at least 0.4, at least 0.5, at least 0.6, at least 0.7, at least 0.8, at least 0.9, or at least 1.0. In yet other aspects of this embodiment, a porous material comprising an elastomer matrix includes pores having a roundness of, e.g., at most 0.1, at most 0.2, at most 0.3, at most 0.4, at most 0.5, at most 0.6, at most 0.7, at most 0.8, at most 0.9, or at most 1.0. In still other aspects of this embodiment, a porous material comprising an elastomer matrix includes pores having a roundness of, e.g., about 0.1 to about 1.0, about 0.2 to about 1.0, about 0.3 to about 1.0, about 0.4 to about 1.0, about 0.5 to about 1.0, about 0.6 to about 1.0, about 0.7 to about 1.0, about 0.8 to about 1.0, about 0.9 to about 1.0, about 0.1 to about 0.9, about 0.2 to about 0.9, about 0.3 to about 0.9, about 0.4 to about 0.9, about 0.5 to about 0.9, about 0.6 to about 0.9, about 0.7 to about 0.9, about 0.8 to about 0.9, about 0.1 to about 0.8, about 0.2 to about 0.8, about 0.3 to about 0.8, about 0.4 to about 0.8, about 0.5 to about 0.8, about 0.6 to about 0.8, about 0.7 to about 0.8, about 0.1 to about 0.7, about 0.2 to about 0.7, about 0.3 to about 0.7, about 0.4 to about 0.7, about 0.5 to about 0.7, about 0.6 to about 0.7, about 0.1 to about 0.6, about 0.2 to about 0.6, about 0.3 to about 0.6, about 0.4 to about 0.6, about 0.5 to about 0.6, about 0.1 to about 0.5, about 0.2 to about 0.5, about 0.3 to about 0.5, or about 0.4 to about 0.5.

In another embodiment, substantially all pores within a porous material comprise an elastomer matrix having a similar diameter. In aspects of this embodiment, at least 90% of all pores within a porous material comprising an elastomer matrix have a similar diameter, at least 95% of all pores within a porous material comprising an elastomer matrix have a similar diameter, or at least 97% of all pores within a porous material comprising an elastomer matrix have a similar diameter. In another aspect of this embodiment, difference in the diameters of two pores is, e.g., less than about 20% of the larger diameter, less than about 15% of the larger diameter, less than about 10% of the larger diameter, or less than about 5% of the larger diameter.

In another embodiment, a porous material comprises an elastomer matrix including pores having a mean diameter sufficient to allow tissue growth into the array of interconnected pores. In aspects of this embodiment, a porous material comprising an elastomer matrix includes pores having mean pore diameter of, e.g., about 50 µm, about 75 µm, about 100 µm, about 150 µm, about 200 µm, about 250 µm, about 300 µm, about 350 µm, about 400 µm, about 450 µm, or about 500 µm. In other aspects, a porous material comprising an elastomer matrix includes pores having mean pore diameter of, e.g., about 500 µm, about 600 µm, about 700 µm, about 800 µm, about 900 µm, about 1000 µm, about 1500 µm, about 2000 µm, about 2500 µm, or about 3000 µm. In yet other aspects of this embodiment, a porous material comprising an elastomer matrix includes pores having mean pore diameter of, e.g., at least 50 µm, at least 75 µm, at least 100 µm, at least 150 µm, at least 200 µm, at least 250 µm, at least 300 µm, at least 350 µm, at least 400 µm, at least 450 µm, or at least 500 µm. In still other aspects, a porous material comprising an elastomer matrix includes pores having mean pore diameter of, e.g., at least 500 µm, at least 600 µm, at least 700 µm, at least 800 µm, at least 900 µm, at least 1000 µm, at least 1500 µm, at least 2000 µm, at least 2500 µm, or at least 3000 µm. In further aspects of this embodiment, a porous material comprising an elastomer matrix includes pores having mean pore diameter of, e.g., at most 50 µm, at most 75 µm, at most 100 µm, at most 150 µm, at most 200 µm, at most 250 µm, at most 300 µm, at most 350 µm, at most 400 µm, at most 450 µm, or at most 500 µm. In yet further aspects of this embodiment, a porous material comprising an elastomer matrix includes pores having mean pore diameter of, e.g., at most 500 µm, at most 600 µm, at most 700 µm, at most 800 µm, at most 900 µm, at most 1000 µm, at most 1500 µm, at most 2000 µm, at most 2500 µm, or at most 3000 µm. In still further aspects of this embodiment, a porous material comprising an elastomer matrix includes pores having mean pore diameter in a range from, e.g., about 300 µm to about 600 µm, about 200 µm to about 700 µm, about 100 µm to about 800 µm, about 500 µm to about 800 µm, about 50 µm to about 500 µm, about 75 µm to about 500 µm, about 100 µm to about 500 µm, about 200 µm to about 500 µm, about 300 µm to about 500 µm, about 50 µm to about 1000 µm, about 75 µm to about 1000 µm, about 100 µm to about 1000 µm, about 200 µm to about 1000 µm, about 300 µm to about 1000 µm, about 50 µm to about 1000 µm, about 75 µm to about 3000 µm, about 100 µm to about 3000 µm, about 200 µm to about 3000 µm, or about 300 µm to about 3000 µm.

In another embodiment, a porous material comprises an elastomer matrix includes pores having a mean elastomer strut thickness sufficient to allow tissue growth into the array of interconnected pores. In aspects of this embodiment, a porous material comprising an elastomer matrix includes pores having a mean elastomer strut thickness of, e.g., about 10 µm, about 20 µm, about 30 µm, about 40 µm, about 50 µm, about 60 µm, about 70 µm, about 80 µm, about 90 µm, about 100 µm, about 110 µm, about 120 µm, about 130 µm, about 140 µm, about 150 µm, about 160 µm, about 170 µm, about 180 µm, about 190 µm, or about 200 µm. In other aspects of this embodiment, a porous material comprising an elastomer matrix includes pores having a mean elastomer strut thickness of, e.g., at least 10 µm, at least 20 µm, at least 30 µm, at least 40 µm, at least 50 µm, at least 60 µm, at least 70 µm, at least 80 µm, at least 90 µm, at least 100 µm, at least 110 µm, at least 120 µm, at least 130 µm, at least 140 µm, at least 150 µm, at least 160 µm, at least 170 µm, at least 180 µm, at least 190 µm, or at least 200 µm. In yet other aspects of this embodiment, a porous material comprising an elastomer matrix includes pores having a mean elastomer strut thickness of, e.g., at most 10 µm, at most 20 µm, at most 30 µm, at most 40 µm, at most 50 µm, at most 60 µm, at most 70 µm, at most 80 µm, at most 90 µm, at most 100 µm, at most 110 µm, at most 120 µm, at most 130 µm, at most 140 µm, at most 150 µm, at most 160 µm, at most 170 µm, at most 180 µm, at most 190 µm, or at most 200 µm. In still aspects of this embodiment, a porous material comprising an elastomer matrix includes pores having a mean elastomer strut thickness of, e.g., about 50 µm to about 110 µm, about 50 µm to about 120 µm, about 50 µm to about 130 µm, about 50 µm to about 140 µm, about 50 µm to about 150 µm, about 60 µm to about 110 µm, about 60 µm to about 120 µm, about 60 µm to about 130 µm, about 60 µm to about 140 µm, about 70 µm to about 110 µm, about 70 µm to about 120 µm, about 70 µm to about 130 µm, or about 70 µm to about 140 µm.

In another embodiment, a porous material comprises an elastomer matrix including pores connected to a plurality of other pores. In aspects of this embodiment, a porous material comprising an elastomer matrix comprises a mean pore connectivity, e.g., about two other pores, about three other pores, about four other pores, about five other pores, about six other pores, about seven other pores, about eight other pores, about nine other pores, about ten other pores, about 11 other pores, or about 12 other pores. In other aspects of this embodiment, a porous material comprising an elastomer matrix comprises a mean pore connectivity, e.g., at least two other pores, at least three other pores, at least four other pores, at least five other pores, at least six other pores, at least seven other pores, at least eight other pores, at least nine other pores, at least ten other pores, at least 11 other pores, or at least 12 other pores. In yet other aspects of this embodiment, a porous material comprising an elastomer matrix comprises a mean pore connectivity, e.g., at most two other pores, at least most other pores, at least most other pores, at least most other pores, at most six other pores, at most seven other pores, at most eight other pores, at most nine other pores, at most ten other pores, at most 11 other pores, or at most 12 other pores.

In still other aspects of this embodiment, a porous material comprises an elastomer matrix including pores connected to, e.g., about two other pores to about 12 other pores, about two other pores to about 11 other pores, about two other pores to about ten other pores, about two other pores to about nine other pores, about two other pores to about eight other pores, about two other pores to about seven other pores, about two other pores to about six other pores, about two other pores to about five other pores, about three other pores to about 12 other pores, about three other pores to about 11 other pores, about three other pores to about ten other pores, about three other pores to about nine other pores, about three other pores to about eight other pores, about three other pores to about seven other pores, about three other pores to about six other pores, about three other pores to about five other pores, about four other pores to about 12 other pores, about four other pores to about 11 other pores, about four other pores to about ten other pores, about four other pores to about nine other pores, about four other pores to about eight other pores, about four other pores to about seven other pores, about four other pores to about six other pores, about four other pores to about five other pores, about five other pores to about 12 other pores, about five other pores to about 11 other pores, about five other pores to about ten other pores, about five other pores to about nine other pores, about five other pores to about eight other pores, about five other pores to about seven other pores, or about five other pores to about six other pores.

In another embodiment, a porous material comprises an elastomer matrix including pores where the diameter of the connections between pores is sufficient to allow tissue growth into the array of interconnected pores. In aspects of this embodiment, a porous material comprising an elastomer matrix includes pores where the diameter of the connections between pores is, e.g., about 10% the mean pore diameter, about 20% the mean pore diameter, about 30% the mean pore diameter, about 40% the mean pore diameter, about 50% the mean pore diameter, about 60% the mean pore diameter, about 70% the mean pore diameter, about 80% the mean pore diameter, or about 90% the mean pore diameter. In other aspects of this embodiment, a porous material comprising an elastomer matrix includes pores where the diameter of the connections between pores is, e.g., at least 10% the mean pore diameter, at least 20% the mean pore diameter, at least 30% the mean pore diameter, at least 40% the mean pore diameter, at least 50% the mean pore diameter, at least 60% the mean pore diameter, at least 70% the mean pore diameter, at least 80% the mean pore diameter, or at least 90% the mean pore diameter. In yet other aspects of this embodiment, a porous material comprising an elastomer matrix includes pores where the diameter of the connections between pores is, e.g., at most 10% the mean pore diameter, at most 20% the mean pore diameter, at most 30% the mean pore diameter, at most 40% the mean pore diameter, at most 50% the mean pore diameter, at most 60% the mean pore diameter, at most 70% the mean pore diameter, at most 80% the mean pore diameter, or at most 90% the mean pore diameter.

In still other aspects of this embodiment, a porous material comprises an elastomer matrix including pores where the diameter of the connections between pores is, e.g., about 10% to about 90% the mean pore diameter, about 15% to about 90% the mean pore diameter, about 20% to about 90% the mean pore diameter, about 25% to about 90% the mean pore diameter, about 30% to about 90% the mean pore diameter, about 35% to about 90% the mean pore diameter, about 40% to about 90% the mean pore diameter, about 10% to about 80% the mean pore diameter, about 15% to about 80% the mean pore diameter, about 20% to about 80% the mean pore diameter, about 25% to about 80% the mean pore diameter, about 30% to about 80% the mean pore diameter, about 35% to about 80% the mean pore diameter, about 40% to about 80% the mean pore diameter, about 10% to about 70% the mean pore diameter, about 15% to about 70% the mean pore diameter, about 20% to about 70% the mean pore diameter, about 25% to about 70% the mean pore diameter, about 30% to about 70% the mean pore diameter, about 35% to about 70% the mean pore diameter, about 40% to about 70% the mean pore diameter, about 10% to about 60% the mean pore diameter, about 15% to about 60% the mean pore diameter, about 20% to about 60% the mean pore diameter, about 25% to about 60% the mean pore diameter, about 30% to about 60% the mean pore diameter, about 35% to about 60% the mean pore diameter, about 40% to about 60% the mean pore diameter, about 10% to about 50% the mean pore diameter, about 15% to about 50% the mean pore diameter, about 20% to about 50% the mean pore diameter, about 25% to about 50% the mean pore diameter, about 30% to about 50% the mean pore diameter, about 10% to about 40% the mean pore diameter, about 15% to about 40% the mean pore diameter, about 20% to about 40% the mean pore diameter, about 25% to about 40% the mean pore diameter, or about 30% to about 40% the mean pore diameter.

The present specification discloses, in part, a porous material comprising an elastomer matrix that defines an array of interconnected pores having a porosity that is sufficient to allow tissue growth into the array of interconnected pores as disclosed in the present specification. As such, the porosity should support aspects of tissue growth such as, e.g., cell migration, cell proliferation, cell differentiation, nutrient exchange, and/or waste removal. As used herein, the term "porosity" refers to the amount of void space in a porous material comprising an elastomer matrix. As such, the total volume of a porous material comprising an elastomer matrix disclosed herein is based upon the elastomer space and the void space.

Thus, in an embodiment, a porous material comprises an elastomer matrix that defines an array of interconnected pores having a porosity sufficient to allow tissue growth into the array of interconnected pores. In aspects of this embodiment, a porous material comprising an elastomer matrix comprises a porosity of, e.g., about 40% of the total volume of an elastomer matrix, about 50% of the total volume of an elastomer matrix, about 60% of the total volume of an elastomer matrix, about 70% of the total volume of an elastomer matrix, about 80% of the total volume of an elastomer matrix, about 90% of the total volume of an elastomer matrix, about 95% of the total volume of an elastomer matrix, or about 97% of the total volume of an elastomer matrix. In other aspects of this embodiment, a porous material comprising an elastomer matrix comprises a porosity of, e.g., at least 40% of the total volume of an elastomer matrix, at least 50% of the total volume of an elastomer matrix, at least 60% of the total volume of an elastomer matrix, at least 70% of the total volume of an elastomer matrix, at least 80% of the total volume of an elastomer matrix, at least 90% of the total volume of an elastomer matrix, at least 95% of the total volume of an elastomer matrix, or at least 97% of the total volume of an elastomer matrix. In yet other aspects of this embodiment, a porous material comprising an elastomer matrix comprises a porosity of, e.g., at most 40% of the total volume of an elastomer matrix, at most 50% of the total volume of an elastomer matrix, at most 60% of the total volume of an elastomer matrix, at most 70% of the total volume of an elastomer matrix, at most 80% of the total volume of an elastomer matrix, at most 90% of the total volume of an elastomer matrix, at most 95% of the total volume of an elastomer matrix, or at most 97% of the total volume of an elastomer matrix. In yet other aspects of this embodiment, a porous material comprising an elastomer matrix comprises a porosity of, e.g., about 40% to about 97% of the total volume of an elastomer matrix, about 50% to about 97% of the total volume of an elastomer matrix, about 60% to about 97% of the total volume of an elastomer matrix, about 70% to about 97% of the total volume of an elastomer matrix, about 80% to about 97% of the total volume of an elastomer matrix, about 90% to about 97% of the total volume of an elastomer matrix, about 40% to about 95% of the total volume of an elastomer matrix, about 50% to about 95% of the total volume of an elastomer matrix, about 60% to about 95% of the total volume of an elastomer matrix, about 70% to about 95% of the total volume of an elastomer matrix, about 80% to about 95% of the total volume of an elastomer matrix, about 90% to about 95% of the total volume of an elastomer matrix, about 40% to about 90% of the total volume of an elastomer matrix, about 50% to about 90% of the total volume of an elastomer matrix, about 60% to about 90% of the total volume of an elastomer matrix, about 70% to about 90% of the total volume of an elastomer matrix, or about 80% to about 90% of the total volume of an elastomer matrix.

The present specification discloses, in part, a porous material comprising an elastomer matrix that defines an array of interconnected pores having a mean open pore value and/or a mean closed pore value that is sufficient to allow tissue growth into the array of interconnected pores as disclosed in the present specification. As used herein, the term "mean open pore value" or "mean open pore" refers to the average number of pores that are connected to at least one other pore present in the elastomer matrix. As used herein, the term "mean closed pore value" or "mean closed pore" refers to the average number of pores that are not connected to any other pores present in the elastomer matrix.

Thus, in an embodiment, a porous material comprises an elastomer matrix defining an array of interconnected pores that has a mean open pore value sufficient to allow tissue growth into the array of interconnected pores. In aspects of this embodiment, a porous material comprising an elastomer matrix has a mean open pore value of, e.g., about 70%, about 75%, about 80%, about 85%, about 90%, about 95%, or about 97%. In other aspects of this embodiment, a porous material comprising an elastomer matrix comprises a mean open pore value of, e.g., at least 70%, at least 75%, at least 80%, at least 85%, at least 90%, at least 95%, or at least 97%. In yet other aspects of this embodiment, a porous material comprising an elastomer matrix has a mean open pore value of, e.g., at most 70%, at most 75%, at most 80%, at most 85%, at most 90%, at most 95%, or at most 97%. In still aspects of this embodiment, a porous material comprising an elastomer matrix has a mean open pore value of, e.g., about 70% to about 90%, about 75% to about 90%, about 80% to about 90%, about 85% to about 90%, about 70% to about 95%, about 75% to about 95%, about 80% to about 95%, about 85% to about 95%, about 90% to about 95%, about 70% to about 97%, about 75% to about 97%, about 80% to about 97%, about 85% to about 97%, or about 90% to about 97%.

In another embodiment, a porous material comprises an elastomer matrix that defines an array of interconnected pores having a mean closed pore value sufficient to allow tissue growth into the array of interconnected pores. In aspects of this embodiment, a porous material comprising an elastomer matrix has a mean closed pore value of, e.g., about 5%, about 10%, about 15%, or about 20%. In other aspects of this embodiment, a porous material comprising an elastomer matrix has a mean closed pore value of, e.g., about 5% or less, about 10% or less, about 15% or less, or about 20% or less. In yet other aspects of this embodiment, a porous material comprising an elastomer matrix has a mean closed pore value of, e.g., about 5% to about 10%, about 5% to about 15%, or about 5% to about 20%.

The present specification discloses, in part, a porous material that comprises an elastomer matrix defining an array of interconnected pores having a void space that is sufficient to allow tissue growth into the array of interconnected pores. As such, the void space should support aspects of tissue growth such as, e.g., cell migration, cell proliferation, cell differentiation, nutrient exchange, and/or waste removal. As used herein, the term "void space" refers to actual or physical space in a porous material comprising an elastomer matrix. As such, the total volume of a porous material comprising an elastomer matrix disclosed herein is based upon the elastomer space and the void space.

Thus, in an embodiment, an elastomer matrix defining an array of interconnected pores has a void volume sufficient to allow tissue growth into the array of interconnected pores. In aspects of this embodiment, a porous material comprising an elastomer matrix comprises a void space of, e.g., about 50% of the total volume of an elastomer matrix, about 60% of the total volume of an elastomer matrix, about 70% of the total volume of an elastomer matrix, about 80% of the total volume of an elastomer matrix, about 90% of the total volume of an elastomer matrix, about 95% of the total volume of an elastomer matrix, or about 97% of the total volume of an elastomer matrix. In other aspects of this embodiment, a porous material comprising an elastomer matrix comprises a void space of, e.g., at least 50% of the total volume of an elastomer matrix, at least 60% of the total volume of an elastomer matrix, at least 70% of the total volume of an elastomer matrix, at least 80% of the total volume of an elastomer matrix, at least 90% of the total volume of an elastomer matrix, at least 95% of the total volume of an elastomer matrix, or at least 97% of the total volume of an elastomer matrix. In yet other aspects of this embodiment, a porous material comprising an elastomer matrix comprises a void space of, e.g., at most 50% of the total volume of an elastomer matrix, at most 60% of the total volume of an elastomer matrix, at most 70% of the total volume of an elastomer matrix, at most 80% of the total volume of an elastomer matrix, at most 90% of the total volume of an elastomer matrix, at most 95% of the total volume of an elastomer matrix, or at most 97% of the total volume of an elastomer matrix. In yet other aspects of this embodiment, a porous material comprising an elastomer matrix comprises a void space of, e.g., about 50% to about 97% of the total volume of an elastomer matrix, about 60% to about 97% of the total volume of an elastomer matrix, about 70% to about 97% of the total volume of an elastomer matrix, about 80% to about 97% of the total volume of an elastomer matrix, about 90% to about 97% of the total volume of an elastomer matrix, about 50% to about 95% of the total volume of an elastomer matrix, about 60% to about 95% of the total volume of an elastomer matrix, about 70% to about 95% of the total volume of an elastomer matrix, about 80% to about 95% of the total volume of an elastomer matrix, about 90% to about 95% of the total volume of an elastomer matrix, about 50% to about 90% of the total volume of an elastomer matrix, about 60% to about 90% of the total volume of an elastomer matrix, about 70% to about 90% of the total volume of an elastomer matrix, or about 80% to about 90% of the total volume of an elastomer matrix.

The present specification discloses, in part, a porous material comprising an elastomer matrix defining an array of interconnected pores allowing substantial tissue growth into the interconnected pores in a time sufficient to reduce or prevent formation of fibrous capsules that can result in capsular contracture or scarring.

Thus, in an embodiment, a porous material comprises an elastomer matrix that defines an array of interconnected pores to allow tissue growth into the interconnected pores in a time sufficient to reduce or prevent formation of fibrous capsules that can result in capsular contracture or scarring. In aspects of this embodiment, a porous material comprising an elastomer matrix defining an array of interconnected pores allows tissue growth into the interconnected pores sufficient to reduce or prevent formation of fibrous capsules in, e.g., about 2 days after implantation, about 3 days after implantation, about 4 days after implantation, about 5 days after implantation, about 6 days after implantation, about 7 days, about 2 weeks after implantation, about 3 weeks after implantation, or about 4 weeks after implantation. In other aspects of this embodiment, a porous material comprising an elastomer matrix defining an array of interconnected pores allows tissue growth into the interconnected pores sufficient to reduce or prevent formation of fibrous capsules in, e.g., at least 2 days after implantation, at least 3 days after implantation, at least 4 days after implantation, at least 5 days after implantation, at least 6 days after implantation, at least 7 days, at least 2 weeks after implantation, at least 3 weeks after implantation, or at least 4 weeks after implantation. In yet other aspects of this embodiment, a porous material comprising an elastomer matrix defining an array of interconnected pores allows tissue growth into the interconnected pores sufficient to reduce or prevent formation of fibrous capsules in, e.g., at most 2 days after implantation, at most 3 days after implantation, at most 4 days after implantation, at most 5 days after implantation, at most 6 days after implantation, at most 7 days, at most 2 weeks after implantation, at most 3 weeks after implantation, or at most 4 weeks after implantation. In still other aspects of this embodiment, a porous material comprising an elastomer matrix defining an array of interconnected pores allows tissue growth into the interconnected pores sufficient to reduce or prevent formation of fibrous capsules in, e.g., about 2 days to about 4 days after implantation, about 2 days to about 5 days after implantation, about 2 days to about 6 days after implantation, about 2 days to about 7 days after implantation, about 1 week to about 2 weeks after implantation, about 1 week to about 3 weeks after implantation, or about 1 week to about 4 weeks after implantation.

In one embodiment, a porous material comprises an elastomer matrix that generally has a low level of microporosity. As used herein, the term "microporosity" refers to a measure of the presence of small micropores within a porous material comprising an elastomer matrix itself (as opposed to the pores defined by an elastomer matrix). In some embodiments, all or substantially all of the micropores in a porous material comprising an elastomer matrix are between about 0.1 µm and about 5 µm, such as between about 0.1 µm and about 3 µm or between about 0.1 µm and about 2 µm. The term "low level of microporosity" means that micropores represent less than 2% of the volume of a porous material comprising an elastomer matrix, as measured by measuring the percentage void space in a cross-section through an elastomer matrix.

Figure 3A:
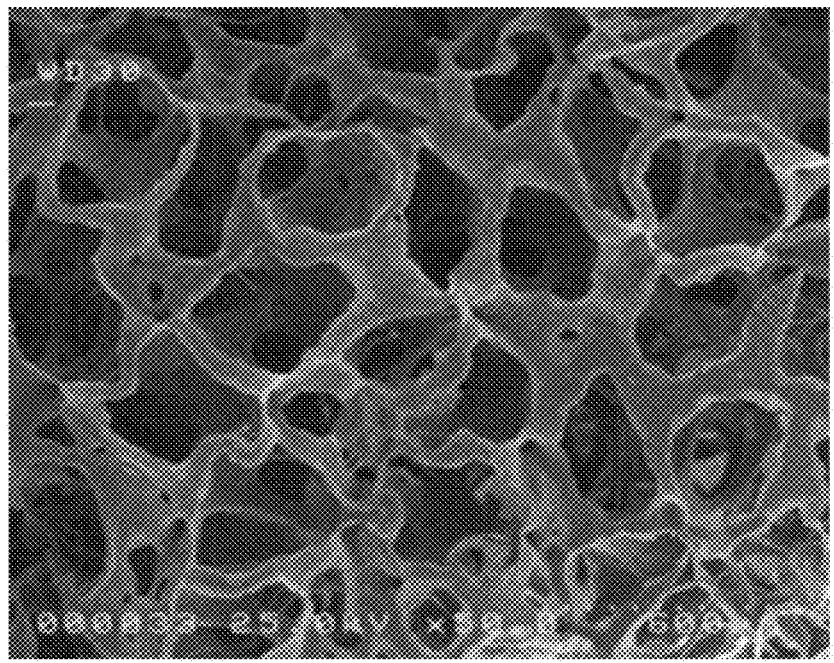
FIG. 3A is a scanning electron micrograph image at 50× magnification.
Figure 3B:
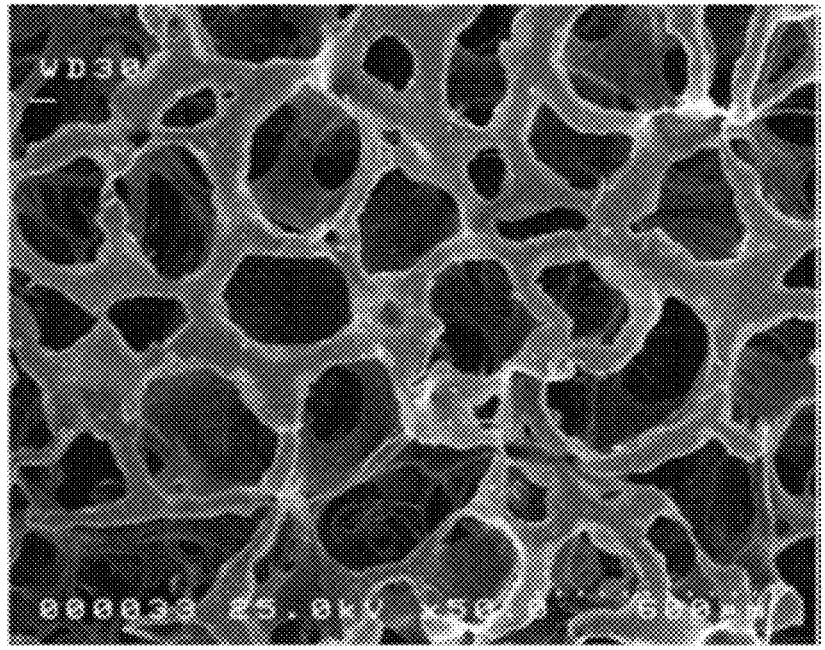
FIG. 3B is a scanning electron micrograph image at 50× magnification.

The shape, roundness, and diameter of pores, the connections between pores, the total volume of the porous material, the void volume, and the elastomer matrix volume can all be assessed using scanning electron microscopy. See, e.g., FIGS. 3A and 3B.

The present specification discloses in part, a biocompatible implantable device comprising a layer of porous material as disclosed in the present specification, wherein the porous material covers a surface of the device. See, e.g., FIGS. 4-10. As used herein, the term "implantable" refers to any material that can be embedded into, or attached to, tissue, muscle, organ or any other part of an animal body. As used herein, the term "animal" includes all mammals including a human. A biocompatible implantable device is synonymous with "medical device," "biomedical device," "implantable medical device" or "implantable biomedical device" and includes, without limitation, pacemakers, dura matter substitutes, implantable cardiac defibrillators, tissue expanders, and tissue implants used for prosthetic, reconstructive, or aesthetic purposes, like breast implants, muscle implants or implants that reduce or prevent scarring. Examples of biocompatible implantable devices that the porous material disclosed herein can be attached to are described in, e.g., Schuessler, Rotational Molding System for Medical Articles, U.S. Pat. No. 7,628,604; Smith, Mastopexy Stabilization Apparatus and Method, U.S. Pat. No. 7,081,135; Knisley, Inflatable Prosthetic Device, U.S. Pat. No. 6,936,068; Falcon, Reinforced Radius Mammary Prostheses and Soft Tissue Expanders, U.S. Pat. No. 6,605,116; Schuessler, Rotational Molding of Medical Articles, U.S. Pat. No. 6,602,452; Murphy, Seamless Breast Prosthesis, U.S. Pat. No. 6,074,421; Knowlton, Segmental Breast Expander For Use in Breast Reconstruction, U.S. Pat. No. 6,071,309; VanBeek, Mechanical Tissue Expander, U.S. Pat. No. 5,882,353; Hunter, Soft Tissue Implants and Anti-Scarring Agents, Schuessler, Self-Sealing Shell For Inflatable Prostheses, U.S. Patent Publication 2010/0049317; U.S. 2009/0214652; Schraga, Medical Implant Containing Detection Enhancing Agent and Method For Detecting Content Leakage, U.S. Patent Publication 2009/0157180; Schuessler, All-Barrier Elastomeric Gel-Filled Breast Prosthesis, U.S. Patent Publication 2009/0030515; Connell, Differential Tissue Expander Implant, U.S. Patent Publication 2007/0233273; and Hunter, Medical implants and Anti-Scarring Agents, U.S. Patent Publication 2006/0147492; Van Epps, Soft Filled Prosthesis Shell with Discrete Fixation Surfaces, International Patent Publication WO/2010/019761; Schuessler, Self Sealing Shell for Inflatable Prosthesis, International Patent Publication WO/2010/022130; Yacoub, Prosthesis Implant Shell, International Application No. PCT/US09/61045, each of which is hereby incorporated by reference in its entirety.

A biocompatible implantable device disclosed herein can be implanted into the soft tissue of an animal during the normal operation of the device. Such implantable devices may be completely implanted into the soft tissue of an animal body (i.e., the entire device is implanted within the body), or the device may be partially implanted into an animal body (i.e., only part of the device is implanted within an animal body, the remainder of the device being located outside of the animal body). A biocompatible implantable device disclosed herein can also be affixed to soft tissue of an animal during the normal operation of the medical device. Such devices are typically affixed to the skin of an animal body.

The present specification discloses, in part, a porous material that covers a surface of the biocompatible implantable device. Any of the porous materials disclosed herein can be used as the porous material covering a surface of a biocompatible implantable device. In general, the surface of a biocompatible implantable device is one exposed to the surrounding tissue of an animal in a manner that promotes tissue growth, and/or reduces or prevents formation of fibrous capsules that can result in capsular contracture or scarring.

Thus, in an embodiment, a porous material covers the entire surface of a biocompatible implantable device. In another embodiment, a porous material covers a portion of a surface of a biocompatible implantable device. In aspects of this embodiment, a porous material covers a front surface of a biocompatible implantable device or a back surface of a biocompatible implantable device. In other aspects, a porous material covers only to, e.g., about 20%, about 30%, about 40%, about 50%, about 60%, about 70% about 80% or about 90% of the entire surface of a biocompatible implantable device, a front surface of a biocompatible implantable device, or a back surface of a biocompatible implantable device. In yet other aspects, a porous material is applied only to, e.g., at least 20%, at least 30%, at least 40%, at least 50%, at least 60%, at least 70% at least 80% or at least 90% of the entire surface of a biocompatible implantable device, a front surface of a biocompatible implantable device, or a back surface of a biocompatible implantable device. In still other aspects, a porous material is applied only to, e.g., at most 20%, at most 30%, at most 40%, at most 50%, at most 60%, at most 70% at most 80% or at most 90% of the entire surface of a biocompatible implantable device, a front surface of a biocompatible implantable device, or a back surface of a biocompatible implantable device. In further aspects, a porous material is applied only to, e.g., about 20% to about 100%, about 30% to about 100%, about 40% to about 100%, about 50% to about 100%, about 60% to about 100%, about 70% to about 100%, about 80% to about 100%, or about 90% to about 100% of the entire surface of a biocompatible implantable device, a front surface of a biocompatible implantable device, or a back surface of a biocompatible implantable device.

The layer of porous material covering a biocompatible implantable device can be of any thickness with the proviso that the material thickness allows tissue growth within the array of interconnected pores of an elastomer matrix in a manner sufficient to reduce or prevent formation of fibrous capsules that can result in capsular contracture or scarring.

Thus, in an embodiment, a layer of porous material covering a biocompatible implantable device is of a thickness that allows tissue growth within the array of interconnected pores of an elastomer matrix in a manner sufficient to reduce or prevent formation of fibrous capsules that can result in capsular contracture or scarring. In aspects of this embodiment, a layer of porous material covering a biocompatible implantable device comprises a thickness of, e.g., about 100 µm, about 200 µm, about 300 µm, about 400 µm, about 500 µm, about 600 µm, about 700 µm, about 800 µm, about 900 µm, about 1 mm, about 2 mm, about 3 mm, about 4 mm, about 5 mm, about 6 mm, about 7 mm, about 8 mm, about 9 mm, or about 10 mm. In other aspects of this embodiment, a layer of porous material covering a biocompatible implantable device comprises a thickness of, e.g., at least 100 µm, at least 200 µm, at least 300 µm, at least 400 µm, at least 500 µm, at least 600 µm, at least 700 µm, at least 800 µm, at least 900 µm, at least 1 mm, at least 2 mm, at least 3 mm, at least 4 mm, at least 5 mm, at least 6 mm, at least 7 mm, at least 8 mm, at least 9 mm, or at least 10 mm. In yet other aspects of this embodiment, a layer porous material covering a biocompatible implantable device comprises a thickness of, e.g., at most 100 µm, at most 200 µm, at most 300 µm, at most 400 µm, at most 500 µm, at most 600 µm, at most 700 µm, at most 800 µm, at most 900 µm, at most 1 mm, at most 2 mm, at most 3 mm, at most 4 mm, at most 5 mm, at most 6 mm, at most 7 mm, at most 8 mm, at most 9 mm, or at most 10 mm. In still other aspects of this embodiment, a layer of porous material covering a biocompatible implantable device comprises a thickness of, e.g., about 100 µm to about 500 µm, about 100 µm to about 1 mm, about 100 µm to about 5 mm, about 500 µm to about 1 mm, about 500 µm to about 2 mm, about 500 µm to about 3 mm, about 500 µm to about 4 mm, about 500 µm to about 5 mm, about 1 mm to about 2 mm, about 1 mm to about 3 mm, about 1 mm to about 4 mm, about 1 mm to about 5 mm, or about 1.5 mm to about 3.5 mm.

The present specification discloses in part, a method for making biocompatible implantable device comprising a porous material. In an aspect, a method for making biocompatible implantable device comprises the step of attaching a porous material to the surface of a biocompatible implantable device. In another aspect, a method for making biocompatible implantable device comprises the steps of a) preparing a surface of a biocompatible implantable device to receive porous material; b) attaching a porous material to the prepared surface of the device. Any of the porous materials disclosed herein can be used as the porous material attached to a surface of a biocompatible implantable device.

In yet another aspect, a method for making biocompatible implantable device comprises the step of: a) coating a mandrel with an elastomer base; b) curing the elastomer base to form a base layer; c) coating the cured base layer with an elastomer base; d) coating the elastomer base with porogens to form an elastomer coated porogen mixture; e) treating the elastomer coated porogen mixture to form a porogen scaffold comprising fused porogens and cure the elastomer; and f) removing the porogen scaffold, wherein porogen scaffold removal results in a porous material, the porous material comprising a non-degradable, biocompatible, elastomer matrix defining an array of interconnected pores. In this method steps (c) and (d) can be repeated multiple times until the desired thickness of the material layer is achieved.

The present specification discloses, in part, preparing a surface of a biocompatible implantable device to receive porous material. Preparing a surface of a biocompatible implantable device to receive porous material can be accomplished by any technique that does not destroy the desired properties of the porous material or the biocompatible implantable device. As a non-limiting example, a surface of a biocompatible implantable device can be prepared by applying a bonding substance. Non-limiting examples of bonding substances include silicone adhesives, such as, e.g., RTV silicone and HTV silicone. The bonding substance is applied to the surface of a biocompatible implantable device, the porous material, or both, using any method known in the art, such as, e.g., cast coating, spray coating, dip coating, curtain coating, knife coating, brush coating, vapor deposition coating, and the like.

The present specification discloses, in part, attaching a porous material to a surface of a biocompatible implantable device. The porous material can be attached to the entire surface of the device, or only to portions of the surface of the device. As a non-limiting example, porous material is attached only to the front surface of the device or only the back surface of the device. Attachment of a porous material to a surface of a biocompatible implantable device can be accomplished by any technique that does not destroy the desired properties of the porous material or the biocompatible implantable device.

For example, attachment can occur by adhering an already formed porous material onto a surface of a biocompatible implantable device using methods known in the art, such as, e.g., gluing, bonding, melting. For instance, a dispersion of silicone is applied as an adhesive onto a surface of a biocompatible implantable device, a porous material sheet, or both, and then the two materials are placed together in a manner that allows the adhesive to attach the porous material to the surface of the device in such a way that there are no wrinkles on the surface of the device. The silicone adhesive is allowed to cure and then the excess material is cut off creating a uniform seam around the device. This process results in a biocompatible implantable device comprising a porous material disclosed in the present specification. Examples 2 and 4 illustrate method of this type of attachment.

Alternatively, attachment can occur by forming the porous material directly onto a surface of a biocompatible implantable device using methods known in the art, such as, e.g., cast coating, spray coating, dip coating, curtain coating, knife coating, brush coating, vapor deposition coating, and the like. For instance, an elastomer base is applied to a mandrel and cured to form a base layer of cured elastomer. The base layer is then initially coated with an elastomer base and then subsequently with porogens to create a elastomer coated porogen mixture. This mixture is then treated as disclosed herein to form a porogen scaffold and cure the elastomer. The porogen scaffold is then removed, leaving a layer of porous material on the surface of the device. The thickness of the porous material layer can be increased by repeated coatings of additional elastomer base and porogens. Examples 5-8 illustrate method of this type of attachment.

Regardless of the method of attachment, the porous material can be applied to the entire surface of a biocompatible implantable device, or only to portions of the surface of a biocompatible implantable device. As a non-limiting example, porous material is applied only to the front surface of a biocompatible implantable device or only the back surface of a biocompatible implantable device.

Thus, in an embodiment, a porous material is attached to a surface of a biocompatible implantable device by bonding a porous material to a surface of a biocompatible implantable device. In aspects of this embodiment, a porous material is attached to a surface of a biocompatible implantable device by gluing, bonding, or melting the porous material to a surface of a biocompatible implantable device.

In another embodiment, a porous material is attached to a surface of a biocompatible implantable device by forming the porous material onto a surface of a biocompatible implantable device. In aspects of this embodiment, a porous material is attached to a surface of a biocompatible implantable device by cast coating, spray coating, dip coating, curtain coating, knife coating, brush coating, or vapor deposition coating.

In another aspect of this embodiment, forming a porous material on a surface of a biocompatible implantable device comprises coating a cured elastomer base layer with an elastomer base and then coating the uncured elastomer base with porogens to form an elastomer coated porogen mixture. In other aspects of this embodiment, coating a cured elastomer base layer with an uncured elastomer base and then coating the uncured elastomer base with porogens to form an elastomer coated porogen mixture can be repeated, e.g., at least once, at least twice, at least three times, at least four times, at least five times, at least six times, at least seven times, at least eight times, at least nine times, or at least ten times, before the mixture is treated.

In another embodiment, a porous material is applied to the entire surface of a biocompatible implantable device. In another embodiment, a porous material is applied to a portion of a surface of a biocompatible implantable device. In aspects of this embodiment, a porous material is applied to a front surface of a biocompatible implantable device or a back surface of a biocompatible implantable device. In other aspects, a porous material is applied only to, e.g., about 20%, about 30%, about 40%, about 50%, about 60%, about 70% about 80% or about 90% of the entire surface of a biocompatible implantable device, a front surface of a biocompatible implantable device, or a back surface of a biocompatible implantable device. In yet other aspects, a porous material is applied only to, e.g., at least 20%, at least 30%, at least 40%, at least 50%, at least 60%, at least 70% at least 80% or at least 90% of the entire surface of a biocompatible implantable device, a front surface of a biocompatible implantable device, or a back surface of a biocompatible implantable device. In still other aspects, a porous material is applied only to, e.g., at most 20%, at most 30%, at most 40%, at most 50%, at most 60%, at most 70% at most 80% or at most 90% of the entire surface of a biocompatible implantable device, a front surface of a biocompatible implantable device, or a back surface of a biocompatible implantable device. In further aspects, a porous material is applied only to, e.g., about 20% to about 100%, about 30% to about 100%, about 40% to about 100%, about 50% to about 100%, about 60% to about 100%, about 70% to about 100%, about 80% to about 100%, or about 90% to about 100% of the entire surface of a biocompatible implantable device, a front surface of a biocompatible implantable device, or a back surface of a biocompatible implantable device.

The layer of porous material applied to a biocompatible implantable device can be of any thickness with the proviso that the material thickness allows tissue growth within the array of interconnected pores of an elastomer matrix in a manner sufficient to reduce or prevent formation of fibrous capsules that can result in capsular contracture or scarring.

Thus, in an embodiment, a layer of porous material applied to a biocompatible implantable device is of a thickness that allows tissue growth within the array of interconnected pores of an elastomer matrix in a manner sufficient to reduce or prevent formation of fibrous capsules that can result in capsular contracture or scarring. In aspects of this embodiment, a layer porous material applied to a biocompatible implantable device comprises a thickness of, e.g., about 100 µm, about 200 µm, about 300 µm, about 400 µm, about 500 µm, about 600 µm, about 700 µm, about 800 µm, about 900 µm, about 1 mm, about 2 mm, about 3 mm, about 4 mm, about 5 mm, about 6 mm, about 7 mm, about 8 mm, about 9 mm, or about 10 mm. In other aspects of this embodiment, a layer of porous material applied to a biocompatible implantable device comprises a thickness of, e.g., at least 100 µm, at least 200 µm, at least 300 µm, at least 400 µm, at least 500 µm, at least 600 µm, at least 700 µm, at least 800 µm, at least 900 µm, at least 1 mm, at least 2 mm, at least 3 mm, at least 4 mm, at least 5 mm, at least 6 mm, at least 7 mm, at least 8 mm, at least 9 mm, or at least 10 mm. In yet other aspects of this embodiment, a layer of porous material applied to a biocompatible implantable device comprises a thickness of, e.g., at most 100 µm, at most 200 µm, at most 300 µm, at most 400 µm, at most 500 µm, at most 600 µm, at most 700 µm, at most 800 µm, at most 900 µm, at most 1 mm, at most 2 mm, at most 3 mm, at most 4 mm, at most 5 mm, at most 6 mm, at most 7 mm, at most 8 mm, at most 9 mm, or at most 10 mm. In still other aspects of this embodiment, a layer of porous material applied to a biocompatible implantable device comprises a thickness of, e.g., about 100 µm to about 500 µm, about 100 µm to about 1 mm, about 100 µm to about 5 mm, about 500 µm to about 1 mm, about 500 µm to about 2 mm, about 500 µm to about 3 mm, about 500 µm to about 4 mm, about 500 µm to about 5 mm, about 1 mm to about 2 mm, about 1 mm to about 3 mm, about 1 mm to about 4 mm, about 1 mm to about 5 mm, or about 1.5 mm to about 3.5 mm.

The present specification also discloses a method of implanting a prosthesis, the method comprising the step of implanting the prosthesis in a patient, the prosthesis covered by a porous material disclosed herein; wherein at any time after implantation, if a capsule has formed, the capsule has a thickness of 75 μm or less, has fiber disorganization comprising 50% or more of the fibers that are not parallel to the prosthesis surface, has tissue growth into the biomaterial of the prosthesis of 100 μm or more, has less than 40% collagen content, adheres to tissue with a peak force of at least 8 N and/or and has a stiffness of 20 mmHg/mL or less.

The present specification also discloses a method of implanting a prosthesis, the method comprising the step of implanting the prosthesis in a patient, the prosthesis covered by a porous material disclosed herein; wherein at any time after implantation, if a capsule has formed, the capsule has a thickness of 50 μm or less, has fiber disorganization comprising 60% or more of the fibers that are parallel to the prosthesis surface, has tissue growth into the biomaterial of the prosthesis of 125 μm or more, has less than 30% collagen content, adheres to tissue with a peak force of at least 9 N and/or and has a stiffness of 15 mmHg/mL or less.

The present specification also discloses a method of implanting a prosthesis, the method comprising the step of implanting the prosthesis in a patient, the prosthesis covered by a porous material disclosed herein; wherein at any time after implantation, if a capsule has formed, the capsule has a thickness of 25 μm or less, has fiber disorganization comprising 70% or more of the fibers that are not parallel to the prosthesis surface, has tissue growth into the biomaterial of the prosthesis of 150 μm or more, has less than 20% collagen content, adheres to tissue with a peak force of at least 10 N and/or and has a stiffness of 10 mmHg/mL or less.

The present specification also discloses a method of implanting a prosthesis, the method comprising the step of implanting the prosthesis in a patient, the prosthesis covered by a porous material disclosed herein; wherein at any time after implantation, if a capsule has formed, the capsule has a thickness of about 5 μm to about 75 μm, has fiber disorganization comprising about 50% to about 90% of the fibers that are not parallel to the prosthesis surface, has tissue growth into the biomaterial of the prosthesis of about 100 μm to about 300 μm, has about 5% to about 40% collagen content, adheres to tissue with a peak force of about 8 N to about 11N, and/or and has a stiffness of about 5 mmHg/mL to about 20 mmHg/mL.

In one embodiment, the present specification discloses an apparatus for implantation within a patient's gastrointestinal tract, specifically for implantation to the internal mucosal lining of the gastrointestinal tract. The apparatus may include an implant device, or biocompatible implant device for implantation to the internal mucosal lining of the gastrointestinal tract. The apparatus may include a porous material in a form disclosed in this application, including, but not limited to, a non-degradable, biocompatible, elastomer matrix defining an array of interconnected pores. The non-degradable porous material may also have properties of being non-resorbable, which means that the porous material is not broken down and assimilated into the body. The porous material may include an array of interconnected pores structured to receive tissue ingrowth from the mucosal lining to anchor the implant device to the mucosal lining. The porous material may be structured to include the features disclosed in this application regarding tissue ingrowth into the array of interconnected pores, including sufficient pore shape, roundness, diameter of connections between pores, pore mean diameter, mean elastomer strut thickness, porosity, mean open pore value and/or mean closed pore value, void space, and void volume.

The porous material may comprise any portion or part of an implant device configured to be implanted within the patient's gastrointestinal tract. The porous material may comprise the entirety of an implant device configured to be implanted within the patient's gastrointestinal tract.

The implant device may be configured as any device for implantation within a patient's gastrointestinal tract. In certain embodiments, the implant device may comprise a medically therapeutic device capable of treating a medical condition of the patient. Such implants may include a stent, a drug elution device, a tissue graft, an intragastric volume occupying device, a sensor, or a device structured to form a stoma within the gastrointestinal tract.

In one embodiment, the porous material for attachment to the mucosal lining of the patient's gastrointestinal tract may be made from a process in which the implant device is first dipped with an elastomer dispersion, which may include a silicone dispersion, such as PN-3206 or Nusil products, or any other biocompatible silicone disclosed in this application. A solvent such as xylene may be applied and allowed to evaporate for a duration of a 1-3 minutes, or for any duration as desired. The wet elastomer surface, including a silicone surface is then coated with porogens, which may comprise sugar particles or polyethylene glycol particles, as desired. Other porogen particles may include poly(lactic-co-glycolic acid) particles or polycaprolactone particles. Any other porogen disclosed in this application may be used that results in a biocompatible porogen material. The porogens may include a core material and a shell material as disclosed in this application. The porogen size may range from 30 microns to up to 1000 microns.

The combined thickness of the elastomer coating and porogens upon the implant device may vary from 50 microns to 200 microns. The elastomer and porogens may be heated at approximately 126° C. to fuse the shells of the porogens together and to cure the elastomer, which may comprise silicone. The steps of elastomer dipping, porogen coating, and heating may be repeated as desired to produce thicker coatings of an elastomer.

The coated implant device may then be soaked in hot water to remove the porogens, which may include sugar or polyethylene glycol particles, leaving an elastomeric porous material. The coated implant device is then dried to produce an implant device having an elastomeric porous material. In one embodiment, the remaining elastomeric porous material may have a porosity of between 10% to 80%.

In one embodiment, a porous material for attachment to the mucosal lining of the patient's gastrointestinal tract may be made separate from the implant device, according to any method disclosed in this application. In this embodiment, the porous material may then be laminated onto the implant device, using a method disclosed in this application.

In one embodiment, a porous material for use with an implant device structured to be anchored within a patient's gastrointestinal tract may be made by the steps of providing porogens each having a core material and a shell material surrounding the core material; fusing the shell material of the porogens to form a porogen scaffold of fused porogens; coating the porogen scaffold with an elastomer base to form an elastomer coated porogen scaffold; curing the elastomer coated porogen scaffold to form a cured elastomer coated porogen scaffold; and removing the porogen scaffold from the cured elastomer coated porogen scaffold, wherein removal of the porogen scaffold results in the elastomer material. In one embodiment, the shell material may be a salt and/or its derivatives, a sugar and/or its derivatives, a polysaccharide and/or its derivatives, a wax and/or its derivatives, a metal and/or its derivatives, a surfactant and/or its derivatives, a water soluble solid and/or its derivatives, and/or a polymer and/or its derivatives. In one embodiment, the core material may be a salt and/or its derivatives, a ceramic and/or its derivatives, a sugar and/or its derivatives, a polysaccharide and/or its derivatives, a wax and/or its derivatives, a metal and/or its derivatives, a water soluble solid and/or its derivatives, and/or a polymer and/or its derivatives.

In one embodiment, the porous material for attachment to the mucosal lining of the patient's gastrointestinal tract may include a mixture of an elastomer, and an acid-resistant material, including a fluorotype silicone, a polybutadiene, or a styrenebutadiene. In one embodiment, the porous material may be entirely made from an acid-resistant material, including a fluorotype silicone, a polybutadiene, or a styrenebutadiene. The acid-resistant material may be utilized in an embodiment in which the implant device is to be implanted within a patient's stomach. The acid-resistant material may protect the porous material of the implant device from damage from the acid within the patient's body. The acid-resistant material may also be used in any other embodiment of the porous material disclosed in this application.

In one embodiment, the porous material including the acid-resistant material may have a porosity of at least 10% and exhibit an elastic elongation of at least 80%. The porous material may exhibit an ultimate strength of at least 1 Mega Pascals, may exhibit a flexural strength of at most 50 Mega Pascals, and may exhibit a compressibility of at most 30 kilo Pascals. In other embodiments, the properties of the porous material may be modified, as disclosed in regard to other porous materials disclosed in this application.

A porous material for implantation to the mucosal lining of the patient's gastrointestinal tract may be made through any other method discussed throughout this application, as long as the resulting porous material is biocompatible for implantation within a patient's gastrointestinal tract.

The porous material for implant to the mucosal lining of the patient's gastrointestinal tract has a structure of a scaffold that promotes a scarring response, an inflammatory response, a stimulation of tissue growth, or any combination therein on the mucosal lining of the gastrointestinal tract, which in-turn stimulates tissue in-growth into and within the scaffold, thereby creating a means for fixating devices within the body through natural processes. The porous material may still be considered a biocompatible material because the response of the mucosal lining is desired.

A benefit of the porous material for implant to the mucosal lining of the patient's gastrointestinal tract is that an implant device may be fixed to the mucosal lining of the gastrointestinal tract without requiring the use of anchors. Implant devices typically include sutures, barbs, or hooks that tie a device to the patient's body. However, such anchors may come loose, or otherwise damage or irritate the patient's body. The porous material for implant to the mucosal lining of the patient's gastrointestinal tract is designed such that these anchors are no longer required. Rather, fixation to the patient's mucosal lining is organic, and produced by the patient's body itself.

In one embodiment, the implant device with a porous material is implanted into the patient's gastrointestinal tract endoscopically. In such embodiments, the implant device may be inserted through an endoscope, or through any other endoscopic device that allows for passage of the implant device through the gastrointestinal lumen. The gastrointestinal lumen includes the portions of a patient's body including the esophagus, the stomach, and the small and large intestines, including the colon.

Figure 11:
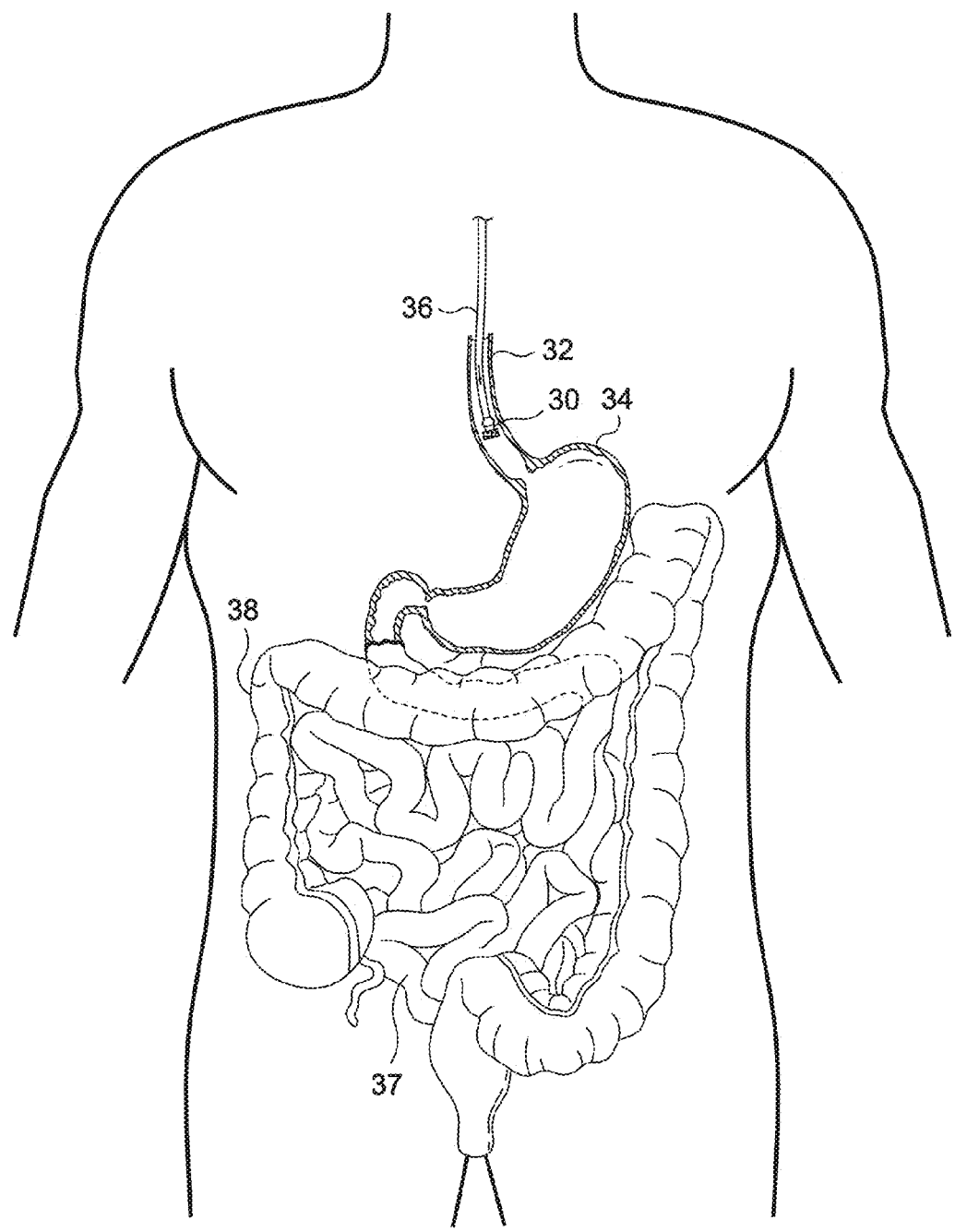
FIG. 11 illustrates an embodiment of a method of implanting an implant device having a porous material in a form disclosed in this application.

FIG. 11 illustrates an embodiment of a method of implanting an implant device having a porous material in a form disclosed in this application. The implant device is anchored to a mucosal lining of a patient's gastrointestinal tract. The steps of anchoring the implant device generally include inserting the implant device into the patient's gastrointestinal tract, and placing the implant device within the patient's gastrointestical tract such that the array of interconnected pores contacts the mucosal lining and receives tissue ingrowth from the mucosal lining to anchor the implant device to the mucosal lining.

FIG. 11 illustrates an implant device 30 being passed through a patient's esophagus 32 and into the patient's stomach 34. The implant device 30 was inserted into the patient's gastrointestinal tract through the patient's mouth. An endoscopic device 36 guides the implant device 30 for delivery into the patient's stomach 34. The implant device 30 is latched to the endoscopic device 36 through an appropriate latching mechanism, for example, graspers as shown in FIG. 11.

In this embodiment, the implant device 30 comprises a drug elution device, although the method may be practiced with any variety of implant devices, which may be discussed in this application.

At least a portion of the implant device 30 includes the porous material in a form disclosed in this application, including, but not limited to, a non-resorbable, biocompatible, elastomer matrix defining an array of interconnected pores structured to receive tissue ingrowth from the mucosal lining of the patient's gastrointestinal tract to anchor the implant device to the mucosal lining.

To help facilitate mucosal tissue ingrowth into the textured implant surface, secondary and/or temporary anchoring devices may be used. Devices commonly practiced with surgeons and endoscopists include clips, bioresorbable sutures, stents, and/or micro hooks for tissue adhesion. These devices help initiate the mucosal tissue ingrowth response, and could be resorbed into, or removed from, the body leaving behind only the natural anchoring of the tissue adhesion into the implant device 30.

In the embodiment shown in FIG. 11, the implant device is delivered through the esophageal lumen until it is positioned as desired within the patient's gastrointestinal tract. The stomach 34 may comprise a desired location for the implant device 30 to be fixed, although in other embodiments, the implant device 30 may be fixed to any other desired location of the gastrointestinal tract, including the esophagus 32, the small intestine 37, or the large intestine 38.

Figure 12:
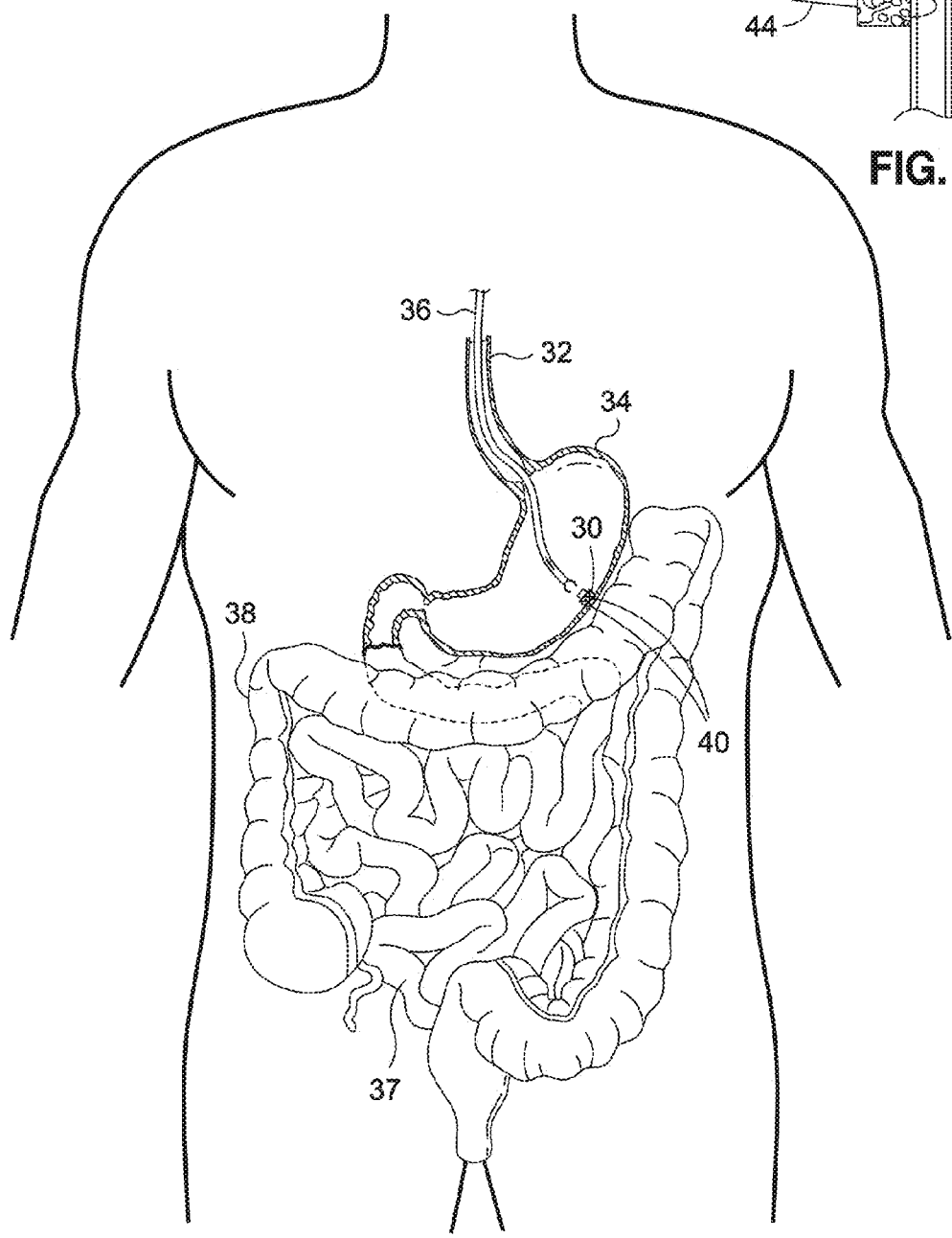
FIG. 12 illustrates an embodiment of a method of implanting an implant device having a porous material in a form disclosed in this application.

FIG. 12 illustrates the implant device 30 of FIG. 11 being placed within the patient's gastrointestinal tract such that the mucosal lining contacts the array of interconnected pores. The implant device 30 is placed at the interior mucosal lining of the stomach 34. The implant device 30 is preferably placed against the mucosal lining of the gastrointestinal tract such that the porous material contacts the mucosal lining of the gastrointestinal tract. In one embodiment, pressure may be applied to press the implant device 30 against the mucosal lining.

The implant device 30 may also be fixed to the stomach 34 via an anchor 40. An anchor for use with the implant device 30 may include clips, bioresorbable sutures, stents, and/or micro hooks for tissue adhesion, or the like. In the embodiment shown in FIG. 12, the anchor 40 comprises temporary sutures that join the implant device 30 to the patient's stomach 34 for a defined period of time. The anchor 40 may be manipulated through an appropriate mechanism to be secured in position, for example, endoscopic graspers or the like.

Once the implant device 30 is placed against the mucosal lining of the gastrointestinal tract as desired, the endoscopic device 36 is withdrawn. In one embodiment, the step of placing the implant device 30 may include releasing, or dropping, the implant device 30 within the patient's gastrointestinal tract such that the implant device 30 eventually contacts and rests against the mucosal lining.

The contact between the porous material of the implant device 30 and the mucosal lining of the gastrointestinal tract causes the porous material to integrate with the array of interconnected pores of the implant device 30. The tissue of the mucosal lining may fuse with the array of interconnected pores and form a bond with the array of interconnected pores.

Figure 13:
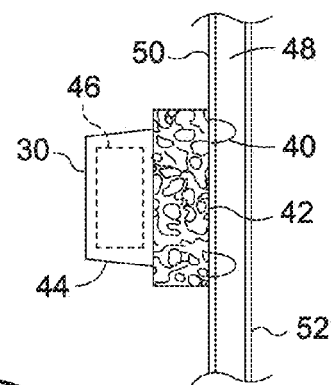
FIG. 13 illustrates a close-up view of an embodiment of an implant device bonded to the tissue of the gastrointestinal tract.

FIG. 13 illustrates a close-up view of the implant device 30 bonded to tissue of the gastrointestinal lining, in the state shown in FIG. 12. The implant device 30 is more clearly shown to include an outer surface 42 that is made of a porous material. A portion 44 of the implant device 30 is not made of a porous material. A drug reservoir 46 is included within the implant device 30 to allow the implant device 30 to serve as a drug elution device. In the embodiment shown in FIG. 13, anchors 40 in the form of temporary sutures fix the implant device 30 to the stomach wall 48. The anchors 40 cause the outer surface 42 of the implant device 30 to hold against the mucosal lining 50 of the stomach wall 48. The implant device 30 does not contact the outer serosa 52 of the stomach wall 48. In another embodiment, the implant device 30 may be configured to serve as a drug elution device by having a time-delayed or engineered degradation of a drug coated texture for drug delivery. In other embodiments, any other structure to deliver drugs into the patient's body may be used.

In the embodiment shown in FIG. 13, the contact between the porous material of the outer surface 42 of the implant device 30 and the mucosal lining 50 causes the mucosal lining to detect the porous material of the outer surface 42 as a foreign object within the patient's body. In response, the mucosal lining 50 undergoes a scarring response, an inflammatory response, a stimulation of tissue growth, or any combination therein, to cause tissue ingrowth into the porous material. The porous material provides an array of interconnected pores that allows tissue to enter therein during this biological response. The tissue from the mucosal lining entering the array of interconnected pores causes the mucosal lining to fuse to the implant device 30, and anchor the implant device to the mucosal lining 50.

Figure 14:
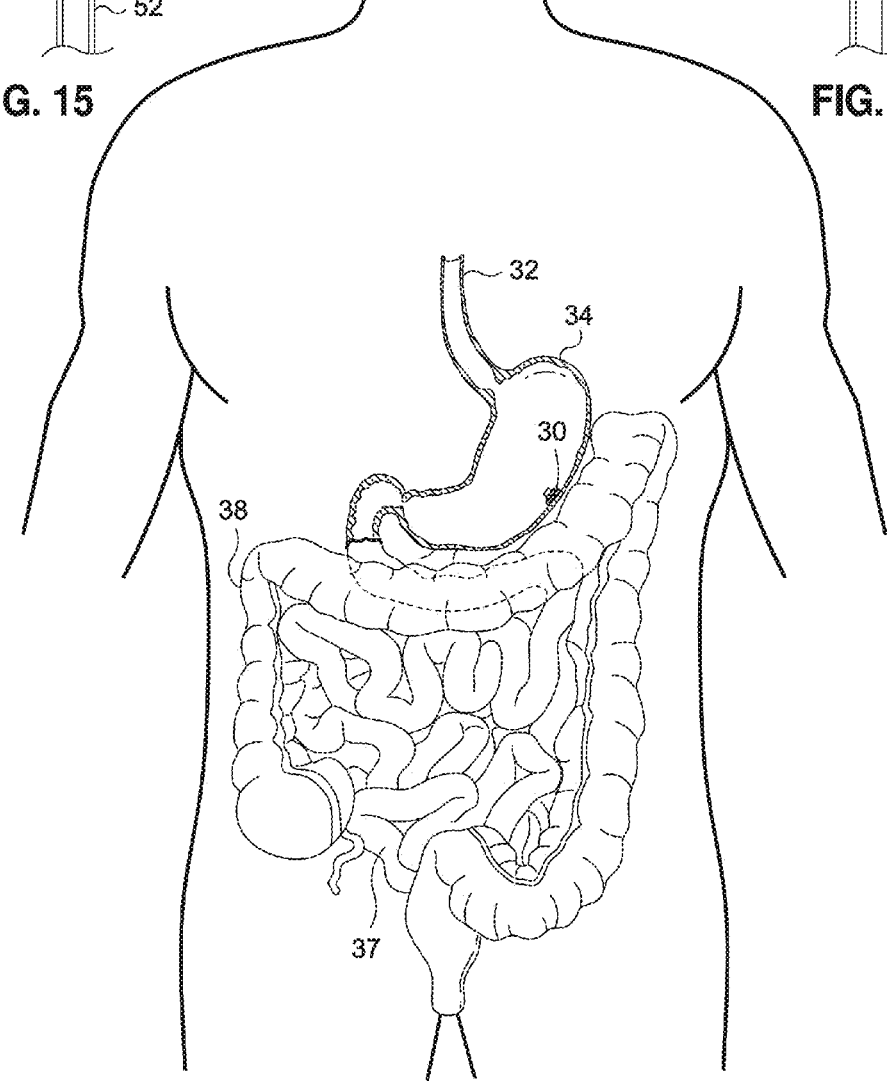
FIG. 14 illustrates an embodiment of a method of implanting an implant device having a porous material in a form disclosed in this application.

FIG. 14 illustrates the implant device 30 after tissue has entered the array of interconnected pores and has fused to the implant device 30. The temporary sutures that comprised the anchor members 40 shown in FIG. 13 have dissolved over time, within the patient's body. The endoscopic device 36 shown in FIG. 12 has been removed from the patient's body.

Figure 15:
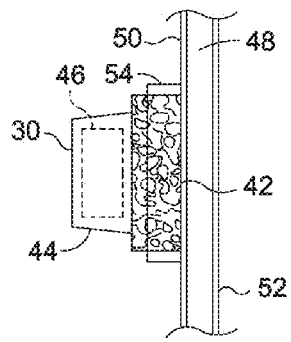
FIG. 15 illustrates a close-up view of an embodiment of an implant device bonded to the tissue of the gastrointestinal tract.

FIG. 15 illustrates a close-up view of the implant device 30 with tissue 54 ingrown into the porous material of the implant device 30, as in the state shown in FIG. 14. The tissue 54 extends in a direction towards the interior of the patient's stomach and integrates with the porous material of the implant device 30. The anchors 40 shown in FIG. 13 have dissolved. The implant device 30 is solely held in place against the mucosal lining 50 by the bond of the tissue 54 growth into the porous material.

Figure 16:
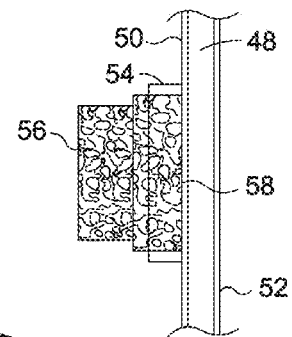
FIG. 16 illustrates a close-up view of an embodiment of an implant device bonded to the tissue of the gastrointestinal tract.

FIG. 16 illustrates an embodiment of an implant device in which a porous material covers the entirety of the outer surface 58 of the implant device 56. In this embodiment, the tissue 54 from the mucosal layer 50 of the stomach may enter any portion of the outer surface of the implant device 56. A greater bonding strength may therefore be possible than in the embodiment shown in FIG. 15, for example. The implant device 56 may comprise a drug elution device, similar to the implant device 30 shown in FIG. 15, although a drug reservoir is not shown in FIG. 16.

Figure 17:
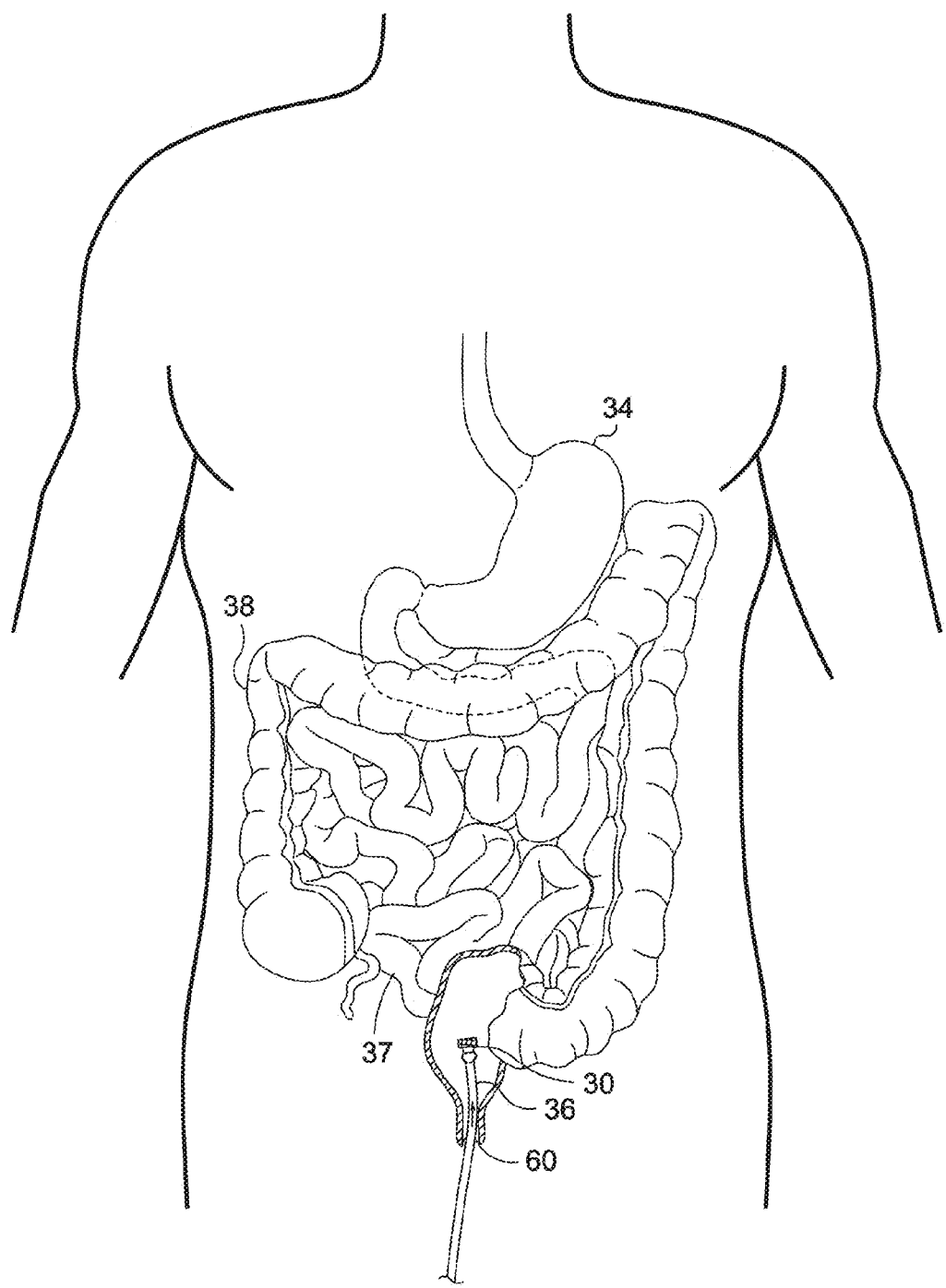
FIG. 17 illustrates an embodiment of a method of implanting an implant device having a porous material in a form disclosed in this application.

FIG. 17 illustrates an embodiment for a method of implanting an implant device having a porous material in a form disclosed in this application. The embodiment shown in FIG. 17 differs from the embodiment shown in FIG. 11, for example, because the endoscopic device 36 is inserted into the patient's large intestine 38 through the patient's anus 60. The implantation method shown in FIG. 17 is otherwise identical to that shown in FIG. 11, namely, the implant device 30 is inserted into the patient's gastrointestinal tract and placed within the gastrointestinal tract such that the mucosal lining contacts the array of interconnected pores.

Figure 18:
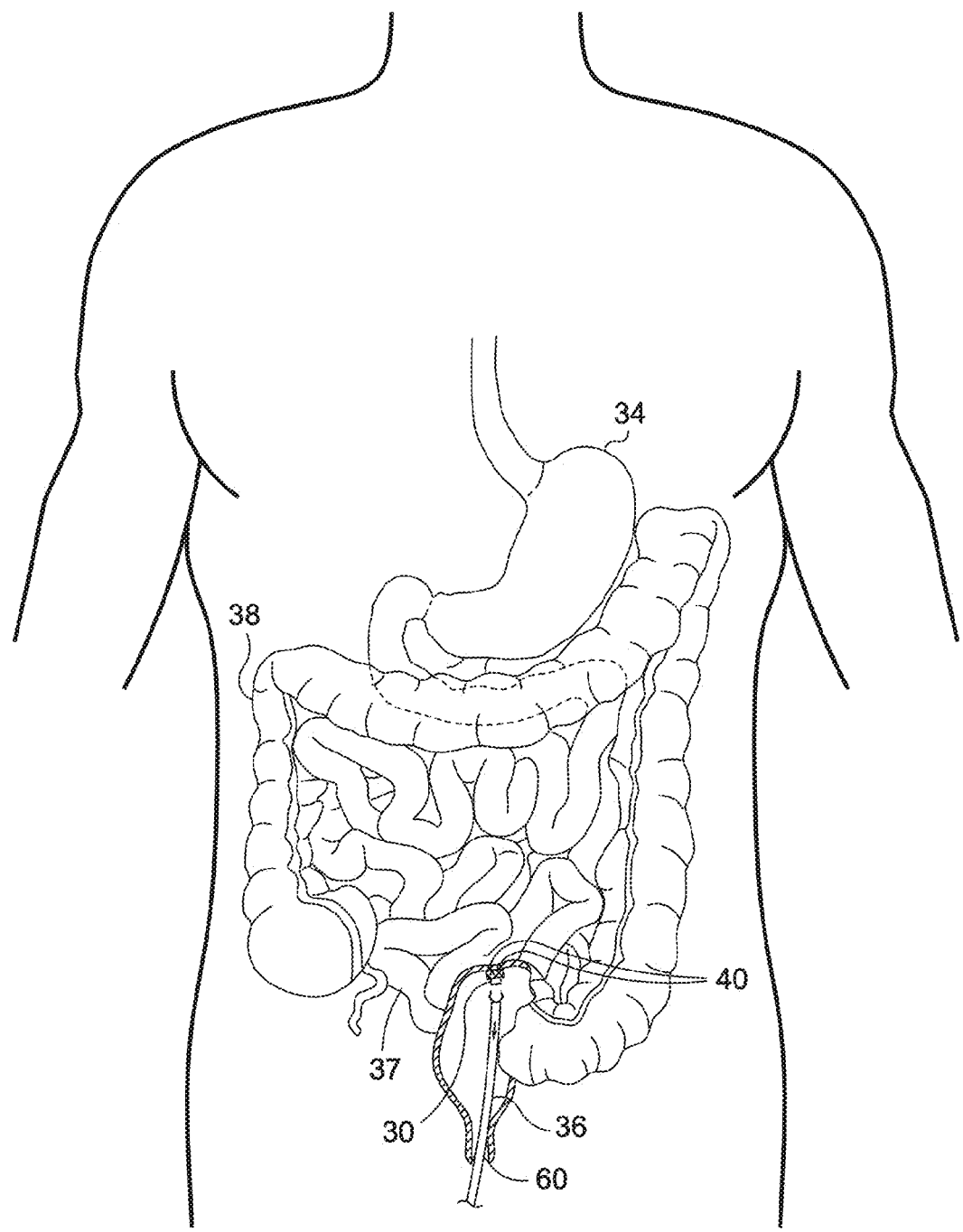
FIG. 18 illustrates an embodiment of a method of implanting an implant device having a porous material in a form disclosed in this application.

FIG. 18 illustrates the implant device 30 after it has been anchored to the patient's rectum, using anchors 40, similar to the embodiment shown in FIG. 12. An outer surface of the implant device 30 comprises a porous material that contacts the mucosal lining of the large intestine 38, specifically the colon. The endoscopic device 36 exits from the patient's anus 60 after implantation.

Figure 19:
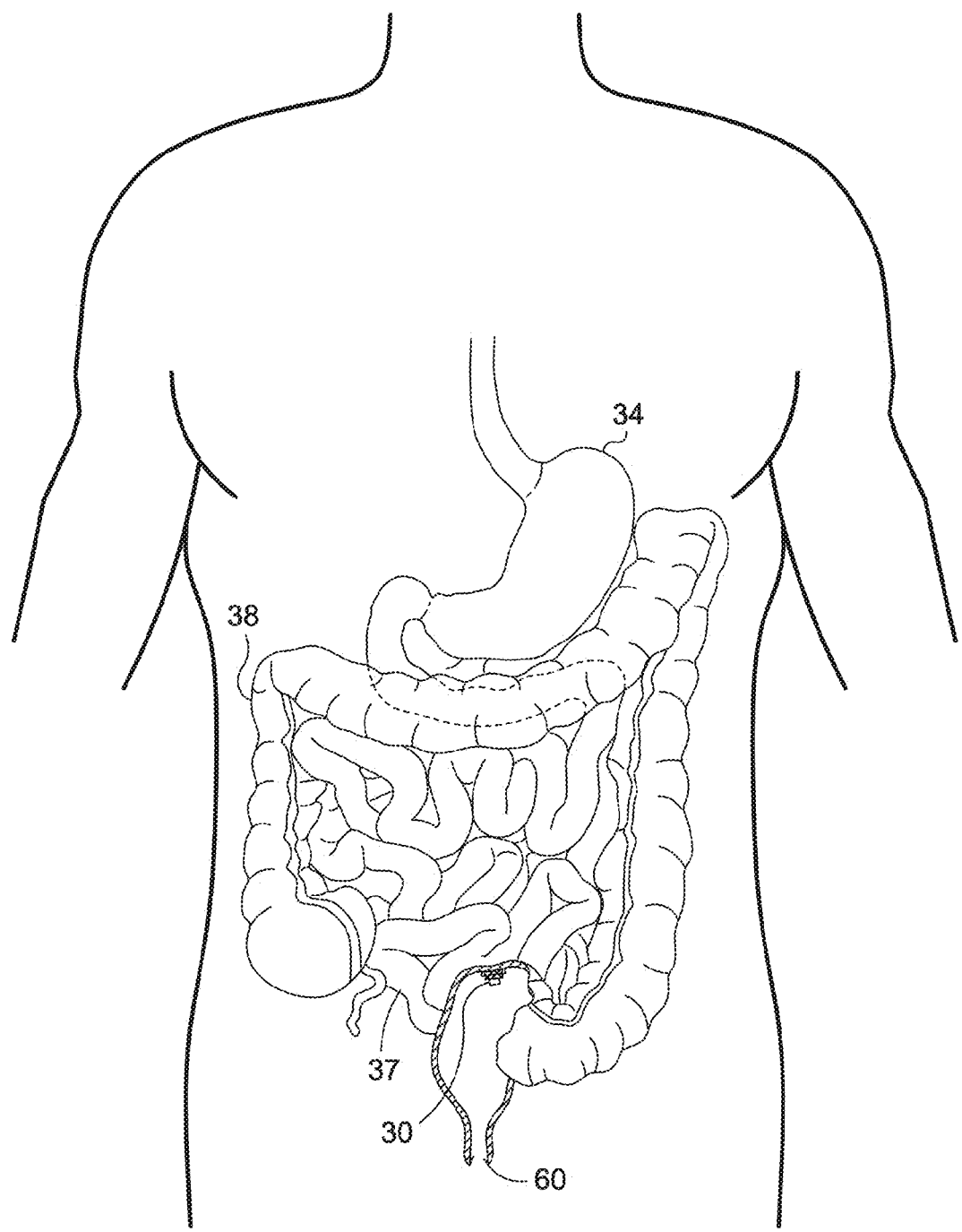
FIG. 19 illustrates an embodiment of a method of implanting an implant device having a porous material in a form disclosed in this application.

FIG. 19 illustrates the implant device 30 after tissue of the mucosal lining of the large intestine has integrated with the porous material of the implant device 30. The implant device 30 has fused to the tissue of the mucosal lining and the anchors 40 have dissolved.

Figure 20:
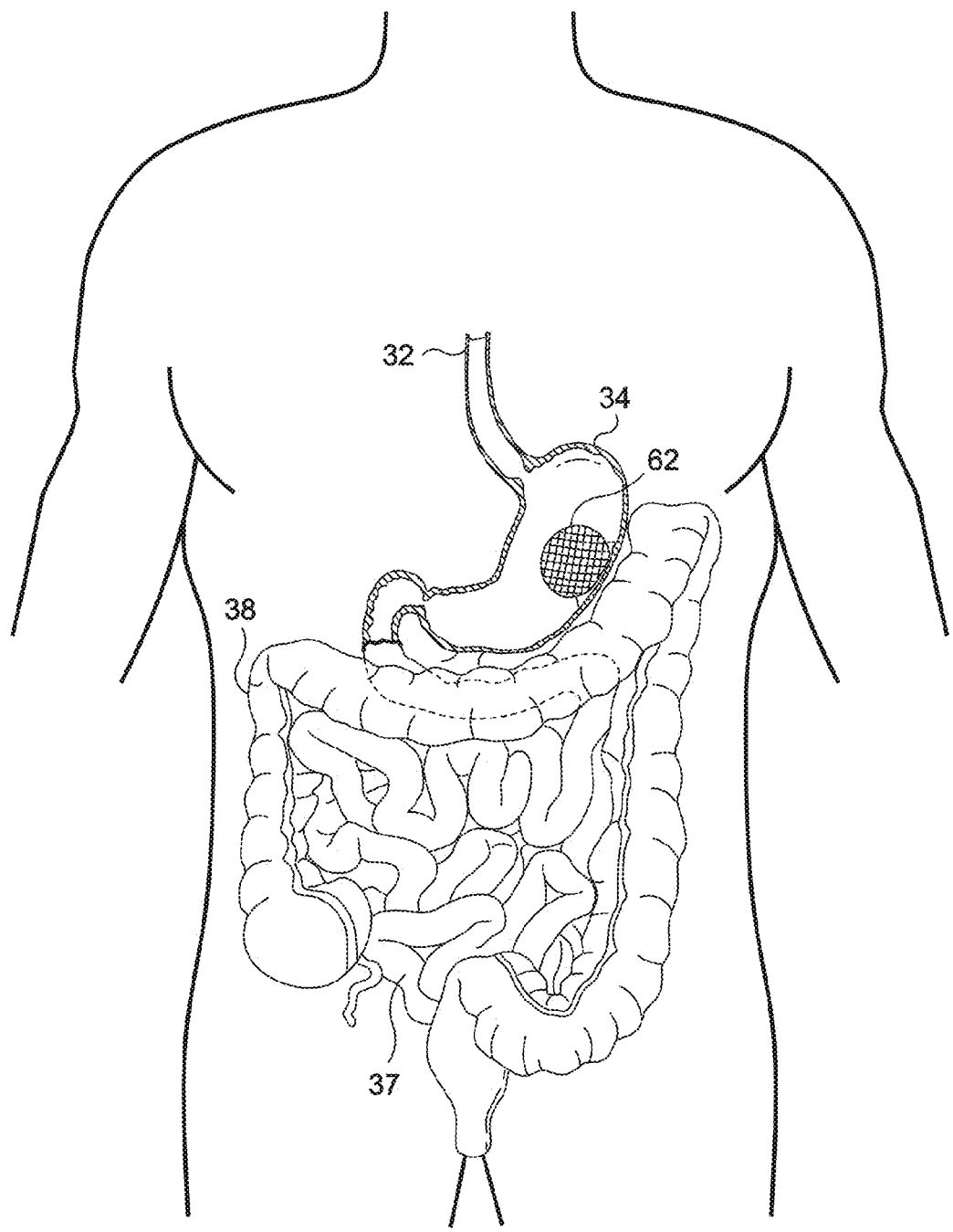
FIG. 20 illustrates an embodiment of an implant device having a porous material in a form disclosed in this application implanted within a patient's gastrointestinal tract.

FIG. 20 illustrates an embodiment of an implant device 62 in which at least a portion of the implant device 62 includes the porous material in a form disclosed in this application, including, but not limited to, a non-resorbable, biocompatible, elastomer matrix defining an array of interconnected pores structured to receive tissue ingrowth from the mucosal lining of the patient's gastrointestinal tract to anchor the implant device to the mucosal lining. The porous material may cover a portion or the entirety of the outer surface of the implant device 62. The implant device 62 in this embodiment comprises an intragastric volume occupying device configured to occupy space within the patient's stomach 34. The intragastric volume occupying device may have a sphere or spheroid shape, or any other shape designed to occupy volume within a stomach. In certain embodiments, the intragastric volume occupying device may be configured to be filled with fluid, to cause the device to take up a larger amount of space within the stomach 34. In other embodiments, the intragastric volume occupying device may include any other material that may occupy space within the stomach 34, including an expandable scaffold structure, an expandable foam structure, or the like. The implant device 62 in an intragastric volume occupying device embodiment is designed to treat obesity by reducing the effective size of the stomach, and causing a patient to feel full more quickly when eating food. The patient consumes less food and subsequently loses weight.

The implant device 62 in the embodiment shown in FIG. 20 may be implanted in a similar manner as shown in FIGS. 11-15, or FIGS. 17-19. Namely, the implant device 62 may be inserted into a patient's gastrointestinal tract endoscopically. In the embodiment shown in FIG. 20, the implant device 62 may be inserted into the patient's stomach 62 in a collapsed state, in which the implant device 62 is sized to pass through the esophagus 32. The implant device 62 may then expand into an expanded state as shown in FIG. 20, in which the implant device 62 is sized to occupy a large amount of volume within the patient's stomach 34. The porous material of the implant device 62 fuses to the mucosal lining of the stomach 34 to anchor the implant device 62 in position.

Figure 21:
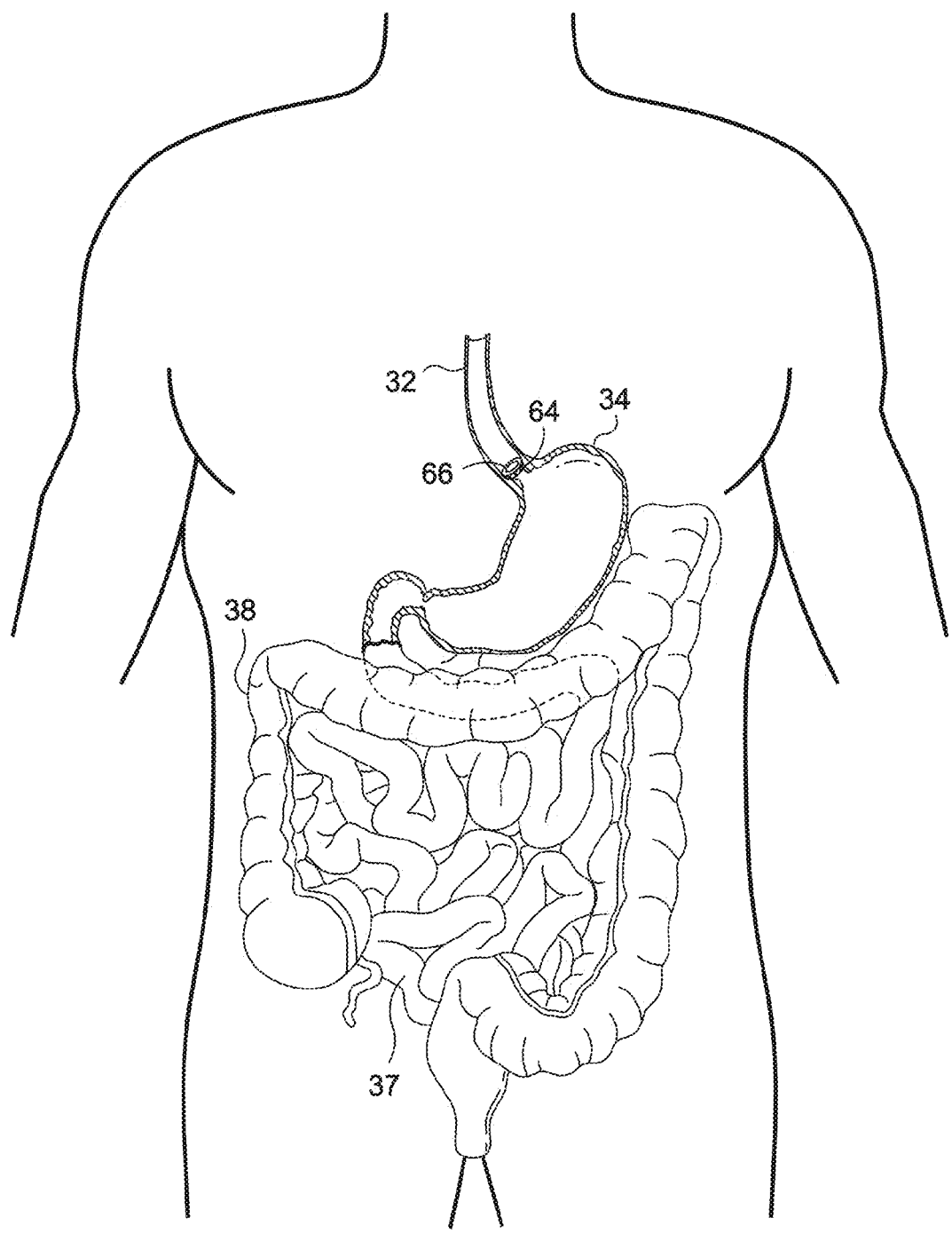
FIG. 21 illustrates an embodiment of an implant device having a porous material in a form disclosed in this application implanted within a patient's gastrointestinal tract.

FIG. 21 illustrates an embodiment of an implant device 64 in which at least a portion of the implant device 64 includes the porous material in a form disclosed in this application, including, but not limited to, a non-resorbable, biocompatible, elastomer matrix defining an array of interconnected pores structured to receive tissue ingrowth from the mucosal lining of the patient's gastrointestinal tract to anchor the implant device to the mucosal lining. The porous material may cover a portion or the entirety of the outer surface of the implant device 64. The implant device 64 in this embodiment comprises a gastric ring configured to form a stoma 66 within the patient's gastrointestinal tract. The gastric ring may comprise an annular shaped device that has an aperture therethrough defining the stoma 66. In certain embodiments, the gastric ring may be capable of varying the size of the stoma 66 to vary the amount of food that may pass through the stoma 66. In certain embodiments, the gastric ring may have any size or shape as desired. The implant device 64 in a gastric ring embodiment is designed to treat obesity by reducing the flow of food to the stomach, and causing a patient to feel full more quickly when eating food. The patient consumes less food and subsequently loses weight.

The implant device 64 in the embodiment shown in FIG. 21 may be implanted in a similar manner as shown in FIGS. 11-15, or FIGS. 17-19. Namely, the implant device 64 may be inserted into a patient's gastrointestinal tract endoscopically. In the embodiment shown in FIG. 21, the implant device 64 may be inserted into the patient's esophagus 32 in a collapsed state, in which the implant device 64 is sized to pass through the esophagus 32. The implant device 64 may then expand into an expanded state shown in FIG. 21, in which the implant device 64 anchors within the patent's esophagus 32, or the esophageal junction between the esophagus 32 and the stomach 34. The porous material of the implant device 64 fuses to the mucosal lining of the patient's esophagus 32, or the esophageal junction between the esophagus 32 and the stomach 34, to anchor the implant device 64 in position.

Figure 22:
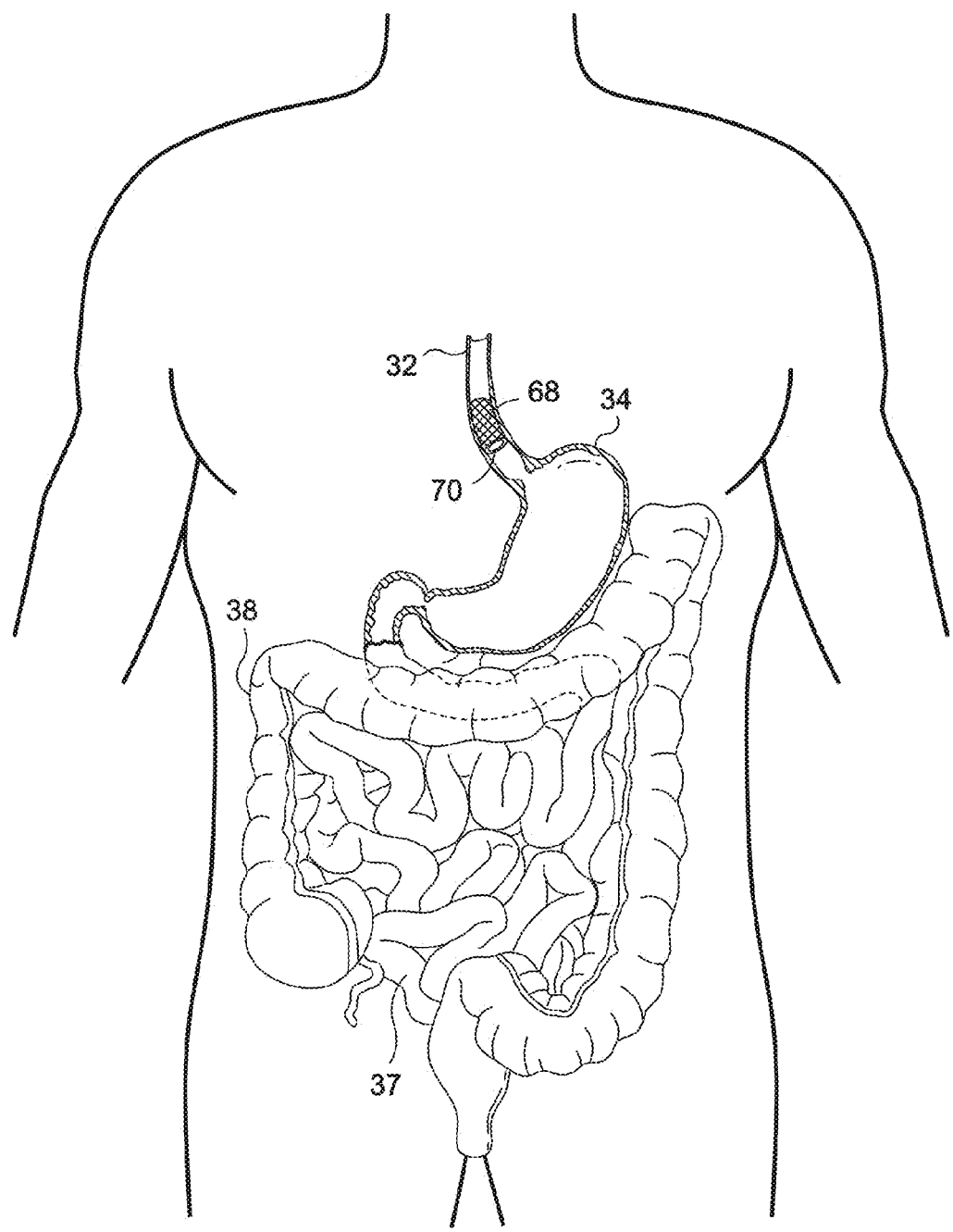
FIG. 22 illustrates an embodiment of an implant device having a porous material in a form disclosed in this application implanted within a patient's gastrointestinal tract.

FIG. 22 illustrates an embodiment of an implant device 68 in which at least a portion of the implant device 68 includes the porous material in a form disclosed in this application, including, but not limited to, a non-resorbable, biocompatible, elastomer matrix defining an array of interconnected pores structured to receive tissue ingrowth from the mucosal lining of the patient's gastrointestinal tract to anchor the implant device to the mucosal lining. The porous material may cover a portion or the entirety of the outer surface of the implant device 68. The implant device 68 in this embodiment comprises a stent configured to form a stoma 70 within the patient's gastrointestinal tract. The stent may comprise a sleeve having a diaphragm at one end, with an aperture therethrough defining the stoma 70. In certain embodiments, the stent may be capable of varying the size of the stoma 70 to vary the amount of food that may pass through the stoma 70. In certain embodiments, the stent may have any size or shape as desired. The implant device 68 in a stent embodiment is designed to treat obesity by reducing the flow of food to the stomach, and causing a patient to feel full more quickly when eating food. The patient consumes less food and subsequently loses weight.

The implant device 68 in the embodiment shown in FIG. 22 may be implanted in a similar manner as shown in FIGS. 11-15, or FIGS. 17-19. Namely, the implant device 68 may be inserted into a patient's gastrointestinal tract endoscopically. In the embodiment shown in FIG. 22, the implant device 68 may be inserted into the patient's esophagus 32 in a collapsed state, in which the implant device 68 is sized to pass through the esophagus 32. The implant device 68 may then expand into an expanded state shown in FIG. 22, in which the implant device 68 anchors within the patient's esophagus 32, or the esophageal junction between the esophagus 32 and the stomach 34. The porous material of the implant device 68 fuses to the mucosal lining of the patient's esophagus 32, or the esophageal junction between the esophagus 32 and the stomach 34, to anchor the implant device 68 in position.

Figure 23:
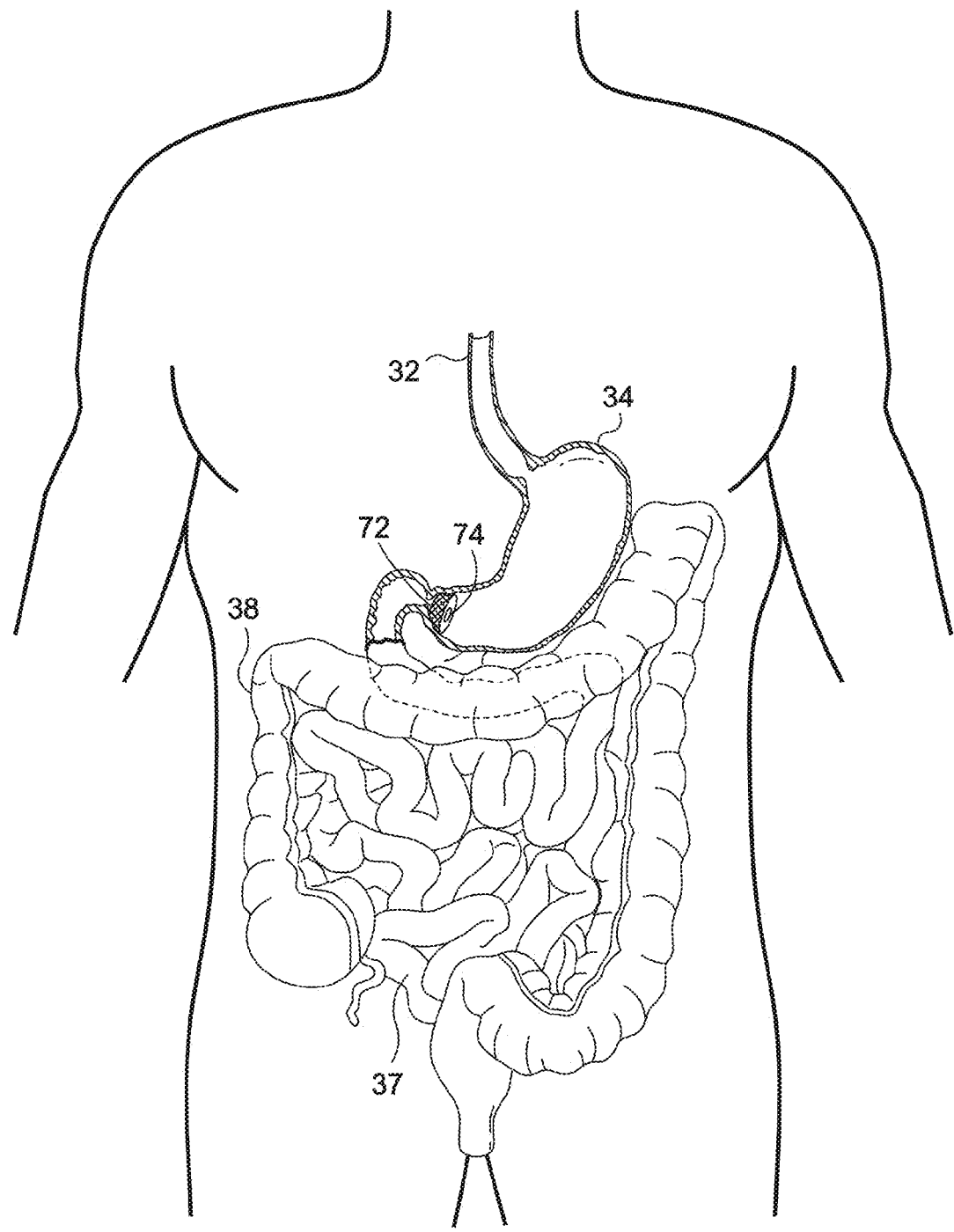
FIG. 23 illustrates an embodiment of an implant device having a porous material in a form disclosed in this application implanted within a patient's gastrointestinal tract.

FIG. 23 illustrates an embodiment of an implant device 72 in which at least a portion of the implant device 72 includes the porous material in a form disclosed in this application, including, but not limited to, a non-resorbable, biocompatible, elastomer matrix defining an array of interconnected pores structured to receive tissue ingrowth from the mucosal lining of the patient's gastrointestinal tract to anchor the implant device to the mucosal lining. The porous material may cover a portion or the entirety of the outer surface of the implant device 72. The implant device 72 in this embodiment comprises a sleeve configured to form a stoma 74 within the patient's gastrointestinal tract. The sleeve may have a diaphragm at one end, with an aperture therethrough defining the stoma 74. In certain embodiments, the sleeve may be capable of varying the size of the stoma 74 to vary the amount of food that may pass through the stoma 74. In certain embodiments, the sleeve may have any size or shape as desired. The implant device 72 in the sleeve embodiment is designed to treat obesity by reducing the flow of food to the intestines 37, 38, and causing a patient's stomach to remain full for a longer period of time than without the implant device 72. In addition, a portion of the sleeve may reduce the amount of food that contacts the intestines 37, 38, reducing the efficiency of food absorption by the patient's body, thereby reducing caloric intake and causing the patient to lose weight.

The implant device 72 in the embodiment shown in FIG. 23 may be implanted in a similar manner as shown in FIGS. 11-15, or FIGS. 17-19. Namely, the implant device 72 may be inserted into a patient's gastrointestinal tract endoscopically. In the embodiment shown in FIG. 23, the implant device 72 may be inserted into the patient's esophagus 32 in a collapsed state, in which the implant device 72 is sized to pass through the esophagus 32. The implant device 68 may then extend into position within the patient's intestines 37, 38. The implant device 72 may anchor around the stomach's 34 pyloric valve, or the connection between the stomach 34 and the duodenum of the small intestine 37, as shown in FIG. 23. The porous material of the implant device 72 fuses to the mucosal lining of the patient's stomach 34, small intestines 37, or large intestines 38, to anchor the implant device 72 in position.

Figure 24:
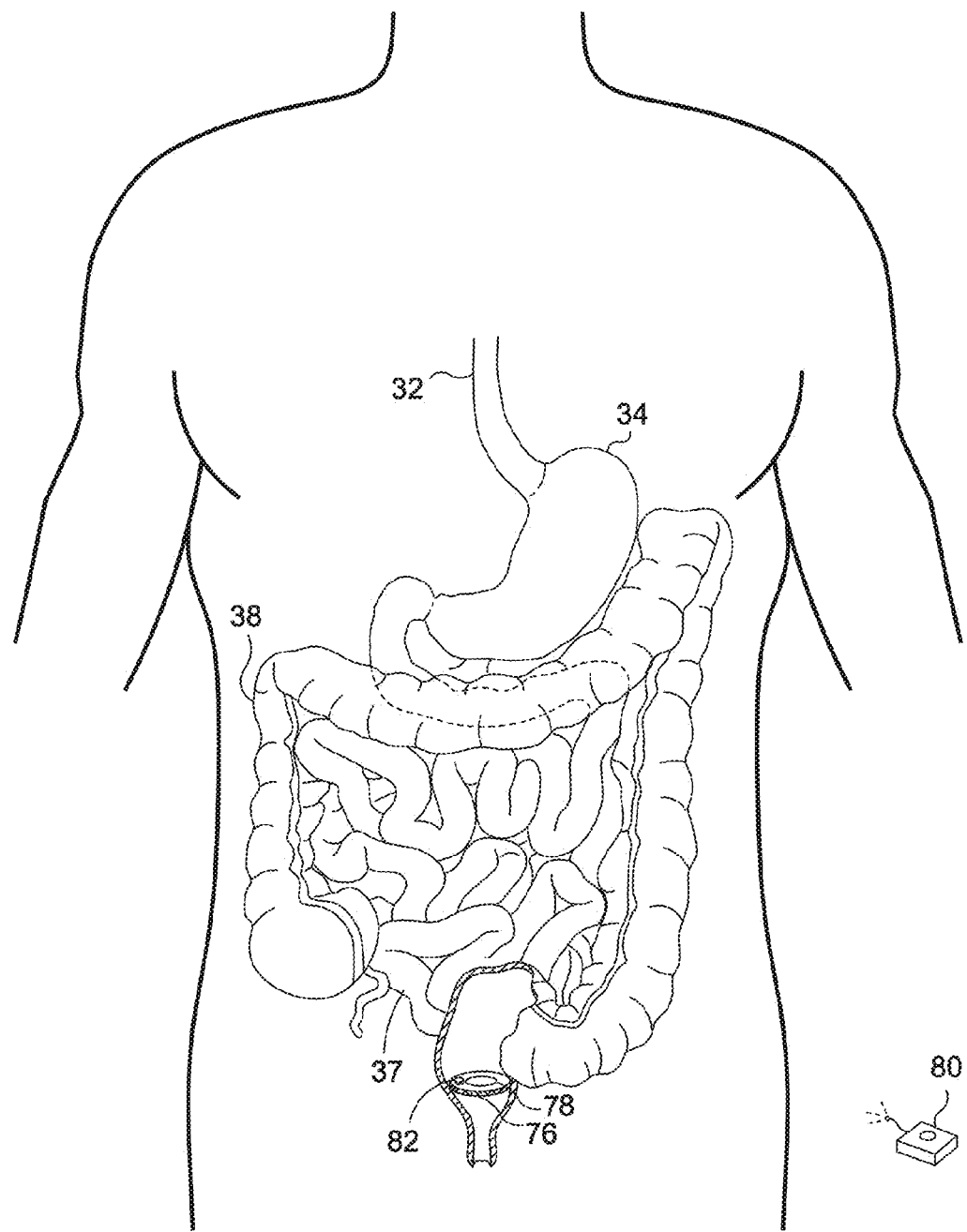
FIG. 24 illustrates an embodiment of an implant device having a porous material in a form disclosed in this application implanted within a patient's gastrointestinal tract.

FIG. 24 illustrates an embodiment of an implant device 76 in which at least a portion of the implant device 76 includes the porous material in a form disclosed in this application, including, but not limited to, a non-resorbable, biocompatible, elastomer matrix defining an array of interconnected pores structured to receive tissue ingrowth from the mucosal lining of the patient's gastrointestinal tract to anchor the implant device to the mucosal lining. The porous material may cover a portion or the entirety of the outer surface of the implant device 76. The implant device 76 in this embodiment comprises an artificial sphincter configured to form a stoma 78 within the patient's gastrointestinal tract. The sphincter has an aperture therethrough defining the stoma 78. In certain embodiments, the sphincter may be capable of varying the size of the stoma 78 to vary the amount of fecal matter that exits through the patient's anus 60. In certain embodiments, the sphincter may have any size or shape as desired. In certain embodiments, the sphincter may be controlled remotely through a remote control device 80. The remote control device 80 may communicate with a receiver 82 within the patient's body that operates to control the size of the stoma 78. A user may then remotely and selectively control the size of the stoma 78, to determine when and how much fecal matter should pass through the stoma 78.

The implant device 76 in the embodiment shown in FIG. 24 may be implanted in a similar manner as shown in FIGS. 11-15, or FIGS. 17-19. Namely, the implant device 76 may be inserted into a patient's gastrointestinal tract endoscopically. In the embodiment shown in FIG. 24, the implant device 76 may be inserted into the patient's gastrointestinal tract in a collapsed state, in which the implant device 76 is sized to pass through the patient's anus 60, for example. The implant device 76 may then extend into position within the patient's large intestines 38, including the rectum. The implant device 76 may anchor within the walls of the patient's rectum. The porous material of the implant device 76 fuses to the mucosal lining of the patient's large intestine 38, to anchor the implant device 76 in position.

Figure 25:
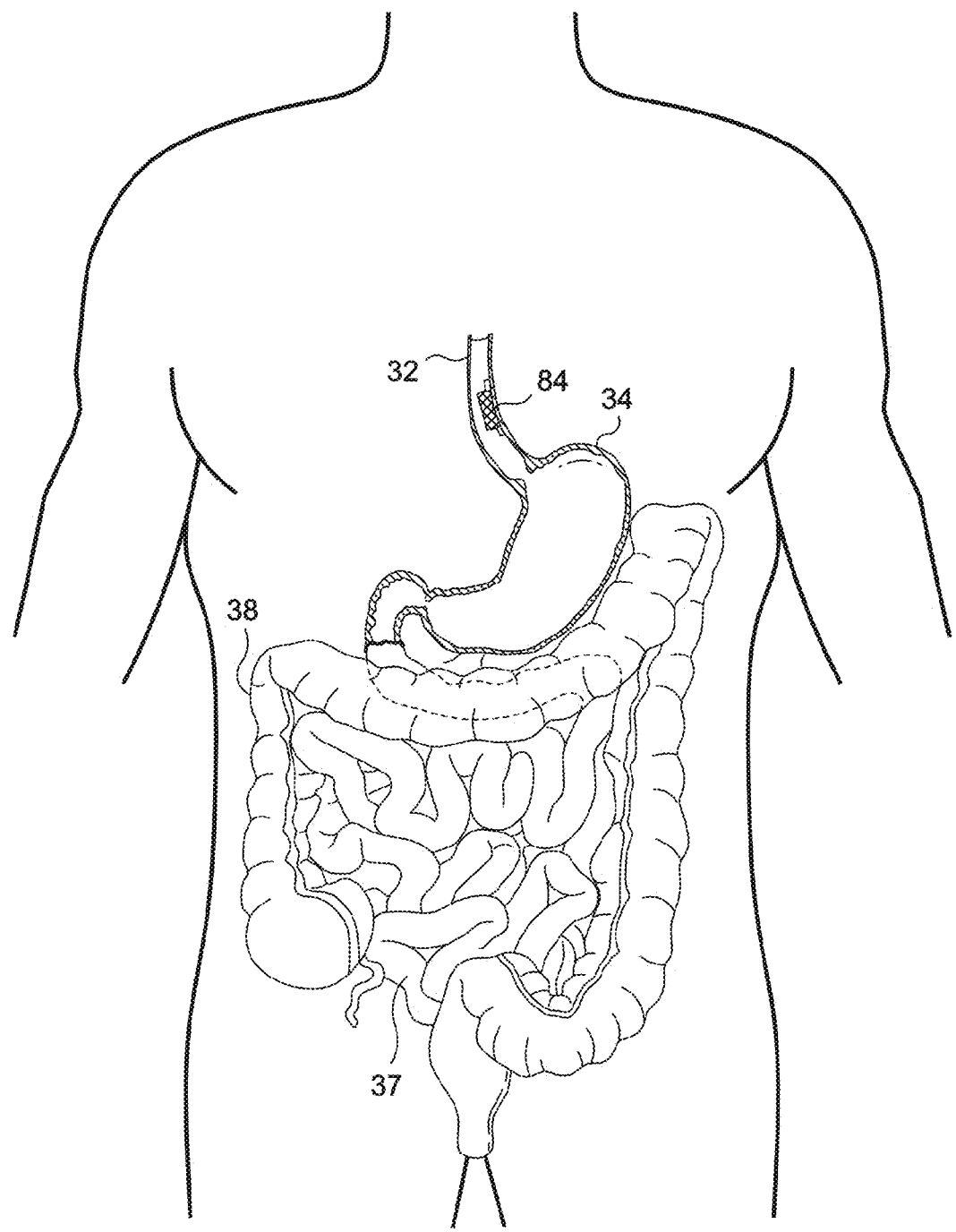
FIG. 25 illustrates an embodiment of an implant device having a porous material in a form disclosed in this application implanted within a patient's gastrointestinal tract.

FIG. 25 illustrates an embodiment of an implant device 84 in which at least a portion of the implant device 84 includes the porous material in a form disclosed in this application, including, but not limited to, a non-resorbable, biocompatible, elastomer matrix defining an array of interconnected pores structured to receive tissue ingrowth from the mucosal lining of the patient's gastrointestinal tract to anchor the implant device to the mucosal lining. The porous material may cover a portion or the entirety of the outer surface of the implant device 84. The implant device 84 in this embodiment comprises a tissue graft configured to restore tissue within the patient's gastrointestinal tract.

The implant device 84 in the embodiment shown in FIG. 25 may be implanted in a similar manner as shown in FIGS. 11-15, or FIGS. 17-19. Namely, the implant device 84 may be inserted into a patient's gastrointestinal tract endoscopically. In the embodiment shown in FIG. 25, the implant device 84 may be inserted into the patient's esophagus 32 in a collapsed state, in which the implant device 84 is sized to pass through the esophagus 32. The implant device 84 may then be extended into position within the desired portion of the gastrointestinal tract, for example, the esophagus 32. The porous material of the implant device 84 fuses to the mucosal lining of the patient's gastrointestinal tract to anchor the implant device 84 in position.

Figure 26:
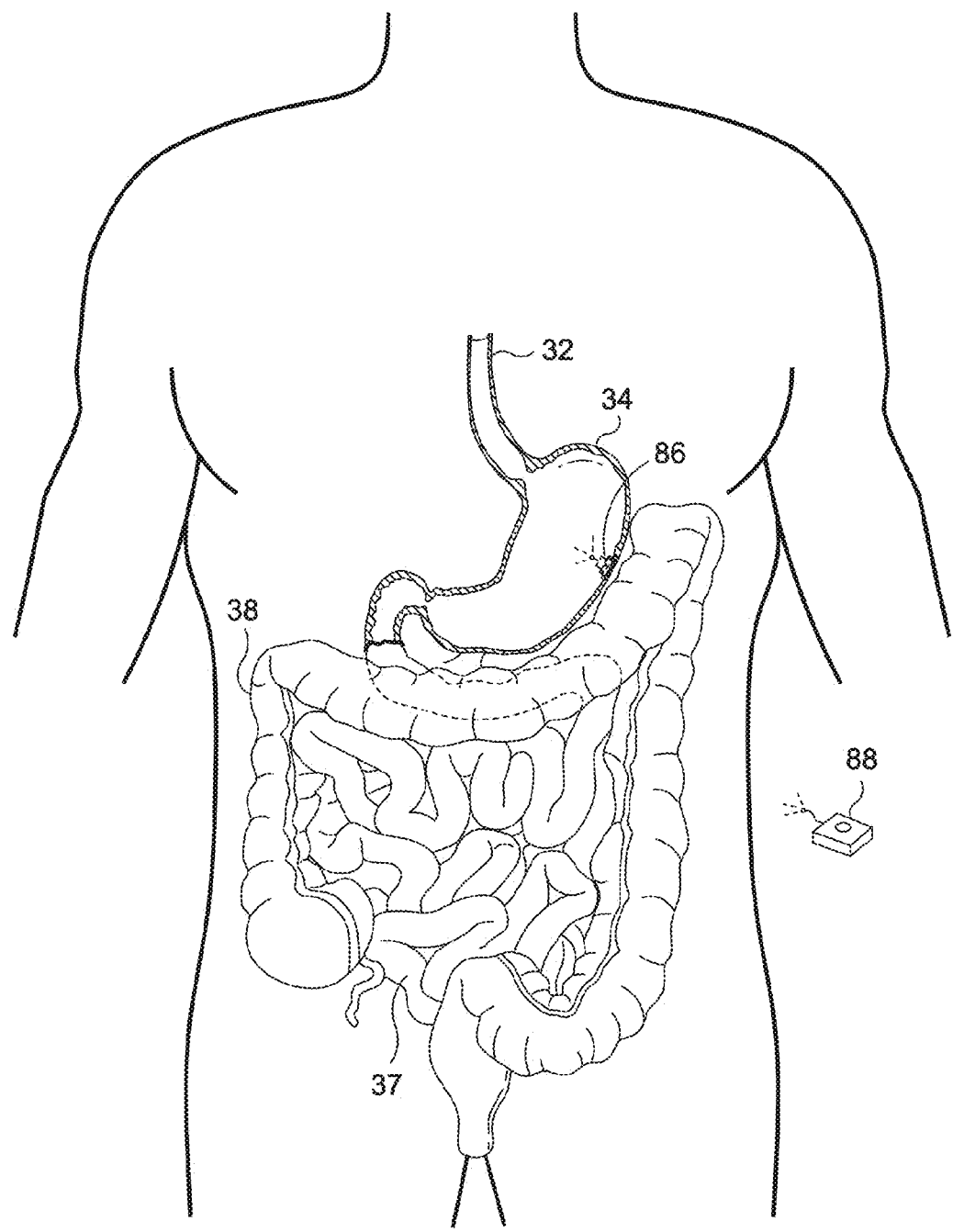
FIG. 26 illustrates an embodiment of an implant device having a porous material in a form disclosed in this application implanted within a patient's gastrointestinal tract.

FIG. 26 illustrates an embodiment of an implant device 86 in which at least a portion of the implant device 86 includes the porous material in a form disclosed in this application, including, but not limited to, a non-resorbable, biocompatible, elastomer matrix defining an array of interconnected pores structured to receive tissue ingrowth from the mucosal lining of the patient's gastrointestinal tract to anchor the implant device to the mucosal lining. The porous material may cover a portion or the entirety of the outer surface of the implant device 86. The implant device 86 in this embodiment comprises a sensor configured to sense a biological condition within the patient's body, including within the patient's gastrointestinal tract. The biological condition may include a hormone or other chemical within a patient's body, or any other biological condition within the patient's body. The sensor may communicate wirelessly with a receiver 88 positioned outside the patient's body, to receive data produced by the sensor.

The implant device 86 in the embodiment shown in FIG. 26 may be implanted in a similar manner as shown in FIGS. 11-15, or FIGS. 17-19. Namely, the implant device 86 may be inserted into a patient's gastrointestinal tract endoscopically. In the embodiment shown in FIG. 26, the implant device 86 may be inserted into the patient's esophagus 32 in a collapsed state, in which the implant device 86 is sized to pass through the esophagus 32. The implant device 86 may then be extended into position within the desired portion of the gastrointestinal tract, for example, the stomach 34. The porous material of the implant device 86 fuses to the mucosal lining of the patient's gastrointestinal tract to anchor the implant device 86 in position.

EXAMPLES

The following examples illustrate representative embodiments now contemplated, but should not be construed to limit the disclosed porous materials, methods of forming such porous materials, biocompatible implantable devices comprising such porous materials, and methods of making such biocompatible implantable devices.

Example 1

A Method of Making a Porous Material Sheet

This example illustrates how to make a sheet of porous material using the porogen compositions disclosed herein.

To coat porogens with a substance, an appropriate amount of porogens comprising a sugar core of about 335 μm and a polyethylene glycol shell of about 15 μm were mixed with an appropriate amount of about 35% (v/v) silicon in xylene (PN-3206-1; NuSil Technology LLC, Carpinteria, Calif.). In other experiments, the porogen composition used were porogens comprising a sugar core of about 335 μm and a polyethylene glycol shell of about 53 μm, porogens comprising a sugar core of about 390 μm and a polyethylene glycol shell of about 83 μm, or porogens comprising a sugar core of about 460 μm and a polyethylene glycol shell of about 104 μm. The mixture was filtered through a 43 μm sieve to remove the excess silicone and was poured into an about 20 cm×20 cm square mold coated with a non-stick surface.

To treat a substance coated porogen mixture to allow fusing of the porogens to form a porogen scaffold and stabilization of the substance, the porogen/silicone mixture was placed into an oven and heated at a temperature of about 75° C. for about 60 min, and then about 126° C. for about 75 minutes. In another experiment, the porogen/silicone mixture was treated by placing into an oven and heated at a temperature of about 126° C. for about 75 minutes, or heated at a temperature of about 145° C. for about 150 minutes, or heated at a temperature of about 126° C. for about 85 min, and then about 30° C. for about 60 minutes. After curing, the sheet of cured elastomer coated porogen scaffold was removed.

To remove a porogen scaffold from the cured substance, the cured elastomer/porogen scaffold was immersed in hot water. After about 30 minutes, the hot water was removed and the resulting 20 cm×20 cm×1.5 mm sheet of porous material was air dried at an ambient temperature of about 18° C. to about 22° C. This process results in a porous material sheet as disclosed herein.

A sample from the sheet of porous material can be characterized by microCT analysis and/or scanning electron microscopy (SEM).

Example 2

A Method of Making a Porous Material Sheet

This example illustrates how to make a sheet of porous material using the porogen compositions disclosed herein.

To coat porogens with a substance, an appropriate amount of porogens were mixed with an appropriate amount of about 35% (v/v) silicon in xylene (PN-3206-1; NuSil Technology LLC, Carpinteria, Calif.). The porogens comprised a core of about 450 µm to about 500 µm in diameter comprising sucrose and corn starch and a PEG shell of about 50 µm to about 75 µm in depth, for a mean porogen diameter of about 550 µm. The mixture was filtered through a 43 µm sieve to remove the excess silicone and was poured into an about 30 cm×30 cm square mold coated with a non-stick surface.

To treat a substance coated porogen mixture to allow fusing of the porogens to form a porogen scaffold and stabilization of the substance, the porogen/silicone mixture was placed into an oven and heated at a temperature of about 126° C. for about 75 minutes. In another experiments, the porogen/silicone mixture was treated by placing into an oven and heated at a temperature of about 126° C. for about 60 minutes to about 90 minutes. After curing, the sheet of cured elastomer coated porogen scaffold was removed.

To remove a porogen scaffold from the cured substance, the cured elastomer/porogen scaffold was immersed in hot water. After about 30 minutes, the hot water was removed and the resulting 30 cm×30 cm×2 mm sheet of porous material was air dried at an ambient temperature of about 18° C. to about 22° C. This process results in a porous material sheet as disclosed herein.

A sample from the sheet of porous material can be characterized by microCT analysis and/or scanning electron microscopy (SEM).

Example 3

A Method of Making a Biocompatible Implantable Device Comprising a Porous Material This example illustrates how to make a biocompatible implantable device comprising a porous material formed using the porogen compositions disclosed herein.

Sheets of porous material comprising an elastomer matrix defining an interconnected array of pores is obtained as described in Example 1 or 2.

To attach a porous material to a biocompatible implantable device, a first porous material sheet is coated with a thin layer of silicone and then placed in the bottom cavity of a mold, adhesive side up. A biocompatible implantable device is then placed on top of the material surface coated with the adhesive. A second porous material sheet is then coated with a thin layer of silicone and applied to the uncovered surface of the biocompatible implantable device. The top piece of the mold cavity is then fixed in place pressing the two material sheets together creating a uniform interface. The silicone adhesive is allowed to cure by placing the covered device into an oven and heated at a temperature of about 126° C. for about 75 minutes. After curing, excess material is trimmed off creating a uniform seam around the biocompatible implantable device. This process results in a biocompatible implantable device 10 as disclosed herein, for example in FIGS. 4A-4D. FIG. 4A is a top view of an implantable device covered with a porous material 10. FIG. 4B is a side view of an implantable device covered with a porous material 10 to show a bottom 12 of the implantable device 10 and a top 14 of the implantable device 10. FIGS. 4C and 4D illustrate the cross-sectional view of the biocompatible implantable device covered with a porous material 10 to show an implantable device 16, a porous material layer 20 including an internal surface 22 and an external surface 24, where the internal surface 22 is attached to an implantable device surface 18. Due to the presence of the porous material on the device surface of the biocompatible implantable device there will be a reduction or prevention of the formation of fibrous capsules that can result in capsular contracture or scarring.

Alternatively, the porous material can be laminated onto a biocompatible implantable device while the device is still on a mandrel. In this process, a first porous material sheet is coated with a thin layer of silicone and then draped over the device on the mandrel in such a way that there are no wrinkles on the surface. After curing the silicone adhesive, as described above, another coating of silicone is applied to the uncovered surface of the biocompatible implantable device and a second porous material is stretched up to cover the back of the device. After curing the silicone adhesive, as described above, the biocompatible implantable device is then taken off the mandrel and the excess porous material is trimmed to create a uniform seam around the device. This process results in a biocompatible implantable device comprising a porous material as disclosed herein. See, e.g., FIG. 4A-4D.

Example 4

A Method of Making a Porous Material Shell

This example illustrates how to make a porous material shell using the porogen compositions disclosed herein.

To coat porogens with a substance, an appropriate amount of a porogen composition comprising a sugar core of about 335 µm and a polyethylene glycol shell of about 53 µm are mixed with an appropriate amount of about 35% (v/v) silicon in xylene (PN-3206-1; NuSil Technology LLC, Carpinteria, Calif.). In other experiments, the porogen composition used are porogens comprising a sugar core of about 335 µm and a polyethylene glycol shell of about 65 µm, porogens comprising a sugar core of about 320 µm and a polyethylene glycol shell of about 30 µm, or porogens comprising a sugar core of about 350 µm and a polyethylene glycol shell of about 50 µm. Alternatively, porogens comprising a core of about 450 µm to about 500 µm in diameter comprising sucrose and corn starch and a PEG shell of about 50 µm to about 75 µm in depth, for a mean porogen diameter of about 550 µm may be used. The mixture is filtered through a 43 µm sieve to remove the excess silicone.

To pour a substance coated porogen mixture into a mold, the filtered elastomer coated porogen mixture is poured into a mold in the shape of a breast implant shell and the mold is mechanically agitated to pack firmly the mixture. The thickness of the shell is controlled based upon the design of the shell mold.

To treat a substance coated porogen mixture to allow fusing of the porogens to form a porogen scaffold and cure the elastomer, the porogen/silicone mixture is placed into an oven and is heated at a temperature of about 75° C. for about 45 min, and then about 126° C. for about 75 minutes. In another experiment, the porogen/silicone mixture is treated by placing into an oven and heated at a temperature of about 126° C. for about 75 minutes, or heated at a temperature of about 145° C. for about 60 minutes. After treating, the shell mold is dismantled and the cured elastomer coated porogen scaffold is removed.

Figure 5A:
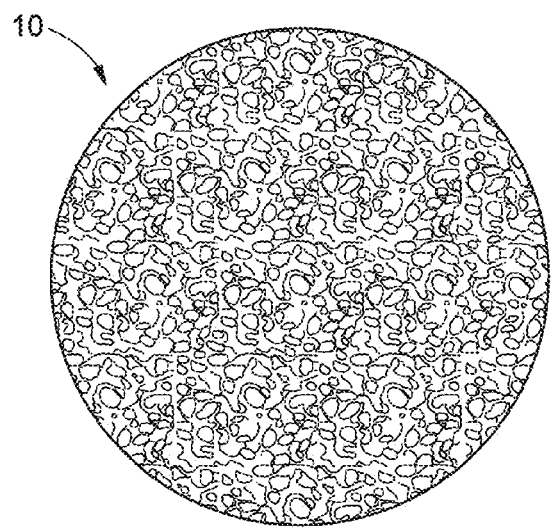
FIG. 5A is a top view of a material shell.
Figure 5B:
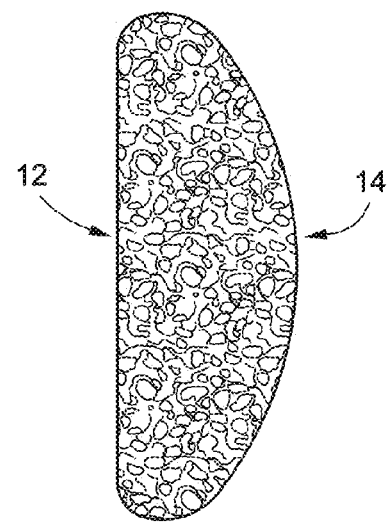
FIG. 5B is a side view of a material shell.
Figure 5C:
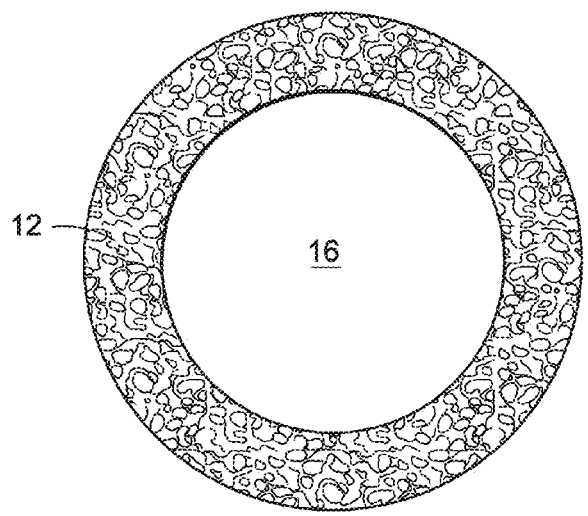
FIG. 5C is a bottom view of a material shell.
Figure 5D:
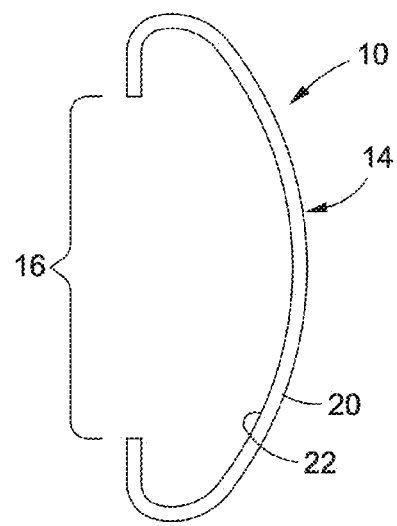
FIG. 5D illustrates the cross-sectional view of the material shell.

To remove a porogen scaffold from the cured substance, the cured elastomer/porogen scaffold is immersed in hot water. After about 3 hours, the hot water is removed and the resulting shell of porous material is dried in an oven of about 126° C. for 30 minutes. This process results in a porous material shell 10 as disclosed herein, for example in FIGS. 5A-5D. FIG. 5A is a top view of a material shell 10. FIG. 5B is a side view of a material shell 10 to show a bottom 12 of the material shell 10 and a top 14 of the material shell 10. FIG. 5C is a bottom view of a material shell 10 to show a hole 16 from which a biocompatible implantable device may be subsequently inserted through. FIG. 5D illustrate the cross-sectional view of the material shell 10 to show the hole 16, an internal surface 20 of the material shell 10 and an external surface 22 of the material shell 10.

A sample from the sheet of porous material can be characterized by microCT analysis and/or scanning electron microscopy (SEM).

Example 5

A Method of Making a Biocompatible Implantable Device Comprising a Porous Material This example illustrates how to make a biocompatible implantable device comprising a porous material formed using the porogen compositions disclosed herein.

A porous material shell comprising a matrix defining an interconnected array of pores is obtained as described in Example 4.

Figure 6A:
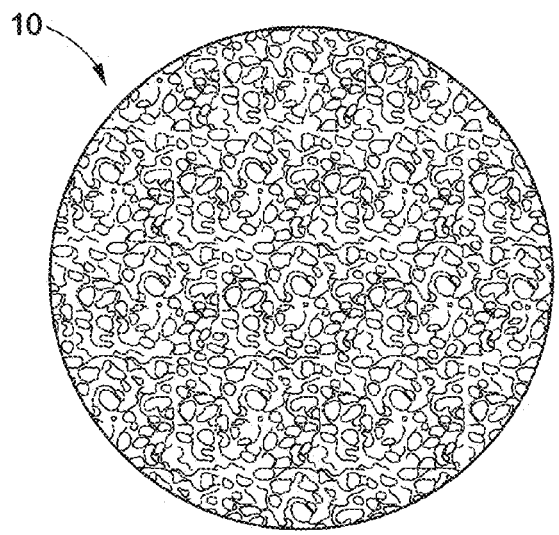
FIG. 6A is a top view of an implantable device covered with a porous material.
Figure 6B:
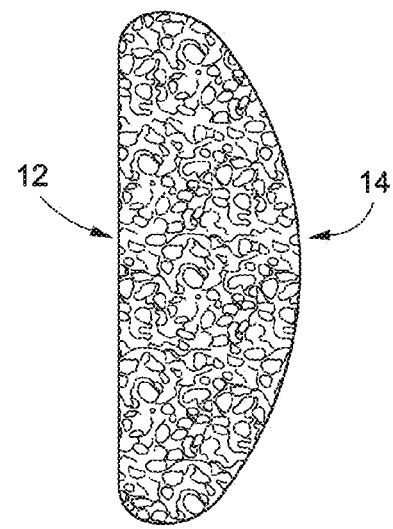
FIG. 6B is a side view of an implantable device covered with a porous material.
Figure 6C:
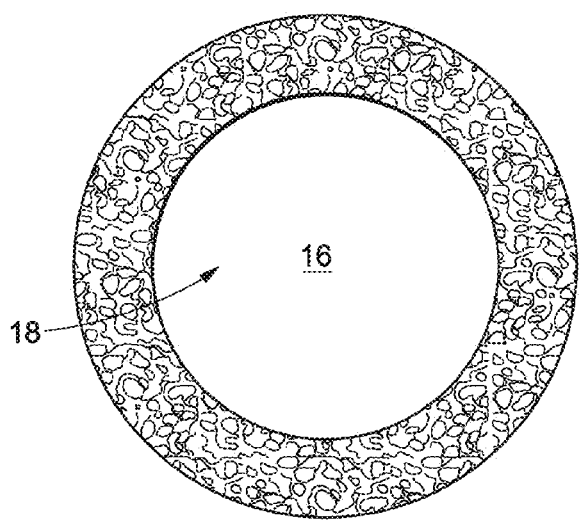
FIG. 6C is a bottom view of a biocompatible implantable device covered with a porous material.
Figure 6D:
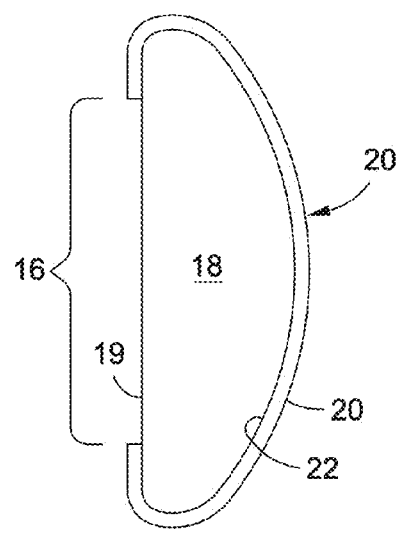
FIG. 6D illustrates the cross-sectional view of the biocompatible implantable device covered with a porous material.

To attach the porous material shell to a biocompatible implantable device, the surface of the device is coated with a thin layer of silicone. The material shell is then placed over the adhesive coated device in a manner that ensures no wrinkles in the material form. The silicone adhesive is allowed to cure by placing the covered device into an oven and heating at a temperature of 126° C. for 75 minutes. After curing, excess material is trimmed off creating a uniform seam around the biocompatible implantable device. This process results in a biocompatible implantable device comprising a porous material 10 as disclosed herein, for example FIGS. 6A-6D. FIG. 6A is a top view of an implantable device covered with a porous material 10. FIG. 6B is a side view of an implantable device covered with a porous material 10 to show a bottom 12 of the implantable device 10 and a top 14 of the implantable device 10. FIG. 6C is a bottom view of a biocompatible implantable device covered with a porous material 10 to show a hole 16 and an implantable device 18. FIG. 6D illustrates the cross-sectional view of the biocompatible implantable device covered with a porous material 10 to show an implantable device 18, a porous material layer 20 including an internal surface 22 and an external surface 24, where the internal surface 22 is attached to implantable device surface 19. Due to the presence of the porous material on the device surface of the biocompatible implantable device there will be a reduction or prevention of the formation of fibrous capsules that can result in capsular contracture or scarring.

Example 6

A Method of Making an Implant Comprising a Porous Material

This example illustrates how to make an implant comprising a porous material disclosed herein of about 0.5 mm to about 1.5 mm in thickness.

To preparing the surface of a device to receive a porous material, a base layer of 35% (w/w) silicon in xylene (PN-3206-1; NuSil Technology LLC, Carpinteria, Calif.) was coated on a mandrel (LR-10), placed into an oven, and cured at a temperature of about 126° C. for about 75 minutes. Alternatively, a previously made biocompatible implantable device, such as, e.g., a base shell disclosed herein, can be attached to a mandrel and then processed beginning with the next step.

To coat the base layer with a mixture comprising a substance and porogens, the cured base layer was dipped first in about 35% (w/w) silicon in xylene (PN-3206-1; NuSil Technology LLC, Carpinteria, Calif.) and then air dried for about 3 minutes to allow the xylene to evaporate. After xylene evaporation, the mandrel with the uncured silicone was dipped in a porogen composition comprising a sugar core of about 335 µm and a polyethylene glycol shell of about 53 µm until the maximum amount of porogens were absorbed into the uncured silicone. In other experiments, the porogen composition used were porogens comprising a sugar core of about 335 µm and a polyethylene glycol shell of about 60 µm, porogens comprising a sugar core of about 390 µm and a polyethylene glycol shell of about 83 µm, or porogens comprising a sugar core of about 460 µm and a polyethylene glycol shell of about 104 µm. The mandrel with the uncured silicon/porogen coating was air dried for about 60 minutes to allow the xylene to evaporate.

To treat a substance coated porogen mixture to allow fusing of the porogens to form a porogen scaffold and stabilization of the substance, the mandrel coated with the uncured silicone/porogen mixture was placed into an oven and cured at a temperature of about 75° C. for 30 min, and then about 126° C. for 75 minutes. In another experiments, the porogen/silicone mixture was treated by placing into an oven and heated at a temperature of about 126° C. for about 75 minutes, or heated at a temperature of about 145° C. for about 60 minutes.

To remove porogen scaffold, the cured silicon/porogen scaffold was immersed in hot water. After about 3 hours, the hot water was removed and the resulting implant comprising a porous material of about 0.5 mm to about 1.5 mm was dried in an oven of about 126° C. for 30 minutes. This process resulted in a biocompatible implantable device comprising a porous material as disclosed herein. See, e.g., FIGS. 4A-4D and FIGS. 6A-6D.

Figure 27A:
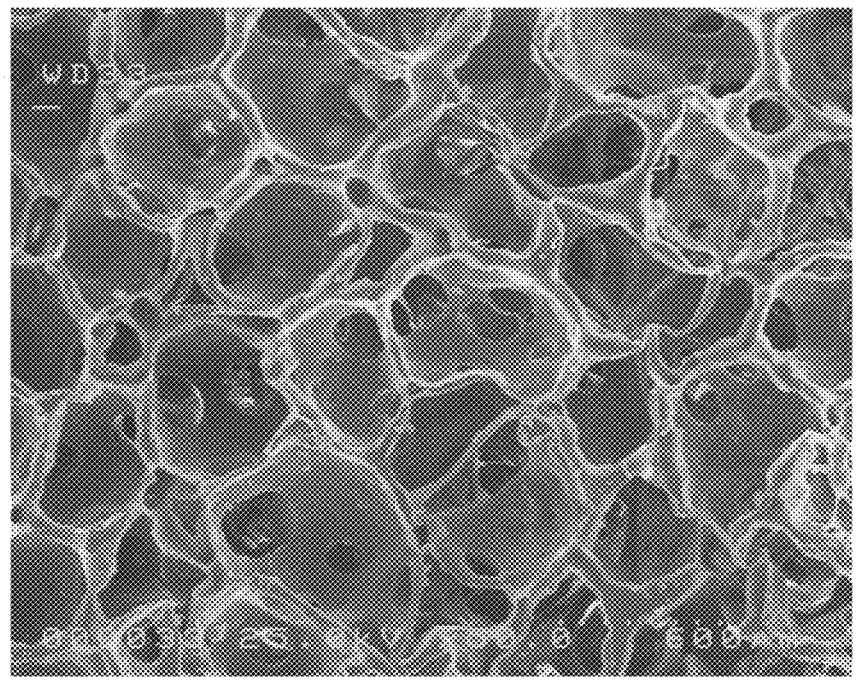
FIG. 27A is scanning electron micrograph image at 50× magnification of the top-view of the porous material.
Figure 27B:
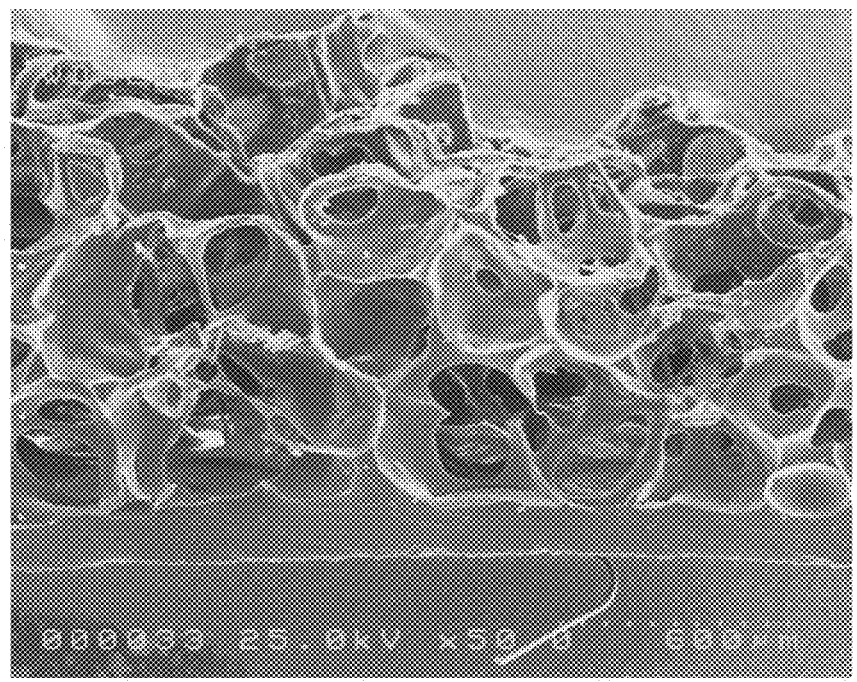
FIG. 27B is scanning electron micrograph image at 50× magnification of the cross-section of the porous material.

A sample from the implant was characterized by microCT analysis. This analysis revealed that the porous material was about 1.4 mm to about 1.6 mm in thickness with a porosity of about 80%, with open pores comprising at least 80% and close pores comprising at most 0.07%. The mean strut thickness was about 90 µm, with a mean pore size of about 400 µm. The porous material has a compressive modulus of about 20 kPa, elongation at break of about 350%, and a tensile strength of about 14 pPa. Scanning electron analysis of the porous material is shown in FIGS. 27A-27B.

To increase the thickness of the porous material covering the base layer, multiple dippings were performed to produce a mandrel coated with multiple layers of an uncured silicone/porogen mixture. Dippings were repeated until the desired thickness is achieved. Examples 7-9 below describe specific examples of this multiple dipping technique.

Example 7

A Method of Making an Implant Comprising a Porous Material

This example illustrates how to make an implant comprising a porous material of about 1 mm to about 2.5 mm in thickness formed using the porogen compositions disclosed herein.

A mandrel comprising a base layer of elastomer was prepared as described in Example 6 or a previously made biocompatible implantable device, such as, e.g., a base shell disclosed herein, can be attached to the mandrel as described in Example 6 and then processed beginning with the next step.

To coat the base layer with a mixture comprising a substance and porogens, the cured base layer was dipped first in about 35% (w/w) silicon in xylene (PN-3206-1; NuSil Technology LLC, Carpinteria, Calif.) and then air dried for about 3 minutes to allow the xylene to evaporate. After xylene evaporation, the mandrel with the uncured silicone was dipped in a porogen composition comprising a sugar core of about 335 μm and a polyethylene glycol shell of about 53 μm until the maximum amount of porogens were absorbed into the uncured silicone. In other experiments, the porogen composition used were porogens comprising a sugar core of about 335 μm and a polyethylene glycol shell of about 60 μm, porogens comprising a sugar core of about 390 μm and a polyethylene glycol shell of about 83 μm, or porogens comprising a sugar core of about 460 μm and a polyethylene glycol shell of about 104 μm. The mandrel with the uncured silicon/porogen mixture coating was air dried for about 60 minutes to allow the xylene to evaporate. After xylene evaporation, the mandrel coated with the uncured silicone/porogen mixture was dipped first in about 35% (w/w) silicon in xylene, air dried to allow xylene evaporation (about 3 minutes), and then dipped in porogen composition until the maximum amount of porogens were absorbed into the uncured silicone. The mandrel with the second coating of uncured silicon/porogen mixture was air dried for about 60 minutes to allow the xylene to evaporate.

The mandrel comprising the two coats of uncured silicone/porogen mixture was treating as described in Example 6.

Removal of the porogen scaffold was as described in Example 5, and the resulting implant comprising a porous material of about 1 mm to about 2.5 mm was dried in an oven of about 126° C. for 30 minutes. This process resulted in a biocompatible implantable device comprising a porous material as disclosed herein. See, e.g., FIGS. 4A-4D and FIGS. 6A-6D.

Figure 28A:
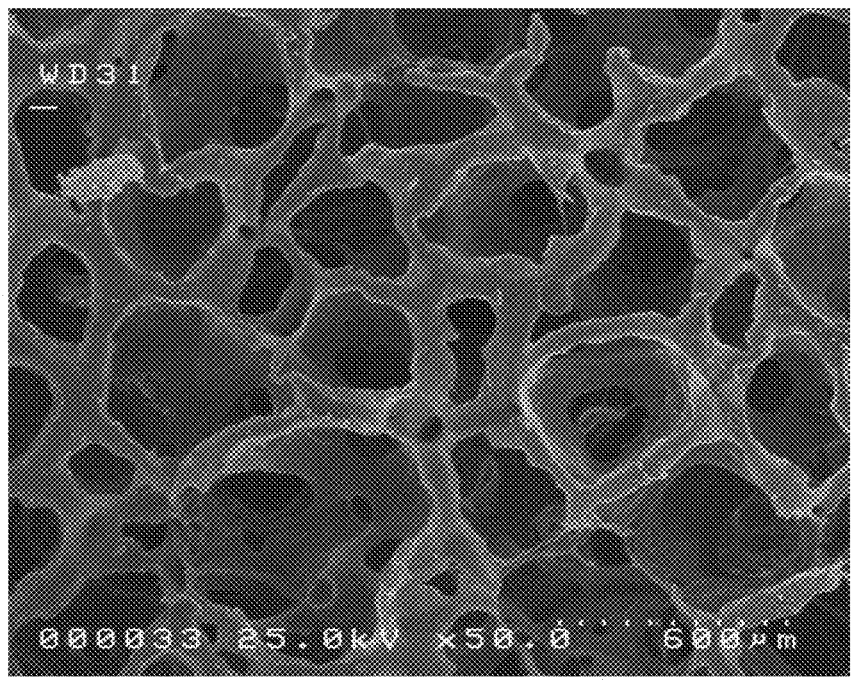
FIG. 28A is scanning electron micrograph image at 50× magnification of the top-view of the porous material.
Figure 28B:
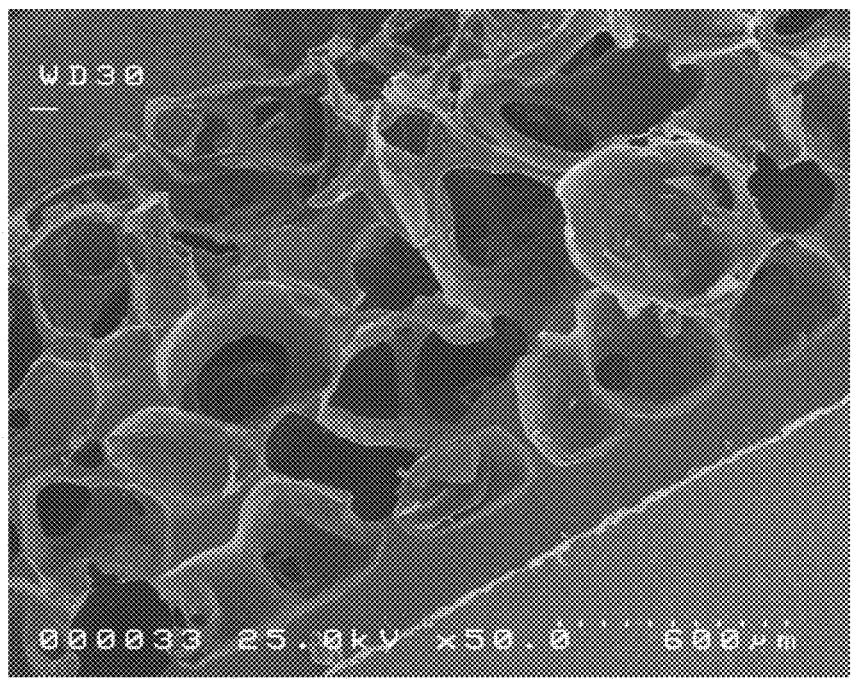
FIG. 28B is scanning electron micrograph image at 50× magnification of the cross-section of the porous material.

A sample from the implant was characterized by microCT analysis. This analysis revealed that the porous material was about 1.0 mm to about 3.0 mm in thickness with a porosity of about 85%, with open pores comprising at least 80% and close pores comprising at most 10%. The mean strut thickness was about 90 μm, with a mean pore size of about 400 μm. The porous material has a compressive modulus of about 20 kPa, elongation at break of about 300%, and a tensile strength of about 14 pPa. Scanning electron analysis of the porous material is shown in FIGS. 28A-28B.

Example 8

A Method of Making an Implant Comprising a Porous Material

This example illustrates how to make an implant comprising a porous material of about 2.5 mm to about 4.5 mm in thickness formed using the porogen compositions disclosed herein.

A mandrel comprising a base layer of elastomer was prepared as described in Example 6 or a previously made biocompatible implantable device, such as, e.g., a base shell disclosed herein, can be attached to the mandrel as described in Example 6 and then processed beginning with the next step.

To coat the base layer with a mixture comprising a substance and porogens, the cured base layer was dipped first in about 35% (w/w) silicon in xylene (PN-3206-1; NuSil Technology LLC, Carpinteria, Calif.) and then air dried for about 3 minutes to allow the xylene to evaporate. After xylene evaporation, the mandrel with the uncured silicone was dipped in a porogen composition comprising a sugar core of about 335 μm and a polyethylene glycol shell of about 53 μm until the maximum amount of porogens were absorbed into the uncured silicone. In other experiments, the porogen composition used were porogens comprising a sugar core of about 335 μm and a polyethylene glycol shell of about 60 μm, porogens comprising a sugar core of about 390 μm and a polyethylene glycol shell of about 83 μm, or porogens comprising a sugar core of about 460 μm and a polyethylene glycol shell of about 104 μm. The mandrel with the uncured silicon/PGLA coating was air dried for about 60 minutes to allow the xylene to evaporate. After xylene evaporation, the mandrel coated with the uncured silicone/porogen mixture was dipped first in about 35% (w/w) silicon in xylene, air dried to allow xylene evaporation (about 3 minutes), and then dipped in the porogen composition until the maximum amount of porogens were absorbed into the uncured silicone. The mandrel with the second coating of uncured silicon/porogen mixture was air dried for about minutes to allow the xylene to evaporate. After xylene evaporation, the mandrel coated with the two layers of the uncured silicone/porogen mixture was dipped first in about 32% (w/w) silicon in xylene, air dried to allow xylene evaporation (about 3 minutes), and then dipped in the porogen composition until the maximum amount of porogens were absorbed into the uncured silicone. The mandrel with the third coating of uncured silicon/porogen mixture was air dried for about 60 minutes to allow the xylene to evaporate.

The mandrel comprising the three coats of uncured silicone/porogen mixture was treating as described in Example 6.

Removal of the porogen scaffold was as described in Example 5, and the resulting implant comprising a porous material of about 2.5 mm to about 4.5 mm was air dried at an ambient temperature of about 18° C. to about 22° C. This process resulted in a biocompatible implantable device comprising a porous material as disclosed herein. See, e.g., FIGS. 4A-4D and FIGS. 6A-6D.

Figure 29A:
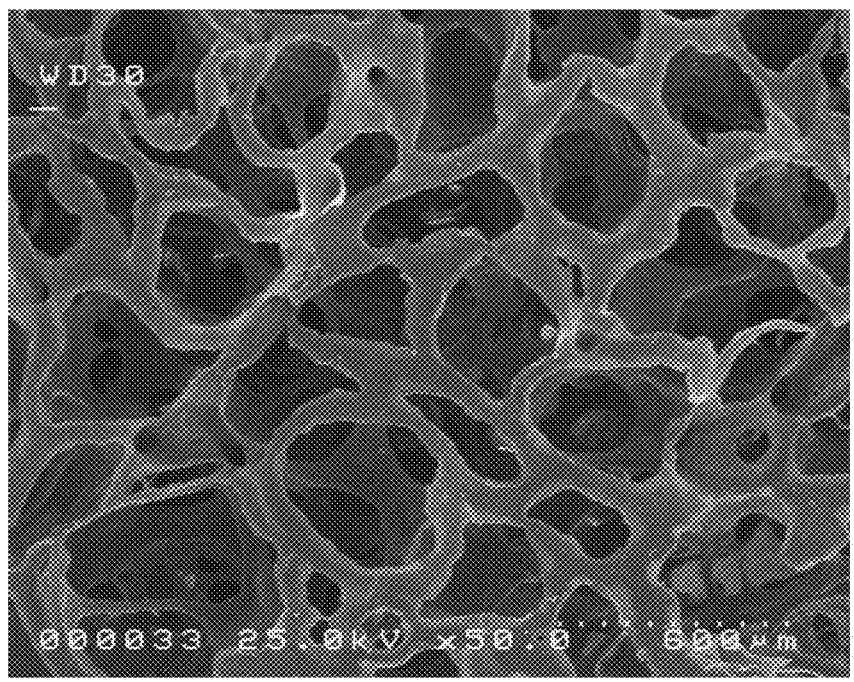
FIG. 29A is scanning electron micrograph image at 50× magnification of the top-view of the porous material.
Figure 29B:
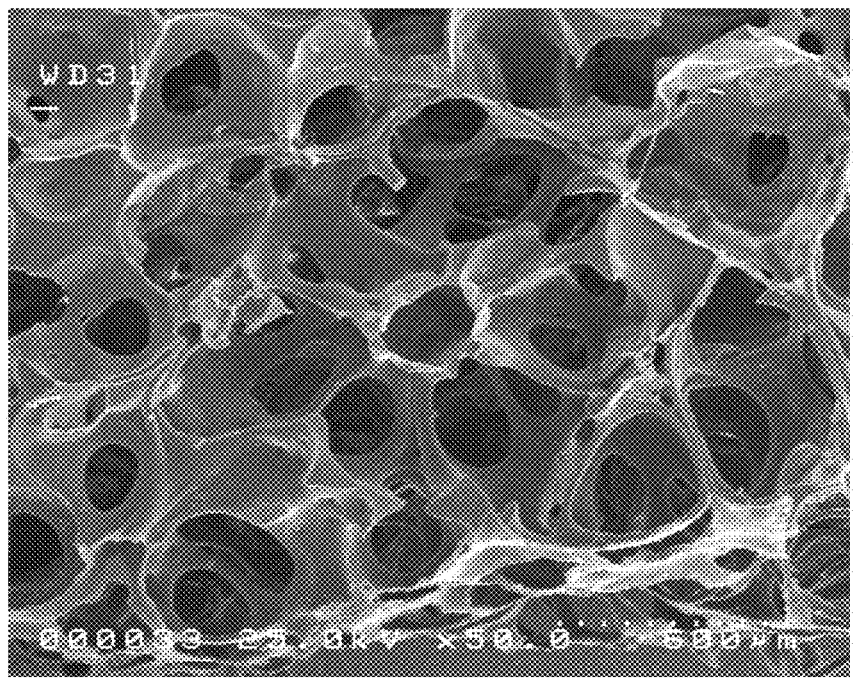
FIG. 29B is scanning electron micrograph image at 50× magnification of the cross-section of the porous material.

A sample from the implant was characterized by microCT analysis. This analysis revealed that the porous material was about 2.0 mm to about 3.0 mm in thickness with a porosity of about 80%, with open pores comprising at least 75% and close pores comprising at most 25%. The mean strut thickness was about 100 μm, with a mean pore size of about 90 μm. Scanning electron analysis of the porous material is shown in FIGS. 29A-29B.

Example 9

A Method of Making an Implant Comprising a Porous Material

This example illustrates how to make an implant comprising a porous material of about 3.5 mm to about 5.5 mm in thickness formed using the porogen compositions disclosed herein.

A mandrel comprising a base layer of elastomer was prepared as described in Example 6 or a previously made biocompatible implantable device, such as, e.g., a base shell disclosed herein, can be attached to the mandrel as described in Example 6 and then processed beginning with the next step.

To coat the base layer with a mixture comprising a substance and porogens, the cured base layer was dipped first in about 35% (w/w) silicon in xylene (PN-3206-1; NuSil Technology LLC, Carpinteria, Calif.) and then air dried for about 3 minutes to allow the xylene to evaporate. After xylene evaporation, the mandrel with the uncured silicone was dipped in a porogen composition comprising a sugar core of about 335 µm and a polyethylene glycol shell of about 53 µm until the maximum amount of porogens were absorbed into the uncured silicone. In other experiments, the porogen composition used were porogens comprising a sugar core of about 335 µm and a polyethylene glycol shell of about 60 µm, porogens comprising a sugar core of about 390 µm and a polyethylene glycol shell of about 80 µm, or porogens comprising a sugar core of about 460 µm and a polyethylene glycol shell of about 104 µm. The mandrel with the uncured silicon/porogen mixture coating was air dried for about 60 minutes to allow the xylene to evaporate. After xylene evaporation, the mandrel coated with the uncured silicone/porogen mixture was dipped first in about 35% (w/w) silicon in xylene, air dried to allow xylene evaporation (about 3 minutes), and then dipped in the porogen composition until the maximum amount of porogens were absorbed into the uncured silicone. The mandrel with the second coating of uncured silicon/porogen mixture was air dried for about minutes to allow the xylene to evaporate. After xylene evaporation, the mandrel coated with the two layers of the uncured silicone/porogen mixture was dipped first in about 32% (w/w) silicon in xylene, air dried to allow xylene evaporation (about 3 minutes), and then dipped in the porogen composition until the maximum amount of porogens were absorbed into the uncured silicone. The mandrel with the third coating of uncured silicon/porogen mixture was air dried for about 60 minutes to allow the xylene to evaporate. After xylene evaporation, the mandrel coated with the three layers of the uncured silicone/porogen mixture was dipped first in about 28% (w/w) silicon in xylene, air dried to allow xylene evaporation (about 3 minutes), and then dipped in the porogen composition until the maximum amount of porogens were absorbed into the uncured silicone. The mandrel with the fourth coating of uncured silicon/porogen mixture was air dried for about 60 minutes to allow the xylene to evaporate.

The mandrel comprising the four coats of uncured silicone/porogen mixture was treating as described in Example 6.

Removal of the porogen scaffold was as described in Example 5, and the resulting implant comprising a porous material of about 3.5 mm to about 5.5 mm was dried in an oven of about 126° C. for 30 minutes. This process resulted in a biocompatible implantable device comprising a porous material as disclosed herein. See, e.g., FIGS. 4A-4D and FIGS. 6A-6D.

Figure 30A:
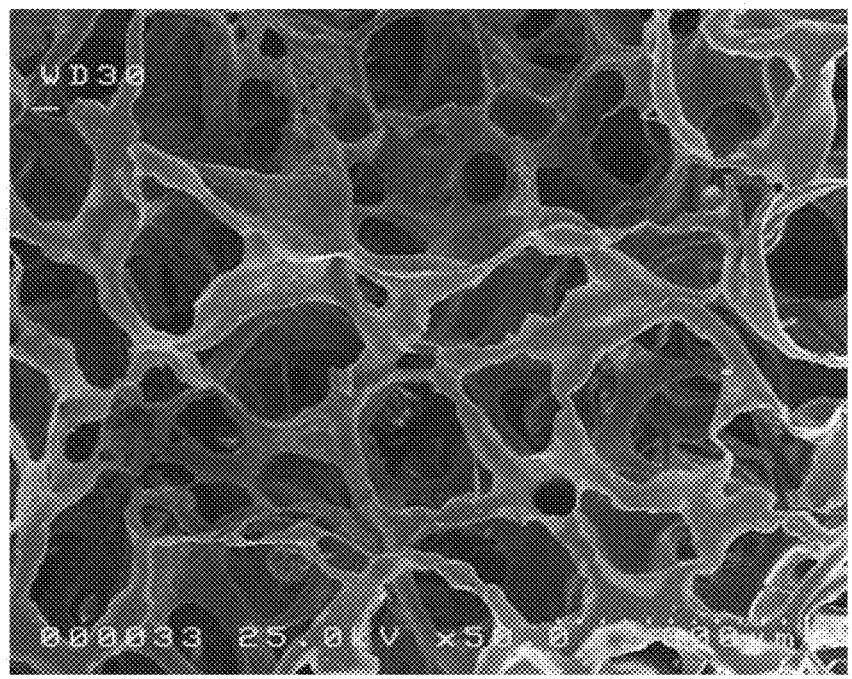
FIG. 30A is scanning electron micrograph image at 50× magnification of the top-view of the porous material.
Figure 30B:
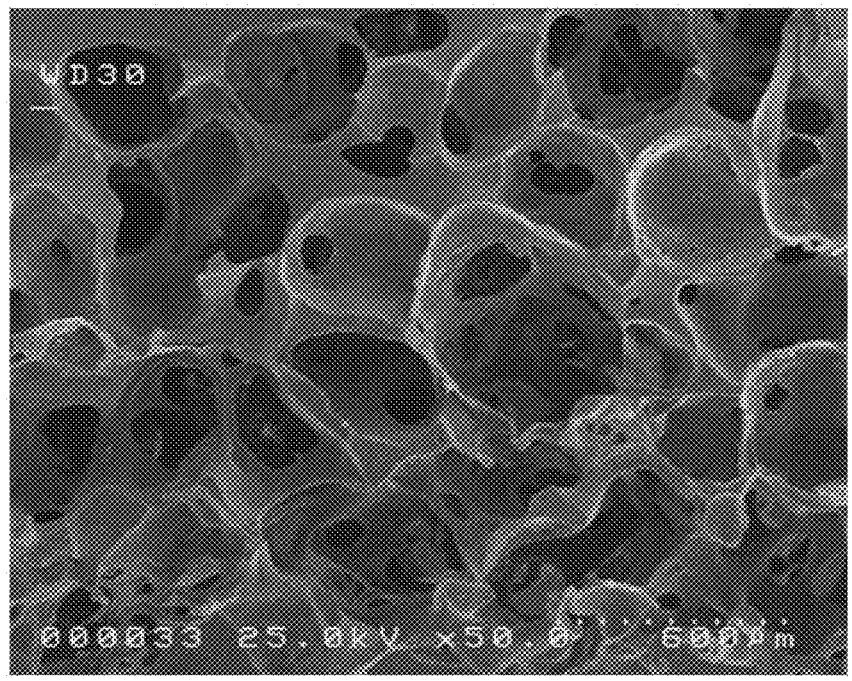
FIG. 30B is scanning electron micrograph image at 50× magnification of the cross-section of the porous material.

A sample from the implant will be characterized by microCT analysis. Scanning electron analysis of the porous material is shown in FIGS. 30A-30B.

Example 10

A Method of Making an Implant Comprising a Porous Material

This example illustrates how to make a biocompatible implantable device (an implant) comprising a porous material layer as disclosed herein, wherein the porous material layer is about 2.5 mm to about 4.5 mm in thickness. Except as otherwise indicated, all steps in this Example were conducted at 25° C.

A substance coated porogen mixture was created, the substance in this Example being silicone. To prepare a surface to act as the base for the substance coated porogen mixture, a base layer of 35% (w/w) silicone in xylene (PN-3206-1; NuSil Technology LLC, Carpinteria, Calif.) was coated on a mandrel (LR-10), placed into an oven, and cured at a temperature of 126° C. for 75 minutes. Alternatively, a previously made biocompatible implantable device, such as, e.g., a base shell disclosed herein, can be attached to a mandrel and then processed beginning with the next step.

The cured base layer was then dipped in about 35% (w/w) silicone in xylene (PN-3206-1; NuSil Technology LLC, Carpinteria, Calif.) and air dried for about 18 minutes to about 22 minutes to allow the xylene to evaporate (devolatilization), thus creating a tacky pore coat.

The mandrel with the base layer covered by the tacky pore coat was then dipped in a composition of core/shell porogens until the maximum amount of porogens were absorbed into the uncured silicone, to create a texture bead coat. The core/shell porogens comprised a core of about 450 µm to about 500 µm comprising sucrose and corn starch, and a PEG shell of about 50 µm to about 75 µm in depth, for a mean porogen diameter of about 550 µm. The total composition of the porogens was about 45% sucrose, about 10% starch and about 45% PEG. The texture bead coat (uncured silicone/porogen coating) was then air dried for about 4.5 minutes to about 5.5 minutes to allow for continued devolatilization.

The texture bead coat was then dipped again in silicone as described above to add additional pore coat, and permitted to devolatilize for about 4 minutes to about 5 minutes. The pore coat was then dipped again in porogens as described above to create another layer of texture bead coat, and permitted to devolatilize for about 25 minutes to about 35 minutes. The texture bead coat was then dipped a third time in silicone as described above to create another layer of pore coat, and permitted to devolatilize for about minutes to about 5 minutes. Then the pore coat was dipped in porogens a final time as described above, and permitted to devolatilize for at least 45 minutes. The process resulted in a substance coated porogen mixture having three layers of texture bead (porogen) coat.

To treat the substance coated porogen mixture to allow fusing of the porogens to form a porogen scaffold and to stabilize the substance, the substance coated porogen mixture was placed into an oven at a temperature of about 126° C. for about 85 minutes. This treatment permitted fusion of the PEG shells of the porogens to form a PEG scaffold, followed by stabilization (curing) of the silicone substance. After curing, the shell mold is dismantled and the cured elastomer coated porogen scaffold is removed.

To remove the porogen scaffold, the cured silicone/porogen scaffold was then subjected to more than one repetition of soaking in hot water followed by rinsing in water until all scaffold was dissolved and removed from the substance. In this Example, the substance coated porogen mixture was immersed in hot water (about 60° C.) for about 8 minutes to about 10 minutes, followed by rinsing in water (less than 45° C.). The mixture was then immersed again in hot water (about 60° C.) for about 20 minutes to about 30 minutes, and rinsed again. Finally the substance was immersed one more time in hot water (about 60° C.) for about 20 minutes to about 30 minutes, followed by rinsing in water while massaging (squeezing) the submerged substance about 10 to about 15 times to remove the now dissolved porogen scaffold material.

This process resulted in a biocompatible implantable device comprising an outer porous material layer (or shell) comprising a layer of interconnected pores, as disclosed herein. See, e.g., FIGS. 4A-4D and 6A-6D. Because the diameter of the porogens was about 550 µm, the average pore size of the porous material was likewise about 550 µm. A sample from the porous material was characterized by microCT analysis. This analysis revealed that the porous material was about 0.8 mm to about 3.0 mm in thickness, with a porosity of about 85% or more, with a surface openness (pore area/total area) of about 60-75%. The porous material has an elongation at break of 450%.

As an alternative example of creating a biocompatible implantable device comprising a porous material layer, the porous material layer is created separately and then attached to the device. In such example, a first porous material layer is created as described above, and is coated with a thin layer of adhesive, for example silicone, and then placed in the bottom cavity of a mold, adhesive side up. A biocompatible implantable device is then placed on top of the porous material surface coated with the adhesive. A second porous material layer is then coated with a thin layer of adhesive such as silicone and applied to the uncovered surface of the biocompatible implantable device. The top piece of the mold cavity is then fixed in place, pressing the two porous material sheets together to create a uniform interface. The silicone adhesive is allowed to cure by placing the covered device into an oven and heated at a temperature of 126° C. for 75 minutes. After curing, excess material is trimmed off creating a uniform seam around the biocompatible implantable device. This process results in a biocompatible implantable device comprising a porous material as disclosed herein.

Alternatively, the porous material created as described above can be laminated onto a biocompatible implantable device while the device is still on a mandrel. In this process, a first porous material layer is coated with a thin layer of silicone and then draped over the device on the mandrel in such a way that there are no wrinkles on the surface. After curing the silicone adhesive, as described above, another coating of silicone is applied to the uncovered surface of the biocompatible implantable device and a second porous material layer is stretched up to cover the back of the device. After curing the silicone adhesive, as described above, the biocompatible implantable device is then taken off the mandrel and the excess porous material is trimmed to create a uniform seam around the device. This process results in a biocompatible implantable device comprising a porous material as disclosed herein. See, e.g., FIGS. 4A-4D and 6A-6D.

Example 11

A Method of Making a Porogen Composition

This example illustrates how to make porogen compositions disclosed herein.

To make a porogen composition comprising a sugar core material and a polymer shell material, sugar particles suitable for a core material were purchased from Paular Corp, (Cranbury, N.J.). These sugar particles were sieved through an about 40 to about 60 mesh to separate particles of about 250 μm about 450 μm in size. To coat sugar core particles with a polymer, poly(ethylene glycol) was coated onto the sugar core material to a thickness of about 53 μm by fluidization using a fluid bed dryer. The resulting porogen compositions yielded porogens comprising a sugar core material of about 335 μm in diameter and a poly(ethylene glycol) shell material of about 53 μm in thickness.

To make a porogen composition comprising a polymer core material and a wax shell material, a polycaprolactone (PCL) core material will be made using a solvent evaporation process. Briefly, about 500 mL of a 30% (w/v) solution of PCL in dichloromethane will be poured into 3 L of a 6% (w/v) solution of poly(vinyl alcohol), MW 23000, with constant stirring. The mixture will be continuously stirred for enough time to allow methylene chloride to evaporate. The resulting PCL particles of core material will be filtered to remove debris and then will be washed with deionized water to remove the poly(vinyl alcohol). This process will result in about 100 g of PCL particles of core material with a mean diameter of about 400 μm to about 500 μm. To coat polymer core particles with a wax, paraffin will be coated onto the PCL core material to a thickness of about 50 μm by fluidization using a fluid bed dryer. The resulting porogen compositions will yield porogens comprising a polymer core material of about 450 μm in diameter and a paraffin shell material of about 50 μm in thickness.

To make a porogen composition comprising a salt core material and a surfactant shell material, sodium chloride particles suitable for a core material will be purchased from a commercial supplier. These salt particles will be sieved through an about 40 to about 60 mesh to separate particles of about 250 μm about 450 μm in size. To coat salt core particles with a surfactant, polysorbate 20 will be coated onto the salt core material to a thickness of about 15 μm by fluidization using a fluid bed dryer. The resulting porogen compositions will yield porogens comprising a salt core material of about 350 μm in diameter and a polysorbate 20 shell material of about 15 μm in thickness.

To make a porogen composition comprising a PGLA (50:50) core and a PCL shell material, PGLA (50:50) and poly-caprolactone (PCL) were co-dissolved in methylene chloride, where at least 2 parts of PGLA (50:50) and at most at 1 part of PCL were dissolved in methylene chloride. Solvent evaporation was applied to form microparticles. A PGLA (50:50) core with PCL shell was formed by annealing the microparticles at 60° C. to allow phase separation between PGLA and PCL. About 500 mL of a 30% (w/v) solution of PGLA (50:50) and PCL in dichloromethane was poured into 3 L of a 6% (w/v) solution of poly(vinyl alcohol), MW 23000, with constant stirring until the methylene chloride evaporated. The resulting particles in polyvinyl alcohol dispersions were heated at 60° C. to allow phase separation between PGLA (50:50) and PCL. After cooling down, the microparticles were filtered to remove debris and then washed with deionized water to remove the poly(vinyl alcohol). This process resulted in about 100 g of a PGLA (50:50) core and PCL shell composition with a mean diameter of about 400 μm to about 500 μm.

Example 12

A Method of Making a Porogen Composition

This example illustrates how to make porogen compositions disclosed herein.

To make a porogen composition comprising a sugar core material comprising two compounds and a polymer shell material, sugar particles suitable for a core material were purchased from Paular Corp. (#703540 MESH 35-40; Cranbury, N.J.), comprising about 75% sucrose with about 25% corn starch binder. To coat sugar core particles with a polymer, poly(ethylene glycol) (PEG with a molecular weight=8000 nominal (PEG 8000)) was coated onto the sugar core material to a thickness of about 50 μm by fluidization using a fluid bed dryer. The total composition of the porogens in this Example was about 45% sucrose, about 10% starch and about 45% PEG. The resulting porogen compositions yielded porogens comprising a sugar core material of about 420-500 μm in diameter and a PEG shell material of about 50 μm in thickness. Particles were sieved through an about 35 US mesh to separate particles of about 500 μm to about 550 μm in size.

Example 13

Capsule Thickness and Disorganization

In order to measure the thickness and disorganization of capsules formed, disks (1 cm in diameter) of various porous biomaterials were implanted subcutaneously in Sprague-Dawley rats using standard procedures. The biomaterials tested were taken from commercially available implants or experimentally produced as follows: Smooth 1, a biomaterial having a smooth surface (NATRELLE®, Allergan, Inc., Irvine, Calif.); Smooth 2, a biomaterial having a smooth surface (MEMORYGEL®, Mentor, Inc., Santa Barbara, Calif.); Textured 1, a biomaterial having a closed-cell textured surface produced from a lost-salt method (BIOCELL® Allergan, Inc., Irvine, Calif.); Textured 2, a biomaterial having a closed-cell textured surface produced from an imprinting method (SILTEX®, Mentor, Inc., Santa Barbara, Calif.); Textured 3, a biomaterial having a closed-cell textured surface produced from either an imprinting or gas foam method (SILIMED®, Sientra, Inc., Santa Barbara, Calif.); Textured 4, a biomaterial having a closed-cell textured surface produced from an imprinting method (Perouse Plastie, Mentor, Inc., Santa Barbara, Calif.); Textured 5, a biomaterial having an open-cell polyurethane surface; Textured 6, a biomaterial having an open-cell textured surface produced according to the methods disclosed herein. Samples were harvested at 6 weeks, fixed in formalin, and processed to produce paraffin blocks. The paraffin blocks were sectioned using a microtome at 2 µm thickness and stained with hematoxylin and eosin (H&E).

Capsules were characterized by measuring the thickness and disorganization of the capsule formed over the porous biomaterial. Capsule thickness was measured by acquiring 2 representative 20× images of the H&E stained biomaterials and measuring the thickness of the capsule at 3 points in the image. Capsule disorganization was evaluated by acquiring 3 representative 20× images of the H&E stained biomaterials, and then drawing a reference vector tangent to the implant surface, as well as, drawing vectors along collagen fibers within the capsule. The angle of each vector relative to the reference vector was then measured, and the standard deviation of the angles was calculated, where greater standard deviations reflected a higher degree of disorganization. All image analysis calculations were performed on the Nikon Elements Advanced Research software.

All thickness and disorganization measurements were acquired blinded and each measurement was normalized to the data obtained from Textured 1 biomaterial. For the thickness data collected, a one-way ANOVA was run to determine significant effects ($p<0.05$). If there were any statistically significant effects from the ANOVA analysis, the Tukey's post-hoc test was run for multiple comparisons at $\alpha=0.05$. For the disorganization data collected, a Levene's Test for Equal Variance was used to determine whether there was a statistically significant difference in disorganization between experimental groups ($p<0.05$). Between individual groups, the criteria for non-significance were overlap of confidence intervals (95%), adjusted for the number of groups.

Figure 7A:
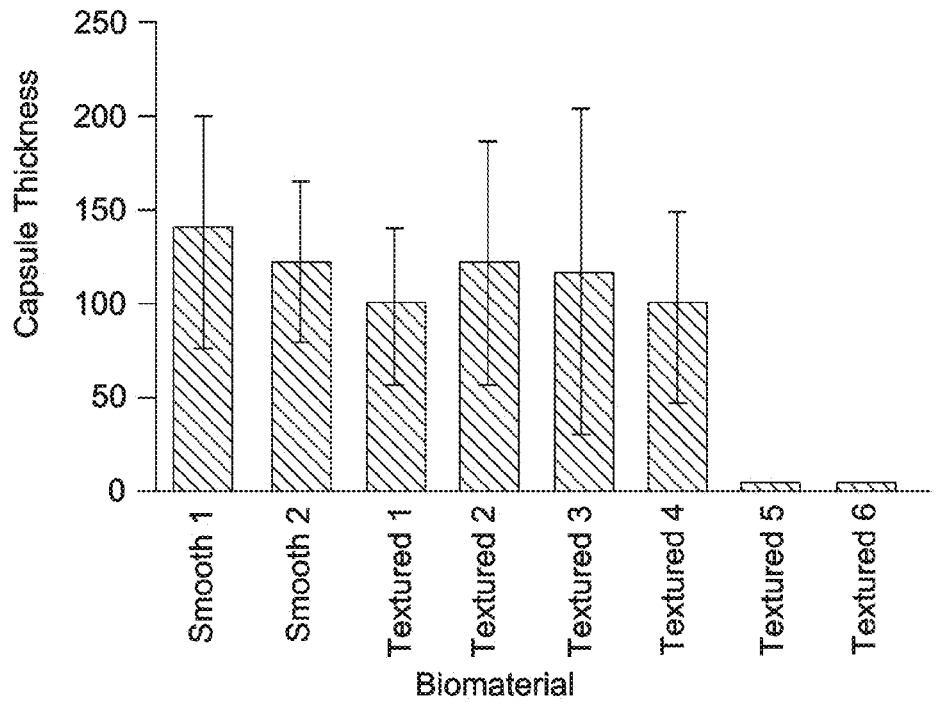
FIG. 7A shows a bar graph of thickness data as normalized mean±normalized standard deviation.
Figure 7B:
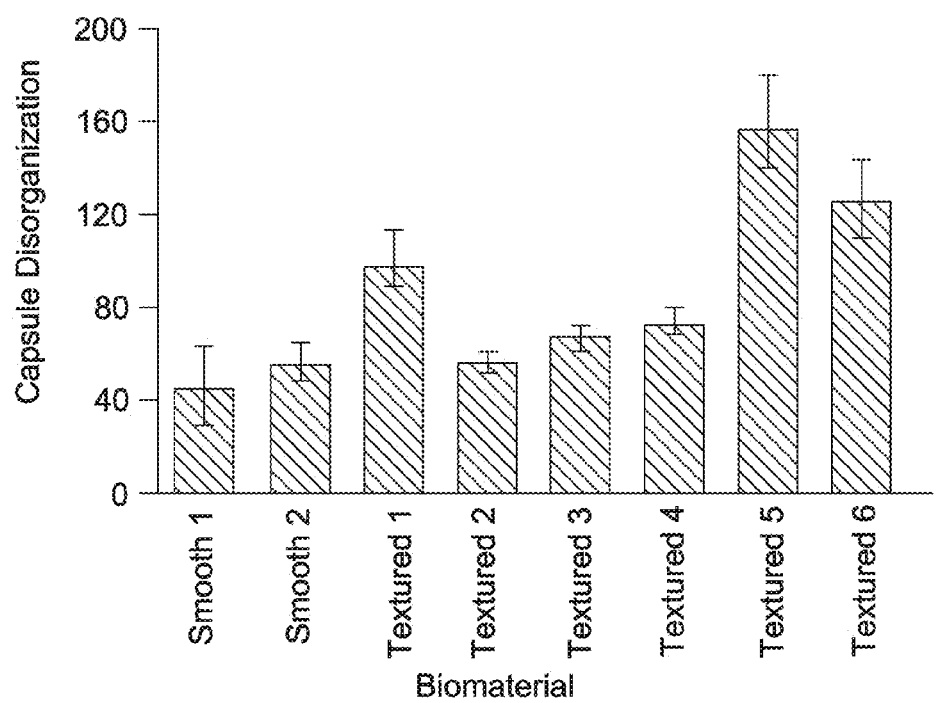
FIG. 7B shows a bar graph of disorganization normalized with a standard deviation with upper and lower bounds of confidence intervals.

The capsule thicknesses and disorganization, normalized to the Texture 1 biomaterial within each respective study, are shown in FIG. 7A-7B. Smooth Texture 1 and 2 biomaterials, and Textures 1-4 biomaterials (having closed-cell texture) exhibited pronounced capsule formation, and the capsules formed were of equivalent thicknesses of about 100 µm to about 140 µm (FIG. 7A). Texture 5-6 biomaterials exhibited minimal capsule formation with capsules formed having a thickness of less than 10 µm (FIG. 7A). With respect to capsule organization, it was found that Texture 1 biomaterial resulted in a capsule that was more disorganized than Smooth 1 and 2 and Texture 2-4 biomaterials (FIG. 7B). Texture 5 and 6 biomaterials demonstrated extensive ingrowth (about 200 µm) that was interconnected and significantly more disorganized (50% of fibers were not parallel to implant surface) than Smooth 1 and 2 and Texture 1-4 biomaterials (FIG. 7B). These findings show that Smooth 1 and 2 biomaterials (smooth surface) and Textures 1-4 biomaterials (closed-cell textured surfaces) resulted in a capsule with predominantly organized collagen. Textures 5-6 biomaterials (open-cell textured surfaces), in contrast, induce significant ingrowth that can eliminate capsule and disorganize the tissue at the material-tissue interface.

Example 14

Capsule Collagen

In order to measure the collagen content of capsules formed, disks (1 cm in diameter) of various porous biomaterials were implanted subcutaneously in Sprague-Dawley rats using standard procedures. The biomaterials tested were taken from commercially available implants or experimentally produced as follows: Smooth 1, a biomaterial having a smooth surface (NATRELLE®, Allergan, Inc., Irvine, Calif.); Smooth 2, a biomaterial having a smooth surface (MEMORYGEL®, Mentor, Inc., Santa Barbara, Calif.); Textured 1, a biomaterial having a closed-cell textured surface produced from a lost-salt method (BIOCELL®, Allergan, Inc., Irvine, Calif.); Textured 2, a biomaterial having a closed-cell textured surface produced from an imprinting method (SILTEX®, Mentor, Inc., Santa Barbara, Calif.); Textured 3, a biomaterial having a closed-cell textured surface produced from an imprinting method (Perouse Plastie, Mentor, Inc., Santa Barbara, Calif.); Textured 4, a biomaterial having a closed-cell textured surface produced from either an imprinting or gas foam method (SILIMED®, Sientra, Inc., Santa Barbara, Calif.); Textured 5, a biomaterial having an inverse foam polyurethane-polyethylene glycol surface; Textured 6, a biomaterial having an inverse foam polyurethane-polyethylene glycol surface; Textured 7, a biomaterial having an open-cell polyurethane surface; Textured 8, a biomaterial having a non-woven felt surface. Samples were harvested at 6 weeks, fixed in formalin, and processed to produce paraffin blocks. The paraffin blocks were sectioned using a microtome at 2 µm thickness and stained with aniline blue.

Capsules were characterized by measuring staining darkness of the capsule formed over the implanted porous biomaterials. The darkness of the capsule was measured from 5 representative 20× images, with overall intensity averaged over the capsules to reflect the depth of staining. To account for variations in parameters, such as section thickness and precise staining times, all measurements were normalized to the intensity measured within the dermis of the same section, which was utilized as a standard due to the consistent staining that was observed in this region. A one-way ANOVA was run to determine significant effects ($p<0.05$). If there were any statistically significant effects from the ANOVA analysis, the Tukey's post-hoc test was run for multiple comparisons at $\alpha=0.05$.

Figure 8:
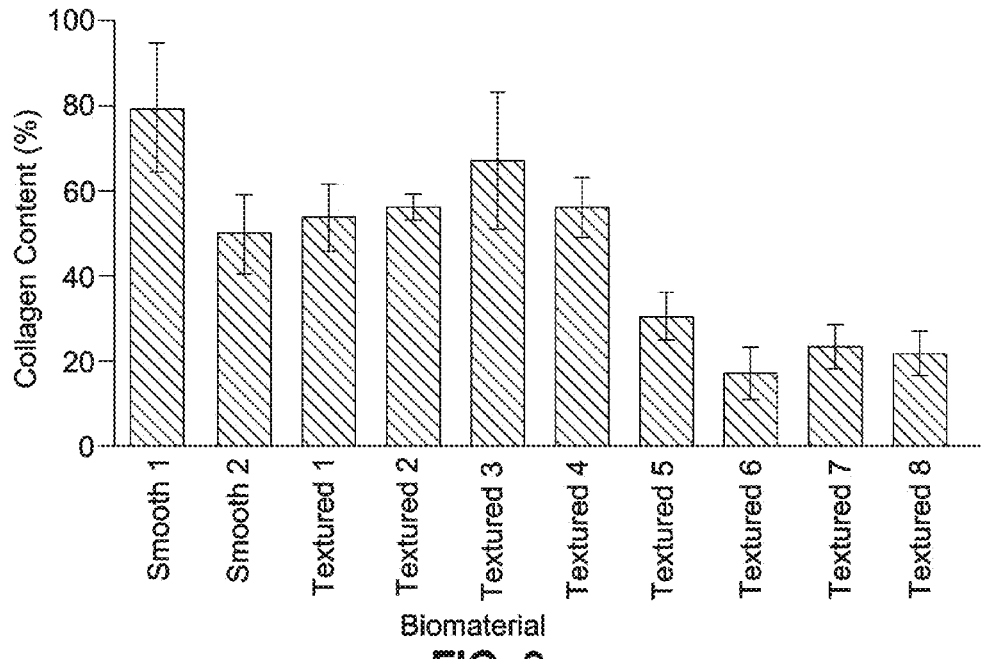
FIG. 8 is a bar graph showing data of collagen content of capsules formed over various biomaterials (n=6). Results are shown as mean±standard deviation. Asterisks (*) indicate a statistically significant Texture 1 biomaterial.

FIG. 8 shows the mean collagen density of capsules and ingrowth formed over smooth and textured porous biomaterials. It was found that the capsules formed over Smooth 1 and 2 biomaterials and Textured 1-4 biomaterials (closed-cell textured surfaces) showed a statistically significant increase in collagen density over the Texture 5 and 6 biomaterials (inverse foam textured surface), Textured 7 biomaterial (open-cell textured surface), and Textured 8 biomaterial (non-woven felt textured surface). As such, the prevention of capsule formation was shown to be linked to significant ingrowth into an open, interconnected texture, where the ingrowth has a low collagen density.

Example 15

Tissue Adhesion

In order to evaluate the effect of texture on tissue adhesion to a porous biomaterial, strips of various biomaterial were implanted subcutaneously in a Sprague-Dawley rat using standard procedures. The biomaterials tested were taken from commercially available implants or experimentally produced as follows: Smooth 1, n=38, a biomaterial having a smooth surface (NATRELLE®, Allergan, Inc., Irvine, Calif.); Textured 1, n=64, a biomaterial having a closed-cell textured surface produced from a lost-salt method (BIOCELL®, Allergan, Inc., Irvine, Calif.); Textured 2, n=6, a biomaterial having a closed-cell textured surface produced from an imprinting method (SILTEX®, Mentor, Inc., Santa Barbara, Calif.); Textured 3, n=6, a biomaterial having an inverse foam polyurethane-polyethylene glycol surface; Textured 4, n=45, a biomaterial having an inverse foam polyurethane-polyethylene glycol surface; Textured 5, n=45, a biomaterial having an open-cell polyurethane surface; Textured 6, n=6, a biomaterial having an open-cell polyurethane surface; Textured 7, n=6, a biomaterial having an open-cell textured surface of 0.8 mm produced according to the methods disclosed herein; Textured 8, n=6, a biomaterial having an open-cell textured surface of 1.5 mm produced according to the methods disclosed herein. Samples were harvested at 4 weeks, and tissue was pulled from the test strip on a mechanical tester with a pullout speed of 2 mm/second. Adhesion strength was measured as the peak force required to separate the implant from the surrounding tissue. A one-way ANOVA was run to determine significant effects ($p<0.05$). If there were any statistically significant effects from the ANOVA analysis, the Tukey's post-hoc test was run for multiple comparisons at $\alpha=0.05$.

Figure 9:
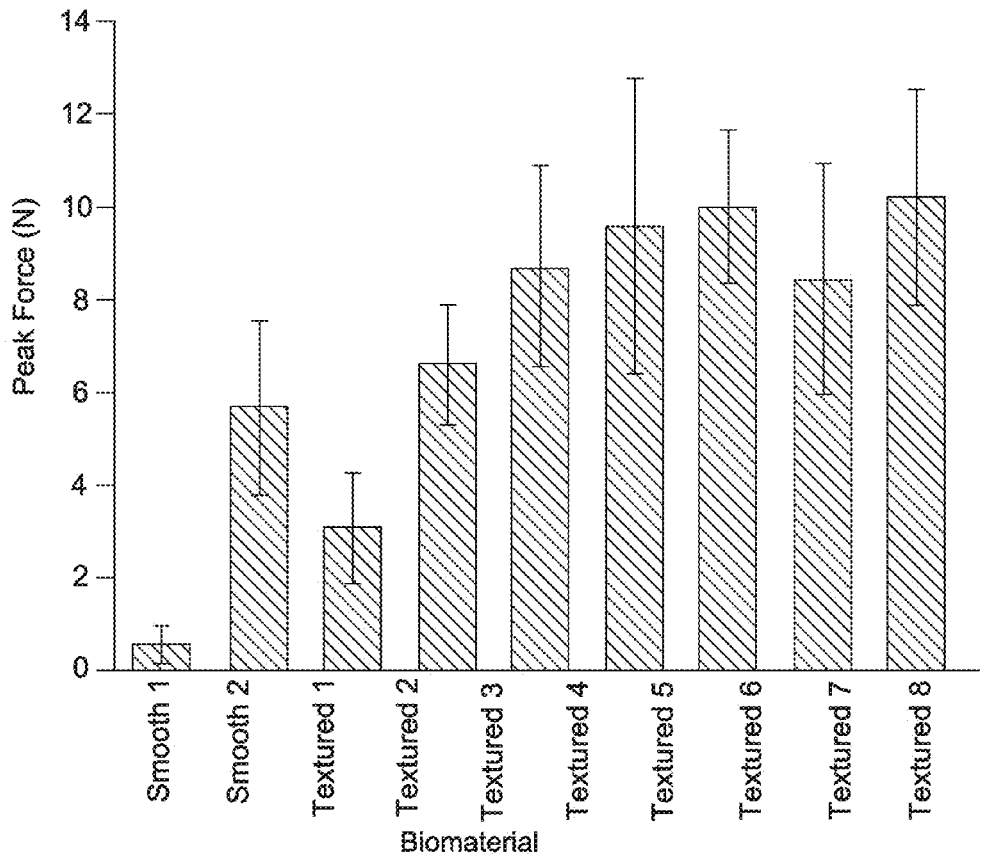
FIG. 9 is a bar graph showing data from a tissue adhesion test of various biomaterials. Results are shown as mean±standard deviation.

Smooth 1 biomaterial showed little adhesion, as there were no significant protrusions above a micro-scale and had minimal drag on the surrounding tissue (FIG. 9). Textured 1 and 2 biomaterials (closed-cell textured surfaces) exhibited limited amount of tissue interaction and showed greater adhesion than Smooth 1 (FIG. 7). Textured 3 and 4 biomaterials (inverse Foam textured surface) and Textures 5-8 biomaterials (open-cell textured surfaces) showed the highest degree of tissue adhesion (FIG. 9). As such, Textured 5-8 biomaterials promoted significant tissue infiltration/ingrowth because of the highly porous and interconnected textures.

Example 16

Capsule Stiffness

In order to evaluate stiffness of capsules/ingrowth formed over a porous biomaterial, 7 mL mini-expanders comprising silicone biomaterial of various textures were implanted subcutaneously in a Sprague-Dawley rat using standard procedures. The biomaterials tested were taken from commercially available implants or experimentally produced as follows: Smooth 1, a biomaterial having a smooth surface (NATRELLE®, Allergan, Inc., Irvine, Calif.); Textured 1, a biomaterial having a closed-cell textured surface produced from a lost-salt method (BIOCELL®, Allergan, Inc., Irvine, Calif.); Textured 2, a biomaterial having an open-cell textured surface of 0.8 mm produced according to the methods disclosed herein; Textured 3, a biomaterial having an open-cell textured surface of 1.5 mm produced according to the methods disclosed herein. At time 0 (immediately post-implantation) and at 6 weeks, saline was incrementally added to each expander, and the resulting pressure exerted on and by the expander at each step was measured with a digital manometer. Stiffness was calculated by fitting a trend-line to the linear region of the pressure-volume curve and measuring the slope of the line. Increases in the stiffness of the capsule/ingrowth were reflected by increases in the slope. To account for expander-to-expander variability, each stiffness measurement was normalized to the stiffness of the expander itself. A one-way ANOVA was run to determine significant effects ($p<0.05$). If there were any statistically significant effects from the ANOVA analysis, the Tukey's post-hoc test was run for multiple comparisons at $\alpha=0.05$.

Figure 10:
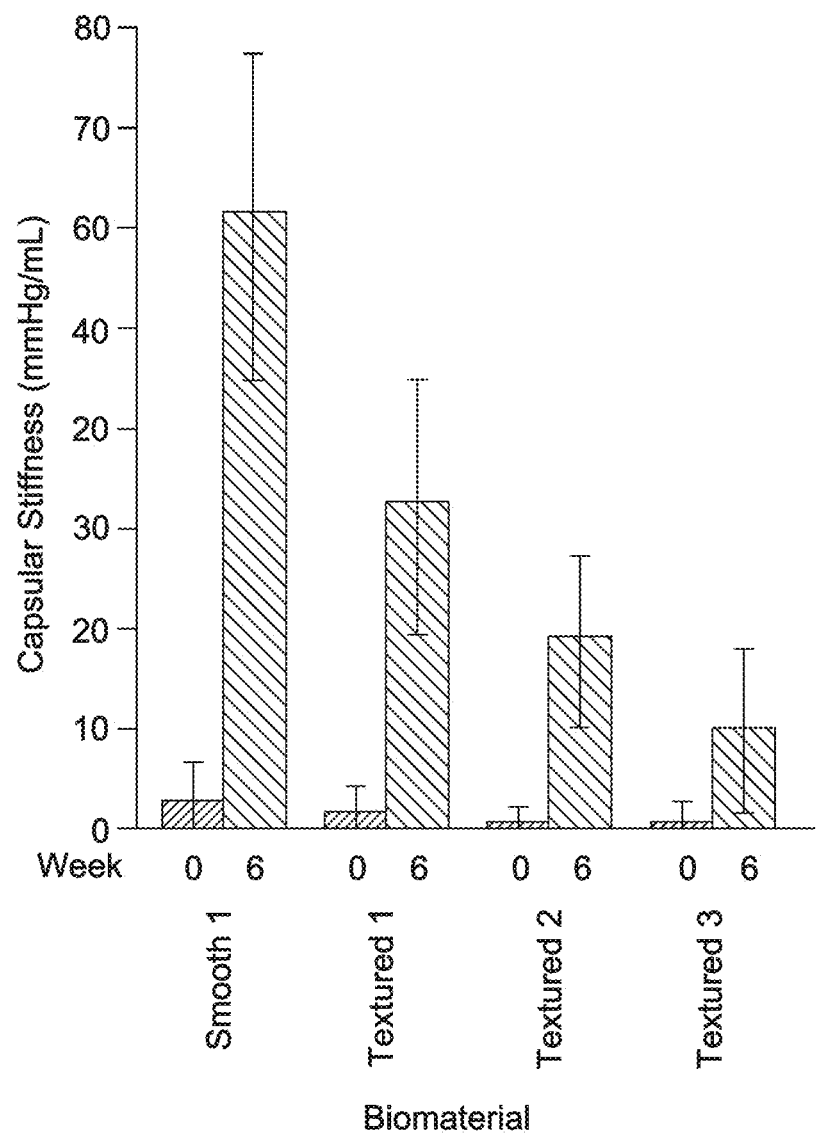
FIG. 10 is a bar graph showing data of stiffness of capsule/ingrowth formed over various tissue expanders at time 0 and at 6 weeks (n=8). Results are shown as mean±standard deviation.

Capsules formed over Smooth 1 biomaterial expander showed the greatest stiffness after 6 weeks (FIG. 10). Textured 1 biomaterial expander (closed-cell textured surface) showed lower stiffness than Smooth 1 biomaterial expander but greater stiffness than the Textured 2 and 3 biomaterial expanders (open-cell textured surface) (FIG. 10). This data demonstrates that closed-cell biomaterials result in capsules that are stiffer than those that result from open-cell biomaterials that support ingrowth and prevent capsule formation.

Example 17

Bleeding and Capsule Response

In order to identify critical morphological and physical characteristics of the porous biomaterials disclosed herein, disks (1 cm in diameter) of various biomaterials were implanted subcutaneously in a Sprague-Dawley rat using standard procedures and the response to such implantation in terms of capsule formation and bleeding were determined. The morphological and physical characteristics tested for each biomaterial are given in Tables 1 and 2.

TABLE 1

Morphological Characteristics of Biomaterials

| Biomaterial | Mean thickness (mm) | Mean porosity (%) | Mean pore size (μm) | Mean inter connections/pore | Mean inter connection size (μm) |
|---|---|---|---|---|---|
| Polyurethane 1 | 2.40 ± 0.10 | 98.0 ± 0.4 | 522 ± 87 | 14.2 ± 3.2 | 166 ± 48 |
| Polyurethane 2 | 2.90 ± 0.01 | 98.0 ± 0.0 | 488 ± 119 | 14.2 ± 1.4 | 230 ± 69 |
| Mesh 1 | 0.89 ± 0.06 | 72.2 ± 1.5 | 522 ± 137 | N/A | N/A |
| Mesh 2 | 1.38 ± 0.10 | 70.9 ± 2.9 | 560 ± 134 | N/A | N/A |
| Fused Porogen 1 | 0.56 ± 0.38 | 55.6 ± 0.5 | 530 ± 150 | 7.0 ± 3.1 | 325 ± 242 |
| Fused Porogen 2 | 0.79 ± 0.06 | 72.6 ± 5.4 | 458 ± 48 | 7.8 ± 1.5 | 151 ± 59 |
| Fused Porogen 3 | 1.10 ± 0.00 | 77.6 ± 1.0 | 596 ± 150 | 4.6 ± 1.9 | 106 ± 42 |
| Fused Porogen 4 | 1.14 ± 0.09 | 66.4 ± 3.2 | 424 ± 68 | 8.0 ± 1.1 | 111 ± 49 |

TABLE 1-continued

Morphological Characteristics of Biomaterials

| Bio-material | Mean thickness (mm) | Mean porosity (%) | Mean pore size (μm) | Mean interconnections/pore | Mean inter connection size (μm) |
|---|---|---|---|---|---|
| Fused Porogen 5 | 1.32 ± 0.02 | 77.9 ± 0.9 | 408 ± 64 | 7.6 ± 2.0 | 118 ± 44 |
| Fused Porogen 6 | 1.60 ± 0.10 | 77.8 ± 1.2 | N/D | N/D | N/D |
| Fused Porogen 7 | 1.60 ± 0.10 | 81.2 ± 1.3 | 608 ± 268 | 4.9 ± 1.9 | 130 ± 85 |
| Fused Porogen 8 | 1.60 ± 0.00 | 85.3 ± 1.4 | 421 ± 48 | 8.2 ± 2.1 | 128 ± 38 |
| Fused Porogen 9 | 1.61 ± 0.03 | 80.3 ± 1.0 | 456 ± 81 | 7.4 ± 1.6 | 154 ± 50 |
| Fused Porogen 10 | 1.80 ± 1.20 | 80.6 ± 0.4 | 634 ± 124 | 7.5 ± 2.6 | 95 ± 33 |
| Fused Porogen 11 | 1.93 ± 0.78 | 82.8 ± 0.5 | 456 ± 65 | 7.1 ± 2.2 | 133 ± 46 |
| Fused Porogen 12 | 1.95 ± 0.19 | 76.5 ± 2.0 | 431 ± 57 | 7.0 ± 1.2 | 114 ± 58 |
| Fused Porogen 13 | 2.34 ± 0.06 | 74.0 ± 0.5 | 478 ± 112 | 7.1 ± 2.0 | 141 ± 47 |
| Fused Porogen 14 | 2.36 ± 0.12 | 81.1 ± 0.5 | 399 ± 93 | 7.4 ± 0.8 | 126 ± 64 |

TABLE 2

Physical Characteristics of Biomaterials

| Biomaterial | Compressive Response (kPa) | | | Elongation |
|---|---|---|---|---|
| | at 5% strain | at 10% strain | at 20% strain | at Break (%) |
| Polyurethane 1 | 1.74 ± 0.40 | 2.60 ± 0.53 | 3.38 ± 0.52 | N/D |
| Polyurethane 2 | 1.41 ± 0.13 | 2.63 ± 0.03 | 2.89 ± 0.20 | 454 ± 7 |
| Mesh 1 | 0.07 ± 0.01 | 0.20 ± 0.02 | 0.74 ± 0.08 | 336 ± 39 |
| Mesh 2 | 0.09 ± 0.04 | 0.22 ± 0.09 | 0.74 ± 0.39 | 439 ± 56 |
| Fused Porogen 1 | 0.05 ± 0.00 | 0.18 ± 0.01 | 1.01 ± 0.14 | N/D |
| Fused Porogen 2 | 0.05 ± 0.03 | 0.23 ± 0.10 | 1.59 ± 0.46 | N/D |
| Fused Porogen 3 | 0.04 ± 0.01 | 0.14 ± 0.06 | 0.86 ± 0.36 | N/D |
| Fused Porogen 4 | 0.55 ± 0.21 | 1.55 ± 0.50 | 5.21 ± 1.18 | 287 ± 78 |
| Fused Porogen 5 | 0.13 ± 0.02 | 0.59 ± 0.14 | 3.26 ± 0.64 | N/D |
| Fused Porogen 6 | 0.10 ± 0.02 | 0.38 ± 0.11 | 2.24 ± 0.92 | N/D |
| Fused Porogen 7 | 0.094 ± 0.00 | 0.35 ± 0.06 | 1.86 ± 0.36 | N/D |
| Fused Porogen 8 | 0.04 ± 0.01 | 0.15 ± 0.04 | 0.61 ± 0.13 | 222 ± 33 |
| Fused Porogen 9 | 0.11 ± 0.03 | 0.46 ± 0.12 | 2.00 ± 0.26 | N/D |
| Fused Porogen 10 | 0.14 ± 0.01 | 0.43 ± 0.03 | 1.48 ± 0.01 | N/D |
| Fused Porogen 11 | 0.17 ± 0.00 | 0.64 ± 0.01 | 2.15 ± 0.03 | N/D |
| Fused Porogen 12 | 0.42 ± 0.14 | 1.07 ± 0.29 | 3.17 ± 0.61 | 384 ± 20 |
| Fused Porogen 13 | 0.19 ± 0.04 | 0.84 ± 0.16 | 3.48 ± 0.39 | N/D |
| Fused Porogen 14 | 0.06 ± 0.02 | 0.16 ± 0.06 | 0.61 ± 0.10 | 335 ± 11 |

Implanted porous biomaterials were harvested, fixed in formalin, and processed to produce paraffin blocks. The paraffin blocks were sectioned using a microtome at 2 μm thickness and stained with hematoxylin and eosin (H&E). Depending on the morphological characteristic being assessed, capsule response was measured by acquiring at least 3 representative lx, 4×, 20×, or 50× images of sectioned biomaterial, digitally capturing the images, and measuring the characteristic at 3 or more point in each captured image. All image analysis calculations were performed on the Nikon Elements Advanced Research software. Bleeding response and physical characteristics were measured using routine methods. See, e.g., Winnie, Softness Measurements for Open-Cell Foam Materials and Human Soft Tissue, Measurement Science and Technology (2006).

The summary of the results obtained from this analysis are given in Table 3. The results indicate that porous biomaterials having a wide range in porosity are well tolerated in that in only a very narrow range of porosity (74-86%) was bleeding observed in some of the biomaterials tested. In terms of capsule formation, increased porosity resulted in decreased capsule formation. Interconnection diameter between pores also influenced the bleeding response in that increased diameter resulted in a decreased bleeding response (Table 3). More strikingly, increasing the number of interconnections per pore decreased both the bleeding response and capsule formation seen in the animals in response to the implanted biomaterials (Table 3). Lastly, a fine balance in the stiffness of a biomaterial, as measured by compressive forces, was needed to provide the optimal in vivo responses. This is because increased stiffness of a biomaterial resulted in decreased bleeding, whereas decreased stiffness was needed in order to decease capsule formation (Table 3).

TABLE 3

Bleeding and Capsule Response of Biomaterials

| Characteristic | Bleeding Response | | Capsule Response | |
|---|---|---|---|---|
| | No Bleeding | Bleeding | No Capsule | Capsule |
| Mean thickness (mm) | 0.6-2.9 | 1.6-2.3 | 0.8-2.9 | 0.6-2.9 |
| Mean porosity (%) | 56-98 | 74-86 | 72-98 | 56-81 |
| Mean pore size (μm) | 408-624 | 456-608 | 456-641 | 408-634 |
| Mean interconnections/pore | 7-14 | 4.9-9.5 | 7.1-14 | 4.6-9.5 |
| Mean interconnection size (μm) | 118-325 | 130-153 | 456-641 | 408-634 |
| Compressive at 5% strain (kPa) | 0.05-2.57 | 0.10-0.20 | 0.05-1.70 | 0.00-2.57 |
| Compressive at 10% strain (kPa) | 0.18-8.00 | 0.10-4.20 | 0.22-4.17 | 0.10-8.00 |
| Compressive at 20% strain (kPa) | 1.00-16.0 | 1.90-3.50 | 1.10-7.60 | 0.90-16.0 |

Analyzing all the data obtained from these experiments revealed optimal morphological and physical characteristics for a porous material produced from the porogen method disclosed herein, was as follows: having a porosity of about 80% to about 88%, having an interconnection size of about 110 μm to about 140 μm, having about 7 to about 11 interconnections per pore, having a compressive force of about 0.50 kPa to about 0.70 kPa at 5% strain, having a compressive force of about 1.0 kPa to about 2.0 kPa at 10% strain, and having a compressive force of about 3.5 kPa to about 5.5 kPa at 20% strain. In an aspect of this embodiment, optimal morphological and physical characteristics for a porous material produced from the porogen method disclosed herein, was as follows: having a porosity of about 83% to about 85%, having an interconnection size of about 120 μm to about 130 μm, having about 8 to about 10 interconnections per pore, having a compressive force of about 0.55 kPa to about 0.65 kPa at 5% strain, having a compressive force of about 1.3 kPa to about 1.7 kPa at 10% strain, and having a compressive force of about 4.0 kPa to about 5.0 kPa at 20% strain.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method for anchoring an implant device to a mucosal lining of a patient's gastrointestinal tract comprising:
   inserting a pre-formed implant device into the patient's gastrointestinal lumen, which defines a passage that allows for passage therethrough of the pre-formed implant and food, at least a portion of the implant device being formed of a substantially non-resorbable, biocompatible, elastomer matrix defining an array of interconnected pores structured to receive tissue ingrowth from the mucosal lining of the patient's gastrointestinal lumen to anchor the implant device to the mucosal lining; and placing the implant device within the passage defined by the patient's gastrointestinal lumen such that the array of interconnected pores contacts the mucosal lining such that the implant rests against the mucosal lining and extends into the passage defined by the gastrointestinal lumen and receives tissue ingrowth from the mucosal lining to anchor the implant device to the mucosal lining.

2. The method of claim 1, wherein the step of placing includes pressing the array of interconnected pores against the mucosal lining.

3. The method of claim 1, wherein the step of inserting includes inserting the implant device into the patient's gastrointestinal tract with an endoscopic device.

4. The method of claim 1, wherein the step of inserting includes inserting the implant device into the patient's esophagus through the patient's mouth or inserting the implant device into the patient's large intestine through the patient's anus.

5. The method of claim 1, wherein the step of placing includes suturing the implant device to the patient's gastrointestinal tract such that the array of interconnected pores contacts the mucosal lining.

6. The method of claim 1, wherein the array of interconnected pores forms an outer surface of the implant device.

7. The method of claim 1, wherein each of the pores of the array of interconnected pores has a size of between about 30 microns to about 1000 microns.

8. The method of claim 1, wherein the elastomer matrix has a porosity of between about 10% to about 80%.

9. The method of claim 1, wherein the elastomer matrix is a silicone-based elastomer matrix.

10. The method of claim 1, wherein the implant device is selected from a group consisting of a stent, a drug elution device, a tissue graft, an intragastric volume occupying device, a sensor, a device structured to form a stoma within the gastrointestinal tract, and combinations thereof.

11. A method for anchoring an implant device to a mucosal lining of a patient's gastrointestinal tract comprising:

inserting a pre-formed implant device into the patient's gastrointestinal lumen, which defines a passage that allows for passage therethrough of the pre-formed implant and food, at least a portion of the implant device being formed of a substantially non-resorbable, biocompatible, elastomer matrix defining an array of interconnected pores structured to receive tissue ingrowth from the mucosal lining of the patient's gastrointestinal lumen to anchor the implant device to the mucosal lining; and placing the implant device within the passage defined by the patient's gastrointestinal lumen such that the array of interconnected pores contacts the mucosal lining such that the implant does not extend into the mucosal lining and receives tissue ingrowth from the mucosal lining to anchor the implant device to the mucosal lining.

12. The method according to claim 11, wherein the implant is placed such that it does not pass through a surface of the mucosal lining.

13. A method for anchoring an implant device to a mucosal lining of a patient's gastrointestinal tract comprising:

inserting a pre-formed implant device into the patient's gastrointestinal lumen, which defines a passage that allows for passage therethrough of the pre-formed implant and food, without cutting any tissue of the patient, at least a portion of the implant device being formed of a substantially non-resorbable, biocompatible, elastomer matrix defining an array of interconnected pores structured to receive tissue ingrowth from the mucosal lining of the patient's gastrointestinal lumen to anchor the implant device to the mucosal lining; and placing the implant device within the passage defined by the patient's gastrointestinal lumen such that the array of interconnected pores contacts the mucosal lining and receives tissue ingrowth from the mucosal lining to anchor the implant device to the mucosal lining.

\* \* \* \* \*